US012593845B2

(12) United States Patent
Teranishi et al.

(10) Patent No.: US 12,593,845 B2
(45) Date of Patent: Apr. 7, 2026

(54) 2,6-DIOXO-3,6-DIHYDROPYRIMIDINE COMPOUND, AGRICULTURAL AND HORTICULTURAL BACTERICIDE, NEMATICIDE, AND MEDICAL AND VETERINARY ANTIFUNGAL AGENT

(71) Applicant: Nippon Soda Co., Ltd., Tokyo (JP)

(72) Inventors: Takaaki Teranishi, Kanagawa (JP); Raito Kuwahara, Kanagawa (JP); Yohei Munei, Kanagawa (JP); Hajime Shimomura, Kanagawa (JP); Tatsuhiro Kawasaki, Kanagawa (JP); Takuma Ishihara, Kanagawa (JP); Jun Iwata, Kanagawa (JP); Tomoyuki Saiga, Kanagawa (JP); Chihiro Nishino, Kanagawa (JP)

(73) Assignee: Nippon Soda Co., Ltd., Tokyo (JP)

(*) Notice: Subject to any disclaimer, the term of this patent is extended or adjusted under 35 U.S.C. 154(b) by 904 days.

(21) Appl. No.: 17/767,749

(22) PCT Filed: Oct. 26, 2020

(86) PCT No.: PCT/JP2020/040135

§ 371 (c)(1),
(2) Date: Apr. 8, 2022

(87) PCT Pub. No.: WO2021/085389

PCT Pub. Date: May 6, 2021

(65) Prior Publication Data

US 2024/0114908 A1 Apr. 11, 2024

(30) Foreign Application Priority Data

Oct. 28, 2019 (JP) ................................ 2019-195484
Mar. 24, 2020 (JP) ................................ 2020-053191

(51) Int. Cl.

| | |
|---|---|
| ***A01N 43/54*** | (2006.01) |
| ***A01N 43/60*** | (2006.01) |
| ***A01N 43/647*** | (2006.01) |
| ***A01N 43/707*** | (2006.01) |
| ***A01N 43/78*** | (2006.01) |
| ***A01N 43/82*** | (2006.01) |
| ***A01N 43/84*** | (2006.01) |
| ***A01P 3/00*** | (2006.01) |
| ***C07D 239/54*** | (2006.01) |
| ***C07D 253/075*** | (2006.01) |
| ***C07D 401/06*** | (2006.01) |
| ***C07D 401/12*** | (2006.01) |
| ***C07D 403/06*** | (2006.01) |
| ***C07D 403/10*** | (2006.01) |
| ***C07D 403/12*** | (2006.01) |
| ***C07D 405/12*** | (2006.01) |
| ***C07D 417/12*** | (2006.01) |

(52) U.S. Cl.
CPC ............. *A01N 43/54* (2013.01); *A01N 43/60* (2013.01); *A01N 43/647* (2013.01); *A01N 43/707* (2013.01); *A01N 43/78* (2013.01); *A01N 43/82* (2013.01); *A01N 43/84* (2013.01); *A01P 3/00* (2021.08); *C07D 239/54* (2013.01); *C07D 253/075* (2013.01); *C07D 401/06* (2013.01); *C07D 401/12* (2013.01); *C07D 403/06* (2013.01); *C07D 403/10* (2013.01); *C07D 403/12* (2013.01); *C07D 405/12* (2013.01); *C07D 417/12* (2013.01)

(58) Field of Classification Search
CPC ..... C07D 401/06; C07D 239/54; A01N 43/54
See application file for complete search history.

(56) References Cited

U.S. PATENT DOCUMENTS

| | | | |
|---|---|---|---|
| 5,166,399 | A | 11/1992 | Schuetz et al. |
| 5,859,014 | A | 1/1999 | Bantle et al. |
| 2011/0082153 | A1 | 4/2011 | Aslanian et al. |
| 2015/0313232 | A1 | 11/2015 | Braun et al. |

FOREIGN PATENT DOCUMENTS

| | | | |
|---|---|---|---|
| EP | 0 748 800 | A2 | 12/1996 |
| JP | 09-100269 | A | 4/1997 |
| JP | 2010-538068 | A | 12/2010 |
| WO | WO-2013/071169 | A1 | 5/2013 |
| WO | WO-2014/053473 | A1 | 4/2014 |

OTHER PUBLICATIONS

"Opportunities for Chiral Agrochemicals," Williams, A., Pestic. Sci., 46, 3-9, 1995.*
Patrick, G. L. "An Introduction to Medicinal Chemistry," 6th Edition, Oxford, 2017, pp. 223-253, at 224-225, 230-231.*
Kubinyi (3D QSAR in Drug Design: Ligand-Protein Interactions and Molecular Similarity, vol. 2-3, Springer, 1998, see p. 243).*
Sahin et al., "Identifying the Novel Pyrimidine-Based CDK2 Inhibitors as Anticancer Agents Using Text-Mining and Combined Molecular Modeling Approaches," Journal of the Turkish Chemical Society Section A: Chemistry, Jun. 23, 2020, 7(2):383-404.
Baruah et al., "Studies On pyrimidine%u2014annelated heterocycles: synthesis of novel pyrazolo[3',4':4,5]pyrido[2,3%u2014d]pyrimidines by intramolecular 1,3%u2014dipolar cycloadditions," J. Chem. Soc., Perkin Trans. 1, 1996, 16:1999-2003.
Kim et al., "The Reactions of 2,6-Dichlorobenzonitrile Oxide with Pyrimidine Derivatives," Heterocycles, 1992, 34(7):1423-1434.

* cited by examiner

*Primary Examiner* — Valerie Rodriguez-Garcia
(74) *Attorney, Agent, or Firm* — Millen, White, Zelano & Branigan, P.C.; Brion P. Heaney

(57) ABSTRACT

An object of the present invention is to provide a 2,6-dioxo-3,6-dihydropyrimidine compound that has excellent bactericidal and antimicrobial activity, has excellent safety, and can be industrially favorably synthesized, and an agricultural and horticultural fungicide, a nematicide, and an antifungal agent for use in medicine/animals that contain the compound as an active ingredient.

4 Claims, No Drawings

2,6-DIOXO-3,6-DIHYDROPYRIMIDINE COMPOUND, AGRICULTURAL AND HORTICULTURAL BACTERICIDE, NEMATICIDE, AND MEDICAL AND VETERINARY ANTIFUNGAL AGENT

The present invention relates to 2,6-dioxo-3,6-dihydropyrimidine compounds and agricultural and horticultural fungicides. More particularly, the present invention relates to a 2,6-dioxo-3,6-dihydropyrimidine compound that has excellent bactericidal and antimicrobial activity, has excellent safety, and can be industrially favorably synthesized, and an agricultural and horticultural fungicide containing the compound as an active ingredient. The present invention further relates to a nematicide containing the compound as an active ingredient. The present invention further relates to an antifungal agent for use in medicine/animals containing the compound as an active ingredient.

The present application is the U.S. National Stage of PCT/JP2020/040135, filed Oct. 26, 2020, which claims priority to Japanese unexamined Patent Application No. 2019-195484, filed on Oct. 28, 2019 and Japanese unexamined Patent Application No. 2020-053191, filed on Mar. 24, 2020, the contents of which are incorporated herein by reference.

TECHNICAL FIELD

The present invention relates to 2,6-dioxo-3,6-dihydropyrimidine compounds and agricultural and horticultural fungicides. More particularly, the present invention relates to a 2,6-dioxo-3,6-dihydropyrimidine compound that has excellent bactericidal and antimicrobial activity, has excellent safety, and can be industrially favorably synthesized, and an agricultural and horticultural fungicide containing the compound as an active ingredient. The present invention further relates to a nematicide containing the compound as an active ingredient. The present invention further relates to an antifungal agent for use in medicine/animals containing the compound as an active ingredient.

The present application claims priority to Japanese unexamined Patent Application No. 2019-195484, filed on Oct. 28, 2019 and Japanese unexamined Patent Application No. 2020-053191, filed on Mar. 24, 2020, the contents of which are incorporated herein by reference.

BACKGROUND ART

In agricultural and horticultural crop cultivation, various compounds having control activity on crop diseases have been suggested. In order to practically use such a compound as an agricultural and horticultural fungicide, the compound is required not only to have sufficiently high efficacy but also to be unlikely to cause drug resistance, to be unlikely to cause phytotoxicity to plants and soil contamination, and to have low toxicity to livestock and fish.

Incidentally, Patent Document 1 discloses a compound of formula (A) and the like.

(A)

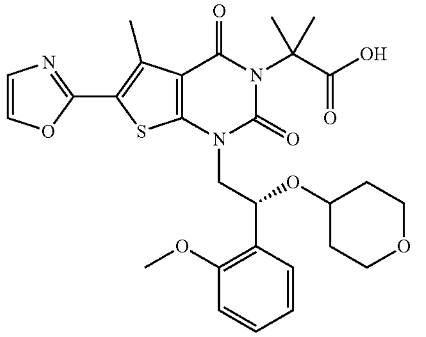

PRIOR ART DOCUMENTS

Patent Documents

Patent Document 1 WO 2013/071169A

SUMMARY OF THE INVENTION

Object to be Solved by the Invention

An object of the present invention is to provide a 2,6-dioxo-3,6-dihydropyrimidine compound that has excellent antimicrobial and bactericidal activity, has excellent safety, and can be industrially favorably synthesized (hereinbelow, may be simply referred to as the "dihydropyrimidine compound") and an agricultural and horticultural fungicide containing the compound as an active ingredient. Another object of the present invention is to provide a nematicide containing the compound as an active ingredient. Another object of the present invention is to provide an antifungal agent for use in medicine/animals containing the compound as an active ingredient.

Means to Solve the Object

The present inventors have made intensive studies to achieve the above-mentioned objects, having completed the present invention including the following aspects.

[1] A compound of formula (II) or a salt thereof:

(II)

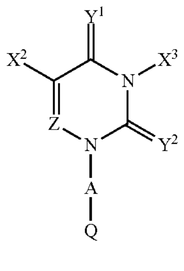

[wherein, $Y^1$ represents an oxygen atom or a sulfur atom;

$Y^2$ represents an oxygen atom or a sulfur atom;

Z represents a group represented by C—$X^1$ or a nitrogen atom;

$X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1$—CO—, a carboxy group, a group represented by $R^2$—O—CO—, a group represented by $R^3R^4N$—, a group represented by $R^3R^4N$—CO—, a group represented by $R^1$—CO—O—, a group represented by $R^1$—CO—$NR^5$—, a group represented by $R^2$—O—CO—O—, a group represented by $R^2$—O—CO—$NR^5$—, a group represented by $R^3R^4N$—CO—O—, a group represented by $R^3R^4N$—CO—$NR^5$—, a group represented by $R^2SO_2$—$NR^5$—, a group represented by $R^3R^4N$—$SO_2$—, or a group represented by $R^1O$—N═$CR^6$—;

each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^4$ independently represents a hydrogen atom, a substituted or unsubstituted C1-6 alkyl group, or a substituted or unsubstituted C6-10 aryl group, where $R^3$ and $R^4$ can together form a divalent organic group, each $R^5$ independently represents a hydrogen atom, a substituted or unsubstituted C1-6 alkyl group, or a substituted or unsubstituted C6-10 aryl group, $R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group;

$X^2$ represents a group represented by $R^1O$—N═$CR^6$—, a group represented by $R^1CO$—O—N═$CR^6$—, a group represented by $R^3R^4N$—CO—O—N═$CR^6$—, a group represented by $R^3R^4N$—N═$CR^6$—, or a group represented by $R^7$—N═$CR^6$—; $R^1$, $R^3$, $R^4$, and $R^6$ have the same meaning as those in $X^1$; $R^7$ represents a substituted or unsubstituted 5-membered ring heterocyclyl group;

$X^3$ represents a substituted or unsubstituted linear C1-6 alkyl group, a substituted or unsubstituted linear C2-6 alkenyl group, a substituted or unsubstituted linear C2-6 alkynyl group, a group represented by $R^1$—CO—, a substituted or unsubstituted C3-6 cycloalkyl group, a substituted or unsubstituted C6-10 aryl group, or a substituted or unsubstituted 4 to 6-membered ring heterocyclyl group;

A represents a substituted or unsubstituted C1-6 alkylene group, a substituted or unsubstituted C2-6 alkenylene group, a substituted or unsubstituted C2-6 alkynylene group, or a substituted or unsubstituted C3-6 cycloalkylene group; and Q represents a substituted or unsubstituted C6-10 aryl group or a substituted or unsubstituted 5 to 10-membered ring heterocyclyl group.].

[2] The compound or a salt thereof according to [1], wherein Formula (II) is of formula (I):

(I)

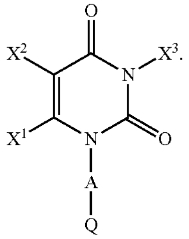

[wherein $X^1$, $X^2$, $X^3$, A, and Q have the same meaning as those in [1].].

[3] The compound or a salt thereof according to [1] or [2], wherein a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group in $X^3$ is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^cR^dN$—, a group represented by $R^cR^dN$—CO—, a group represented by $R^cR^dN$—$NR^d$—CO—, a group represented by $R^a$—CO—O—, a group represented by $R^a$—CO—$NR^e$—, a group represented by $R^a$—CO—CO—$NR^e$—, a group represented by $R^a$—CO—$NR^e$—$NR^e$—, a group represented by $R^a$—CO—$NR^e$—$NR^e$—CO—, a group represented by $R^b$—O—CO—O—, a group represented by $R^b$—O—CO—$NR^e$—, a group represented by $R^cR^dN$—CO—O—, a group represented by $R^cR^dN$—CO—$NR^e$—, a group represented by $R^cR^dN$—CO—CO—$NR^e$—, a group represented by $R^a$—CS—$NR^e$—, a group represented by $R^cR^dN$—CS—$NR^e$—, a group represented by $R^bSO_2$—$NR^e$—, a group represented by $R^cR^dN$—$SO_2$—, a group represented by $R^aO$—N═$CR^f$—, a group represented by $R^hR^jC$═N—O—, a group represented by $R^a$—C(═$NR^g$)—$NR^e$—, a group represented by a group represented by $R^cR^dN$—C(═$NR^g$)—, a group represented by $R^hR^iS$(═O)═N—CO—, and a group represented by $R^hR^iS$═N—CO—;

each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group, each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 10-membered ring heterocyclyl group, each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^c$ and $R^d$ can together form a divalent organic group, each $R^e$ independently represents a hydrogen atom, a substituted or unsubstituted C1-6 alkyl group, a substituted or unsubstituted C1-6 alkoxy group, or a substituted or unsubstituted C6-10 aryl group, $R^f$ represents a hydrogen atom, an amino group, or a substituted or unsubstituted C1-6 alkyl group, each $R^g$ independently represents a hydrogen atom, a substituted or unsubstituted C1-6 alkyl group, or a substituted or unsubstituted C6-10 aryl group, each $R^h$ independently represents a substituted or unsubstituted C1-6 alkyl group or a substituted or unsubstituted C6-10 aryl group, each $R^i$ independently represents a substituted or unsubstituted C1-6 alkyl group or a substituted or unsubstituted C6-10 aryl group, where $R^h$ and $R^i$ can together form a divalent organic group; and when two or more substituents are present on the linear C1-6 alkyl group, two of the substituents can together form a divalent organic group.

[4] The compound or a salt thereof according to any of [1] to [3], wherein a substituent on the C1-6 alkylene group or the C2-6 alkenylene group in A is one or more substituents selected from the group consisting of a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a mercapto group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 6-membered ring heterocyclyl group, a substituted or unsubstituted 3 to 6-membered ring heterocyclyloxy group, a nitro group, a cyano group, a group represented by $R^{a1}$—CO—, a carboxy group, a group represented by $R^{b1}$—O—CO—, a group represented by $R^{c1}R^{d1}N$—, a group represented by $R^{c1}R^{d1}N$—CO—, a group represented by $R^{a1}$—CO—O—, a group represented by $R^{a1}$—CO—$NR^{e1}$—, a group represented by $R^{b1}$—O—CO—O—, a group represented by $R^{b1}$—O—CO—$NR^{e1}$—, a group represented by $R^{c1}R^{d1}N$—CO—O—, a group represented by $R^{c1}R^{d1}N$—CO—$NR^{e1}$—, a group represented by $R^{b1}SO_2$—$NR^{e1}$—, a group represented by $R^{c1}R^{d1}N$—$SO_2$—, a group represented by $R^{a1}O$—N═$CR^{f1}$—, a group represented by $R^{g1}R^{h1}C$═N—O—, an oxo group (O═), a thioxo group (S═), a divalent group represented by $R^{a1}$—N═, a divalent group represented by $R^{a1}O$—N═, a divalent group represented by $R^{c1}R^{d1}N$—N═, a divalent group represented by $R^{a1}$—CO—$NR^{e1}$—N═, a divalent group represented by $R^{b1}$—O—CO—$NR^{e1}$—N═, and a divalent group represented by $R^{b1}SO_2$—$NR^{e1}$—N═;

each $R^{a1}$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^{b1}$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^{c1}$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^{d1}$ independently represents a hydrogen atom, a substituted or unsubstituted C1-6 alkyl group, or a substituted or unsubstituted C6-10 aryl group, where $R^{c1}$ and $R^{d1}$ can together form a divalent organic group, each $R^{e1}$ independently represents a hydrogen atom, a substituted or unsubstituted C1-6 alkyl group, or a substituted or unsubstituted C6-10 aryl group, $R^{f1}$ represents a hydrogen atom or a substituted or unsubstituted C1-6 alkyl group, $R^{g1}$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, $R^{h1}$ represents a hydrogen atom or a substituted or unsubstituted C1-6 alkyl group, where $R^{g1}$ and $R^{h1}$ can together form a divalent organic group; and when two or more substituents are present on the C1-6 alkylene group or the C2-6 alkenylene group, two of the substituents can together form a divalent organic group.

[5] An agricultural and horticultural fungicide containing at least one selected from the group consisting of the compound according to any of [1] to [4] and a salt thereof as an active ingredient.

[6] The agricultural and horticultural fungicide according to [5], wherein the fungicide is for seed treatment.

[7] A nematicide containing at least one selected from the group consisting of the compound according to any of [1] to [4] and a salt thereof as an active ingredient.

[8] An antifungal agent for use in medicine/animals containing at least one selected from the group consisting of the compound according to any of [1] to [4] and a salt thereof as an active ingredient.

[9] A compound of formula (III) or a salt thereof:

(III)

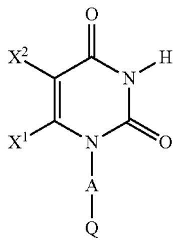

[wherein, $X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1$—CO—, a carboxy group, a group represented by $R^2$—O—CO—, a group represented by $R^3R^4N$—, a group represented by $R^3R^4N$—CO—, a group represented by $R^1$—CO—O—, a group represented by $R^1$—CO—$NR^5$—, a group represented by $R^2$—O—CO—O—, a group represented by $R^2$—O—CO—$NR^5$—, a group represented by $R^3R^4N$—CO—O—, a group represented by $R^3R^4N$—CO—$NR^5$—, a group represented by $R^2SO_2$—$NR^5$—, a group represented by $R^3R^4N$—$SO_2$—, or a group represented by $R^1O$—N═$CR^6$—;

each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^4$ independently represents a hydrogen atom, a substituted or unsubstituted C1-6 alkyl group, or a substituted or unsubstituted C6-10 aryl group, where $R^3$ and $R^4$ can together form a divalent organic group, each $R^5$ independently represents a hydrogen atom, a substituted or unsubstituted C1-6 alkyl group, or a substituted or unsubstituted C6-10 aryl group, $R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group;

$X^2$ represents a group represented by $R^1O$—N═$CR^6$—, a group represented by $R^1CO$—O—N═$CR^6$—, a group represented by $R^3R^4N$—CO—O—N═$CR^6$—, a group represented by $R^3R^4N$—N═$CR^6$—, or a group represented by $R^7$—N═$CR^6$—; $R^1$, $R^3$, $R^4$, and $R^6$ have the same meaning as those in $X^1$; $R^7$ represents a substituted or unsubstituted 5-membered ring heterocyclyl group;

A represents a substituted or unsubstituted C1-6 alkylene group, a substituted or unsubstituted C2-6 alkenylene group, a substituted or unsubstituted C2-6 alkynylene group, or a substituted or unsubstituted C3-6 cycloalkylene group; and Q represents a substituted or unsubstituted C6-10 aryl group or a substituted or unsubstituted 5 to 10-membered ring heterocyclyl group.].

[10] A compound of formula (IV) or a salt thereof:

(IV)

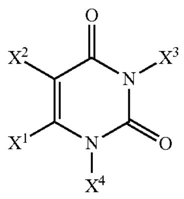

[wherein, $X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1$—CO—, a carboxy group, a group represented by $R^2$—O—CO—, a group represented by $R^3R^4N$—, a group represented by $R^3R^4N$—CO—, a group represented by $R^1$—CO—O—, a group represented by $R^1$—CO—$NR^5$—, a group represented by $R^2$—O—CO—O—, a group represented by $R^2$—O—CO—$NR^5$—, a group represented by $R^3R^4N$—CO—O—, a group represented by $R^3R^4N$—CO—$NR^5$—, a group represented by $R^2SO_2$—$NR^5$—, a group represented by $R^3R^4N$—$SO_2$—, or a group represented by $R^1O$—N═$CR^6$—;

each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^4$ independently represents a hydrogen atom, a substituted or unsubstituted C1-6 alkyl group, or a substituted or unsubstituted C6-10 aryl group, where $R^3$ and $R^4$ can together form a divalent organic group, each $R^5$ independently represents a hydrogen atom, a substituted or unsubstituted C1-6 alkyl group, or a substituted or unsubstituted C6-10 aryl group, $R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group;

$X^2$ represents a group represented by $R^1O$—N═$CR^6$—, a group represented by $R^1CO$—O—N═$CR^6$—, a group represented by $R^3R^4N$—CO—O—N═$CR^6$—, a group represented by $R^3R^4NR^3R^4N$—N═$CR^6$—, or a group represented by $R^7$—N═$CR^6$—; $R^1$, $R^3$, $R^4$, and $R^6$ have the same meaning as those in $X^1$; $R^7$ represents a substituted or unsubstituted 5-membered ring heterocyclyl group;

$X^3$ represents a substituted or unsubstituted linear C1-6 alkyl group, a substituted or unsubstituted linear C2-6 alkenyl group, a substituted or unsubstituted linear C2-6 alkynyl group, a group represented by $R^1$—CO—, a substituted or unsubstituted C3-6 cycloalkyl group, a substituted or unsubstituted C6-10 aryl group, or a substituted or unsubstituted 4 to 6-membered ring heterocyclyl group; and $X^4$ represents a hydrogen atom or a C1-6 alkoxymethyl group.].

Effect of the Invention

The dihydropyrimidine compound of the present invention has excellent antimicrobial and bactericidal activity, reliably exerts its effects, has excellent safety, and can be industrially favorably synthesized.

The agricultural and horticultural fungicide and the nematicide of the present invention have an excellent control effect, cause no phytotoxicity to plants, and give little influence on humans, livestock, and fish.

The antifungal agent for use in medicine/animals of the present invention has an excellent antimicrobial effect and has little toxicity to humans, livestock, and fish.

MODE OF CARRYING OUT THE INVENTION

[Dihydropyrimidine Compound]

The dihydropyrimidine compound of the present invention is a compound of formula (II) (hereinbelow, sometimes referred to as the compound (II)) or a salt of the compound (II).

(II)

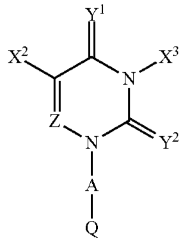

The dihydropyrimidine compound is preferably a compound of formula (I) (hereinbelow, sometimes referred to as the compound (I)) or a salt of the compound (I).

(I)

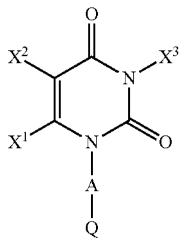

In the present invention, the term “unsubstituted” means that the group has only a group forming a mother nucleus. Descriptions using only the name of the group forming a mother nucleus, unless otherwise stated, mean “unsubstituted”.

On the other hand, the term “substituted” means that any of the hydrogen atoms of the group forming a mother nucleus is replaced with a group which has the same structure as or a different structure from that of the mother nucleus. Thus, the term “substituent” refers to another group bonded to a group forming a mother nucleus. There may be one substituent or two more substituents. The two or more substituents may be the same as or different from each other.

A “substituent” is not particularly limited as long as it is chemically acceptable and has the effects of the present invention.

Specific examples of groups that may become the “substituent” include the following groups:

a halogeno group such as a fluoro group, a chloro group, a bromo group, and an iodo group;

a C1-6 alkyl group such as a methyl group, an ethyl group, a n-propyl group, an i-propyl group, a n-butyl group, a s-butyl group, an i-butyl group, a t-butyl group, a n-pentyl group, and a n-hexyl group;

a C2-6 alkenyl group such as a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group;

a C2-6 alkynyl group such as an ethynyl group, a 1-propynyl group, a 2-propynyl group, a 1-butynyl group, a 2-butynyl group, a 3-butynyl group, a 1-methyl-2-propynyl group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group;

a C3-6 cycloalkyl group such as a cyclopropyl group, a cyclobutyl group, a cyclopentyl group, and a cyclohexyl group;

a C3-6 cycloalkenyl group such as a 2-cyclopropenyl group, a 2-cyclopentenyl group, and a 3-cyclohexenyl group;

a C6-10 aryl group such as a phenyl group and a naphthyl group;

a C6-10 aryl C1-6 alkyl group such as a benzyl group and a phenethyl group;

a 3 to 6-membered ring heterocyclyl group;

a 3 to 6-membered ring heterocyclyl C1-6 alkyl group;

a hydroxy group;

a C1-6 alkoxy group such as a methoxy group, an ethoxy group, a n-propoxy group, an i-propoxy group, a n-butoxy group, a s-butoxy group, an i-butoxy group, and a t-butoxy group;

a C2-6 alkenyloxy group such as a vinyloxy group, an allyloxy group, a propenyloxy group, and a butenyloxy group;

a C2-6 alkynyloxy group such as an ethynyloxy group and a propargyloxy group;

a C6-10 aryloxy group such as a phenoxy group and a naphthoxy group;

a C6-10 aryl C1-6 alkoxy group such as a benzyloxy group and a phenethyloxy group;

a carboxy group;

a formyl group;

a C1-6 alkylcarbonyl group such as an acetyl group and a propionyl group;

a formyloxy group;

a C1-6 alkylcarbonyloxy group such as an acetyloxy group and a propionyloxy group a C1-6 alkoxycarbonyl group such as a methoxycarbonyl group, an ethoxycarbonyl group, a n-propoxycarbonyl group, an i-propoxycarbonyl group, a n-butoxycarbonyl group, and a t-butoxycarbonyl group;

a C1-6 haloalkyl group such as a chloromethyl group, a chloroethyl group, a trifluoromethyl group, a 1,2-dichloro-n-propyl group, a 1-fluoro-n-butyl group, and a perfluoro-n-pentyl group;

a C2-6 haloalkenyl group such as a 2-chloro-1-propenyl group and a 2-fluoro-1-butenyl group;

a C2-6 haloalkynyl group such as a 4,4-dichloro-1-butynyl group, a 4-fluoro-1-pentynyl group, and a 5-bromo-2-pentynyl group;

a C3-6 halocycloalkyl group such as a 3,3-difluorocyclobutyl group;

a C1-6 haloalkoxy group such as a 2-chloro-n-propoxy group, a 2,3-dichlorobutoxy group, a trifluoromethoxy group, and a 2,2,2-trifluoroethoxy group;

a C2-6 haloalkenyloxy group such as a 2-chloropropenyloxy group and a 3-bromobutenyloxy group;

a C1-6 haloalkylcarbonyl group such as a chloroacetyl group, a trifluoroacetyl group, and a trichloroacetyl group;

an amino group;

a C1-6 alkyl-substituted amino group such as a methylamino group, a dimethylamino group, and a diethylamino group;

a C6-10 arylamino group such as an anilino group and a naphthylamino group;

a C6-10 aryl C1-6 alkylamino group such as a benzylamino group and phenethylamino group;

- a formylamino group;
- a C1-6 alkylcarbonylamino group such as an acetylamino group, a propionylamino group, a butyrylamino group, and an i-propylcarbonylamino group;
- a C1-6 alkoxycarbonylamino group such as a methoxycarbonylamino group, an ethoxycarbonylamino group, a n-propoxycarbonylamino group, and an i-propoxycarbonylamino group;
- an unsubstituted or substituted aminocarbonyl group such as a carbamoyl group, a dimethylaminocarbonyl group, a phenylaminocarbonyl group, and a N-phenyl-N-methylaminocarbonyl group;
- an imino C1-6 alkyl group such as an iminomethyl group, a (1-imino) ethyl group, and a (1-imino)-n-propyl group;
- a substituted or unsubstituted N-hydroxyimino C1-6 alkyl group such as a N-hydroxy-iminomethyl group, a (1-(N-hydroxy)-imino)ethyl group, a (1-(N-hydroxy)-imino)propyl group, a N-methoxy-iminomethyl group, and a (1-(N-methoxy)-imino)ethyl group;
- an aminocarbonyloxy group;
- a C1-6 alkyl-substituted aminocarbonyloxy group such as an ethylaminocarbonyloxy group and a dimethylaminocarbonyloxy group;
- a mercapto group;
- a C1-6 alkylthio group such as a methylthio group, an ethylthio group, a n-propylthio group, an i-propylthio group, a n-butylthio group, an i-butylthio group, a s-butylthio group, and a t-butylthio group;
- a C1-6 haloalkylthio group such as a trifluoromethylthio group and a 2,2,2-trifluoroethylthio group;
- a C2-6 alkenylthio group such as a vinylthio group and an arylthio group;
- a C2-6 alkynylthio group such as an ethynylthio group and a propargylthio group;
- a C1-6 alkylsulfinyl group such as a methylsulfinyl group, an ethylsulfinyl group, and a t-butylsulfinyl group;
- a C1-6 haloalkylsulfinyl group such as a trifluoromethylsulfinyl group and a 2,2,2-trifluoroethylsulfinyl group;
- a C2-6 alkenylsulfinyl group such as an arylsulfinyl group;
- a C2-6 alkynylsulfinyl group such as a propargylsulfinyl group;
- a C1-6 alkylsulfonyl group such as a methylsulfonyl group, an ethylsulfonyl group, and a t-butylsulfonyl group;
- a C1-6 haloalkylsulfonyl group such as a trifluoromethylsulfonyl group and a 2,2,2-trifluoroethylsulfonyl group;
- a C2-6 alkenylsulfonyl group such as an allylsulfonyl group;
- a C2-6 alkynylsulfonyl group such as a propargylsulfonyl group;
- an aminothiocarbonyl group;
- a C1-6 alkylsulfoxyimino group such as a S,S-dimethylsulfoxyimino group;
- a tri C1-6 alkyl-substituted silyl group such as a trimethylsilyl group, a triethylsilyl group, and a t-butyldimethylsilyl group;
- a tri C6-10 aryl-substituted silyl group such as a triphenylsilyl group;
- a cyano group; and a nitro group.

The term "C1 to 6" or the like means that the number of carbon atoms in a group forming a mother nucleus is 1 to 6 or the like. The number of carbon atoms does not include the number of carbon atoms present in substituents. For example, an ethoxybutyl group, which has a butyl group as the group forming a mother nucleus and has an ethoxy group as a substituent, is classified into C2 alkoxy C4 alkyl groups.

The "3 to 6-membered ring heterocyclyl group" described above includes 1 to 4 hetero atoms selected from the group consisting of a nitrogen atom, an oxygen atom, and a sulfur atom as a constituent atom(s) of the ring. Examples of the "3 to 6-membered ring heterocyclyl group" include a 3 to 6-membered ring saturated heterocyclyl group, a 5 to 6-membered ring heteroaryl group, and a 5 to 6-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5-membered ring heteroaryl group can include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 6-membered ring heteroaryl group can include a pyridyl group, a pyrazinyl group, a pyrimidinyl group, a pyridazinyl group, and a triazinyl group.

Examples of the 5-membered ring partially unsaturated heterocyclyl group include a pyrrolinyl group, a dihydrofuranyl group, an imidazolinyl group, a pyrazolinyl group, and an oxazolinyl group.

Examples of the 6-membered ring partially unsaturated heterocyclyl group can include an isoxazolinyl group and a dihydropyranyl group.

Any hydrogen atoms in these "substituents" may be substituted with a group having a different structure.

[$Y^1$ and $Y^2$]

$Y^1$ represents an oxygen atom or a sulfur atom, and $Y^2$ represents an oxygen atom or a sulfur atom.

In the present invention, $Y^1$ is preferably an oxygen atom, and $Y^2$ is a preferably oxygen atom.

[Z]

Z represents a group represented by C—$X^1$ or a nitrogen atom.

[$X^1$]

$X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1$—CO—, a carboxy group, a group represented by $R^2$—O—CO—, a group represented by $R^3R^4N$—, a group represented by $R^3R^4N$—CO—, a group represented by $R^1$—CO—O—, a group represented by $R^1$—CO—$NR^5$—, a group represented by $R^2$—O—CO—O—, a group represented by $R^2$—O—CO—$NR^5$—, a group represented by $R^3R^4N$—CO—O—, a group represented by $R^3R^4N$—CO—$NR^5$—, a group represented by $R^2SO_2$—$NR^5$—, a group represented by $R^3R^4N$—$SO_2$—, or a group represented by $R^1O$—N═$CR^6$—.

Each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^4$ independently represents a hydrogen atom, a substituted or unsubstituted C1-6 alkyl group, or a substituted or unsubstituted C6-10 aryl group.

Here, $R^3$ and $R^4$ may together form a divalent organic group.

Each $R^5$ independently represents a hydrogen atom, a substituted or unsubstituted C1-6 alkyl group, or a substituted or unsubstituted C6-10 aryl group.

$R^6$ represents a hydrogen atom, a halogeno group, an amino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group.

Examples of the "halogeno group" in $X^1$ can include a fluoro group, a chloro group, a bromo group, and an iodo group.

The "C1-6 alkyl group" in $X^1$ may be a linear chain or may be a branched chain. Examples of the "C1-6 alkyl group" in $X^1$ can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in $X^1$ can include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Examples of the "C2-6 alkynyl group" in $X^1$ can include an ethynyl group, a 1-propyny group, a 2-propyny group, a 1-butynyl group, a 2-butynyl group, a 3-butynyl group, a 1-methyl-2-propyny group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C1-6 alkoxy group" in $X^1$ can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the "C2-6 alkenyloxy group" in $X^1$ can include a vinyloxy group, an allyloxy group, a propenyloxy group, and a butenyloxy group.

Examples of the "C2-6 alkynyloxy group" in $X^1$ can include an ethynyloxy group and a propargyloxy group.

Examples of the "C1-6 alkylthio group" in $X^1$ can include a methylthio group, an ethylthio group, a n-propylthio group, a n-butylthio group, a n-pentylthio group, a n-hexylthio group, and an i-propylthio group.

Examples of the "C1-6 alkylsulfinyl group" in $X^1$ can include a methylsulfinyl group, an ethylsulfinyl group, and a t-butylsulfinyl group.

Examples of the "C1-6 alkylsulfonyl group" in $X^1$ can include a methylsulfonyl group, an ethylsulfonyl group, and a t-butylsulfonyl group.

The substituent on the "C1-6 alkyl group", the "C2-6 alkenyl group", the "C2-6 alkynyl group", the "C1-6 alkoxy group", the "C2-6 alkenyloxy group", the "C2-6 alkynyloxy group", the "C1-6 alkylthio group", the "C1-6 alkylsulfinyl group", or the "C1-6 alkylsulfonyl group" in $X^1$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in $X^1$ can include a cyclopropyl group, a cyclobutyl group, a cyclopentyl group, and a cyclohexyl group.

Examples of the "C3-6 cycloalkyloxy group" in $X^1$ can include a cyclopropyloxy group, a cyclobutyloxy group, a cyclopentyloxy group, and a cyclohexyloxy group.

Examples of the "C6-10 aryl group" in $X^1$ can include a phenyl group, a naphthyl group, an indanyl group, an indenyl group, and a tetralinyl group.

Examples of the "C6-10 aryloxy group" in $X^1$ can include a phenoxy group and a naphthoxy group.

Examples of the "C6-10 arylthio group" in $X^1$ can include a phenylthio group and a naphthylthio group.

Examples of the "C6-10 arylsulfinyl group" in $X^1$ can include a phenylsulfinyl group and a naphthylsulfinyl group.

Examples of the "C6-10 arylsulfonyl group" in $X^1$ can include a phenylsulfonyl group and a naphthylsulfonyl group.

The "5 to 6-membered ring heterocyclyl group" in $X^1$ is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. Examples of the "5 to 6-membered ring heterocyclyl group" can include a 5 to 6-membered ring saturated heterocyclyl group, a 5 to 6-membered ring heteroaryl group, and a 5 to 6-membered ring partially unsaturated heterocyclyl group.

Examples of the 5 to 6-membered ring saturated heterocyclyl group can include a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 6-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered ring heteroaryl group such as a pyridyl group, a pyrazinyl group, a pyrimidinyl group, a pyridazinyl group, and a triazinyl group.

Examples of the 5 to 6-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; and a 6-membered ring partially unsaturated heterocyclyl group such as an isoxazolinyl group and a dihydropyranyl group.

The "5 to 6-membered ring heterocyclyloxy group" in $X^1$ has a structure in which a 5 to 6-membered ring heterocyclyl group is bonded to an oxy group. Specific examples thereof can include a thiazolyloxy group and a pyridyloxy group.

The substituent on the "C3-6 cycloalkyl group", the "C3-6 cycloalkyloxy group", the "C6-10 aryl group", the "C6-10 aryloxy group", the "C6-10 arylthio group", the "C6-10 arylsulfinyl group", the "C6-10 arylsulfonyl group", the "5 to 6-membered ring heterocyclyl group", or the "5 to 6-membered ring heterocyclyloxy group" in $X^1$ is preferably a halogeno group such as a fluoro group, a chloro group, a bromo group, or an iodo group; a C1-6 alkyl group such as a methyl group, an ethyl group, an n-propyl group, an i-propyl group, an n-butyl group, an s-butyl group, an i-butyl group, a t-butyl group, an n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such a methoxy group, an ethoxy group, a n-propoxy group, an i-propoxy group, a n-butoxy group, a s-butoxy group, an i-butoxy group, and a t-butoxy group; a C1-6 haloalkoxy group such as a 2-chloro-n-propoxy group, a 2,3-dichlorobutoxy group, and a trifluoromethoxy group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Further, as the substituent on the "C3-6 cycloalkyl group", the "C3-6 cycloalkyloxy group", the "5 to 6-membered ring heterocyclyl group", or the "5 to 6-membered ring heterocyclyloxy group", an oxo group is also preferred.

In the "group represented by $R^1$—CO—" in $X^1$, $R^1$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Examples of the "C1-6 alkyl group" in $R^1$ can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in $R^1$ can include a vinyl group and 1-propenyl group.

Examples of the "C2-6 alkynyl group" in $R^1$ can include an ethynyl group and a 1-propyny group.

The substituent on the "C1-6 alkyl group", the "C2-6 alkenyl group", or the "C2-6 alkynyl group" in $R^1$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, or a cyclopentyl group, cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in $R^1$ can include a cyclopropyl group, a cyclobutyl group, a cyclopentyl group, and a cyclohexyl group.

Examples of the "C6-10 aryl group" in $R^1$ can include a phenyl group, a naphthyl group, an indenyl group, an indanyl group, and a tetralinyl group.

The "5 to 6-membered ring heterocyclyl group" in $R^1$ is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. Examples of the "5 to 6-membered ring heterocyclyl group" can include a 5 to 6-membered ring saturated heterocyclyl group, a 5 to 6-membered ring heteroaryl group, and a 5 to 6-membered ring partially unsaturated heterocyclyl group.

Examples of the 5 to 6-membered ring saturated heterocyclyl group can include a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 6-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered ring heteroaryl group such as a pyridyl group, a pyrazinyl group, a pyrimidinyl group, a pyridazinyl group, and a triazinyl group.

Examples of the 5 to 6-membered ring partially unsaturated heterocyclyl group include a 5-membered ring partially unsaturated heterocyclyl group such as a pyrrolinyl group, a dihydrofuranyl group, an imidazolinyl group, a pyrazolinyl group, and an oxazolinyl group; and a 6-membered ring partially unsaturated heterocyclyl group such as an isoxazolinyl group and a dihydropyranyl group.

The substituent on the "C3-6 cycloalkyl group", the "C6-10 aryl group", or the "5 to 6-membered ring heterocyclyl group" in $R^1$ is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or an n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, or an i-butoxy group, or t-butoxy group; a C1-6 haloalkoxy group such as a 2-chloro-n-propoxy group, a 2,3-dichlorobutoxy group, or a trifluoromethoxy group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Further, as the substituent on the "C3-6 cycloalkyl group" or the "5 to 6-membered ring heterocyclyl group", an oxo group is also preferred.

Specific examples of the "group represented by $R^1$—CO—" can include a formyl group, an acetyl group, a propionyl group, a butyryl group, and an i-propylcarbonyl group.

In the "group represented by $R^2$—O—CO—" in $X^1$, $R^2$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Specific examples of the substituent in $R^2$ can include the same as those exemplified for $R^1$.

Specific examples of the "group represented by $R^2$—O—CO—" can include a methoxycarbonyl group, an ethoxycarbonyl group, and a t-butoxycarbonyl group.

In the "group represented by $R^3R^4N$—" in $X^1$, $R^3$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^4$ represents a hydrogen atom, a substituted or unsubstituted C1-6 alkyl group, or a substituted or unsubstituted C6-10 aryl group.

Specific examples of the substituent in $R^3$ or $R^4$ can include the same as those exemplified for $R^1$.

Here, $R^3$ and $R^4$ may together form a divalent organic group.

Examples of the divalent organic group that can be formed can include a substituted or unsubstituted C2-5 alkylene group or a substituted or unsubstituted C1-3 alkyleneoxy C1-3 alkylene group.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

The substituent on the "C2-5 alkylene group" or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

Specific examples of the "group represented by $R^3R^4N$—" can include an amino group, a methylamino group, a dimethylamino group, and an i-propylamino group.

In the "group represented by $R^3R^4N$—CO—" in $X^1$, $R^3$ and $R^4$ have the same meaning as those in the above "group represented by $R^3R^4N$—".

Specific examples of the "group represented by $R^3R^4N$—CO—" can include a carbamoyl group, a N,N-dimethylaminocarbonyl group, a N-(i-propyl) aminocarbonyl group, and a N-(i-propyl)-N-methylaminocarbonyl group.

In the "group represented by $R^1$—CO—O—" in $X^1$, $R^1$ represents the same meaning as that in the above "group represented by $R^1$—CO—".

Specific examples of the "group represented by $R^1$—CO—O—" can include an acetyloxy group and an i-propylcarbonyloxy group.

In the "group represented by $R^1$—CO—$NR^5$—" in $X^1$, $R^1$ represents the same meaning as that in the above "group represented by $R^1$—CO—".

$R^5$ represents a hydrogen atom, a substituted or unsubstituted C1-6 alkyl group, or a substituted or unsubstituted C6-10 aryl group.

Specific examples of the substituent in $R^5$ can include the same as those exemplified for $R^1$.

Specific examples of the "group represented by $R^1$—CO—$NR^5$—" can include an acetylamino group and an i-propylcarbonylamino group.

In the "group represented by $R^2$—O—CO—O—" in $X^1$, $R^2$ represents the same meaning as that in the above "group represented by $R^2$—O—CO—".

Specific examples of the "group represented by $R^2$—O—CO—O—" can include a methoxycarbonyloxy group and an ethoxycarbonyloxy group.

In the "group represented by $R^2$—O—CO—$NR^5$—" in $X^1$, $R^2$ represents the same meaning as that in the above "group represented by $R^2$—O—CO—". $R^5$ represents the same meaning as that in the above "group represented by $R^1$—CO—$NR^5$—".

Specific examples of the "group represented by $R^2$—O—CO—$NR^5$—" can include a methoxycarbonylamino group.

In the "group represented by $R^3R^4N$—CO—O—" in $X^1$, $R^3$ and $R^4$ have the same meaning as those in the above "group represented by $R^3R^4N$—".

Specific examples of the "group represented by $R^3R^4N$—CO—O—" can include a carbamoyloxy group and a N,N-dimethylaminocarbonyloxy group.

In the "group represented by $R^3R^4N$—CO—$NR^5$—" in $X^1$, $R^3$ and $R^4$ have the same meaning as those in the above "group represented by $R^3R^4N$—". $R^5$ represents the same meaning as that in the above "group represented by $R^1$—CO—$NR^5$—".

Specific examples of the "group represented by $R^3R^4N$—CO—$NR^5$—" can include a carbamoylamino group and a N,N-dimethylaminocarbonylamino group.

In the "group represented by $R^2SO_2$—$NR^5$—" in $X^1$, $R^2$ represents the same meaning as that in the above "group represented by $R^2$—O—CO—". $R^5$ represents the same meaning as that in the above "group represented by $R^1$—CO—$NR^5$—".

Specific examples of the "group represented by $R^2SO_2$—$NR^5$—" can include a methanesulfonylamino group.

In the "group represented by $R^3R^4N$—$SO_2$—" in $X^1$, $R^3$ and $R^4$ have the same meaning as those in the above "group represented by $R^3R^4N$—".

Specific examples of the "group represented by $R^3R^4N$—$SO_2$—" can include a N,N-dimethylaminosulfonyl group.

In the "group represented by $R^1O$—N═$CR^6$—" in $X^1$, $R^1$ represents the same meaning as that in the above "group represented by $R^1$—CO—".

$R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group.

Specific examples of the "substituted or unsubstituted C1-6 alkyl group" or the "substituted or unsubstituted 5 to 6-membered ring heterocyclyl group" in $R^6$ can include the same as those exemplified for $R^1$.

Examples of the "halogeno group" in $R^6$ can include a fluoro group, a chloro group, a bromo group, and an iodo group.

Examples of the "mono C1-6 alkylamino group" of the "substituted or unsubstituted mono C1-6 alkylamino group" in $R^6$ can include a methylamino group, an ethylamino group, and an i-propylamino group.

Examples of the "di C1-6 alkylamino group" of the "substituted or unsubstituted di C1-6 alkylamino group" in $R^6$ can include a dimethylamino group, a diethylamino group, and a N-methyl-N-i-propylamino group.

Examples of the "C1-6 alkoxy group" of the "substituted or unsubstituted C1-6 alkoxy group" in $R^6$ can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the "C1-6 alkylthio group" in the "substituted or unsubstituted C1-6 alkylthio group" in $R^6$ can include a methylthio group, an ethylthio group, a n-propylthio group, a n-butylthio group, a n-pentylthio group, a n-hexylthio group, and an i-propylthio group.

Examples of the substituent on the "C1-6 alkoxy group", the "mono C1-6 alkylamino group", the "di C1-6 alkylamino group", or the "C1-6 alkylthio group" in $R^6$ can include the same as the substituents on the "C1-6 alkyl group" exemplified for $R^1$.

Specific examples of the "group represented by $R^1O$—N═$CR^6$—" can include a (hydroxyimino)methyl group, an (ethoxyimino)methyl group, and 1-(i-propoxyimino)ethyl group.

In the present invention, examples of preferred $X^1$ can include a hydrogen atom or a substituted or unsubstituted C1-6 alkyl group. As $X^1$, a hydrogen atom is further preferred.

[$X^2$]

$X^2$ represents a group represented by $R^1O$—N═$CR^6$—, a group represented by a group represented by $R^1CO$—O—N═$CR^6$—, a group represented by $R^3R^4N$—CO—O—N═$CR^6$—, a group represented by $R^3R^4N$—N═$CR^6$—, or a group represented by $R^7$—N═$CR^6$—.

$R^1$, $R^3$, $R^4$, and $R^6$ have the same meaning as those in $X^1$.

$R^7$ represents a substituted or unsubstituted 5-membered ring heterocyclyl group.

Specific examples of the substituent in $X^2$ can include the same as those exemplified for $X^1$.

The “5-membered ring heterocyclyl group” in $R^7$ includes 1 to 4 hetero atoms selected from the group consisting of a nitrogen atom, an oxygen atom, and a sulfur atom as a constituent atom(s) of the ring. Examples of the “5-membered ring heterocyclyl group” can include a 5-membered ring saturated heterocyclyl group, a 5-membered ring heteroaryl group, and a 5-membered ring partially unsaturated heterocyclyl group.

Examples of the 5-membered ring saturated heterocyclyl group can include a pyrrolidinyl group, a tetrahydrofuranyl group, a thiazolidinyl group, and a dioxolanyl group.

Examples of the 5-membered ring heteroaryl group can include a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group.

Examples of the 5-membered ring partially unsaturated heterocyclyl group include a pyrrolinyl group, a dihydrofuranyl group, an imidazolinyl group, a pyrazolinyl group, and an oxazolinyl group.

The substituent on the “5-membered ring heterocyclyl group” in $R^7$ is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C6-10 aryl group such as a phenyl group or a naphthyl group; a C6-10 aryl group substituted with any one or more substituents of a halogeno group, a C1-6 haloalkyl group, or a C1-6 haloalkoxy group, such as a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

In the present invention, examples of preferred $X^2$ can include a group represented by $R^1O—N═CR^6—$.

As $R^1$, preferred is a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group. As $R^6$, preferred is a hydrogen atom or a substituted or unsubstituted C1-6 alkyl group.

Specific examples of the “group represented by $R^1O—N═CR^6—$” can include a (hydroxyimino)methyl group, an (ethoxyimino)methyl group, a 1-(ethoxyimino)ethyl group, and a 1-(i-propoxyimino)ethyl group.

[Q]

Q represents a substituted or unsubstituted C6-10 aryl group or a substituted or unsubstituted 5 to 10-membered ring heterocyclyl group.

Examples of the “C6-10 aryl group” in Q can include a phenyl group, a naphthyl group, an indenyl group, an indanyl group, and a tetralinyl group.

The “5 to 10-membered ring heterocyclyl group” in Q is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. The group may be either monocyclic or polycyclic.

Examples of the “5 to 10-membered ring heterocyclyl group” can include a 5 to 6-membered ring saturated heterocyclyl group, a 5 to 10-membered ring heteroaryl group, and a 5 to 10-membered ring partially unsaturated heterocyclyl group.

Examples of the 5 to 6-membered ring saturated heterocyclyl group can include a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 10-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered ring heteroaryl group such as a pyridyl group, a pyrazinyl group, a pyrimidinyl group, a pyridazinyl group, and a triazinyl group; a 9-membered heteroaryl group such as an indolyl group, an isoindolyl group, a benzofuranyl group, a benzothienyl group, an indazolyl group, a benzimidazolyl group, a benzoxazolyl group, a benzisoxazolyl group, a benzothiazolyl group, and a benzisothiazolyl group; and a 10-membered heteroaryl group such as a quinolinyl group, an isoquinolinyl group, a cinnolinyl group, a phthalazinyl group, a quinazolinyl group, and a quinoxalinyl group.

Examples of the 5 to 10-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; a 6-membered ring partially unsaturated heterocyclyl group such as an isoxazolinyl group and a dihydropyranyl group; a 9-membered ring partially unsaturated heterocyclyl group such as an indolinyl group, an isoindolinyl group, a 2,3-dihydrobenzofuranyl group, and a 1,3-dihydrobenzofuranyl group; and a 10-membered ring partially unsaturated heterocyclyl group such as a 1,2,3,4-tetrahydroquinolinyl group.

The substituent on the “C6-10 aryl group” or the “5 to 10-membered ring heterocyclyl group” in Q is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C2-6 alkenyl group such as a vinyl group; a C2-6 alkynyl group such as an ethynyl group; a C1-6 haloalkyl group such as a chloromethyl group, a chloroethyl group, a trifluoromethyl group, a 1,2-dichloro-n-propyl group, or a 1-fluoro-n-butyl group; a C1-6 alkoxy C1-6 alkyl group such as a methoxymethyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a hydroxy C1-6 alkoxy group such as a hydroxyethoxy group; a C1-6 alkoxyalkoxy group such as a methoxymethoxy group or a methoxyethoxy group; a tri C1-6 alkyl-substituted silyloxy C1-6 alkoxy group such as a trimethylsilyloxyethoxy group or a t-butyldimethylsilyloxyethoxy group; a C1-6 haloalkoxy group such as a 2-chloro-n-propoxy group, a 2,3-dichlorobutoxy group, or a trifluoromethoxy group; a C3-6 cycloalkyl C1-6 alkoxy group; a C6-10 aryl C1-6 alkoxy group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 5-membered ring heteroaryl C1-6 alkoxy group; a (5-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 6-membered ring heteroaryl C1-6 alkoxy group; a (6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C1-6 haloalkylthio group such as a trifluoromethylthio group or a 2,2,2-trifluoroethylthio group; a C1-6 haloalkylsulfinyl group such as a trifluoromethylsulfinyl group or a 2,2,2-trifluoroethylsulfinyl group; a C1-6 haloalkylsulfonyl group such as a trifluoromethylsulfonyl group or a 2,2,2-trifluoroethylsulfonyl group; a C3-6 cycloalkyl group such as a cyclopropyl group, a cyclobutyl group, or a cyclopentyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C3-6 cycloalkenyl group such as a cyclopropenyl group, a cyclobutenyl group, or a cyclopentenyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-fluorophenyl group, a 4-trifluoromethylphenyl group, or a 4-trifluoromethoxyphenyl group; a 3 to 4-membered ring saturated heterocyclyl group such as an aziridinyl group, an epoxy group, an azetidinyl group, or an oxetanyl group; a 3 to 4-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5 to 6-membered ring saturated heterocyclyl group such as a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, or a dioxanyl group; a 5 to 6-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; 5-membered ring partially unsaturated heterocyclyl group such as a pyrrolinyl group, a dihydrofuranyl group, an imidazolinyl group, a pyrazolinyl group, or an oxazolinyl group; a 5-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; 6-membered ring partially unsaturated heterocyclyl group such as an isoxazolinyl group or a dihydropyranyl group; a 6-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group;

a group represented by $R^{Q1}$—CO— (wherein $R^{Q1}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{Q1}$ below.);

a carboxy group;

a group represented by $R^{Q2}$—O—CO— (wherein $R^{Q2}$ represents a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group)

C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{Q2}$ below.);

a group represented by $R^{Q1}R^{Q1}N$— (wherein $R^{Q1}$ in the formula may be the same or different; $R^{Q1}$ may together form a trimethylene group, a tetramethylene group, a pentamethylene group, or a dimethyleneoxydimethylene group.);

a group represented by $R^{Q1}R^{Q1}N$—CO— (wherein $R^{Q1}$ in the formula may be the same or different; $R^{Q1}$ may together form a trimethylene group, a tetramethylene group, a pentamethylene group, or a dimethyleneoxydimethylene group.);

a group represented by $R^{Q1}$—CO—O—; a group represented by $R^{Q1}$—CO—$NR^{Q3}$— (wherein $R^{Q3}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; or a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; the same applies to $R^{Q3}$ below.);

a group represented by $R^{Q2}$—O—CO—O—; a group represented by $R^{Q2}$—O—CO—$NR^{Q3}$—; a group represented by $R^{Q1}R^{Q1}N$—CO—O— (wherein $R^{Q1}$ in the formula may be the same or different; $R^{Q1}$ may together form a trimethylene group, a tetramethylene group, a pentamethylene group, or a dimethyleneoxydimethylene group.);

a group represented by $R^{Q1}R^{Q1}N$—CO—$NR^{Q3}$— (wherein $R^{Q1}$ in the formula may be the same or different; $R^{Q1}$ may together form a trimethylene group, a tetramethylene group, a pentamethylene group, or a dimethyleneoxydimethylene group.); a group represented by $R^{Q2}SO_2$—$NR^{Q3}$—; a group represented by RQ'RQ'N—$SO_2$— (wherein $R^{Q1}$ in the formula may be the same or different; $R^{Q1}$ may together form a trimethylene group, a tetramethylene group, a pentamethylene group, or a dimethyleneoxydimethylene group.);

a group represented by $R^{Q1}$—O—N═C($R^{Q4}$)— (wherein $R^{Q4}$ represents a hydrogen atom or a C1-6 alkyl group.); a group represented by $(R^{Q1})_2C$═N—O— (wherein $R^{Q1}$ in the formula may be the same or different; $R^{Q1}$ may together form a trimethylene group, a tetramethylene group, a pentamethylene group, or a dimethyleneoxydimethylene group.);

a pentafluorosulfanyl group, a trimethylsilylethynyl group, a nitro group, or a cyano group.

Further, as the substituent on the "5 to 10-membered ring heterocyclyl group", an oxo group is also preferred.

[$X^3$]

$X^3$ represents a substituted or unsubstituted linear C1-6 alkyl group, a substituted or unsubstituted linear C2-6 alkenyl group, a substituted or unsubstituted linear C2-6 alkynyl group, a group represented by $R^1$—CO—, a substituted or unsubstituted C3-6 cycloalkyl group, a substituted or unsubstituted C6-10 aryl group, or a substituted or unsubstituted 4 to 6-membered ring heterocyclyl group.

Examples of the "linear C1-6 alkyl group" in $X^3$ can include a methyl group, an ethyl group, a n-propyl group, a n-butyl group, a n-pentyl group, and a n-hexyl group.

Examples of the "linear C2-6 alkenyl group" in $X^3$ can include a vinyl group, a 1-propenyl group, a 2-propenyl group, a 1-butenyl group, a 2-butenyl group, a 3-butenyl group, a 1-pentenyl group, a 2-pentenyl group, 3-pentenyl group, a 4-pentenyl group, a 1-hexenyl group, a 2-hexenyl group, a 3-hexenyl group, a 4-hexenyl group, and a 5-hexenyl group.

Examples of the "linear C2-6 alkynyl group" in $X^3$ can include an ethynyl group, a 1-propyny group, a 2-propyny group, a 1-butynyl group, a 2-butynyl group, a 3-butynyl group, a 1-pentynyl group, a 2-pentynyl group, a 3-pentynyl group, a 4-pentynyl group, and a 1-hexynyl group.

Examples of the "4-membered ring heterocyclyl group" in $X^3$ can include an azetidinyl group and an oxetanyl group.

Specific examples of other substituents in $X^3$ can include the same as those exemplified for $X^1$.

In the present invention, examples of preferred $X^3$ can include a substituted or unsubstituted linear C1-6 alkyl group, a substituted or unsubstituted C3-6 cycloalkyl group, or a substituted or unsubstituted C6-10 aryl group.

Examples of a substituent on the linear C1-6 alkyl group, a substituent on the linear C2-6 alkenyl group, a substituent on the linear C2-6 alkynyl group, a substituent on the C3-6 cycloalkyl group, a substituent on the C6-10 aryl group, or a substituent on the 4 to 6-membered ring heterocyclyl group can include one or more substituents selected from a group of substituents below (hereinbelow, this substituent sometimes referred to by a symbol "G".).

When two or more substituents (G) are present, two of the substituents may together form a divalent organic group. The group of substituents is shown below:

a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 10-membered ring heterocyclyl group, a substituted or unsubstituted 3 to 10-membered ring heterocyclyloxy group, a nitro group, a cyano group, a group represented by $R^a$—CO—, a carboxy group, a group represented by $R^b$—O—CO—, a group represented by $R^cR^dN$—, a group represented by $R^cR^dN$—CO—, a group represented by $R^cR^dN$—$NR^d$—CO—, a group represented by $R^a$—CO—O—, a group represented by $R^a$—CO—$NR^e$—, a group represented by $R^a$—CO—

CO—$NR^e$—, a group represented by $R^a$—CO—$NR^e$—$NR^e$—, a group represented by $R^a$—CO—$NR^e$—$NR^e$—CO—, a group represented by $R^b$—O—CO—O—, a group represented by $R^b$—O—CO—$NR^e$—, a group represented by $R^cR^d$N—CO—O—, a group represented by $R^cR^d$N—CO—$NR^e$—, a group represented by $R^cR^d$N—CO—CO—$NR^e$—, a group represented by $R^a$—CS—$NR^e$—, a group represented by $R^cR^d$N—CS—$NR^e$—, a group represented by $R^bSO_2$—$NR^e$—, a group represented by $R^cR^d$N—$SO_2$—, a group represented by $R^a$O—N═$CR^f$—, a group represented by $R^hR^i$C═N—O—, a group represented by $R^a$—C(═$NR^g$)—$NR^e$—, a group represented by $R^cR^d$N—C(═$NR^g$)—, a group represented by $R^hR^i$S(═O)═N—CO—, and a group represented by $R^hR^i$S═N—CO—.

In the group of substituents described above, each $R^a$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group.

Each $R^b$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^c$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Each $R^d$ independently represents a hydrogen atom, a substituted or unsubstituted C1-6 alkyl group, a substituted or unsubstituted C1-6 alkoxy group, or a substituted or unsubstituted C6-10 aryl group, where $R^c$ and $R^d$ may together form a divalent organic group.

Each $R^e$ independently represents a hydrogen atom, a substituted or unsubstituted C1-6 alkyl group, a substituted or unsubstituted C1-6 alkoxy group, or a substituted or unsubstituted C6-10 aryl group.

$R^f$ represents a hydrogen atom, an amino group, or a substituted or unsubstituted C1-6 alkyl group.

Each $R^g$ independently represents a hydrogen atom, a substituted or unsubstituted C1-6 alkyl group, or a substituted or unsubstituted C6-10 aryl group.

Each $R^h$ independently represents a substituted or unsubstituted C1-6 alkyl group or a substituted or unsubstituted C6-10 aryl group.

Each $R^i$ independently represents a substituted or unsubstituted C1-6 alkyl group or a substituted or unsubstituted C6-10 aryl group, where $R^h$ and $R^i$ may together form a divalent organic group.

Examples of the "halogeno group" in G can include a fluoro group, a chloro group, a bromo group, and an iodo group.

The "C1-6 alkyl group" in G may be a linear chain or may be a branched chain.

Examples of the "C1-6 alkyl group" in G can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in G can include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Examples of the "C2-6 alkynyl group" in G can include an ethynyl group, a 1-propyny group, a 2-propyny group, a 1-butynyl group, a 2-butynyl group, a 3-butynyl group, a 1-methyl-2-propyny group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C1-6 alkoxy group" in G can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the "C2-6 alkenyloxy group" in G can include a vinyloxy group, an allyloxy group, a propenyloxy group, and a butenyloxy group.

Examples of the "C2-6 alkynyloxy group" in G can include an ethynyloxy group and a propargyloxy group.

Examples of the "C1-6 alkylthio group" in G can include a methylthio group, an ethylthio group, a n-propylthio group, a n-butylthio group, a n-pentylthio group, a n-hexylthio group, and an i-propylthio group.

Examples of the "C1-6 alkylsulfinyl group" in G can include a methylsulfinyl group, an ethylsulfinyl group, and a t-butylsulfinyl group.

Examples of the "C1-6 alkylsulfonyl group" in G can include a methylsulfonyl group, an ethylsulfonyl group, and a t-butylsulfonyl group.

The substituent on the "C1-6 alkyl group", the "C2-6 alkenyl group", the "C2-6 alkynyl group", the "C1-6 alkoxy group", the "C2-6 alkenyloxy group", the "C2-6 alkynyloxy group", the "C1-6 alkylthio group", the "C1-6 alkylsulfinyl group", or the "C1-6 alkylsulfonyl group" in G is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in G can include a cyclopropyl group, a cyclobutyl group, a cyclopentyl group, and a cyclohexyl group.

Examples of the "C3-6 cycloalkyloxy group" in G can include a cyclopropyloxy group, a cyclobutyloxy group, a cyclopentyloxy group, and a cyclohexyloxy group.

Examples of the "C6-10 aryl group" in G can include a phenyl group and a naphthyl group.

Examples of the "C6-10 aryloxy group" in G can include a phenoxy group and a naphthoxy group.

Examples of the "C6-10 arylthio group" in G can include a phenylthio group and a naphthylthio group.

Examples of the "C6-10 arylsulfinyl group" in G can include a phenylsulfinyl group and a naphthylsulfinyl group.

Examples of the "C6-10 arylsulfonyl group" in G can include a phenylsulfonyl group and a naphthylsulfonyl group.

The "3 to 10-membered ring heterocyclyl group" in G is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. The group may be either monocyclic or polycyclic.

Examples of the "3 to 10-membered ring heterocyclyl group" can include a 3 to 6-membered ring saturated heterocyclyl group, a 5 to 10-membered ring heteroaryl group, and a 5 to 10-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 10-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered ring heteroaryl group such as a pyridyl group, a pyrazinyl group, a pyrimidinyl group, a pyridazinyl group, and a triazinyl group; a 9-membered heteroaryl group such as an indolyl group, an isoindolyl group, a benzofuranyl group, a benzothienyl group, an indazolyl group, a benzimidazolyl group, a benzoxazolyl group, a benzisoxazolyl group, a benzothiazolyl group, and a benzisothiazolyl group; and a 10-membered heteroaryl group such as a quinolinyl group, an isoquinolinyl group, a cinnolinyl group, a phthalazinyl group, a quinazolinyl group, and a quinoxalinyl group.

Examples of the 5 to 10-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; a 6-membered ring partially unsaturated heterocyclyl group such as an isoxazolinyl group and a dihydropyranyl group; a 9-membered ring partially unsaturated heterocyclyl group such as an indolinyl group, an isoindolinyl group, a 2,3-dihydrobenzofuranyl group, and a 1,3-dihydrobenzofuranyl group; and a 10-membered ring partially unsaturated heterocyclyl group such as a 1,2,3,4-tetrahydroquinolinyl group.

The "3 to 10-membered ring heterocyclyloxy group" in G has a structure in which a 3 to 10-membered ring heterocyclyl group is bonded to an oxy group. Specific examples thereof can include a thiazolyloxy group and a pyridyloxy group.

The substituent on the "C3-6 cycloalkyl group", the "C3-6 cycloalkyloxy group", the "C6-10 aryl group", the "C6-10 aryloxy group", the "C6-10 arylthio group", the "C6-10 arylsulfinyl group", the "C6-10 arylsulfonyl group", the "3 to 10-membered ring heterocyclyl group", or the "3 to 10-membered ring heterocyclyloxy group" in G is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as 2-chloro-n-propoxy group, a 2,3-dichlorobutoxy group, or a trifluoromethoxy group; a C3-6 cycloalkyl C1-6 alkoxy group; a C6-10 aryl C1-6 alkoxy group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 5-membered ring heteroaryl C1-6 alkoxy group; a (5-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 6-membered ring heteroaryl C1-6 alkoxy group; a (6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C1-6 haloalkylthio group such as a trifluoromethylthio group or a 2,2,2-trifluoroethylthio group; a C1-6 haloalkylsulfinyl group such as a trifluoromethylsulfinyl group or a 2,2,2-trifluoroethylsulfinyl group; a C1-6 haloalkylsulfonyl group such as a trifluoromethylsulfonyl group or a 2,2,2-trifluoroethylsulfonyl group; a C3-6 cycloalkyl group such as a cyclopropyl group or a cyclobutyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C3-6 cycloalkenyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; 3 to 4-membered ring saturated heterocyclyl group such as an aziridinyl group, an epoxy group, an azetidinyl group, or an oxetanyl group; a 3 to 4-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5 to 6-membered ring saturated heterocyclyl group such as a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, or a dioxanyl group; a 5 to 6-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, a oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; a 5-membered ring partially unsaturated heterocyclyl group such as a pyrrolinyl group, a dihydrofuranyl group, an imidazolinyl group, a pyrazolinyl group, or an oxazolinyl group; a 5-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; a 6-membered ring partially unsaturated heterocyclyl group such as an isoxazolinyl group or a dihydropyranyl group; a 6-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group;

a group represented by $R^{G1}$—CO— (wherein $R^{G1}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{G1}$ below.); a carboxy group;

a group represented by $R^{G2}$—O—CO— (wherein $R^{G2}$ represents a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{G2}$ below.);

a group represented by $R^{G1}R^{G1}$N— (wherein $R^{G1}$ in the formula may be the same or different; $R^{G1}$ may together form a trimethylene group, a tetramethylene group, a pentamethylene group, or a dimethyleneoxydimethylene group.);

a group represented by $R^{G1}R^{G1}$N—CO— (wherein $R^{G1}$ in the formula may be the same or different; $R^{G1}$ may together form a trimethylene group, a tetramethylene group, a pentamethylene group, or a dimethyleneoxydimethylene group.);

a group represented by $R^{G1}$—CO—O—; a group represented by $R^{G1}$—CO—$NR^{G3}$— (wherein $R^{G3}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; or a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; the same applies to $R^{G3}$ below.);

a group represented by $R^{G2}$—O—CO—O—; a group represented by $R^{G2}$—O—CO—$NR^{G3}$—; a group represented by $R^{G1}R^{G1}$N—CO—O— (wherein $R^{G1}$ in the formula may be the same or different; $R^{G1}$ may together form a trimethylene group, a tetramethylene group, a pentamethylene group, or a dimethyleneoxydimethylene group.);

a group represented by $R^{G1}R^{G1}$N—CO—$NR^{G3}$— (wherein $R^{G1}$ in the formula may be the same or different; $R^{G1}$ may together form a trimethylene group, a tetramethylene group, a pentamethylene group, or a dimethyleneoxydimethylene group.); a group represented by $R^{G2}SO_2$—$NR^{G3}$_; a group represented by $R^{G1}R^{G1}N$—$SO_2$— (wherein $R^{G1}$ in the formula may be the same or different; $R^{G1}$ may together form a trimethylene group, a tetramethylene group, a pentamethylene group, or a dimethyleneoxydimethylene group.); a group represented by $R^{G1}$—O—N═C($R^{G4}$)— (wherein $R^{G4}$ represents a hydrogen atom or a C1-6 alkyl group.); a group represented by $(R^{G1})_2C$═N—O— (wherein $R^{G1}$ in the formula may be the same or different; $R^{G1}$ may together form a trimethylene group, a tetramethylene group, a pentamethylene group, or a dimethyleneoxydimethylene group.);

a pentafluorosulfanyl group, a nitro group, or a cyano group.

Further, as the substituent on the "C3-6 cycloalkyl group", the "C3-6 cycloalkyloxy group", the "3 to 10-membered ring heterocyclyl group", or the "3 to 10-membered ring heterocyclyloxy group", an oxo group is also preferred.

In the "group represented by $R^a$—CO—" in G, $R^a$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 3 to 10-membered ring heterocyclyl group.

Examples of the "C1-6 alkyl group" in $R^a$ can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in $R^a$ can include a vinyl group and a 1-propenyl group.

Examples of the "C2-6 alkynyl group" in $R^a$ can include an ethynyl group and a 1-propyny group.

The substituent on the "C1-6 alkyl group", the "C2-6 alkenyl group", or the "C2-6 alkynyl group" in $R^a$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as 2-chloro-n-propoxy group, a 2,3-dichlorobutoxy group, or a trifluoromethoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a carboxy group; a C1-6 alkoxycarbonyl group such as a methoxycarbonyl group, an ethoxycarbonyl group, a n-propoxycarbonyl group, an i-propoxycarbonyl group, a n-butoxycarbonyl group, or a t-butoxycarbonyl group; a C3-6 cycloalkyl group such as a cyclopropyl group, a cyclobutyl group, a cyclopentyl group, or a cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 5-membered ring heteroaryl group such as a pyrrolyl group, a furyl group, a thienyl group, an imidazolyl group, a pyrazolyl group, an oxazolyl group, an isoxazolyl group, a thiazolyl group, a isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; or a cyano group.

Examples of the "C3-6 cycloalkyl group" in $R^a$ can include a cyclopropyl group, a cyclobutyl group, a cyclopentyl group, and a cyclohexyl group.

Examples of the "C6-10 aryl group" in $R^a$ can include a phenyl group, a naphthyl group, an indenyl group, an indanyl group, and a tetralinyl group.

The "3 to 10-membered ring heterocyclyl group" in $R^a$ is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. The group may be either monocyclic or polycyclic.

Examples of the "3 to 10-membered ring heterocyclyl group" can include a 3 to 6-membered ring saturated heterocyclyl group, a 5 to 10-membered ring heteroaryl group, and a 5 to 10-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 10-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; a 6-membered ring heteroaryl group such as a pyridyl group, a pyrazinyl group, a pyrimidinyl group, a pyridazinyl group, and a triazinyl group; a 9-membered heteroaryl group such as an indolyl group, an isoindolyl group, a benzofuranyl group, a benzothienyl group, an indazolyl group, a benzimidazolyl group, a benzoxazolyl group, a benzisoxazolyl group, a benzothiazolyl group, and a benzisothiazolyl group; and a 10-membered heteroaryl group such as a quinolinyl group, an isoquinolinyl group, a cinnolinyl group, a phthalazinyl group, a quinazolinyl group, and a quinoxalinyl group.

Examples of the 5 to 10-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; a 6-membered ring partially unsaturated heterocyclyl group such as an isoxazolinyl group and a dihydropyranyl group; a 9-membered ring partially unsaturated heterocyclyl group such as an indolinyl group, an isoindolinyl group, a 2,3-dihydrobenzofuranyl group, and a 1,3-dihydrobenzofuranyl group; and a 10-membered ring partially unsaturated heterocyclyl group such as a 1,2,3,4-tetrahydroquinolinyl group.

The substituent on the "C3-6 cycloalkyl group", the "C6-10 aryl group", or the "3 to 10-membered ring heterocyclyl group" in $R^a$ is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, a i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl C1-6 alkoxy group; a C6-10 aryl C1-6 alkoxy group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 5-membered ring heteroaryl C1-6 alkoxy group; a (5-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a 6-membered ring heteroaryl C1-6 alkoxy group; a (6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkoxy group; a C1-6 alkylthio group such as a methylthio group or an ethylthio group; a C1-6 alkylsulfinyl group such as a methylsulfinyl group or an ethylsulfinyl group; a C1-6 alkylsulfonyl group such as a methylsulfonyl group or an ethylsulfonyl group; a C1-6 haloalkylthio group such as a trifluoromethylthio group or a 2,2,2-trifluoroethylthio group; a C1-6 haloalkylsulfinyl group such as a trifluoromethylsulfinyl group or a 2,2,2-trifluoroethylsulfinyl group; a C1-6 haloalkylsulfonyl group such as a trifluoromethylsulfonyl group or a 2,2,2-trifluoroethylsulfonyl group; a C3-6 cycloalkyl group such as a cyclopropyl group, a cyclobutyl group, or a cyclopentyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C3-6 cycloalkenyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; a 3 to 4-membered ring saturated heterocyclyl group such as an aziridinyl group, an epoxy group, an azetidinyl group, or an oxetanyl group; a 3 to 4-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5 to 6-membered ring saturated heterocyclyl group such as a pyrrolidinyl group, a tetrahydrofuranyl group, a thiazolidinyl group, a tetrahydro-2H-pyranyl group, a piperidyl group, a piperazinyl group, morpholinyl group, a dioxolanyl group, or a dioxanyl group; a 5 to 6-membered ring saturated heterocyclyl group substituted with any one or more substituents of a C1-6 alkyl group, a C1-6 alkoxy group, a halogeno group, a C1-6 haloalkyl group, or a C1-6 haloalkoxy group; a 5-membered ring heteroaryl group such as a pyrrolyl group, a furyl group, a thienyl group, an imidazolyl group, a pyrazolyl group, an oxazolyl group, an isoxazolyl group, a thiazolyl group, a isothiazolyl group, a triazolyl group, an oxadiazolyl group, a thiadiazolyl group, or a tetrazolyl group; a 5-membered ring heteroaryl group substituted with any one or more substituents of a C1-6 alkyl group, a C1-6 alkoxy group, a halogeno group, a C1-6 haloalkyl group, or a C1-6 haloalkoxy group; a 6-membered ring heteroaryl group such as a pyridyl group, a pyrazinyl group, a pyrimidinyl group, a pyridazinyl group, or a triazinyl group; a 6-membered ring heteroaryl group substituted with any one or more substituents of a C1-6 alkyl group, a C1-6 alkoxy group, a halogeno group, a C1-6 haloalkyl group, or a C1-6 haloalkoxy group; a 5-membered ring partially unsaturated heterocyclyl group such as a pyrrolinyl group, a dihydrofuranyl group, an imidazolinyl group, a pyrazolinyl group, or an oxazolinyl group; a 5-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group; a 6-membered ring partially unsaturated heterocyclyl group such as an isoxazolinyl group or a dihydropyranyl group; a 6-membered ring partially saturated heterocyclyl group substituted with any one or more substituents of a C1-6 alkyl group, a C1-6 alkoxy group, a halogeno group, a C1-6 haloalkyl group, or a C1-6 haloalkoxy group;

a group represented by $R^{q1}$—CO— (wherein $R^{q1}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; a 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{q1}$ below.); a carboxy group;

a group represented by $R^{q2}$—O—CO— (wherein $R^{q2}$ represents a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; a C2-6 alkenyl group; a C2-6 haloalkenyl group; a C2-6 alkynyl group; a C2-6 haloalkynyl group; a C3-6 cycloalkyl group; a C3-6 cycloalkyl group substituted with any one or more substituents of a C1-6 alkyl group, a C1-6 alkoxy group, a halogeno group, a C1-6 haloalkyl group, a C1-6 haloalkoxy group, or a cyano group; a C6-10 aryl group; a C6-10 aryl group substituted with any one or more substituents of a C1-6 alkyl group, a C1-6 alkoxy group, a halogeno group, a C1-6 haloalkyl group, or a C1-6 haloalkoxy group; a 5 to 6-membered ring heteroaryl group; or a 5 to 6-membered ring heteroaryl group substituted with any one or more substituents of a C1-6 alkyl group, a C1-6 alkoxy group, a halogeno group, a C1-6 haloalkyl group, or a C1-6 haloalkoxy group; the same applies to $R^{q2}$ below.); a group represented by $R^{q1}R^{q1}N$— (wherein $R^{q1}$ in the formula may be the same or different; $R^{q1}$ may together form a trimethylene group, a tetramethylene group, a pentamethylene group, or a dimethyleneoxydimethylene group.);

a group represented by $R^{q1}R^{q1}N$—CO— (wherein $R^{q1}$ in the formula may be the same or different; $R^{q1}$ may together form a trimethylene group, a tetramethylene group, a pentamethylene group, or a dimethyleneoxydimethylene group.);

a group represented by $R^{q1}$—CO—O—; a group represented by $R^{q1}$—CO—$NR^{q3}$— (wherein $R^{q3}$ represents a hydrogen atom; a C1-6 alkyl group; a C1-6 alkyl group substituted with any one or more substituents of a halogeno group, a C1-6 alkoxy group, a C1-6 haloalkoxy group, a C3-6 cycloalkyl group, a phenyl group, or a 5 to 6-membered ring heteroaryl group; a (C6-10 aryl substituted with any one or more substituents of a C1-6 alkyl group, a C1-6 alkoxy group, a halogeno group, a C1-6 haloalkyl group, or a C1-6 haloalkoxy group) C1-6 alkyl group; or a (5 to 6-membered ring heteroaryl substituted with any one or more substituents of a C1-6 alkyl group, a C1-6 alkoxy group, a halogeno group, a C1-6 haloalkyl group, or a C1-6 haloalkoxy group) C1-6 alkyl group; the same applies to $R^{q3}$ below.);

a group represented by $R^{q2}$—O—CO—O—; a group represented by $R^{q2}$—O—CO—$NR^{q3}$—; a group represented by $R^{q1}R^{q1}N$—CO—O— (wherein $R^{q1}$ in the formula may be the same or different; $R^{q1}$ may together form a trimethylene group, a tetramethylene group, a pentamethylene group, or a dimethyleneoxydimethylene group.);

a group represented by $R^{q1}R^{q1}N$—CO—$NR^{q3}$— (wherein $R^{q1}$ in the formula may be the same or different; $R^{q1}$ may together form a trimethylene group, a tetramethylene group, a pentamethylene group, or a dimethyleneoxydimethylene group.); a group represented by $R^{q2}SO_2$—$NR^{q3}$—; a group represented by $R^{q1}R^{q1}N$—$SO_2$— (wherein $R^{q1}$ in the formula may be the same or different; $R^{q1}$ may together form a trimethylene group, a tetramethylene group, a pentamethylene group, or a dimethyleneoxydimethylene group.);

a group represented by $R^{q1}$—O—N═C($R^{q4}$)— (wherein $R^{q4}$ represents a hydrogen atom or a C1-6 alkyl group.); a group represented by $(R^{q1})_2C$═N—O— (wherein $R^{q1}$ in the formula may be the same or different; $R^{q1}$ may together form a trimethylene group, a tetramethylene group, a pentamethylene group, or a dimethyleneoxydimethylene group.);

a pentafluorosulfanyl group, a nitro group, or a cyano group.

Further, as the substituent on the "C3-6 cycloalkyl group" or the "3 to 10-membered ring heterocyclyl group", an oxo group is also preferred.

Specific examples of the "group represented by $R^a$—CO—" can include a formyl group, an acetyl group, and an i-propylcarbonyl group.

In "the group represented by $R^b$—O—CO—" in G, $R^b$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Specific examples of the substituent in $R^b$ can include the same as those exemplified for $R^a$.

Specific examples of the "group represented by $R^b$—O—CO—" can include a methoxycarbonyl group, an ethoxycarbonyl group, a n-propoxycarbonyl group, an i-propoxycarbonyl group, a n-butoxycarbonyl group, and a t-butoxycarbonyl group.

In the "group represented by $R^cR^dN$—" in G, $R^c$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^d$ represents a hydrogen atom, a substituted or unsubstituted C1-6 alkyl group, a substituted or unsubstituted C1-6 alkoxy group, or a substituted or unsubstituted C6-10 aryl group.

Specific examples of the substituent in $R^c$ or $R^d$ can include the same as those exemplified for $R^a$.

Examples of the "C1-6 alkoxy group" in $R^d$ can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

The substituent on the "C1-6 alkoxy group" in $R^d$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, or a cyclopentyl group, cyclohexyl group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; or a cyano group.

Here, $R^c$ and $R^d$ may together form a divalent organic group.

Examples of the divalent organic group that can be formed can include a substituted or unsubstituted C2-5 alkylene group, a substituted or unsubstituted C1-3 alkyleneoxy C1-3 alkylene group, a substituted or unsubstituted C1-3 alkylenethio C1-3 alkylene group, or a substituted or unsubstituted C1-3 alkyleneimino C1-3 alkylene group.

Further examples can include a silicon-containing divalent hydrocarbon group such as —$CH_2CH_2$—$Si(CH_3)_2$—$CH_2CH_2$—.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

Examples of the "C1-3 alkylenethio C1-3 alkylene group" can include a dimethylenethiodimethylene group.

Examples of the "C1-3 alkyleneimino C1-3 alkylene group" can include a dimethyleneiminodimethylene group.

Here, the imino group of the "C1-3 alkylenealkyleneimino C1-3 alkylene group" means —NH—.

The substituent on the "C2-5 alkylene group", the "C1-3 alkyleneoxy C1-3 alkylene group", the "C1-3 alkylenethio C1-3 alkylene group", and the "C1-3 alkyleneimino C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; a methylidene group; or a C1-6 haloalkyl group such as a chloromethyl group, a chloroethyl group, a trifluoromethyl group, a 1,2-dichloro-n-propyl group, or a 1-fluoro-n-butyl group.

Specific examples of the "group represented by $R^cR^dN$—" can include an amino group, a methylamino group, a dimethylamino group, and an i-propylamino group.

In the "group represented by $R^cR^dN$—CO—" in G, $R^c$ and $R^d$ have the same meaning as those in the above "group represented by $R^cR^dN$—".

Specific examples of the "group represented by $R^cR^dN$—CO—" can include a carbamoyl group, a N,N-dimethylaminocarbonyl group, a N-(i-propyl) aminocarbonyl group, and a N-(i-propyl)-N-methylaminocarbonyl group.

In the "group represented by $R^cR^dN$—$NR^d$—CO—" in G, $R^c$ and $R^d$ have the same meaning as those in the above "group represented by $R^cR^dN$—".

Specific examples of the "group represented by $R^cR^dN$—$NR^d$—CO—" can include a 2,2-dimethylhydrazine-1-carbonyl group.

In the "group represented by $R^a$—CO—O—" in G, $R^a$ represents the same meaning as that in the above "group represented by $R^a$—CO—".

Specific examples of the "group represented by $R^a$—CO—O—" can include an acetyloxy group.

In the "group represented by $R^a$—CO—$NR^e$—" in G, $R^a$ represents the same meaning as that in the above "group represented by $R^a$—CO—".

$R^e$ represents a hydrogen atom, a substituted or unsubstituted C1-6 alkyl group, a substituted or unsubstituted C1-6 alkoxy group, or a substituted or unsubstituted C6-10 aryl group.

Specific examples of the substituent in $R^e$ can include the same as those exemplified for $R^a$.

Specific examples of the "group represented by $R^a$—CO—$NR^e$—" can include an acetylamino group, a propionylamino group, a butyrylamino group, and an i-propylcarbonylamino group.

In the "group represented by $R^a$—CO—CO—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—CO—$NR^e$—" can include an oxopropanamide group.

In the "group represented by $R^a$—CO—$NR^e$—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—$NR^e$—$NR^e$—" can include an acetylhydrazinyl group and an i-propylcarbonylhydrazinyl group.

In the "group represented by $R^a$—CO—$NR^e$—$NR^e$—CO—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CO—$NR^e$—$NR^e$—CO—" can include a 2-acetylhydrazine-1-carbonyl group.

In the "group represented by $R^b$—O—CO—O—" in G, $R^b$ represents the same meaning as that in the above "group represented by $R^b$—O—CO—".

Specific examples of the "group represented by $R^b$—O—CO—O—" can include a methoxycarbonyloxy group and an ethoxycarbonyloxy group.

In the "group represented by $R^b$—O—CO—$NR^e$—" in G, $R^b$ represents the same meaning as that in the above "group represented by "group represented by $R^b$—O—CO—". $R^e$ represents the same meaning as that in the above "group represented by $R^b$—CO—$NR^e$—".

Specific examples of the "group represented by $R^b$—O—CO—$NR^e$—" can include a methoxycarbonylamino group.

In the "group represented by $R^cR^dN$—CO—O—" in G, $R^c$ and $R^d$ have the same meaning as those in the above "group represented by $R^cR^dN$—".

Specific examples of the "group represented by $R^cR^dN$—CO—O—" can include a carbamoyloxy group and a N,N-dimethylaminocarbonyloxy group.

In the "group represented by $R^cR^dN$—CO—$NR^e$—" in G, $R^c$ and $R^d$ have the same meaning as those in the above "group represented by $R^cR^dN$—". $R^e$ represents the same meaning as that in the above "group represented by $R^a$—CO—$NR^e$—".

Specific examples of the "group represented by $R^cR^dN$—CO—$NR^e$—" can include a carbamoylamino group and a N,N-dimethylaminocarbonylamino group.

In the "group represented by $R^cR^dN$—CO—CO—$NR^e$—" in G, $R^c$ and $R^d$ have the same meaning as those in the above "group represented by $R^CR^dN$—". $R^e$ represents the same meaning as that in the above "group represented by $R^a$—CO—$NR^e$—".

Specific examples of the "group represented by $R^cR^dN$—CO—CO—$NR^e$—" can include a 2-(methylamino)-2-oxoacetamide group and a 2-(t-butylamino)-2-oxoacetamide group.

In the "group represented by $R^a$—CS—$NR^e$—" in G, $R^a$ represents the same meaning as that in the above "group represented by $R^a$—CO—". $R^e$ represents the same meaning as that in the above "group represented by $R^a$—CO—$NR^e$—".

Specific examples of the "group represented by $R^a$—CS—$NR^e$—" can include an ethanethioamide group, a propanethioamide group, and a 2-methylpropanethioamide group.

In the "group represented by $R^cR^dN$—CS—$NR^e$—" in G, $R^C$ and $R^d$ have the same meaning as those in the above "group represented by $R^cR^dN$—". $R^e$ represents the same meaning as that in the above "group represented by $R^a$—CO—$NR^e$—".

Specific examples of the "group represented by $R^cR^dN$—CS—$NR^e$—" can include a 3,3-dimethylthioureido group.

In the "group represented by $R^bSO_2$—$NR^e$—" in G, $R^b$ represents the same meaning as that in the above "group represented by "group represented by $R^b$—O—CO—". $R^e$ represents the same meaning as that in the above "group represented by $R^a$—CO—$NR^e$—".

Specific examples of the "group represented by $R^bSO_2$—$NR^e$—" can include a methanesulfonylamino group.

In the "group represented by $R^cR^dN$—$SO_2$—" in G, $R^c$ and $R^d$ have the same meaning as those in the above "group represented by $R^cR^dN$—".

Specific examples of the "group represented by $R^cR^dN$—$SO_2$—" can include a N,N-dimethylaminosulfonyl group.

In the "group represented by $R^aO$—N═$CR^f$—" in G, $R^a$ represents the same meaning as that in the above "group represented by $R^a$—CO—".

$R^f$ represents a hydrogen atom, an amino group, or a substituted or unsubstituted C1-6 alkyl group.

Specific examples of the substituent in $R^f$ can include the same as those exemplified for $R^a$.

Specific examples of the "group represented by $R^a$O—N═C$R^f$—" can include a (hydroxyimino)methyl group and an (ethoxyimino)methyl group.

In the "group represented by $R^a$—C(═N$R^g$)—N$R^e$—" in G, $R^a$ represents the same meaning as that in the above "group represented by $R^a$—CO—". $R^e$ represents the same meaning as that in the above "group represented by $R^a$—CO—N$R^e$—".

Each $R^g$ independently represents a hydrogen atom, a substituted or unsubstituted C1-6 alkyl group, or a substituted or unsubstituted C6-10 aryl group.

Specific examples of the substituent in $R^g$ can include the same as those exemplified for $R^a$.

In the "group represented by $R^cR^d$N—C(═N$R^g$)—" in G, $R^c$ and $R^d$ have the same meaning as those in the above "group represented by $R^cR^d$N—". $R^g$ represents the same meaning as that in the above "group represented by $R^a$—C(═N$R^g$)—N$R^e$—".

In the "group represented by $R^hR^i$S(═O)═N—CO—" in G, each $R^{h1}$ independently represents a substituted or unsubstituted C1-6 alkyl group or a substituted or unsubstituted C6-10 aryl group, and each $R^i$ independently represents a substituted or unsubstituted C1-6 alkyl group or a substituted or unsubstituted C6-10 aryl group.

Specific examples of the substituent in $R^h$ or $R^i$ can include the same as those exemplified for $R^a$.

Here, $R^h$ and $R^i$ may together form a divalent organic group.

Examples of the divalent organic group that can be formed can include a substituted or unsubstituted C2-5 alkylene group or a substituted or unsubstituted C1-3 alkyleneoxy C1-3 alkylene group.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

The substituent on the "C2-5 alkylene group" or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

In the "group represented by $R^hR^i$S═N—CO—" in G, $R^h$ or $R^i$ represents the same meaning as those in the above "group represented by $R^hR^i$S(═O)═N—CO—".

In the "group represented by $R^hR^j$C═N—O—" in G, $R^h$ and $R^i$ have the same meaning as those in the above "group represented by $R^hR^i$S═N—O—".

Specific examples of the "group represented by $R^hR^j$C═N—O—" can include a (propan-2-ylidenamino)oxy group.

When two or more substituents (G) are present, examples of a divalent organic group that can be formed together by two of the substituents can include a substituted or unsubstituted C1-5 alkylene group, a substituted or unsubstituted oxy C1-4 alkylene group, a substituted or unsubstituted oxy C2-3 alkyleneoxy group, or a substituted or unsubstituted C1-3 alkyleneoxy C1-3 alkylene group.

Examples of the "C1-5 alkylene group" can include a methylene group, a dimethylene group, a trimethylene group, and a tetramethylene group.

Examples of the "oxy C1-4 alkylene group" can include an oxymethylene group and an oxydimethylene group.

Examples of the "oxy C2-3 alkyleneoxy group" can include an oxydimethyleneoxy group.

Examples of the "C1-3 alkyleneoxy C1-3 alkylene group" can include a dimethyleneoxydimethylene group.

The substituent on the "C1-5 alkylene group", the "oxy C1-4 alkylene group", the "oxy C2-3 alkyleneoxy group", and the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

In the present invention, examples of preferred G can include a halogeno group, a substituted or unsubstituted C1-6 alkyl group, a substituted or unsubstituted C1-6 alkoxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C6-10 aryl group, a substituted or unsubstituted 3 to 10-membered ring heterocyclyl group, a group represented by $R^b$—O—CO—, a group represented by $R^cR^d$N—, a group represented by $R^cR^d$N—CO—, a group represented by $R^a$—CO—O—, a group represented by $R^a$—CO—N$R^e$—, a group represented by $R^b$—O—CO—N$R^e$—, a group represented by $R^cR^d$N—CO—O—, a group represented by $R^cR^d$N—CO—N$R^e$—, a group represented by $R^cR^d$N—CS—N$R^e$—, a group represented by $R^bSO_2$—N$R^e$—, a group represented by $R^a$O—N═C$R^f$—, or a group represented by $R^hR^i$C═N—O—.

[A]

A represents a substituted or unsubstituted C1-6 alkylene group, a substituted or unsubstituted C2-6 alkenylene group, a substituted or unsubstituted C2-6 alkynylene group, or a substituted or unsubstituted C3-6 cyclo alkylene group.

Examples of the "C1-6 alkylene group" in A can include a methylene group, a dimethylene group, a trimethylene group, and a tetramethylene group.

Examples of the "C2-6 alkenylene group" in A can include a vinylene group (—CH═CH—), a divinylene group (—CH═CH—CH═CH—), and a propenylene group (—CH═CH—$CH_2$—, —$CH_2$—CH═CH—).

Examples of the "C2-6 alkynylene group" in A can include an ethynylene group (—C≡C—) and a propynylene group (—$CH_2$—C≡C—, —C≡C—$CH_2$—).

Examples of the "C3-6 cycloalkylene group" in A can include a 1,2-cyclopropylene group, a 1,2-cyclobutanediyl group, and a 1,3-cyclobutanediyl group.

In the present invention, examples of preferred A can include a substituted or unsubstituted C1-6 alkylene group or a substituted or unsubstituted C2-6 alkenylene group.

Examples of a substituent on the C1-6 alkylene group or the C2-6 alkenylene group can include one or more substituents selected from a group of substituents below (hereinbelow, this substituent may be denoted by a symbol "Ga".

When two or more substituents (Ga) are present, two of the substituents may together form a divalent organic group. The group of substituents is shown below:

a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a mercapto group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 3 to 6-membered ring heterocyclyl group, a substituted or unsubstituted 3 to 6-membered ring heterocyclyloxy group, a nitro group, a cyano group, a group represented by $R^{a1}$—CO—, a carboxy group, a group represented by $R^{b1}$—O—CO—, a group represented by $R^{c1}R^{d1}N$—, a group represented by $R^{c1}R^{d1}N$—CO—, a group represented by $R^{a1}$—CO—O—, a group represented by $R^{a1}$—CO—$NR^{e1}$—, a group represented by $R^{b1}$—O—CO—O—, a group represented by $R^{b}$1-O—CO—$NR^{e1}$—, a group represented by $R^{c1}R^{d1}N$—CO—O—, a group represented by $R^{c1}R^{d1}N$—CO—$NR^{e1}$—, a group represented by $R^{b1}SO_2$—$NR^{e1}$—, a group represented by $R^{c1}R^{d1}N$—$SO_2$—, a group represented by $R^{a1}O$—N═$CR^{f1}$—, a group represented by $R^{g1}R^{h1}C$═N—O—, an oxo group (0═), a thioxo group (S═), a divalent group represented by $R^{a1}$—N═, a divalent group represented by $R^{a1}O$—N═, a divalent group represented by $R^{c1}R^{d1}N$—N═, a divalent group represented by $R^{a1}$—CO—$NR^{e1}$—N═, a divalent group represented by $R^{b1}$—O—CO—$NR^{e1}$—N═, and a divalent group represented by $R^{b1}SO_2$—$NR^{e1}$—N═.

In the group of the substituents described above, each $R^{a1}$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^{b1}$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^{c1}$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and each $R^{d1}$ independently represents a hydrogen atom, a substituted or unsubstituted C1-6 alkyl group, or a substituted or unsubstituted C6-10 aryl group, where $R^{c1}$ and $R^{d1}$ may together form a divalent organic group.

Each $R^{e1}$ independently represents a hydrogen atom, a substituted or unsubstituted C1-6 alkyl group, or a substituted or unsubstituted C6-10 aryl group, $R^{f1}$ represents a hydrogen atom or a substituted or unsubstituted C1-6 alkyl group, $R^{g1}$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^{h1}$ represents a hydrogen atom or a substituted or unsubstituted C1-6 alkyl group, where $R^{g1}$ and $R^{h1}$ may together form a divalent organic group.

Examples of the "halogeno group" in Ga can include a fluoro group, a chloro group, a bromo group, and an iodo group.

The "C1-6 alkyl group" in Ga may be a linear chain or may be a branched chain. Examples of the "C1-6 alkyl group" in Ga can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in Ga can include a vinyl group, a 1-propenyl group, a 2-propenyl group, a 1-butenyl group, a 2-butenyl group, a 3-butenyl group, a 1-methyl-2-propenyl group, a 2-methyl-2-propenyl group, a 1-pentenyl group, a 2-pentenyl group, a 3-pentenyl group, a 4-pentenyl group, a 1-methyl-2-butenyl group, a 2-methyl-2-butenyl group, a 1-hexenyl group, a 2-hexenyl group, a 3-hexenyl group, a 4-hexenyl group, and a 5-hexenyl group.

Examples of the "C2-6 alkynyl group" in Ga can include an ethynyl group, a 1-propyny group, a 2-propyny group, a 1-butynyl group, a 2-butynyl group, a 3-butynyl group, a 1-methyl-2-propyny group, a 2-methyl-3-butynyl group, a 1-pentynyl group, a 2-pentynyl group, a 3-pentynyl group, a 4-pentynyl group, a 1-methyl-2-butynyl group, a 2-methyl-3-pentynyl group, a 1-hexynyl group, and a 1,1-dimethyl-2-butynyl group.

Examples of the "C1-6 alkoxy group" in Ga can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the "C2-6 alkenyloxy group" in Ga can include a vinyloxy group, an allyloxy group, a propenyloxy group, and a butenyloxy group.

Examples of the "C2-6 alkynyloxy group" in Ga can include an ethynyloxy group and a propargyloxy group.

Examples of the "C1-6 alkylthio group" in Ga can include a methylthio group, an ethylthio group, a n-propylthio group, a n-butylthio group, a n-pentylthio group, a n-hexylthio group, and an i-propylthio group.

Examples of the "C1-6 alkylsulfinyl group" in Ga can include a methylsulfinyl group, an ethylsulfinyl group, and a t-butylsulfinyl group.

Examples of the "C1-6 alkylsulfonyl group" in Ga can include a methylsulfonyl group, an ethylsulfonyl group, and a t-butylsulfonyl group.

The substituent on the "C1-6 alkyl group", the "C2-6 alkenyl group", the "C2-6 alkynyl group", the "C1-6 alkoxy group", the "C2-6 alkenyloxy group", the "C2-6 alkynyloxy group", the "C1-6 alkylthio group", the "C1-6 alkylsulfinyl group", or the "C1-6 alkylsulfonyl group" in Ga is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, a cyclopentyl group, or a cyclohexyl group; a C6-10 aryl group such as a phenyl group and a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; or a cyano group.

Examples of the "C3-6 cycloalkyl group" in Ga can include a cyclopropyl group, a cyclobutyl group, a cyclopentyl group, and a cyclohexyl group.

Examples of the "C3-6 cycloalkyloxy group" in Ga can include a cyclopropyloxy group, a cyclobutyloxy group, a cyclopentyloxy group, and a cyclohexyloxy group.

Examples of the "C6-10 aryl group" in Ga can include a phenyl group, a naphthyl group, an indenyl group, an indanyl group, and a tetralinyl group.

Examples of the "C6-10 aryloxy group" in Ga can include a phenoxy group and a naphthoxy group.

Examples of the "C6-10 arylthio group" in Ga can include a phenylthio group and a naphthylthio group.

Examples of the "C6-10 arylsulfinyl group" in Ga can include a phenylsulfinyl group and a naphthylsulfinyl group.

Examples of the "C6-10 arylsulfonyl group" in Ga can include a phenylsulfonyl group and a naphthylsulfonyl group.

The "3 to 6-membered ring heterocyclyl group" in Ga is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. Examples of the "3 to 6-membered ring heterocyclyl group" include a 3 to 6-membered ring saturated heterocyclyl group, a 5 to 6-membered ring heteroaryl group, and a 5 to 6-membered ring partially unsaturated heterocyclyl group.

Examples of the 3 to 6-membered ring saturated heterocyclyl group can include an aziridinyl group, an epoxy group, an azetidinyl group, an oxetanyl group, a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 6-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered ring heteroaryl group such as a pyridyl group, a pyrazinyl group, a pyrimidinyl group, a pyridazinyl group, and a triazinyl group.

Examples of the 5 to 6-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; and a 6-membered ring partially unsaturated heterocyclyl group such as an isoxazolinyl group and a dihydropyranyl group.

The "3 to 6-membered ring heterocyclyloxy group" in Ga has a structure in which a 3 to 6-membered ring heterocyclyl group is bonded to an oxy group. Specific examples thereof can include a thiazolyloxy group and a pyridyloxy group.

The substituent on the "C3-6 cycloalkyl group", the "C3-6 cycloalkyloxy group", the "C6-10 aryl group", the "C6-10 aryloxy group", the "C6-10 arylthio group", the "C6-10 arylsulfinyl group", the "C6-10 arylsulfonyl group", the "3 to 6-membered ring heterocyclyl group", or the "3 to 6-membered ring heterocyclyloxy group" in Ga is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; or a cyano group.

In the "group represented by $R^{a1}$—CO—" in Ga, $R^{a1}$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Examples of the "C1-6 alkyl group" in $R^{a1}$ can include a methyl group, an ethyl group, a n-propyl group, a n-butyl group, a n-pentyl group, a n-hexyl group, an i-propyl group, an i-butyl group, a s-butyl group, a t-butyl group, an i-pentyl group, a neopentyl group, a 2-methylbutyl group, and an i-hexyl group.

Examples of the "C2-6 alkenyl group" in $R^{a1}$ can include a vinyl group and 1-propenyl group.

Examples of the "C2-6 alkynyl group" in $R^{a1}$ can include an ethynyl group and a 1-propyny group.

The substituent on the "C1-6 alkyl group", the "C2-6 alkenyl group", or the "C2-6 alkynyl group" in $R^{a1}$ is preferably a halogeno group such as a fluoro group, a chloro group, a bromo group, or an iodo group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C3-6 cycloalkyl group such as a cyclopropyl group, a cyclobutyl group, or a cyclopentyl group, cyclohexyl group; a C6-10 aryl group such as a phenyl group or a naphthyl group; a C6-10 aryl group substituted with any one or more substituents of a halogeno group, a C1-6 haloalkyl group, or a C1-6 haloalkoxy group, such as a 4-chlorophenyl group, a 4-trifluoromethylphenyl group, or a 4-trifluoromethoxyphenyl group; or a cyano group.

Examples of the "C3-6 cycloalkyl group" in $R^{a1}$ can include a cyclopropyl group, a cyclobutyl group, a cyclopentyl group, and a cyclohexyl group.

Examples of the "C6-10 aryl group" in $R^{a1}$ can include a phenyl group and a naphthyl group.

The "5 to 6-membered ring heterocyclyl group" in $R^{a1}$ is a group including 1, 2, 3, or 4 hetero atoms selected from the group consisting of a nitrogen atom, an oxygen atom, and a sulfur atom as a constituent atom(s) of the ring. When two or more hetero atoms are included, the hetero atoms may be the same or different. Examples of the "5 to 6-membered ring heterocyclyl group" can include a 5 to 6-membered ring saturated heterocyclyl group, a 5 to 6-membered ring heteroaryl group, and a 5 to 6-membered ring partially unsaturated heterocyclyl group.

Examples of the 5 to 6-membered ring saturated heterocyclyl group can include a pyrrolidinyl group, a tetrahydrofuranyl group, a thiazolidinyl group, a tetrahydro-2H-pyranyl group, a piperidyl group, a piperazinyl group, a morpholinyl group, a dioxolanyl group, and a dioxanyl group.

Examples of the 5 to 6-membered ring heteroaryl group can include a 5-membered ring heteroaryl group such as a pyrrolyl group, a furyl group, a thienyl group, an imidazolyl group, a pyrazolyl group, an oxazolyl group, an isoxazolyl group, a thiazolyl group, an isothiazolyl group, a triazolyl group, an oxadiazolyl group, a thiadiazolyl group, and a tetrazolyl group; and a 6-membered ring heteroaryl group such as a pyridyl group, a pyrazinyl group, a pyrimidinyl group, a pyridazinyl group, and a triazinyl group.

Examples of the 5 to 6-membered ring partially unsaturated heterocyclyl group can include a 5-membered ring partially unsaturated heterocyclyl group such as a pyrrolinyl group, a dihydrofuranyl group, an imidazolinyl group, a pyrazolinyl group, and an oxazolinyl group; and a 6-membered ring partially unsaturated heterocyclyl group such as an isoxazolinyl group and a dihydropyranyl group.

The substituent on the "C3-6 cycloalkyl group", the "C6-10 aryl group", or the "5 to 6-membered ring heterocyclyl group" in $R^{a1}$ is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, a t-butyl group, a n-pentyl group, or a n-hexyl group; a C1-6 haloalkyl group such as a chloromethyl group, a chloroethyl group, a trifluoromethyl group, a 1,2-dichloro-n-propyl group, or a 1-fluoro-n-butyl group; a hydroxy group; a C1-6 alkoxy group such as a methoxy group, an ethoxy group, a n-propoxy group, an i-propoxy group, a n-butoxy group, a s-butoxy group, an i-butoxy group, or a t-butoxy group; a C1-6 haloalkoxy group such as a 2-chloro-n-propoxy group, a 2,3-dichlorobutoxy group, or a trifluoromethoxy group; a C6-10 aryl group such as a phenyl group or a naphthyl group; a C6-10 aryl group substituted with any one or more substituents of a C1-6 alkyl group, a C1-6 alkoxy group, a halogeno group, a C1-6 haloalkyl group, or a C1-6 haloalkoxy group, such as a 4-methylphenyl group, a 4-methoxyphenyl group, a 4-chlorophenyl group, a 4-trifluoromethylphenyl group, or a 4-trifluoromethoxyphenyl group; or a cyano group.

Specific examples of the "group represented by $R^{a1}$—CO—" can include a formyl group and an acetyl group.

In the "group represented by $R^{b}$l-O—CO—" in Ga, $R^{b1}$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group.

Specific examples of the substituent in $R^{b1}$ can include those exemplified for $R^{a1}$.

Specific examples of the "group represented by $R^{b}$l-O—CO—" can include a methoxycarbonyl group, an ethoxycarbonyl group, and a t-butoxycarbonyl group.

In the "group represented by $R^{c1}R^{d1}N$—" in Ga, $R^{c1}$ represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^{d1}$ represents a hydrogen atom, a substituted or unsubstituted C1-6 alkyl group, or a substituted or unsubstituted C6-10 aryl group.

Specific examples of the substituent in $R^{c1}$ or $R^{d1}$ can include the same as those exemplified for $R^{a1}$.

Here, $R^{c1}$ and $R^{d1}$ may together form a divalent organic group. Examples of the divalent organic group that can be formed can include a substituted or unsubstituted C2-5 alkylene group or a substituted or unsubstituted C1-3 alkyleneoxy C1-3 alkylene group.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

The substituent on the "C2-5 alkylene group" or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

Specific examples of the "group represented by $R^{c1}R^{d1}N$—" can include an amino group, a methylamino group, and a dimethylamino group.

In the "group represented by $R^{c1}R^{d1}N$—CO—" in Ga, $R^{c1}$ and $R^{d1}$ have the same meaning as those in the above "group represented by $R^{c1}R^{d1}N$—".

Specific examples of the "group represented by $R^{c1}R^{d1}N$—CO—" can include a carbamoyl group, a N,N-dimethylaminocarbonyl group, a N-(i-propyl)aminocarbonyl group, and a N-(i-propyl)-N-methylaminocarbonyl group.

In the "group represented by $R^{a1}$—CO—O—" in Ga, $R^{a1}$ represents the same meaning as that in the above "group represented by $R^{a1}$—CO—".

Specific examples of the "group represented by $R^{a1}$—CO—O—" can include an acetyloxy group.

In the "group represented by $R^{a1}$—CO—$NR^{e1}$—" in Ga, $R^{a1}$ represents the same meaning as that in the above "group represented by $R^{a1}$—CO—".

$R^{e1}$ represents a hydrogen atom, a substituted or unsubstituted C1-6 alkyl group, or a substituted or unsubstituted C6-10 aryl group.

Specific examples of the substituent in $R^{e1}$ can include those exemplified for $R^{a1}$.

Specific examples of the "group represented by $R^{a1}$—CO—$NR^{e1}$—" can include an acetylamino group.

In the "group represented by $R^b$1-O—CO—O—" in Ga, $R^{b1}$ represents the same meaning as that in the above "group represented by $R^{b1}$—O—CO—".

Specific examples of the "group represented by $R^b$1-O—CO—O—" can include a methoxycarbonyloxy group and an ethoxycarbonyloxy group.

In the "group represented by $R^{b1}$—O—CO—$NR^{e1}$—" in Ga, $R^{b1}$ represents the same meaning as that in the above "group represented by $R^{b1}$—O—CO—". $R^{e1}$ represents the same meaning as that in the above "group represented by $R^{b1}$—CO—$NR^{e1}$—".

Specific examples of the "group represented by $R^b$1-O—CO—$NR^{e1}$—" can include a methoxycarbonylamino group.

In the "group represented by $R^{c1}R^{d1}$N—CO—O—" in Ga, $R^{c1}$ and $R^{d1}$ have the same meaning as those in the above "group represented by $R^{c1}R^{d1}$N—".

Specific examples of the "group represented by $R^{c1}R^{d1}$N—CO—O—" can include a carbamoyloxy group and a N, N-dimethylaminocarbonyloxy group.

In the "group represented by $R^{c1}R^{d1}$N—CO—$NR^{e1}$—" in Ga, $R^{c1}$ and $R^{d1}$ have the same meaning as those in the above "group represented by $R^{c1}R^{d1}$N—". $R^{e1}$ represents the same meaning as that in the above "group represented by $R^{a1}$—CO—$NR^{e1}$—"

Specific examples of the "group represented by $R^{c1}R^{d1}$N—CO—$NR^{e1}$—" can include a carbamoylamino group and a N,N-dimethylaminocarbonylamino group.

In the "group represented by $R^{b1}SO_2$—$NR^{e1}$—" in Ga, $R^{b1}$ represents the same meaning as that in the above "group represented by $R^{b1}$—O—CO—". $R^{e1}$ represents the same meaning as that in the above "group represented by $R^{a1}$—CO—$NR^{e1}$—".

Specific examples of the "group represented by $R^{b1}SO_2$—$NR^{e1}$—" can include a methanesulfonylamino group.

In the "group represented by $R^{c1}R^{d1}N$—$SO_2$—" in Ga, $R^{c1}$ and $R^{d1}$ have the same meaning as those in the above "group represented by $R^{c1}R^{d1}$N—".

Specific examples of the "group represented by $R^{c1}R^{d1}$N—$SO_2$—" can include a N,N-dimethylaminosulfonyl group.

In the "group represented by $R^{a1}$O—N═$CR^{f1}$—" in Ga, $R^{a1}$ represents the same meaning as that in the above "group represented by $R^{a1}$—CO—".

$R^{f1}$ represents a hydrogen atom or a substituted or unsubstituted C1-6 alkyl group.

Specific examples of the substituent in $R^{f1}$ can include the same as those exemplified for $R^a$.

Specific examples of the "group represented by $R^{a1}$O—N═$CR^{f1}$—" can include a (hydroxyimino)methyl group and an (ethoxyimino)methyl group.

In the "group represented by $R^{g1}R^{h1}$C═N—O—" in Ga, $R^{g1}$ represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, and $R^{h1}$ represents a hydrogen atom or a substituted or unsubstituted C1-6 alkyl group.

Specific examples of the substituent in $R^{g1}$ or $R^{h1}$ can include the same as those exemplified for $R^{a1}$.

Here, $R^{g1}$ and $R^{h1}$ may together form a divalent organic group.

Examples of the divalent organic group that can be formed can include a substituted or unsubstituted C2-5 alkylene group or a substituted or unsubstituted C1-3 alkyleneoxy C1-3 alkylene group.

Examples of the "C2-5 alkylene group" can include a dimethylene group, a trimethylene group, and a tetramethylene group.

Examples of the "C1-3 alkyleneoxy C1-3 alkylene group" can include a dimethyleneoxydimethylene group.

The substituent on the "C2-5 alkylene group" or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

Specific examples of the "group represented by $R^{g1}R^{h1}$C═N—O—" can include a (propan-2-ylidenamino) oxy group.

In the "divalent group represented by $R^{a1}$—N═" in Ga, $R^{a1}$ represents the same meaning as that in the above "group represented by $R^{a1}$—CO—".

Specific examples of the "divalent group represented by $R^{a1}$—N═" can include an imino group (HN═) and a methylimino group.

In the "divalent group represented by $R^{a1}$O—N═" in Ga, $R^{a1}$ represents the same meaning as that in the above "group represented by $R^{a1}$—CO—".

Specific examples of the "divalent group represented by $R^{a1}$O—N═" can include a N-hydroxyimino group and a N-methoxyimino group.

In the "divalent group represented by $R^{c1}R^{d1}$N—N═" in Ga, $R^{c1}$ and $R^{d1}$ have the same meaning as those in the above "group represented by $R^{c1}R^{d1}$N—".

Specific examples of the "divalent group represented by $R^{c1}R^{d1}$N—N═" can include a 2,2-dimethylhydrazinylidene group.

In the "divalent group represented by $R^{a1}$—CO—$NR^{e1}$—N═" in Ga, $R^{a1}$ represents the same meaning as that in the above "group represented by $R^{a1}$—CO—". $R^{e1}$ represents the same meaning as that in the above "group represented by $R^{a1}$—CO—$NR^{e1}$—"

In the "divalent group represented by $R^{b1}$—O—CO—$NR^{e1}$—N═" in Ga, $R^{b1}$ represents the same meaning as that in the above "group represented by $R^{b1}$—O—CO—". $R^{e1}$ represents the same meaning as that in the above "group represented by $R^{a1}$—CO—$NR^{e1}$—".

In the "divalent group represented by $R^{b1}SO_2$—$NR^{e1}$—N═" in Ga, $R^{b1}$ represents the same meaning as that in the above "group represented by $R^{b1}$—O—CO—". $R^{e1}$ represents the same meaning as that in the above "group represented by $R^{a1}$—CO—$NR^{e1}$—".

When two or more substituents (Ga) are present, examples of a divalent organic group that can be formed together by two of the substituents can include a substituted or unsubstituted C1-5 alkylene group, a substituted or unsubstituted oxy C1-4 alkylene group, a substituted or unsubstituted oxy C2-3 alkyleneoxy group, or a substituted or unsubstituted C1-3 alkyleneoxy C1-3 alkylene group.

Examples of the "C1-5 alkylene group" can include a methylene group, a dimethylene group, a trimethylene group, and a tetramethylene group.

Examples of the "oxy C1-4 alkylene group" can include an oxymethylene group and an oxydimethylene group.

Examples of the "oxy C2-3 alkyleneoxy group" can include an oxydimethyleneoxy group.

Examples of the "C1-3 alkyleneoxy C1-3 alkylene group" can include a dimethyleneoxydimethylene group.

The substituent on the "C1-5 alkylene group", the "oxy C1-4 alkylene group", the "oxy C2-3 alkyleneoxy group", or the "C1-3 alkyleneoxy C1-3 alkylene group" is preferably a halogeno group such as a fluoro group, a chloro group, a bromo group, or an iodo group; a C1-6 alkyl group such as a methyl group, an ethyl group, a n-propyl group, an i-propyl group, a n-butyl group, a s-butyl group, an i-butyl group, or a t-butyl group; or a C1-6 haloalkyl group such as a chloromethyl group, a chloroethyl group, a trifluoromethyl group, a 1,2-dichloro-n-propyl group, or a 1-fluoro-n-butyl group.

In the present invention, examples of preferred Ga can include a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C3-6 cycloalkyloxy group, a substituted or unsubstituted C6-10 aryloxy group, a substituted or unsubstituted 5 to 6-membered ring heterocyclyloxy group, a group represented by $R^{a1}$—CO—O—, an oxo group (O═), or a divalent group represented by $R^{a1}$O—N═.

In this case, preferable examples of the substituted or unsubstituted 5 to 6-membered ring heterocyclyloxy group can include a tetrahydro-2H-pyran-4-yl group.

In the present invention, examples of more preferred Ga can include a hydroxy group, a substituted or unsubstituted C1-6 alkoxy group, a substituted or unsubstituted C2-6 alkenyloxy group, a substituted or unsubstituted C2-6 alkynyloxy group, a group represented by $R^{a1}$—CO—O—, an oxo group (O═), or a divalent group represented by $R^{a1}$O—N═.

[Salt]

The salts of the compound (II) are not particularly limited as long as the salts are agriculturally and horticulturally acceptable salts. Examples thereof can include a salt of an inorganic acid such as hydrochloric acid and sulfuric acid; a salt of an organic acid such as acetic acid and lactic acid; a salt of an alkali metal such as lithium, sodium, and potassium; a salt of an alkaline earth metal such as calcium and magnesium; a salt of a transition metal such as iron and copper; a salt of an organic base such as triethylamine, tributylamine, pyridine, and hydrazine; and ammonia.

[Production Method]

A method for producing the compound (II) or a salt of the compound (II) is not limited. For example, the compound (II) or a salt of the compound (II) of the present invention can be obtained by a known method described in Examples and the like. The salt of the compound (II) can be obtained also by a known method from the compound (II).

(Reaction Scheme 1)

For example, among the compounds (II), the compound of Formula (I-1) shown below may be prepared by condensing a compound of Formula (III-1) and a compound of Formula (A), as shown in the following reaction scheme 1.

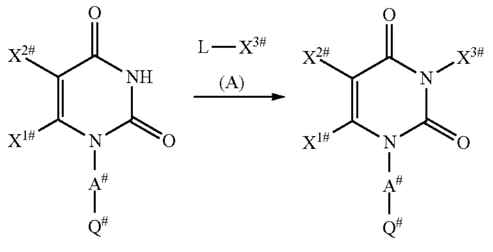

(III-1) (I-1)

In Formula (I-1), $X^{1\#}$ represents the same meaning as $X^1$ in Formula (II) or represents a structure that can be derived into $X^1$ by a common method. $X^{2\#}$ represents the same meaning as $X^2$ in Formula (II) or represents a structure that can be derived into $X^2$ by a common method. $X^{3\#}$ represents the same meaning as $X^3$ in Formula (II) or represents a structure that can be derived into $X^3$ by a common method. $Q^{\#}$ represents the same meaning as Q in Formula (II) or represents a structure that can be derived into Q by a common method. $A^{\#}$ represents the same meaning as A in Formula (II) or represents a structure that can be derived into A by a common method.

The symbols in Formula (III-1) have the same meaning as those in Formula (I-1).

$X^{3\#}$ in Formula (A) represents the same meaning as that in Formula (I-1). L represents a leaving group.

For example, when a compound of Formula (A) having a leaving group such as a methanesulfonyl group as L is used, the compound of Formula (I-1) may be prepared by a reaction in the presence of an inorganic base.

For example, when a compound of Formula (A) in which L is a hydroxy group is used, the compound of Formula (I-1) may be prepared by use of a Mitsunobu reaction.

(Reaction Scheme 2)

The compound of Formula (III-1) may be prepared by condensing a compound of Formula (B) and a compound of Formula (C), as shown in the following reaction scheme 2.

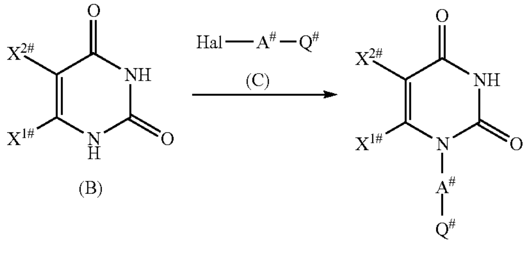

(B) (III-1)

The symbols in Formula (B) have the same meaning as those in Formula (I-1). The symbols in Formula (C) have the same meaning as those in Formula (I-1). Hal represents a halogeno group.

For example, the compound of Formula (III-1) may be prepared by reacting the compound of Formula (B) with the compound of Formula (C) in the presence of an inorganic base.

(Reaction Scheme 3)

Among compounds of Formula (B), a compound of Formula (B-1), in which an $X^2$ moiety is a group represented by $R^1$O—N═$CR^6$—, may be prepared by condensing a compound of Formula (D) and a compound of Formula (E), as shown in the following reaction scheme 3.

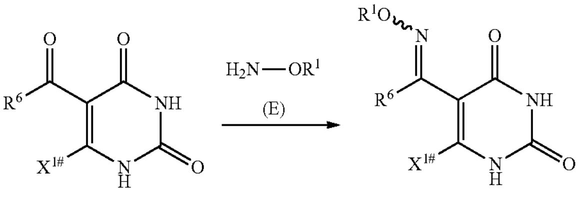

(D) (B-1)

$R^1$ and $R^6$ in Formula (B-1) have the same meaning as those in Formula (II). $X^{1\#}$ represents the same meaning as that in Formula (I-1).

$R^6$ in Formula (D) represents the same meaning as that in Formula (II). $X^{1\#}$ represents the same meaning as that in Formula (I-1).

$R^1$ in Formula (E) represents the same meaning as that in Formula (II). As the compound of Formula (E), a hydrochloride of the compound may be used.

For example, the compound of Formula (B-1) may be prepared by reacting the compound of Formula (D) with the compound of Formula (E) in an alcohol solvent.

(Reaction Scheme 4)

Among compounds of Formula (I-1), a compound of Formula (I-2), in which an $X^2$ moiety is a group represented by $R^1O—N═CR^6—$, may be prepared by condensing a compound of Formula (F) and a compound of Formula (E), as shown in the following reaction scheme 4.

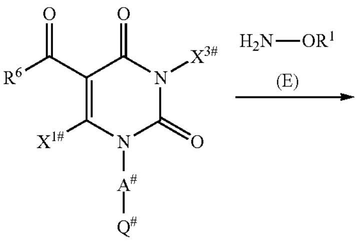

(F)

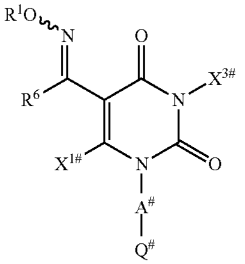

(I-2)

$R^1$ and $R^6$ in Formula (I-2) have the same meaning as those in Formula (II). Other symbols have the same meaning as those in Formula (I-1).

$R^6$ in Formula (F) represents the same meaning as that in Formula (II). Other symbols have the same meaning as those in Formula (I-1).

$R^1$ in Formula (E) represents the same meaning as that in Formula (II). As the compound of Formula (E), a hydrochloride of the compound may be used.

For example, the compound of Formula (I-2) may be prepared by reacting the compound of Formula (F) with the compound of Formula (E) in an alcohol solvent.

(Reaction Scheme 5)

The compound of Formula (I-1) may be prepared also by condensing a compound of Formula (IV-1) and a compound of Formula (C), as shown in the following reaction scheme 5.

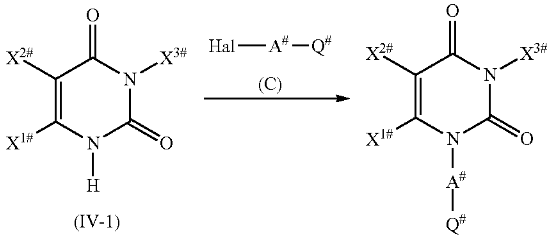

(IV-1)

(I-1)

The symbols in Formula (IV-1) have the same meaning as those in Formula (I-1). The symbols in Formula (C) have the same meaning as those in Formula (I-1). Hal represents a halogeno group.

For example, the compound of Formula (I-1) may be prepared by reacting the compound of Formula (IV-1) with the compound of Formula (C) in the presence of an inorganic base.

[Production Intermediate]

A compound represented by the following Formula (III) or a salt thereof can be used as a production intermediate on producing a compound of formula (II).

(III)

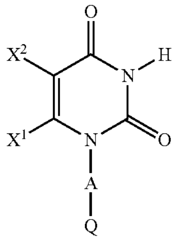

In Formula (III), $X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1—CO—$, a carboxy group, a group represented by $R^2—O—CO—$, a group represented by $R^3R^4N—$, a group represented by $R^3R^4N—CO—$, a group represented by $R^1—CO—O—$, a group represented by $R^1—CO—NR^5—$, a group represented by $R^2—O—CO—O—$, a group represented by $R^2—O—CO—NR^5—$, a group represented by $R^3R^4N—CO—O—$, a group represented by $R^3R^4N—CO—NR^5—$, a group represented by $R^2SO_2—NR^5—$, a group represented by $R^3R^4N—SO_2—$, or a group represented by $R^1O—N═CR^6—$;

each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^4$ independently represents a hydrogen atom, a substituted or unsubstituted C1-6 alkyl group, or a substituted or unsubstituted C6-10 aryl group, where $R^3$ and $R^4$ may together form a divalent organic group, each $R^5$ independently represents a hydrogen atom, a substituted or unsubstituted C1-6 alkyl group, or a substituted or unsubstituted C6-10 aryl group, $R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group;

$X^2$ represents a group represented by $R^1O—N═CR^6—$, a group represented by $R^1CO—O—N═CR^6—$, a group represented by $R^3R^4N—CO—O—N═CR^6—$, a group represented by $R^3R^4N—N═CR^6—$, or a group represented by $R^7—N═CR^6—$; $R^1$, $R^3$, $R^4$, and $R^6$ have the same meaning as those in $X^1$; $R^7$ represents a substituted or unsubstituted 5-membered ring heterocyclyl group;

A represents a substituted or unsubstituted C1-6 alkylene group, a substituted or unsubstituted C2-6 alkenylene group, a substituted or unsubstituted C2-6 alkynylene group, or a substituted or unsubstituted C3-6 cycloalkylene group; and Q represents a substituted or unsubstituted C6-10 aryl group or a substituted or unsubstituted 5 to 10-membered ring heterocyclyl group.

The symbols in Formula (III) have the same meaning as those in Formula (II).

A compound by the following Formula (IV) or a salt thereof can be used as a production intermediate on producing a compound of formula (II).

(IV)

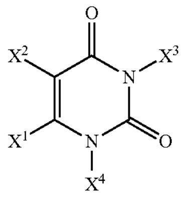

In Formula (IV), $X^1$ represents a hydrogen atom, a halogeno group, a substituted or unsubstituted C1-6 alkyl group, a substituted or unsubstituted C2-6 alkenyl group, a substituted or unsubstituted C2-6 alkynyl group, a hydroxy group, a substituted or unsubstituted C1-6 alkoxy group, a substituted or unsubstituted C2-6 alkenyloxy group, a substituted or unsubstituted C2-6 alkynyloxy group, a substituted or unsubstituted C1-6 alkylthio group, a substituted or unsubstituted C1-6 alkylsulfinyl group, a substituted or unsubstituted C1-6 alkylsulfonyl group, a substituted or unsubstituted C3-6 cycloalkyl group, a substituted or unsubstituted C3-6 cycloalkyloxy group, a substituted or unsubstituted C6-10 aryl group, a substituted or unsubstituted C6-10 aryloxy group, a substituted or unsubstituted C6-10 arylthio group, a substituted or unsubstituted C6-10 arylsulfinyl group, a substituted or unsubstituted C6-10 arylsulfonyl group, a substituted or unsubstituted 5 to 6-membered ring heterocyclyl group, a substituted or unsubstituted 5 to 6-membered ring heterocyclyloxy group, a nitro group, a cyano group, a group represented by $R^1—CO—$, a carboxy group, a group represented by $R^2—O—CO—$, a group represented by $R^3R^4N—$, a group represented by $R^3R^4N—CO—$, a group represented by $R^1—CO—O—$, a group represented by $R^1—CO—NR^5—$, a group represented by $R^2—O—CO—O—$, a group represented by $R^2—O—CO—NR^5—$, a group represented by $R^3R^4N—CO—O—$, a group represented by $R^3R^4N—CO—NR^5—$, a group represented by $R^2SO_2—NR^5—$, a group represented by $R^3R^4N—SO_2—$, or a group represented by $R^1O—N═CR^6—$;

each $R^1$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^2$ independently represents a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^3$ independently represents a hydrogen atom, a substituted or unsubstituted C1-6 alkyl group, a substituted or unsubstituted C2-6 alkenyl group, a substituted or unsubstituted C2-6 alkynyl group, a substituted or unsubstituted C3-6 cycloalkyl group, a substituted or unsubstituted C6-10 aryl group, or a substituted or unsubstituted 5 to 6-membered ring heterocyclyl group, each $R^4$ independently represents a hydrogen atom, a substituted or unsubstituted C1-6 alkyl group, or a substituted or unsubstituted C6-10 aryl group, where $R^3$ and $R^4$ may together form a divalent organic group, each $R^5$ independently represents a hydrogen atom, a substituted or unsubstituted C1-6 alkyl group, or a substituted or unsubstituted C6-10 aryl group, $R^6$ represents a hydrogen atom, a halogeno group, an amino group, a substituted or unsubstituted mono C1-6 alkylamino group, a substituted or unsubstituted di C1-6 alkylamino group, a substituted or unsubstituted C1-6 alkyl group, a substituted or unsubstituted C1-6 alkoxy group, a substituted or unsubstituted C1-6 alkylthio group, or a substituted or unsubstituted 5 to 6-membered ring heterocyclyl group;

$X^2$ represents a group represented by $R^1O—N═CR^6—$, a group represented by $R^1CO—O—N═CR^6—$, a group represented by $R^3R^4N—CO—O—N═CR^6—$, a group represented by $R^3R^4N—N═CR^6—$, or a group represented by $R^7—N═CR^6—$; $R^1$, $R^3$, $R^4$, and $R^6$ have the same meaning as those in $X^1$; $R^7$ represents a substituted or unsubstituted 5-membered ring heterocyclyl group;

$X^3$ represents a substituted or unsubstituted linear C1-6 alkyl group, a substituted or unsubstituted linear C2-6 alkenyl group, a substituted or unsubstituted linear C2-6 alkynyl group, a substituted or unsubstituted C3-6 cycloalkyl group, a substituted or unsubstituted C6-10 aryl group, or a substituted or unsubstituted 5 to 6-membered ring heterocyclyl group; and $X^4$ represents a hydrogen atom or a C1-6 alkoxymethyl group.

The symbols other than $X^4$ in Formula (IV) have the same meaning as those in Formula (II).

Examples of the "C1-6 alkoxy group" of the "C1-6 alkoxymethyl group" in $X^4$ can include a methoxy group, an ethoxy group, a n-propoxy group, a n-butoxy group, a n-pentyloxy group, a n-hexyloxy group, an i-propoxy group, an i-butoxy group, a s-butoxy group, a t-butoxy group, and an i-hexyloxy group.

Examples of the production intermediate for use in production of the compound (II) of the present invention are shown in Table 1 below. In the table, the melting point (m.p.) is also shown as physical properties of each compound.

TABLE 1

| Compound number | Structural formula | Physical properties |
|---|---|---|
| 1 | 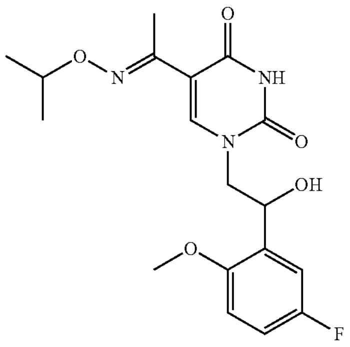 [SMILES: COc1ccc(F)cc1C(O)Cn1cc(/C(C)=N/OC(C)C)c(=O)[nH]c1=O] | m.p. 198-200° C. |
| 2 | 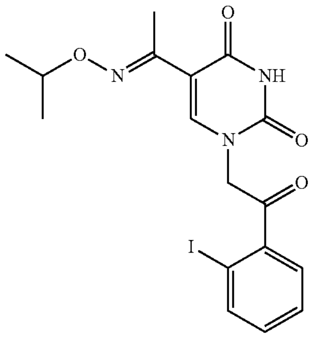 [SMILES: C/C(=N\OC(C)C)c1cn(CC(=O)c2ccccc2I)c(=O)[nH]c1=O] | m.p. 186-187° C. |
| 3 | 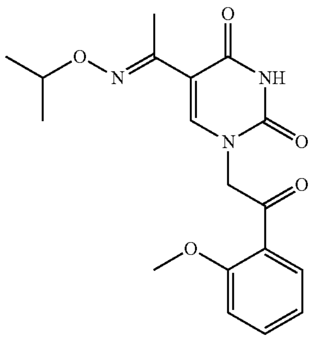 [SMILES: COc1ccccc1C(=O)Cn1cc(/C(C)=N/OC(C)C)c(=O)[nH]c1=O] | m.p. 185-186° C. |

TABLE 1-continued
| Compound number | Structural formula | Physical properties |
|---|---|---|
| 4 | 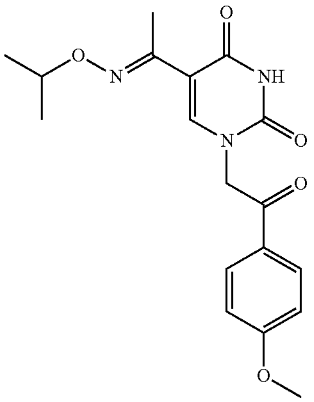 [SMILES: COc1ccc(C(=O)Cn2cc(/C(C)=N/OC(C)C)c(=O)[nH]c2=O)cc1] | m.p. 182-183° C. |
| 5 | 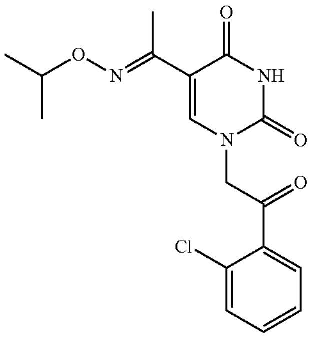 [SMILES: C/C(=N\OC(C)C)c1cn(CC(=O)c2ccccc2Cl)c(=O)[nH]c1=O] | m.p. 157-158° C. |
| 6 | 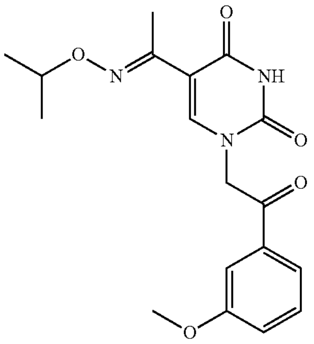 [SMILES: COc1cccc(C(=O)Cn2cc(/C(C)=N/OC(C)C)c(=O)[nH]c2=O)c1] | m.p. 124-125° C. |
| 7 | 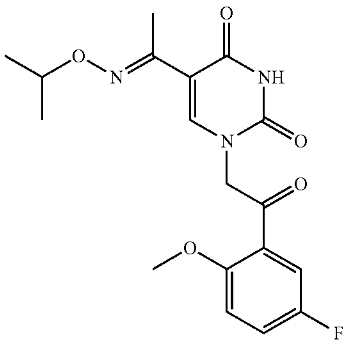 [SMILES: COc1ccc(F)cc1C(=O)Cn1cc(/C(C)=N/OC(C)C)c(=O)[nH]c1=O] | m.p. 199-202° C. |

TABLE 1-continued

| Compound number | Structural formula | Physical properties |
|---|---|---|
| 8 | 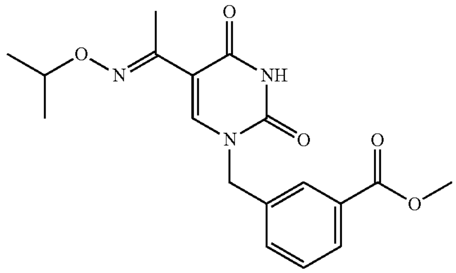 [SMILES: COC(=O)c1cccc(Cn2cc(/C(C)=N/OC(C)C)c(=O)[nH]c2=O)c1] | m.p. 128-129° C. |
| 9 | 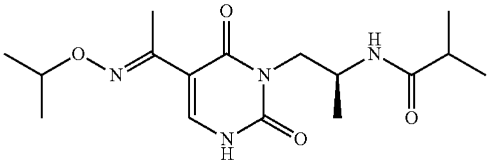 [SMILES: C/C(=N\OC(C)C)c1c[nH]c(=O)n(C[C@H](C)NC(=O)C(C)C)c1=O] | m.p. 205-206° C. |
| 10 | 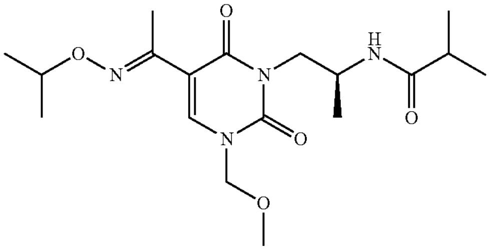 [SMILES: COCn1cc(/C(C)=N/OC(C)C)c(=O)n(C[C@H](C)NC(=O)C(C)C)c1=O] | m.p. 125-126° C. |
| 11 | 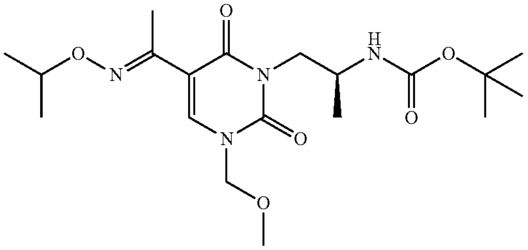 [SMILES: COCn1cc(/C(C)=N/OC(C)C)c(=O)n(C[C@H](C)NC(=O)OC(C)(C)C)c1=O] | viscous oil |

Among the compounds described in Table 1, for the compound having an amorphous or viscous-oil property, the $^1$H-NMR data thereof are shown below.

Compound 11: $^1$H-NMR ($CDCl_3$) 7.49 (1H, s), 5.21-3.70 (7H, m), 3.43 (3H, s), 2.16 (3H, s), 1.35-1.20 (9H, m).

[Agricultural and Horticultural Fungicide]

The agricultural and horticultural fungicide of the present invention contains at least one selected from the compound (II) and a salt thereof as an active ingredient. The amount of the compound (II) or a salt thereof included in the agricultural and horticultural fungicide of the present invention is not particularly limited as long as it shows the bactericidal effect.

The agricultural and horticultural fungicide of the present invention can be used for controlling plant diseases derived from a wide variety of filamentous fungi, for example, fungi belonging to algae fungi (Oomycetes), sac fungi (Ascomycetes), imperfect fungi (Deuteromycetes), Basidiomycete fungi (Basidiomycetes), or conjugation fungi (Zygomycetes).

Examples of plant diseases (pathogens) to be controlled are shown below: Sugar beet: *Cercospora* leaf spot (*Cercospora beticola*), *Aphanomyces* root rot (*Aphanomyces cochlioides*), root rot (*Thanatephorus cucumeris*), leaf blight (*Thanatephorus cucumeris*), rust (*Uromyces betae*), powdery mildew (*Oidium* sp.), Ramularia leaf spot (*Ramularia beticola*), and damping-off (*Aphanomyces cochlioides, Pythium ultimum*).

Peanut: brown leaf spot (*Mycosphaerella arachidis*), leaf mold (*Ascochyta* sp.), rust (*Puccinia arachidis*), damping-off (*Pythium debaryanum*), *Alternaria* leaf spot (*Alternaria alternata*), southern blight (*Sclerotium rolfsii*), leaf spot (*Mycosphaerella berkeleyi*), and pod and root necrosis (*Calonectria ilicicola*).

Cucumber: powdery mildew (*Sphaerotheca fuliginea*), downy mildew (*Pseudoperonospora cubensis*), gummy stem blight (*Mycosphaerella melonis*), Fusarium wilt (*Fusarium oxysporum*), Sclerotinia rot (*Sclerotinia sclerotiorum*), gray mold (*Botrytis cinerea*), anthracnose (*Colletotrichum orbiculare*), scab (*Cladosporium cucumerinum*), *Corynespora* leaf spot (*Corynespora cassiicola*), damping-off (*Pythium debaryanum, Rhizoctonia solani* Kuhn), Phomopsis root rot (*Phomopsis* sp.), and bacterial spot (*Pseudomonas syringae* pv. *Lachrymans*).

Tomato: gray mold (*Botrytis cinerea*), leaf mold (*Cladosporium fulvum*), late blight (*Phytophthora infestans*), *verticillium* wilt (*Verticillium albo-atrum, Verticillium dahliae*), powdery mildew (*Oidium neolycopersici*), early blight (*Alternaria solani*), *Cercospora* leaf mold (*Pseudocercospora fuligena*), bacterial wilt (*Ralstonia solanacearum*), and stem rot (*Sclerotinia sclerotiorum*).

Eggplant: gray mold (*Botrytis cinerea*), black blight (*Corynespora melongenae*), powdery mildew (*Erysiphe cichoracearum*), leaf mold (*Mycovellosiella nattrassii*), stem rot (*Sclerotinia sclerotiorum*), *verticillium* wilt (*Verticillium dahliae*), and brown spot (*Phomopsis vexans*). *Capsicum: phytophthora* blight (*Phytophthora capsici*), gray mold (*Botrytis cinerea*), *Sclerotinia* rot (*Sclerotinia sclerotiorum*), anthracnose (*Colletotrichum aenigma, Colletotrichum capsici, Colletotrichum fructicola, Colletotrichum jiangxiense*), and powdery mildew (*Leveillula taurica*).

Strawberry: gray mold (*Botrytis cinerea*), powdery mildew (*Sphaerotheca humuli*), anthracnose (*Colletotrichum acutatum, Colletotrichum fragariae*), phytophthora rot (*Phytophthora cactorum*), soft rot of fruit (*Rhizopus stolonifer*), Fusarium wilt (*Fusarium oxysporum*), Verticillium wilt (*Verticillium dahliae*), and crown rot (*Sclerotinia sclerotiorum*).

Onion: gray-mold neck rot (*Botrytis allii*), gray mold (*Botrytis cinerea*), gray-mold neck rot (*Botrytis squamosa*), downy mildew (*Peronospora destructor*), leaf blight (*Phytophthora porri*), leaf blight (*Ciborinia allii*), small sclerotial rot (*Botrytis squamosa*), fusarium basal rot (*Fusarium oxysporum*), pink root rot (*Pyrenochaeta terrestris*), white rot (*Sclerotium cepivorum*), rust (*Puccinia allii*), and southern blight (*Sclerotium rolfsii*). Welsh onion: bacterial soft rot (*Pectobacterium carotovorum*), downy mildew (*Peronospora destructor*), leaf blight (*Pleospora allii*), white rot (*Sclerotium cepivorum*), rust (*Puccinia allii*), leaf blight (*Botrytis squamosa*), southern blight (*Sclerotium rolfsii*), and pink root rot (*Pyrenochaeta terrestris*).

Cabbage: clubroot (*Plasmodiophora brassicae*), bacterial soft rot (*Erwinia carotovora*), black rot (*Xanthomonas campesrtis* pv. *campestris*), bacterial leaf spot (*Pseudomonas syringae* pv. *maculicola, P. s.* pv. *alisalensis*), downy mildew (*Peronospora parasitica*), Sclerotinia rot (*Sclerotinia sclerotiorum*), *Alternaria* sooty spot (*Alternaria brassicicola*), gray mold (*Botrytis cinerea*), black leg (*Phoma lingam*), Pythium rot (*Pythium aphanidermatum, Pythium ultimum*), and white rust (*Albugo macrospora*).

Lettuce: bacterial rot (*Pseudomonas cichorii, Pseudomonas marginalis*), soft rot (*Pectobacterium carotovorum*), downy mildew (*Bremia lactucae*), gray mold (*Botrytis cinerea*), stem rot (*Sclerotinia sclerotiorum*), Big-Vein disease (Mirafiori lettuce big-vein ophiovirus), root rot (*Fusarium oxysporum*), bottom rot (*Rhizoctonia solani*), and powdery mildew (*Golovinomyces orontii*). Common bean: stem rot (*Sclerotinia sclerotiorum*), gray mold (*Botrytis cinerea*), anthracnose (*Colletotrichum lindemuthianum*), and angular leaf spot (*Phaeoisariopsis griseola*).

Pea: *Mycosphaerella blight* (*Mycosphaerella blight*), gray mold (*Botrytis cinerea*), Sclerotinia rot (*Sclerotinia sclerotiorum*), and powdery mildew (*Erysiphe pisi*).

Apple: powdery mildew (*Podosphaera leucotricha*), scab (*Venturia inaequalis*), Monilia leaf blight (*Monilinia mali*), fruit spot (*Mycosphaerella pomi*), Valsa canker (*Valsa mali*), Alternaria blotch (*Alternaria mali*), rust (*Gymnosporangium yamadae*), ring rot (*Botryosphaeria berengeriana*), bitter rot (*Glomerella cingulata, Colletotrichum acutatum*), blotch (*Diplocarpon mali*), fly speck (*Zygophiala jamaicensis*), sooty blotch (*Gloeodes pomigena*), violet root rot (*Helicobasidium mompa*), white root rot (*Rosellinia necatrix*), gray mold (*Botrytis cinerea*), fire blight (*Erwinia amylovora*), silver leaf (*Chondrostereum purpureum*), and crown gall (*Rhizobium radiobacter, Rhizobium rhizogenes*).

Japanese apricot: scab (*Cladosporium carpophilum*), gray mold (*Botrytis cinerea*), brown rot (*Monilinia mumecola*), sooty blotch (*Peltaster* sp.), pocket (*Taphrina pruni*), and brown shot hole (*Phloeosporella padi*). Persimmon: powdery mildew (*Phyllactinia kakicola*), anthracnose (*Gloeosporium kaki*), angular leaf spot (*Cercospora kaki*), circular leaf spot (*Mycosphaerella nawae*), gray mold (*Botrytis cinerea*), and fly speck (*Zygophiala jamaicensis*).

Peach: brown rot (*Monilinia fructicola, Monilia fructigena*), scab (*Cladosporium carpophilum*), *Phomopsis* rot (*Phomopsis* sp.), bacterial shot hole (*Xanthomonas campestris* pv. *pruni*), leaf curl (*Taphrina deformans*), anthracnose (*Colletotrichum gloeosporioides*), Cylindrosporium leaf spot (*Phloeosporella padi*), and *Coriolus* stem rot (*Coriolus versicolor*).

Almond: brown rot (*Monilinia laxa*), spot blotch (*Stigmina carpophila*), scab (*Cladosporium carpophilum*), red leaf spot (*Polystigma rubrum*), *Alternaria* blotch (*Alternaria alternata*), and anthracnose (*Colletotrichum gloeospoides*).

Yellow peach: brown rot (*Monilinia fructicola*), anthracnose (*Colletotrichum acutatum*), black spot (*Alternaria* sp.), young-fruit rot (*Monilinia kusanoi*), *Cylindrosporium* leaf spot (*Mycosphaerella cerasella*), and powdery mildew (*Podosphaera tridactyla*).

Grape: gray mold (*Botrytis cinerea*), powdery mildew (*Uncinula necator*), ripe rot (*Glomerella cingulata, Colletotrichum acutatum*), downy mildew (*Plasmopara viticola*), bird's eye rot (*Elsinoe ampelina*), isariopsis leaf spot (*Pseudocercospora vitis*), black rot (*Guignardia bidwellii*), white rot (*Coniella castaneicola*), leaf rust (*Phakopsora ampelopsidis*), cottony bunch (pathogen unidentified), and crown gall (*Rhizobium radiobacter, Rhizobium vitis*).

Pear: scab (*Venturia nashicola*), rust (*Gymnosporangium asiaticum*), black spot (*Alternaria kikuchiana*), ring rot (*Botryosphaeria berengeriana*), powdery mildew (*Phyllactinia mali*), *Phomopsis* canker (*Phomopsis fukushii*), brown spot (*Stemphylium vesicarium*), and anthracnose (*Glomerella cingulata*).

Tea: gray blight (*Pestalotiopsis longiseta, P. theae*), anthracnose (*Colletotrichum theae-sinensis*), net blister blight (*Exobasidium reticulatum*), bacterial shoot blight (*Pseudomonas syringae*), and blister blight (*Exobasidium vexans*).

Citrus fruits: scab (*Elsinoe fawcettii*), blue mold (*Penicillium italicum*), green mold (*Penicillium digitatum*), gray mold (*Botrytis cinerea*), black spot (*Diaporthe citri*), canker (*Xanthomonas campestris* pv. *Citri*), powdery mildew (*Oidium* sp.), late blight (*Phytophthora citrophthora*), and anthracnose (*Colletotrichum fioriniae*).

Kiwifruit: bacterial blossom blight (*Pseudomonas marginalis, Pseudomonas syringae, Pseudomonas viridiflava*), bacterial canker (*Pseudomonas syringae*), gray mold (*Botrytis cinerea*), soft rot (*Botryosphaeria dothidea, Diaporthe* sp., *Lasiodiplodia theobromae*), and sooty spot (*Pseudocercospora actinidiae*).

Olive: anthracnose (*Colletotrichum acutatum, Colletotrichum gloeosporioides*) and peacock spot (*Spilocaea oleaginea*).

Chestnut: anthracnose (*Colletotrichum gloeosporioides*).

Wheat: powdery mildew (*Blumeria graminis* f. sp. *tritici*), Fusarium blight (*Gibberella zeae, Fusarium avenaceum, Fusarium culmorum, Fusarium crookwellense, Microdochium nivale*), brown rust (*Puccinia recondita*), stripe rust (*Puccinia striiformis*), browning root rot (*Pythium iwayamai*), snow mold (*Monographella nivalis*), eye spot (*Pseudocercosporella herpotrichoides*), speckled leaf blotch (*Septoria tritici*), glume blotch (*Leptosphaeria nodorum*), Typhula snow blight (*Typhula incarnata*), Sclerotinia snow blight (*Myriosclerotinia borealis*), take-all (*Gaeumannomyces graminis*), ergot (*Claviceps purpurea*), stinking smut (*Tilletia caries*), loose smut (*Ustilago nuda*), blast (*Pyricularia grisea*), damping-off (*Pythium* spp., *Fusarium* spp., *Rhizoctonia* spp.), and seedling blight (*Pythium* spp., *Fusarium* spp., *Rhizoctonia* spp.).

Barley: stripe (*Pyrenophora graminea*), net blotch (*Pyrenophora teres*), sacald (*Rhynchosporium secalis*), loose smut (*Ustilago tritici, U. nuda*), damping-off (*Pythium* spp., *Fusarium* spp., *Rhizoctonia* spp.), and seedling blight (*Pythium* spp., *Fusarium* spp., *Rhizoctonia* spp.).

Rice: blast (*Pyricularia oryzae*), sheath blight (*Rhizoctonia solani*), "Bakanae" disease (*Gibberella fujikuroi*), brown spot (*Cochliobolus miyabeanus*), seedling blight (*Pythium graminicola*), bacterial leaf blight (*Xanthomonas oryzae*), bacterial seedling blight (*Burkholderia plantarii*), bacterial brown stripe (Acidovorax *avenae*), bacterial grain rot (*Burkholderia glumae*), *Cercospora* leaf spot (*Cercospora oryzae*), false smut (*Ustilaginoidea virens*), discoloured rice grains (*Alternaria alternata, Curvularia intermedia*), kernel discoloration (*Alternaria padwickii*), and pink coloring of rice grains (*Epicoccum purpurascens*).

Tobacco: Sclerotinia stem-rot (*Sclerotinia sclerotiorum*), powdery mildew (*Erysiphe cichoracearum*), and black shank (*Phytophthora nicotianae*).

Tulip: gray mold (*Botrytis cinerea*), *Botrytis* blight (*Botrytis tulipae*), leaf rot (*Rhizoctonia solani*), bulb rot (*Fusarium oxysporum*), and bulb-coat rot (*Rhizoctonia solani*).

Rose: black spot (*Diplocarpon rosae*), powdery mildew (*Erysiphe simulans, Podosphaera pannosa*), and Botrytis blight (*Botrytis cinerea*).

*Chrysanthemum: Botrytis* blight (*Botrytis cinerea*), rust (*Puccinia horiana*), downy mildew (*Paraperonospora minor, Peronospora danica*), Pythium blight (*Pythium aphanidermatum, Pythium dissotocum, Pythium helicoides, Pythium oedochilum, Pythium sylvaticum*), root and stem rot (*Rhizoctonia solani*), and *Fusarium* blight (*Fusarium solani*).

Gerbera: gray mold (*Botrytis cinerea*) and powdery mildew (*Podosphaera xanthii*).

Lily: Botrytis blight (*Botrytis elliptica, Pestalotiopsis* sp.) and gray mold (*Botrytis cinerea*). Sunflower: downy mildew (*Plasmopara halstedii*), Sclerotinia rot (*Sclerotinia sclerotiorum*), and gray mold (*Botrytis cinerea*).

Bent grass: Sclerotinia snow blight (*Sclerotinia borealis*), large patch (*Rhizoctonia solani*), brown patch (*Rhizoctonia solani*), dollar spot (*Sclerotinia homoeocarpa*), blast (*Pyricularia* sp.), *Pythium* red blight (*Pythium aphanidermatum*), and anthracnose (*Colletotrichum graminicola*).

Orchard grass: powdery mildew (*Erysiphe graminis*).

Soy: purple stain (*Cercospora kikuchii*), downy mildew (*Peronospora manshurica*), stem rot (*Phytophthora sojae*), rust (*Phakopsora pachyrhizi*), Sclerotinia rot (*Sclerotinia sclerotiorum*), anthracnose (*Colletotrichum truncatum*), gray mold (*Botrytis cinerea*), *Sphaceloma* scab (*Elsinoe glycines*), pod and stem blight (*Diaporthe phaseolorum* var. *sojae*), damping-off (*Pythium* spp., *Fusarium* spp., *Rhizoctonia* spp.), and seedling blight (*Pythium* spp., *Fusarium* spp., *Rhizoctonia* spp.).

Potato: late blight (*Phytophthora infestans*), early blight (*Alternaria solani*), black scurf (*Thanatephorus cucumeris*), Verticillium wilt (*Verticillium albo-atrum, V. dahliae, V. nigrescens*), black leg (*Pectobacterium atrosepticum*), bacterial soft rot (*Pectobacterium carotovorum*), gray mold (*Botrytis cinerea*), common scab (*Streptomyces* spp.), and Sclerotial rot (*Sclerotinia sclerotiorum*).

Yam: leaf spot (*Cylindrosporium dioscoreae*), anthracnose (*Colletotrichum gloeosporioides*) and blue mold (*Penicillium sclerotigenum*).

Sweet potato: violet root rot (*Helicobasidium mompa*) and stem rot (*Fusarium oxysporum*).

Taro: Phytophthora blight (*Phytophthora colocasiae*) and stem rot (*Rhizoctonia solani*).

Ginger: root rot (*Pythium ultimum, Pythium myriotylum*) and leaf spot (*Phyllosticta zingiberis*).

Banana: Panama disease (*Fusarium oxysporum*) and Sigatoka disease (*Mycosphaerella fijiensis, M. musicola*).

Mango: anthracnose (*Colletotrichum aenigma*), bacterial canker (*Xanthomonas campestris*), stem-end rot (*Diaporthe pseudophoenicicola, Lasiodiplodia theobromae, Lasiodiplodia* spp., *Neofusicoccum parvum, Neofusicoccum* sp.), and gray mold (*Botrytis cinerea*).

Rapeseed: Sclerotinia rot (*Sclerotinia sclerotiorum*), root rot (*Phoma lingam*), gray leaf spot (*Alternaria brassicae*), powdery mildew (*Erysiphe cruciferarum, Erysiphe cichoracearum, Oidium matthiolae*), and downy mildew (*Peronospora parasitica*).

Coffee: rust (*Hemileia vastatrix*), anthracnose (*Colletotrichum coffeanum*), and leaf spot (*Cercospora coffeicola*).

Sugarcane: brown rust (*Puccinia melanocephala*). Corn: zonate leaf spot (*Gloeocercospora sorghi*), rust (*Puccinia sorghi*), southern rust (*Puccinia polysora*), smut (*Ustilago maydis*), southern leaf spot (*Cochliobolus heterostrophus*), leaf blight (*Setosphaeria turcica*), damping-off (*Pythium* spp., *Fusarium* spp., *Rhizoctonia* spp.), and seedling blight (*Pythium* spp., *Fusarium* spp., *Rhizoctonia* spp.).

Cotton: seedling blight (*Pythium* sp.), rust (*Phakopsora gossypii*), frosty mildew (*Mycosphaerella areola*), and anthracnose (*Glomerella gossypii*). Hop: downy mildew (*Pseudoperonospora humuli*), powdery mildew (*Oidium* sp., *Podosphaera macularis*), and gray mold (*Botrytis cinerea*).

[Nematicide]

The dihydropyrimidine compound of the present invention have an excellent control effect on various nematodes that affect plant growth.

The nematicide of the present invention contains at least one selected from the compound (II) and a salt thereof as an active ingredient. The amount of the compound (II) or a salt thereof included in the nematicide of the present invention is not particularly limited as long as it shows the control effect on nematodes.

Specific examples of plant parasitic nematodes that can be controlled by the nematicide of the present invention are shown below: (1) Order Tylenchida (a) nematodes of the family Anguinidae, for example, species belonging to the genus *Anguina* (*Anguina* spp.) such as *Anguina funesta* and *Anguina tritici*; and species belonging to the genus *Ditylenchus* (*Ditylenchus* spp.) such as *Ditylenchus destructor, Ditylenchus dipsaci* and *Ditylenchus myceliophagus;*

(b) nematodes of the family Aphelenchoididae, for example, species belonging to the genus *Aphelenchoides* (*Aphelenchoides* spp.) such as *Aphelenchoides besseyi, Aphelenchoides fragariae*, and *Aphelenchoides ritzemabosi*; and species belonging to the genus *Bursaphelenchus* (*Bursaphelenchus* spp.) such as *Bursaphelenchus xylophilus;*

(c) nematodes of the family Belonolaimidae, for example, species belonging to the genus *Belonolaimus* (*Belonolaimus* spp.) such as *Belonolaimus longicaudatus*; and species belonging to the genus *Tylenchorhynchus* (*Tylenchorhynchus* spp.) such as *Tylenchorhynchus claytoni* and *Tylenchorhynchus dubius;*

(d) nematodes of the family Criconematidae such as *Criconema mutabile;*

(e) nematodes of the family Dolichodoridae such as *Dolichodorus mediterraneus;*

(f) nematodes of the family Ecphyadophoridae such as *Ecphyadophora tenuissima;*

(g) nematodes of the family Hemicycliophoridae such as *Loofia thienemanni;*

(h) nematodes of the family Heteroderidae, for example, species belonging to the genus *Globodera* (*Globodera* spp.) such as *Globodera rostochiensis, Globodera pallida*, and *Globodera tabacum*; and species belonging to the genus *Heterodera* (*Heterodera* spp.) such as *Heterodera avenae, Heterodera cruciferae, Heterodera glycines, Heterodera schachtii*, and *Heterodera trifolii;*

(i) nematodes of the family Hoplolaimidae, for example, species belonging to the genus *Helicotylenchus* (*Helicotylenchus* spp.) such as *Helicotylenchus dihystera* and *Helicotylenchus multicinctus*; species belonging to the genus *Hoplolaimus* (*Hoplolaimus* spp.) such as *Hoplolaimus columbus* and *Hoplolaimus galeatus*; and others such as *Rotylenchus robustus* and *Rotylenchulus reniformis;*

(j) nematodes of the family Meloidogynidae, for example, species belonging to the genus *Meloidogyne* (*Meloidogyne* spp.) such as *Meloidogyne arenaria, Meloidogyne chitwoodi, Meloidogyne hapla, Meloidogyne incognita, Meloidogyne javanica*, and *Meloidogyne thamesi;*

(k) nematodes of the family Nothotylenchidae such as *Nothotylenchus acris;*

(l) nematodes of the family Paratylenchidae, for example, species belonging to the genus *Paratylenchus* (*Paratylenchus* spp.) such as *Paratylenchus curvitatus* and *Paratylenchus elachistus*; and (m) nematodes of the family Pratylenchidae, for example, species belonging to the genus *Pratylenchus* (*Pratylenchus* spp.) such as *Pratylenchus brachyurus, Pratylenchus coffeae, Pratylenchus curvitatus, Pratylenchus fallax, Pratylenchus goodeyi, Pratylencus neglectus, Pratylenchus penetrans, Pratylencus scribneri, Pratylenchus vulnus*, and *Pratylenchus zeae*; and others such as *Nacobbus aberrans, Radopholus similis, Tylenchulus semipenetrans*, and *Radopholus citrophilus.*

(2) Order Dorylaimida (a) nematodes of the family Longidoridae, for example, species belonging to the genus *Longidorus* (*Longidorus* spp.) such as *Longidorus* elongates; and species belonging to the genus *Xiphinema* (*Xiphinema* spp.) such as *Xiphinema americanum, Xiphinema brevicolle, Xiphinema index*, and *Xiphinema diversicaudatum.*

(3) Order Triplonchida (a) nematodes of the family Trichodoridae such as *Trichodorus primitivus* and *Paratrichodorus minor.*

[Application Method and Mixture Agent]

The agricultural and horticultural fungicide or the nematicide of the present invention are preferably used for grains; vegetables; root vegetables; potatoes; trees such as fruit trees, tea, coffee, and cacao; pasture grasses; turf grasses; and plants such as cotton.

The agricultural and horticultural fungicide of the present invention can be applied to each part of plants such as leaves, stems, stalks, flowers, buds, fruits, seeds, sprouts, roots, tubers, tuberous roots, shoots, and cuttings. The nematicide can be applied to roots, tubers, tuberous roots, and the like. The nematicide can be applied also to improved varieties/modified varieties, cultivars, as well as mutants, hybrids and genetically modified organisms (GMO) of these plants.

The agricultural and horticultural fungicide of the present invention can be used for seed treatment, foliage application, soil application, water surface application and the like to be conducted in order to control various diseases occurring in agricultural and horticultural crop plants including flowers, turf grasses, and pasture grasses. The nematicide can be used for seed treatment, soil application, and the like.

The agricultural and horticultural fungicide or the nematicide of the present invention may contain other ingredients than the dihydropyrimidine compound of the present invention. Examples of the other ingredients can include a conventionally-known carrier to be used for formulation. Additional examples of the other ingredients can include a fungicide, an insecticide/acaricide, a nematicide, a soil pesticide, a plant regulator, a synergist, a fertilizer, a soil conditioner, and an animal feed that are conventionally known. Containing such other ingredients may cause a synergistic effect.

That is, one aspect of the present invention can include an agricultural and horticultural fungicide including one or more additional fungicides.

Specific examples of fungicides that can be mixed with or used in combination with the agricultural and horticultural fungicide or the nematicide of the present invention are shown below:

(1) Nucleic Acid Biosynthesis Inhibitors:

(a) RNA polymerase I inhibitors: benalaxyl, benalaxyl-M, furalaxyl, metalaxyl, metalaxyl-M; oxadixyl; clozylacon, ofurace;

(b) adenosine deaminase inhibitors: bupirimate, dimethirimol, ethirimol;

(c) DNA/RNA synthesis inhibitors: hymexazol, octhilinone;

(d) DNA topoisomerase II inhibitors: oxolinic acid.

(2) Antimitotic Agents and Cell Division Inhibitors:

(a) ß-tubulin polymerization inhibitors: benomyl, carbendazim, chlorfenazole, fuberidazole, thiabendazole; thiophanate, thiophanate methyl; diethofencarb; zoxamide; ethaboxam;

(b) cell division inhibitors: pencycuron;

(c) delocalization inhibitors of spectrin-like protein: fluopicolide, fluopimomide.

(3) Respiration Inhibitors:

(a) complex I NADH oxidoreductase inhibitors: diflumetorim; tolfenpyrad;

(b) complex II succinate dehydrogenase inhibitors: benodanil, flutolanil, mepronil; isofetamid; fluopyram; fenfuram, furmecyclox; carboxin, oxycarboxin; thifluzamide; benzovindiflupyr, bixafen, fluxapyroxad, furametpyr, isopyrazam, penflufen, penthiopyrad, sedaxane; boscalid, pydiflumetofen, isoflucypram, pyraziflumid, inpyrfluxam;

(c) complex III ubiquinol oxidase Qo inhibitors: azoxystrobin, coumoxystrobin, coumethoxystrobin, enoxastrobin, flufenoxystrobin, picoxystrobin, pyraoxystrobin; pyraclostrobin, pyrametostrobin, triclopyricarb; kresoxim-methyl, trifloxystrobin; dimoxystrobin, fenaminstrobin, metominostrobin, orysastrobin; famoxadone; fluoxastrobin; fenamidone; pyribencarb; metyltetraprole; mandestrobin;

(d) complex III ubiquinol reductase Qi inhibitors: cyazofamid; amisulbrom; fenpicoxamid;

(e) oxidative phosphorylation uncouplers: binapacryl, meptyldinocap, dinocap; fluazinam; ferimzone;

(f) oxidative phosphorylation inhibitors (ATP synthase inhibitors): fentin acetate, fentin chloride, fentin hydroxide;

(g) ATP production inhibitor: silthiofam;

(h) complex III: Qx (unknown) inhibitor of cytochrome bc1 (ubiquinone reductase): ametoctradin.

(4) Amino Acid and Protein Synthesis Inhibitors:

(a) methionine biosynthesis inhibitors: andoprim, cyprodinil, mepanipyrim, pyrimethanil;

(b) protein synthesis inhibitors: blasticidin-S, kasugamycin, kasugamycin hydrochloride, streptomycin, oxytetracycline.

(5) Signal Transduction Inhibitors:

(a) signal transduction inhibitors: quinoxyfen, proquinazid;

(b) MAP/histidine kinase inhibitors in osmotic signal transduction: fenpiclonil, fludioxonil; chlozolinate, iprodione, procymidone, vinclozolin.

(6) Lipid and Cell Membrane Synthesis Inhibitors:

(a) phospholipid biosynthesis and methyltransferase inhibitors: edifenphos, iprobenfos, pyrazophos; isoprothiolane;

(b) lipid peroxidation agents: biphenyl, chloroneb, dicloran, quintozene, tecnazene, tolclofos-methyl; etridiazole;

(c) agents acting on cell membranes: iodocarb, propamocarb, propamocarb hydrochloride, propamocarb-fosetylate, prothiocarb;

(d) microorganisms disturbing pathogenic cell membranes: *Bacillus subtilis, Bacillus subtilis* strain QST713, *Bacillus subtilis* strain FZB24, *Bacillus subtilis* strain MBI600, *Bacillus subtilis* strain D747;

(e) agents disturbing cell membranes: extracts of *Melaleuca* alternifolia (tea tree).

(7) Sterol Biosynthesis Inhibitors of Cell Membranes:

(a) C14 position demethylation inhibitors in sterol biosynthesis: triforine; pyrifenox, pyrisoxazole; fenarimol, flurprimidol, nuarimol; imazalil, imazalil sulfate, oxpoconazole, pefurazoate, prochloraz, triflumizole, viniconazole; azaconazole, bitertanol, bromuconazole, cyproconazole, diclobutrazol, difenoconazole, diniconazole, diniconazole-M, epoxiconazole, etaconazole, fenbuconazole, fluquinconazole, flusilazole, flutriafol, fluconazole, fluconazole-cis, hexaconazole, imibenconazole, ipconazole, metconazole, myclobutanil, penconazole, propiconazole, simeconazole, tebuconazole, tetraconazole, triadimefon, triadimenol, triticonazole; prothioconazole, voriconazole, mefentrifluconazole;

(b) inhibitors of 014 reductase and 08-07-isomerase in sterol biosynthesis: aldimorph, dodemorph, dodemorph acetate, fenpropimorph, tridemorph; fenpropidin, piperalin; spiroxamine;

(c) 3-keto reductase inhibitors in C4 position demethylation in sterol biosynthesis system: fenhexamid; fenpyrazamine;

(d) squalene epoxidase inhibitors in sterol biosynthesis system: pyributicarb; naftifine, terbinafine.

(8) Cell Wall Synthesis Inhibitors:

(a) trehalase inhibitor: validamycin;

(b) chitin synthetase inhibitors: polyoxin, polyoxorim;

(c) cellulose synthetase inhibitors: dimethomorph, flumorph, pyrimorph; benthiavalicarb, iprovalicarb, valifenalate; mandipropamid.

(9) Melanin Biosynthesis Inhibitors (a) reductase inhibitors in melanin biosynthesis: fthalide; pyroquilon; tricyclazole;

(b) anhydrase inhibitors in melanin biosynthesis: carpropamid; diclocymet; fenoxanil;

(c) polyketide synthesis inhibitors in melanin biosynthesis: tolprocarb.

(10) Resistance Inducers of Host Plants:

(a) agents acting on salicylic acid synthetic pathway: acibenzolar-S-methyl;

(b) other agents: probenazole; tiadinil; isotianil; dichlobentiazox, ipfentrifluconazole, laminarin; extraction liquid of *Fallopia sachalinensis*.

(11) Agents with unknown actions: cymoxanil, fosetyl-aluminium, phosphoric acid (phosphates), tecloftalam, triazoxide, flusulfamide, diclomezine, methasulfocarb, cyflufenamid, metrafenone, pyriofenone, dodine, dodine free base, flutianil.

(12) Agents having multiple points of action: copper (copper salts), Bordeaux mixture, copper hydroxide, copper naphthalate, copper oxide, copper oxychloride, copper sulfate, sulfur, sulfur products, calcium polysulfide; ferbam, mancozeb, maneb, mancopper, metiram, polycarbamate, propineb, thiram, zineb, ziram; captan, captafol, folpet; chlorothalonil; dichlofluanid, tolylfluanid; guazatine, guazatine acetate, iminoctadine acetates (iminoctadine triacetate), iminoctadine albesilates (iminoctadine trialbesilate); anilazine; dithianon; chinomethionate; fluoroimide.

(13) Other agents: DBEDC, fluor folpet, bis(8-quinolinolato) copper (II), propamidine, chloropicrin, cyprofuram, agrobacterium, bethoxazin, diphenylamine, methyl isothiocyanate (MITC), mildiomycin, capsaicin, cufraneb, cyprosulfamide, dazomet, debacarb, dichlorophen, difenzoquat, difenzoquat methylsulfonate, flumetover, fosetyl calcium, fosetyl sodium, irumamycin, natamycin, nitrothal-isopropyl, oxamocarb, pyrrolnitrin, tebufloquin, tolnifanide, zarilamid, algophase, amicarthiazol, oxathiapiprolin, fluoxapiprolin, metiram zinc, benthiazole, trichlamide, uniconazole, oxyfenthiin, picarbutrazox, quinofumelin, florylpicoxamid, pyrapropoyne, fluindapyr, aminopyrifen, pyridachlomethyl, ipflufenoquin, dipymetitrone.

Specific examples of an insecticide/acaricide, a nematicide, a soil pesticide, and an anthelmintic that can be mixed with or used in combination with the agricultural and horticultural fungicide or the nematicide of the present invention are shown below:

(1A) Acetylcholinesterase (AChE) Inhibitors (Carbamate-Based):

alanycarb, aldicarb, bendiocarb, benfuracarb, butocarboxim, butoxycarboxim, carbaryl, carbofuran, carbosulfan, ethiofencarb, fenobucarb, formetanate, furathiocarb, isoprocarb, methiocarb, methomyl, metolcarb, oxamyl, pirimicarb, propoxur, thiodicarb, thiofanox, triazamate, trimethacarb, XMC, xylylcarb.

(1B) Acetylcholinesterase (AChE) Inhibitors (Organophosphorus-Based):

acephate, azamethiphos, azinphos-ethyl, azinphos-methyl, cadusafos, chlorethoxyfos, chlorfenvinphos, chlormephos, chlorpyrifos, chlorpyrifos-methyl, coumaphos, cyanophos, demeton-S-methyl, diazinon, dichlorvos, dicrotophos, dimethoate, dimethylvinphos, disulfoton, EPN, ethion, ethoprophos, famphur, fenamiphos, fenitrothion, fenthion, fosthiazate, heptenophos, imicyafos, isofenphos, isopropyl=O-

(methoxyaminothiophosphoryl)salicylate, isoxathion, malathion, mecarbam, methamidophos, methidathion, mevinphos, monocrotophos, naled, omethoate, oxydemeton-methyl, parathion, parathion-methyl, phenthoate, phorate, phosalone, phosmet, phosphamidon, phoxim, pirimiphos-methyl, profenofos, propetamphos, prothiofos, pyraclofos, pyridaphenthion, quinalphos, sulfotep, tebupirimphos, temephos, terbufos, tetrachlorvinphos, thiometon, triazophos, trichlorfon, vamidothion.

(2) GABA-Gated Chloride Ion (Chlorine Ion) Channel Blockers:

chlordane, endosulfan; ethiprole, fipronil.

flufiprole.

(3A) Sodium channel modulators (pyrethroid-based): acrinathrin, allethrin, d-cis/trans allethrin, d-trans allethrin, bifenthrin, bioallethrin, bioallethrin-S-cyclopentenyl isomers, bioresmethrin, cycloprothrin, cyfluthrin, β-cyfluthrin, cyhalothrin, λ-cyhalothrin, γ-cyhalothrin, cypermethrin, α-cypermethrin, β-cypermethrin, θ-cypermethrin, ζ-cypermethrin, cyphenothrin [(1R)-trans isomers], deltamethrin, empenthrin [(EZ) (1R)-isomers], esfenvalerate, etofenprox, fenpropathrin, fenvalerate, flucythrinate, flumethrin, τ-fluvalinate, halfenprox, imiprothrin, kadethrin, permethrin, phenothrin [(1R)-trans isomers], prallethrin, pyrethrin, resmethrin, silafluofen, tefluthrin, tetramethrin, tetramethrin [(1R)-isomers], tralomethrin, transfluthrin.

κ-bifenthrin, chloropralethurin, heptafluthrin, meperfluthrin, ε-metofluthrin, momfluorothrin, ε-momfluorothrin, κ-tefluthrin, tetramethylfluthrin; bioethanomethrin.

(3B) Sodium Channel Modulators (DDT):

DDT, methoxychlor.

(4) Nicotinic Acetylcholine Receptor (nAChR) Competitive Modulators:

acetamiprid, clothianidin, dinotefuran, imidacloprid, nitenpyram, thiacloprid, thiamethoxam; nicotine; sulfoxaflor; flupyradifurone; triflumezopyrim.

dicloromezotiaz, flupyrimin.

(5) Nicotinic Acetylcholine Receptor (nAChR) Allosteric Modulators:

spinetoram, spinosad.

(6) Glutamatergic Chloride Ion (Chlorine Ion) Channel (GluCl) Allosteric Modulators:

abamectin, emamectin, emamectin benzoate, lepimectin, milbemectin.

doramectin, eprinomectin, ivermectin, moxidectin, selamectin.

(7) Juvenile Hormone Analogous Agents:

hydroprene, kinoprene, methoprene; fenoxycarb; pyriproxyfen.

(8) Other Nonspecific (Multi-Site) Inhibitors:

methyl bromide, halogenated alkyls; chloropicrin; aluminum sodium fluoride, sulfuryl fluoride; borax, boric acid, disodium octaborate, sodium borate, sodium metaborate; tartar emetic; dazomet, metam, metam-potassium, metam-sodium.

(9) Chordotonal Organ TRPV Channel Modulators:

pymetrozine, pyrifluquinazon; afidopyropen.

(10) Mite Growth Inhibitors:

clofentezine, diflovidazin, hexythiazox, etoxazole.

(11) Insect Midgut Inner Membrane Disrupting Agents Derived from Microorganisms:

*B. t.* subsp. *israelensis, B. t.* subsp. *aizawai, B. t.* subsp. *kurstaki, B. t.* subsp. *tenebrionis*; proteins contained in B. t. crops: CrY1Ab, CrY1Ac, CrY1Fa, CrY1A.105, CrY2Ab, Vip3A, mCry3A, Cry3Ab, Cry3Bb, Cry34Ab1/Cry35Ab1; *Bacillus sphaericus.*

(12) Mitochondrial ATP Biosynthetic Enzyme Inhibitors:

diafenthiuron, azocyclotin, cyhexatin, fenbutatin oxide, propargite, tetradifon.

(13) Oxidative Phosphorylation Uncoupling Agents that Disrupt Proton Gradient:

chlorfenapyr, DNOC, sulfluramid.

(14) Nicotinic Acetylcholine Receptor (nAChR) Channel Blocker:

bensultap, cartap hydrochloride, thiocyclam, thiosultap monosodium salt.

(15) Chitin Biosynthesis Inhibitors, Type 0:

bistrifluron, chlorfluazuron, diflubenzuron, flucycloxuron, flufenoxuron, hexaflumuron, lufenuron, novaluron, noviflumuron, teflubenzuron, triflumuron.

(16) Chitin Biosynthesis Inhibitors, Type 1:

buprofezin.

(17) Molting Inhibitors:

cyromazine.

(18) Molting Hormone (Ecdysone) Receptor Agonists:

chromafenozide, halofenozide, methoxyfenozide, tebufenozide.

(19) Octopamine Receptor Agonists:

amitraz.

(20) Mitochondrial Electron Transport System Complex III Inhibitors:

hydramethylnon; acequinocyl; fluacrypyrim; bifenazate.

(21) Mitochondrial Electron Transport System Complex I Inhibitors (METI):

fenazaquin, fenpyroximate, pyridaben, pyrimidifen, tebufenpyrad, tolfenpyrad; rotenone.

(22) Voltage-Dependent Sodium Channel Blockers:

indoxacarb, metaflumizone.

(23) Acetyl CoA Carboxylase Inhibitors:

spirodiclofen, spiromesifen, spirotetramat.

spiropidion.

(24) Mitochondrial Electron Transport System Complex IV Inhibitors:

aluminum phosphide, calcium phosphide, zinc phosphide, phosphine; calcium cyanide, sodium cyanide, potassium cyanide.

(25) Mitochondrial Electron Transport System Complex II Inhibitors:

cyenopyrafen, cyflumetofen, pyflubumide.

(28) Ryanodine Receptor Modulators:

chlorantraniliprole, cyantraniliprole, cyclaniliprole, flubendiamide.

cyhalodiamide, tetrachlorantraniliprole, tetraniliprole.

(29) Chordotonal Organ Modulator, Target Site Unidentified:

flonicamid.

(30) GABA-Gated Chloride Ion (Chlorine Ion) Channel Allosteric Modulators:

broflanilide, fluxametamide.

isocycloseram; afoxolaner, fluralaner, lotilaner, sarolanar.

Other Insecticides/Acaricides:

azadirachtin, benzoximate, bromopropylate, chinomethionate, dicofol, lime sulfur, mancozeb, pyridalyl, sulfur.

acynonapyr, benzpyrimoxan, flometoquin, fluhexafon, oxazosulfyl, tyclopyrazoflor.

Anthelmintics:

(a) Benzimidazole-based anthelmintics: fenbendazole, albendazole, triclabendazole, oxibendazole, mebendazole, oxfendazole, parbendazole, flubendazole; febantel, netobimin, thiophanate; thiabendazole, cambendazole;

(b) Salicylanilide-based anthelmintics: closantel, oxyclozanide, rafoxanide, niclosamide;
(c) Substituted phenol-based anthelmintics: nitroxinil, nitroscanate;
(d) Pyrimidine-based anthelmintics: pyrantel, morantel;
(e) Imidazothiazole-based anthelmintics: levamisole, tetramisole;
(f) Tetrahydropyrimidine-based anthelmintics: praziquantel, epsiprantel;
(g) Other anthelmintics: cyclodien, ryania, clorsulon, metronidazole, demiditraz; piperazine, diethylcarbamazine, dichlorophen, monepantel, tribendimidine, amidantel; thiacetarsamide, melarsomine, arsenamide.

Specific examples of plant regulators that can be mixed with or used in combination with the agricultural and horticultural fungicide or the nematicide of the present invention are shown below:

abscisic acid, kinetin, benzylaminopurine, 1,3-diphenylurea, forchlorfenuron, thidiazuron, chlorphenuron, dihydroseatin, gibberellin A, gibberellin A4, gibberellin A7, gibberellin A3,1-methylcyclopropane, N-acetyl aminoethoxyvinyl glycine (aka: aviglycine), aminooxyacetic acid, silver nitrate, cobalt chloride, IAA, 4-CPA, chloroprop, 2,4-D, MCPB, indole-3-butyric acid, dichlorprop, phenothiol, 1-naphthylacetamide, ethychlozate, croxyfonac, maleic hydrazide, 2,3,5-triiodobenzoic acid, salicylic acid, methyl salicylate, (−)-jasmonic acid, methyl jasmonate, (+)-strigol, (+)-deoxystrigol, (+)-orobanchol, (+)-sorgolactone, 4-oxo-4-(2-phenylethyl) amino butyric acid; ethephon, chlormequat, mepiquat chloride, benzyl adenine, 5-aminolevulinic acid.

[Formulation]

The agricultural and horticultural fungicide or the nematicide of the present invention is are not particularly by dosage forms. Examples of the dosage form can include a wettable powder, an emulsion, a powder, a granule, a water-soluble agent, a suspension, a granular wettable powder, and a tablet. There is no particular limitation on a method of preparing a formulation, and a known preparation method can be used depending on a dosage form.

Several formulation examples are shown below. The pharmaceutical formulations shown below are merely exemplary and can be modified without deviating from the concept of the present invention. The present invention is in no way limited by the following formulation examples. "Parts" represent "parts by weight" unless otherwise noted.

Formulation Example 1: Wettable Powder 40 parts of the dihydropyrimidine compound of the present invention, 53 parts of diatomaceous earth, 4 parts of a higher alcohol sulfuric acid ester, and 3 parts of an alkyl naphthalene sulfonate were uniformly mixed and finely pulverized to obtain a wettable powder containing 40% of the active ingredient.

Formulation Example 2: Emulsion 30 parts of the dihydropyrimidine compound of the present invention, 33 parts of xylene, 30 parts of dimethylformamide, and 7 parts of a polyoxyethylene alkyl allyl ether were mixed and dissolved to obtain an emulsion containing 30% of the active ingredient.

Formulation Example 3: Granule 5 parts of the dihydropyrimidine compound of the present invention, 40 parts of talc, 38 parts of clay, 10 parts of bentonite, and 7 parts of sodium alkyl sulfate were uniformly mixed and finely pulverized, and then granulated into a granular form having a diameter of 0.5 to 1.0 mm to obtain a granule containing 5% of the active ingredient.

Formulation Example 4: Granule 5 parts of the dihydropyrimidine compound of the present invention, 73 parts of clay, 20 parts of bentonite, 1 part of sodium dioctyl sulfosuccinate, and 1 part of potassium phosphate were uniformly mixed and pulverized. Water was added thereto and thoroughly kneaded, followed by granulation and drying to obtain a granule containing 5% of the active ingredient.

Formulation Example 5: Suspension 10 parts of the dihydropyrimidine compound of the present invention, 4 parts of a polyoxyethylene alkyl allyl ether, 2 parts of a polycarboxylic acid sodium salt, 10 parts of glycerin, 0.2 parts of xanthan gum, and 73.8 parts of water were mixed and subjected to wet grinding until the particle size becomes 3 microns or less to obtain a suspension containing 10% of the active ingredient.

Formulation Example 6: Granular Wettable Powder 40 parts of the dihydropyrimidine compound of the present invention, 36 parts of clay, 10 parts of potassium chloride, 1 part of sodium alkylbenzenesulfonate, 8 parts of sodium lignosulfonate, and 5 parts of a formaldehyde condensation product of sodium alkylbenzenesulfonate were uniformly mixed and finely pulverized followed by adding a suitable amount of water and kneading to form a clay-like product. The clay-like product was granulated and dried to obtain a granular wettable powder containing 40% of the active ingredient.

[Medical/Animal (Vererinary) Antifungal Agent]

The dihydropyrimidine compound of the present invention can be used as a prophylactic or therapeutic agent intended to control harmful pathogens, particularly fungi, which infect humans or animals.

The antifungal agent for use in medicine/animals of the present invention contains at least one selected from the compound (II) and a salt thereof as an active ingredient. The amount of the compound (II) or a salt thereof included in the antifungal agent for use in medicine of the present invention is not particularly limited as long as it shows the antifungal effect.

The "animals" herein means vertebrates including companion animals, livestock and poultry, exhibited animals that are reared in zoos or aquariums, captive wild animals, further laboratory/experimental animals, and the like.

Examples thereof include animals below, but specific examples of the animals are not limited only to these:

a mammal such as a sheep, a goat, a pig, a horse, a cow, a buffalo, a donkey, a mule, a camel, a llama, an alpaca, a wild boar, a reindeer, a deer, a mink, an elephant, a bear, a kangaroo, a fox, a dog, a cat, a squirrel, a rabbit, a mouse, a rat, a guinea pig, a hamster, a monkey, and a ferret;

a bird such as a pigeon, a parakeet, a parrot, a Java sparrow, a society finch, a canary, a chicken, a duck, a turkey, a wild duck, a pheasant, a peacock, an ostrich, a swan, a sparrow, a quail, an owl, an eagle, a hawk, and a Japanese cormorant;

- a reptile such as a chameleon, an iguana, a lizard, a snake, a turtle, an alligator, and a gecko;
- an amphibian such as a frog and a newt; and
- a fish such as a carp, a goldfish, a medaka, a tropical fish, a yellowtail, a young yellowtail, a sea bream, a great amberjack, a salmon, a mackerel, a sea bass, a longtooth grouper, a tuna, a horse mackerel, a flounder, and a puffer fish.

As pathogens to which the antifungal agent for use in medicine/animals of the present invention can be applied, examples of fungi (mold) are shown below.

Specific examples thereof are not limited only to these. For example, the genus *Absidia* such as *absidia corymbifera*; the genus *Acremonium*; the genus *Alternaria* such as *Alternaria alternata*; the genus *Aspergillus* such as *Aspergillus flavus, Aspergillus fumigatus, Aspergillus nidulans, Aspergillus niger, Aspergillus parasiticus*, and *Aspergillus terreus*; the genus *Bipolaris*; the genus *Blastomyces* such as *Blastomyces dermatitidis*; the genus *Blumeria* such as *Blumeria graminis*; the genus *Candida* such as *Candida albicans, Candida glabrata, Candida krusei, Candida parapsilosis*, and *Candida tropicalis*; the genus *Cladosporium* such as *Cladosporium cladosporoides* and *Cladosporium* herbarium; the genus *Coccidioides* such as *Coccidioides immitis* and *Coccidioides posadasii*; the genus *Colletotrichium* such as *Colletotrichium trifolii*; the genus *Cryptococcus* such as *Cryptococcus neoformans*; the genus *Curvularia* such as *Curvularia lunata*; the genus *Encephalitozoon* such as *Encephalitozoon cuniculi*; the genus *Epicoccum* such as *Epicoccum nigrum*; the genus *Epidermophyton* such as *Epidermophyton floccosum*; the genus *Exophiala*; the genus *Exserohilum* such as *Exserohilum rostratum*; the genus *Fusarium* such as *Fusarium graminarium, Fusarium solani*, and *Fusarium sporotrichoides*; the genus *Fonsecaea* such as *Fonsecaea monophora*; the genus *Histoplasma* such as *Histoplasma capsulatum*; the genus *Leptosphaeria* such as *Leptosphaeria nodorum*; the genus *Malassezia* such as *Malassezia globosa*; the genus *Microsporum* such as *Microsporum canis*; the genus *Mycosphaerella* such as *Mycosphaerella graminicola*; the genus *Neurospora*; the genus *Paecilomyces* such as *Paecilomyces lilanicus* and *Paecilomyces varioti*; the genus *Penicillium* such as *Penicillium chrysogenum*; the genus *Phytophthora* such as *Phytophthora capsici* and *Phytophthora infestans*; the genus *Plasmopara* such as *Plasmopara viticola*; the genus *Pneumocystis* such as *Pneumocystis jirovecii*; the genus *Pyricularia* such as *Pyricularia oryzae*; the genus *Pythium* such as *Pythium ultimum*; the genus *Puccinia* such as *Puccinia coronata* and *Puccinia graminis*; the genus *Rhizoctonia* such as *Rhizoctonia solani*; the genus *Rhizomucor*; the genus *Scedosporium* such as *Fusarium apiospermum* and *Scedosporium prolificans*; the genus *Scopulariopsis* such as *Scopulariopsis brevicaulis*; the genus *Sporothrix* such as *Sporothrix schenckii*; the genus *Talaromyces* such as *Talaromyces marneffei*; the genus *Trichophyton* such as *Trichophyton mentagrophytes, Trichophyton interdigitale, Trichophyton rubrum, Trichophyton tonsurans*, and *Trichophyton verrucosum*; the genus *Trichosporon* such as *Trichosporon asahii* and *Trichosporon beigelii*, and; the genus *Ustilago*.

Among these, the antifungal agent of the present invention is suitable to the genus *Aspergillus*, the genus *Trichophyton*, or the genus *Candida*, and particularly suitable to *Aspergillus fumigatus* or *Trichophyton tonsurans*.

As infections to which the antifungal agent for use in medicine/animals of the present invention can be applied, examples of mycoses are shown below. Specific examples thereof are not limited only to these.

The antifungal agent for use in medicine/animals of the present invention can be applied to any of systemic mycotic infections, superficial mycotic infections, and the like. Specific examples of mycotic infections can include aspergillosis (*Aspergillus*) such as pulmonary aspergillosis and systemic aspergillosis (likely to occur in immunosuppressed patients such as bone marrow recipients and AIDS patients), candidiasis (*Candida*) such as systemic candidiasis, *Cryptococcus* meningitis (*Cryptococcus*), rhinocerebral mucormycosis, pulmonary mucormycosis, blastomycosis, histoplasmosis, coccidiomycosis, paracoccidiomycosis, lobomycosis, keratomycosis, sporotrichosis, chromoblastomycosis, chromomycosis, phaeohyphomycosis, zygomycosis, cryptococcosis, disseminated sporotrichosis, tinea (ring worm), tinea capitis (trichophytia capitis), tinea corporis (jock itch), tinea cruris (crotch rot), tinea pedis (athlete's foot), tinea unguium (nail tinea), skin, oral, or vaginal candidiasis, *Malassezia* infection, chronic mucocutaneous candidiasis, *pneumocystis* pneumonia, and *Penicillium marneffei*.

The antifungal agent of the present invention can be also applied to allergic diseases caused by fungi, such as allergic bronchopulmonary asthma) (ABPA); asthma, rhinosinusitis, sinusitis, or the like.

The antifungal agent for use in medicine/animals of the present invention can comprise pharmaceutically acceptable additives. The additives are not particularly limited as long as they are used in known medical agents. These are naturally sterile and non-pyrogenic. The additives can be appropriately selected in accordance with the dosage form and the administration method of the antifungal agent.

The dosage form that can be adopted for the antifungal agent for use in medicine/animals of the present invention is not particularly limited, and examples thereof can include a solid agent such as a tablet, a powder, a particulate, a granule, a capsule, a troche (candy), and a pellet; a liquid agent such as a syrup, an emulsion, a suspension, a solution, a pour-on agent, and a spot-on agent; a semi-solid preparation such as an ointment and a gel; a gas agent such as aerosol and vapor; and a nanoparticle formulation.

The antifungal agent for use in medicine of the present invention can be administered by known methods. Examples of the administration method can include subcutaneous, intravenous, intramuscular, or intrasternal infusion (injection); insertion into the anus or the vagina, transdermal administration such as application, spraying, or dropping to the skin surface; oral administration such as ingestion via the mouth, and nasal administration via aspiration.

In the case of a solid agent for oral administration, examples of additives that can be used for the antifungal agent for use in medicine/animals of the present invention can include a dissolution aid such as cyclodextrin or modified cyclodextrin; a diluent such as lactose, dextrose, saccharose, cellulose, corn starch, or potato starch; a lubricant such as silica, talc, stearic acid, magnesium stearate or calcium stearate, and polyethylene glycol; a binding agent such as starch, arabic gum, gelatin, methyl cellulose, carboxy methyl cellulose, or polyvinylpyrrolidone; a disaggregating agent such as starch, alginic acid, alginate, or sodium starch glycolate; an effervescing mixture; a pigment; a sweetener; a humectant such as lecithin, polysorbate, and lauryl sulphate; or a non-toxic and pharmacologically inactive substance commonly used in pharmaceutical formulations. These additives can be included in the antifungal agent for use in medicine of the present invention by known manners, for example, by means of mixing, granulating, tabletting, sugar-coating, or film-coating processes.

In the case of a liquid agent for oral administration, examples of additives that can be used for the antifungal agent for use in medicine/animals of the present invention can include a dissolution aid such as cyclodextrin or modified cyclodextrin, saccharose, glycerin, mannitol, sorbitol, natural gum, agar, sodium alginate, pectin, methyl cellulose, carboxy methyl cellulose, or polyvinyl alcohol.

In the case of a liquid agent for intramuscular injection, examples of additives that can be used for the antifungal agent for use in medicine/animals of the present invention can include sterile water, olive oil, ethyl oleate, a glycol such as propylene glycol, and a dissolution aid such as cyclodextrin or modified cyclodextrin. Further, a suitable amount of lidocaine hydrochloride also can be included, as required.

In the case of a liquid agent for intravenous injection, examples of additives that can be used for the antifungal agent for use in medicine/animals of the present invention can include a carrier such as sterile water; and a dissolution aid such as cyclodextrin or modified cyclodextrin. These can be included also in the form of a sterilized isotonic physiological saline solution.

The content of the compound (II) or a salt thereof contained in the antifungal agent for use in medicine/animals of the present invention is preferably 85% by weight or less and more preferably 50% by weight or less based on the weight of the antifungal agent.

The dose of the antifungal agent for use in medicine/animals of the present invention can be appropriately selected in accordance with the administration method, the type of the fungus caused the infection, the age, body weight, and symptom of the patient, and the like. For example, in the case of oral or parenteral (injection, infusion, or the like) administration for an adult, a dose of 0.1 to 100 mg/kg-body weight can be administered once or several times per day.

The antifungal agent for use in medicine/animals of the present invention also can be used in combination with an agent other than the compound (II).

Next, Synthesis Examples are shown, and the present invention will be more concretely described. However, the present invention is in no way limited by the following synthesis examples.

Example 1

Synthesis of 2-(3-(2-(2-cyanoethoxy)-2-(5-fluoro-2-methoxyphenyl)ethyl)-5-((isopropoxyimino)methyl)-2,6-dioxo-3,6-dihydropyrimidin-1(2H)-yl)-N-isopropylpropanamide (Compound Number A-14)

Step 1

Synthesis of 2-(5-(((tert-butyldimethylsilyl)oxy)methyl)-3-(2-(5-fluoro-2-methoxyphenyl)-2-oxoethyl)-2,6-dioxo-3,6-dihydropyrimidin-1(2H)-yl)-N-isopropylpropanamide

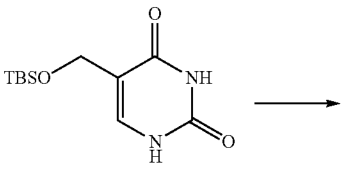

-continued

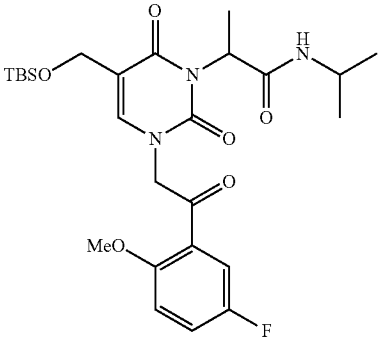

5-(((tert-Butyldimethylsilyl)oxy)methyl)pyrimidine-2,4(1H,3H)-dione (1.50 g) was dissolved in N,N-dimethylformamide (60 ml), potassium carbonate (0.81 g) and 2-bromo-5'-fluoro-2'-methoxyacetophenone (1.45 g) were added under ice cooling, and the resulting mixture was stirred at room temperature for 3 hours. Water was added to the reaction solution, and the resulting solid was filtered.

The obtained solid was dissolved in N,N-dimethylformamide (60 ml), potassium carbonate (0.98 g) and 2-bromo-N-isopropylpropanamide (1.40 g) were added, and the resulting mixture was stirred at 45° C. overnight.

Water was added to the reaction solution. The solution was extracted with ethyl acetate, washed with water and saturated brine, and then dried with anhydrous sodium sulfate. The solvent was removed by vacuum distillation, and the obtained residue was purified by silica gel column chromatography (eluent: hexane/ethyl acetate) to obtain 2.13 g of the target compound. Yield: 68% $^1$H-NMR of the target product obtained is shown below. $^1$H-NMR ($CDCl_3$) δ: 7.63-6.97 (3H, m), 7.08 (1H, s), 5.47-5.01 (4H, m), 4.54 (2H, s), 4.10-4.03 (1H, m), 3.98 (3H, s), 1.61 (3H, d), 1.12 (6H, d), 0.91 (9H, s), 0.12 (6H, s)

Step 2

Synthesis of 2-(5-(((tert-butyldimethylsilyl) oxy) methyl)-3-(2-(2-cyanoethoxy)-2-(5-fluoro-2-methoxyphenyl)ethyl)-2,6-dioxo-3,6-dihydropyrimidin-1(2H)-yl)-N-isopropylpropanamide

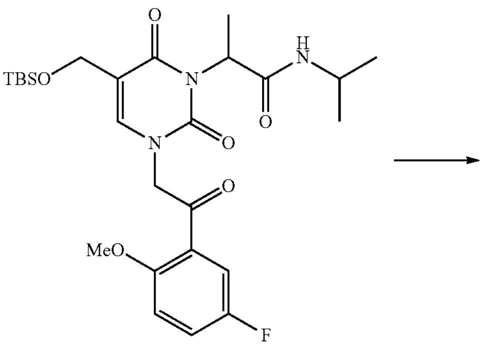

-continued

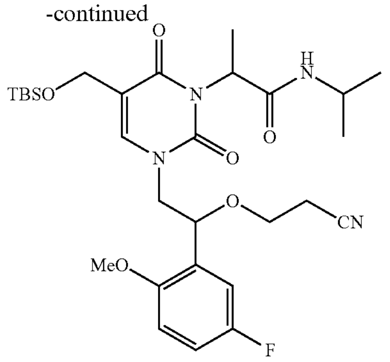

2-(5-(((tert-Butyldimethylsilyl)oxy)methyl)-3-(2-(5-fluoro-2-methoxyphenyl)-2-oxoethyl)-2,6-dioxo-3,6-dihydropyrimidin-1(2H)-yl)-N-isopropylpropanamide (0.15 g) was dissolved in methanol (1.5 ml) and tetrahydrofuran (1.5 ml), sodium borohydride (12 mg) was added under ice cooling, and the resulting mixture was stirred for an hour.

A saturated ammonium chloride aqueous solution was added to the reaction solution. The solution was extracted with ethyl acetate, washed with water and saturated brine, and then dried with anhydrous sodium sulfate. The solvent was removed by vacuum distillation, the obtained residue was dissolved in tetrahydrofuran (1.5 ml), acrylonitrile (0.2 g) and a 40% potassium hydroxide aqueous solution (0.1 ml) were added, and the solution was stirred at room temperature overnight.

Water was added to the reaction solution. The solution was extracted with chloroform and then dried with anhydrous sodium sulfate. The solvent was removed by vacuum distillation, and the obtained residue was purified by silica gel column chromatography (eluent: hexane/ethyl acetate) to obtain 0.08 g of the target compound. Yield: 48%

$^1$H-NMR of the target product obtained is shown below. $^1$H-NMR ($CDCl_3$) δ: 7.19-6.82 (4H, m), 5.82-5.07 (3H, m), 4.49 (2H, s), 4.20-3.41 (5H, m), 3.82 (3H, s), 2.53 (2H, t), 1.55 (3H, d), 1.12 (6H, d), 0.91 (9H, s), 0.12 (6H, s)

Step 3

Synthesis of 2-(3-(2-(2-cyanoethoxy)-2-(5-fluoro-2-methoxyphenyl)ethyl)-5-((isopropoxyimino)methyl)-2,6-dioxo-3,6-dihydropyrimidin-1(2H)-yl)-N-isopropylpropanamide

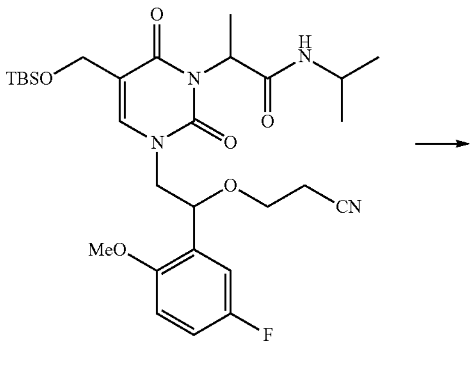

-continued

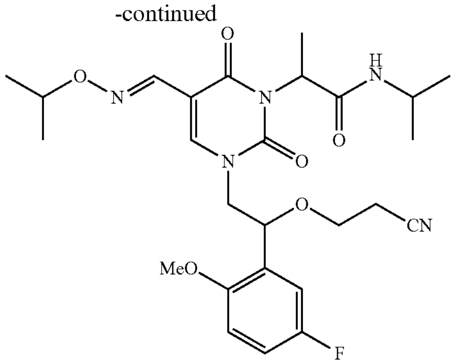

2-(5-(((tert-Butyldimethylsilyl)oxy)methyl)-3-(2-(2-cyanoethoxy)-2-(5-fluoro-2-methoxyphenyl)ethyl)-2,6-dioxo-3,6-dihydropyrimidin-1(2H)-yl)-N-isopropylpropanamide (2.00 g) was dissolved in tetrahydrofuran (8 ml) and water (8 ml), acetic acid (20 ml) was added, and the resulting mixture was stirred at room temperature for 7 hours.

Water was added to the reaction solution. The solution was extracted with ethyl acetate, washed with a saturated sodium hydrogen carbonate aqueous solution and saturated brine, and then dried with anhydrous sodium sulfate. The solvent was removed by vacuum distillation, the obtained residue was dissolved in chloroform (80 ml), manganese dioxide (2.00 g) was added, and the resulting mixture was stirred at room temperature for 3 hours.

The reaction solution was filtered, and the residue obtained by concentration of the mother liquor was dissolved in chloroform (20 ml) and ethanol (20 ml). At room temperature, pyridine (0.40 g) and isopropoxyamine hydrochloride (0.6 g) were added, and the resulting mixture was stirred for 30 minutes.

The reaction solution was concentrated under reduced pressure, and the obtained residue was purified by silica gel column chromatography (eluent: n-hexane/ethyl acetate) to obtain 1.26 g of the target compound (E:Z=1:1). Yield: 70%

$^1$H-NMR of the target product obtained is shown below. $^1$H-NMR ($CDCl_3$) δ: 8.84-7.51 (2H, m) 7.14-6.80 (3H, m), 5.85-5.07 (3H, m), 4.40-3.41 (6H, m), 3.82 (3H, s), 2.65-2.51 (2H, m), 1.55 (3H, d), 1.29-1.13 (12H, m)

Example 2

Synthesis of N-(2-(3-(2-(2-cyanoethoxy)-2-(5-fluoro-2-methoxyphenyl)ethyl)-5-(1-(ethoxyimino)ethyl)-2,6-dioxo-3,6-dihydropyrimidin-1(2H)-yl)ethyl)isobutyramide (Compound number A-38)

Step 1

Synthesis of tert-butyl(2-(5-acetyl-3-(2-(5-fluoro-2-methoxyphenyl)-2-oxoethyl)-2,6-dioxo-3,6-dihydropyrimidin-1(2H)-yl)ethyl)carbamate

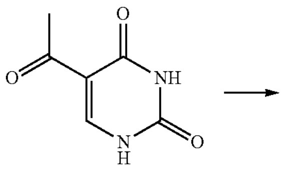

-continued

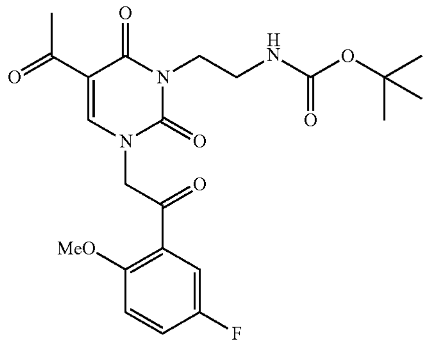

5-Acetyluracil (2.50 g) was dissolved in N,N-dimethylformamide (80 ml), potassium carbonate (2.20 g) and 2-bromo-5'-fluoro-2'-methoxyacetophenone (4.00 g) were added under ice cooling, and the resulting mixture was stirred at room temperature for 3 hours. Water was added to the reaction solution, and the resulting solid was filtered.

The obtained solid was dissolved in N,N-dimethylformamide (120 ml), potassium carbonate (2.40 g) and tert-butyl n-(2-bromoethyl)carbamate (4.80 g) were added, and the resulting mixture was stirred at 80° C. for 5 hours.

Water was added to the reaction solution. The solution was extracted with ethyl acetate, washed with water and saturated brine, and then dried with anhydrous sodium sulfate. The solvent was removed by vacuum distillation, and the obtained residue was purified by silica gel column chromatography (eluent: chloroform/ethyl acetate) to obtain 4.60 g of the target compound. Yield: 61%

$^1$H-NMR of the target product obtained is shown below. $^1$H-NMR ($CDCl_3$) δ: 8.09 (1H, s), 7.64-6.99 (3H, m), 5.21 (2H, s), 4.87 (1H, m), 4.17-3.42 (4H, m), 4.00 (3H, s), 2.65 (3H, s), 1.40 (9H, s)

Step 2

Synthesis of N-(2-(5-acetyl-3-(2-(5-fluoro-2-methoxyphenyl)-2-oxoethyl)-2,6-dioxo-3,6-dihydropyrimidin-1 (2H)-yl)ethyl) isobutyramide

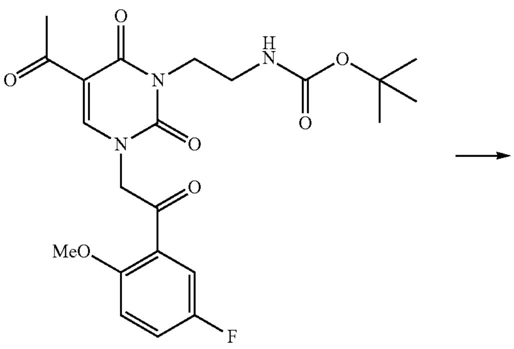

-continued

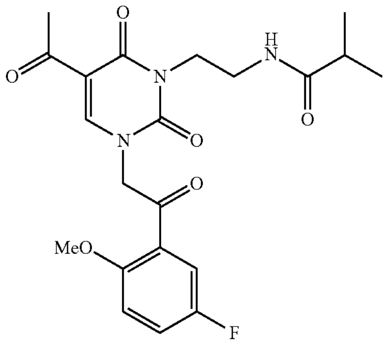

tert-Butyl(2-(5-acetyl-3-(2-(5-fluoro-2-methoxyphenyl)-2-oxoethyl)-2,6-dioxo-3,6-dihydropyrimidin-1(2H)-yl) ethyl)carbamate (1.60 g) was dissolved in 1,4-dioxane (50 ml), a 4 N hydrogen chloride/1,4-dioxane solution (15 ml) was added, and the resulting mixture was stirred at room temperature for 8 hours.

The reaction solution was concentrated, the obtained residue was dissolved in methylene chloride (50 ml), triethylamine (1.5 ml) and isobutyryl chloride (0.7 ml) were added, and the resulting mixture was stirred at room temperature for 3 hours.

The reaction solution was concentrated under reduced pressure, and the obtained residue was purified by silica gel column chromatography (eluent: chloroform/ethyl acetate) to obtain 0.95 g of the target compound. Yield: 64%

$^1$H-NMR of the target product obtained is shown below. $^1$H-NMR ($CDCl_3$) δ: 8.10 (1H, s), 7.64-7.00 (3H, m), 6.00 (1H, m), 5.21 (2H, s), 4.22-3.57 (4H, m), 4.00 (3H, s), 2.64 (3H, s), 2.34-2.27 (1H, m), 1.10 (6H, d)

Step 3

Synthesis of N-(2-(5-(1-(ethoxyimino)ethyl)-3-(2-(5-fluoro-2-methoxyphenyl)-2-oxoethyl)-2,6-dioxo-3,6-dihydropyrimidin-1(2H)-yl)ethyl)isobutyramide (Compound number A-36)

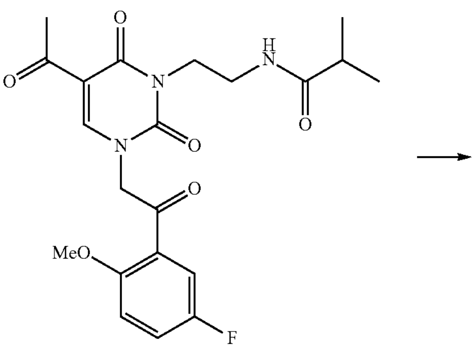

-continued

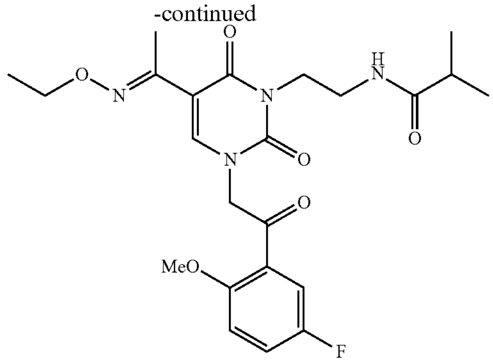

N-(2-(5-Acetyl-3-(2-(5-fluoro-2-methoxyphenyl)-2-oxoethyl)-2,6-dioxo-3,6-dihydropyrimidin-1(2H)-yl)ethyl) isobutyramide (0.50 g) was dissolved in chloroform (8 ml) and ethanol (8 ml), pyridine (0.10 g) and ethoxyamine hydrochloride (0.12 g) were added at room temperature, and the resulting mixture was stirred for 3 hours.

The reaction solution was concentrated under reduced pressure, and the obtained residue was purified by silica gel column chromatography (eluent: n-hexane/ethyl acetate) to obtain 0.45 g of the target compound. Yield: 82%

$^1$H-NMR of the target product obtained is shown below.

$^1$H-NMR ($CDCl_3$) δ: 7.64-7.00 (3H, m), 7.33 (1H, s), 6.15 (1H, m), 5.13 (2H, s), 4.20-3.53 (6H, m), 3.99 (3H, s), 2.34-2.27 (1H, m), 2.19 (3H, s), 1.27 (3H, t), 1.10 (6H, d)

Step 4

Synthesis of N-(2-(5-(1-(ethoxyimino)ethyl)-3-(2-(5-fluoro-2-methoxyphenyl)-2-hydroxyethyl)-2,6-dioxo-3,6-dihydropyrimidin-1(2H)-yl)ethyl)isobutyramide (Compound number A-37)

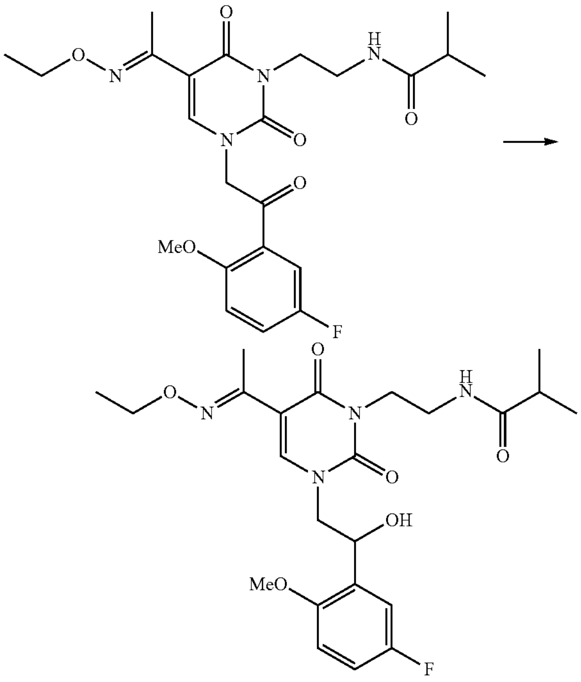

N-(2-(5-(1-(ethoxyimino)ethyl)-3-(2-(5-fluoro-2-methoxyphenyl)-2-oxoethyl)-2,6-dioxo-3,6-dihydropyrimidin-1(2H)-yl)ethyl)isobutyramide (0.25 g) was dissolved in methanol (4 ml) and tetrahydrofuran (4 ml), sodium borohydride (20 mg) was added under ice cooling, and the resulting mixture was stirred for 30 minutes.

A saturated ammonium chloride aqueous solution was added to the reaction solution. The solution was extracted with ethyl acetate, washed with water and saturated brine, and then dried with anhydrous sodium sulfate. The obtained residue was purified by silica gel column chromatography (eluent: n-hexane/ethyl acetate) to obtain 0.25 g of the target compound. Yield: 99% $^1$H-NMR of the target product obtained is shown below.

$^1$H-NMR ($CDCl_3$) δ: 7.40 (1H, s), 7.35-6.80 (3H, m), 5.90-5.48 (2H, m), 4.44-3.24 (9H, m), 3.85 (3H, s), 2.34-2.27 (1H, m), 2.14 (3H, s), 1.27 (3H, t), 1.10 (6H, d)

Step 5

Synthesis of N-(2-(3-(2-(2-cyanoethoxy)-2-(5-fluoro-2-methoxyphenyl)ethyl)-5-(1-(ethoxyimino)ethyl)-2,6-dioxo-3,6-dihydropyrimidin-1(2H)-yl)ethyl)isobutyramide

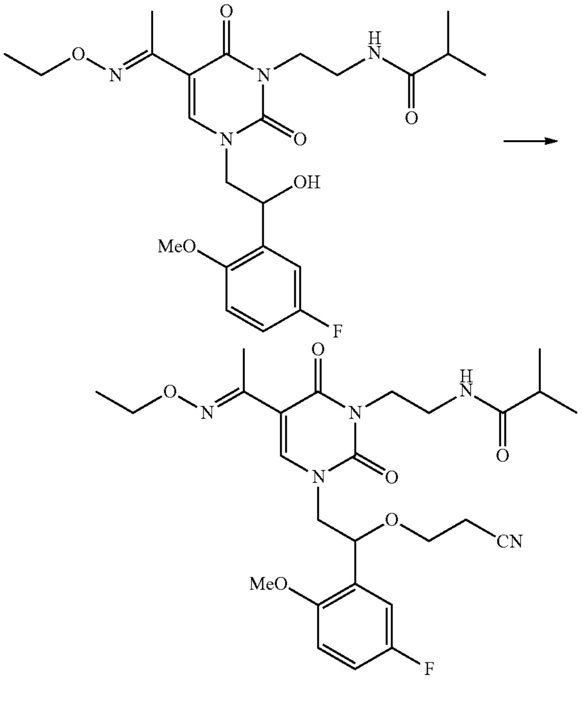

N-(2-(5-(1-(Ethoxyimino)ethyl)-3-(2-(5-fluoro-2-methoxyphenyl)-2-hydroxyethyl)-2,6-dioxo-3,6-dihydropyrimidin-1(2H)-yl)ethyl)isobutyramide (0.23 g) was dissolved in tetrahydrofuran (4 ml), acrylonitrile and (0.27 g) and a 40% potassium hydroxide aqueous solution (0.3 ml) were added, and the resulting mixture was stirred at room temperature overnight.

Water was added to the reaction solution. The solution was extracted with chloroform and then dried with anhydrous sodium sulfate. The solvent was removed by vacuum distillation, and the obtained residue was purified by silica gel column chromatography (eluent: hexane/ethyl acetate) to obtain 0.12 g of the target compound. Yield: 47%

$^1$H-NMR of the target product obtained is shown below. $^1$H-NMR ($CDCl_3$) δ: 7.46 (1H, s), 7.15-6.83 (3H, m), 6.28-5.18 (2H, m), 4.32-3.48 (10H, m), 3.84 (3H, s), 2.64 (2H, t), 2.34-2.27 (1H, m), 2.16 (3H, s), 1.30 (3H, t), 1.10 (6H, d)

Example 3

Synthesis of N-((2S)-1-(3-(2-(5-fluoro-2-methoxyphenyl)-2-hydroxyethyl)-5-((E)-1-(isopropoxyimino) ethyl)-2,6-dioxo-3,6-dihydropyrimidin-1(2H)-yl) propan-2-yl)isobutyramide (Compound numbers A-74 and A-75)

Step 1

Synthesis of (E)-5-(1-(isopropoxyimino)ethyl)pyrimidine-2,4 (1H,3H)-dione

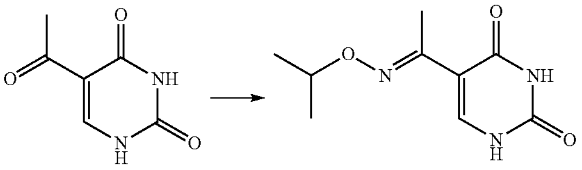

5-Acetylpyrimidine-2,4(1H,3H)-dione (15.4 g) was dissolved in ethanol (200 ml) and chloroform (100 ml), 2-(aminooxy)propane hydrochloride (14.0 g) was added, and the resulting mixture was stirred at 45° C. for 3 hours.

Water was added to the reaction solution. The solution was extracted with methylene chloride and then dried with anhydrous sodium sulfate. The solvent was removed by vacuum distillation to obtain 20.6 g of the target compound. Yield: 98%

$^1$H-NMR of the target product obtained is shown below. $^1$H-NMR (DMSO-$D_6$) δ: 11.26 (1H, s), 11.11 (1H, d, J=5.9 Hz), 7.42 (1H, d, J=5.9 Hz), 4.31-4.25 (1H, m), 1.99 (3H, s), 1.20 (6H, d, J=6.3 Hz).

Step 2

Synthesis of (E)-1-(2-(5-fluoro-2-methoxyphenyl)-2-oxoethyl)-5-(1-(isopropoxyimino)ethyl)pyrimidine-2,4(1H,3H)-dione (production intermediate 7)

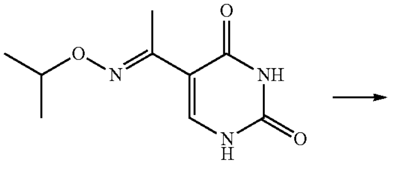

-continued

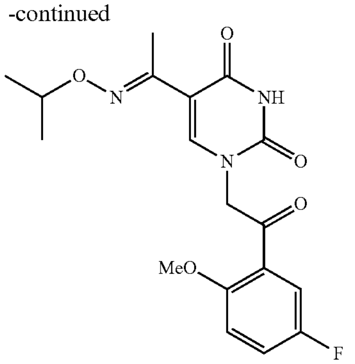

(E)-5-(1-(Isopropoxyimino)ethyl)pyrimidine-2,4(1H, 3H)-dione (2.11 g) was dissolved in N,N-dimethylformamide (30 ml), potassium carbonate (1.50 g) and 2-bromo-5'-fluoro-2'-methoxyacetophenone (2.55 g) were added, and the resulting mixture was stirred at room temperature for 3 hours. Water was added to the reaction solution, and the resulting solid was filtered to obtain 3.39 g of the target product. Yield: 90% $^1$H-NMR of the target product obtained is shown below. $^1$H-NMR ($CDCl_3$) δ: 8.23 (1H, s), 7.67-6.98 (3H, m), 7.34 (1H, s), 5.13 (2H, s), 4.35-4.32 (1H, m), 3.98 (3H, s), 2.19 (3H, s), 1.25 (6H, d, J=6.3 Hz).

Step 3

Synthesis of (S,E)-N-(1-(3-(2-(5-fluoro-2-methoxyphenyl)-2-oxoethyl)-5-(1-(isopropoxyimino)ethyl)-2,6-dioxo-3,6-dihydropyrimidin-1(2H)-yl)propan-2-yl) isobutyramide (Compound number C-221)

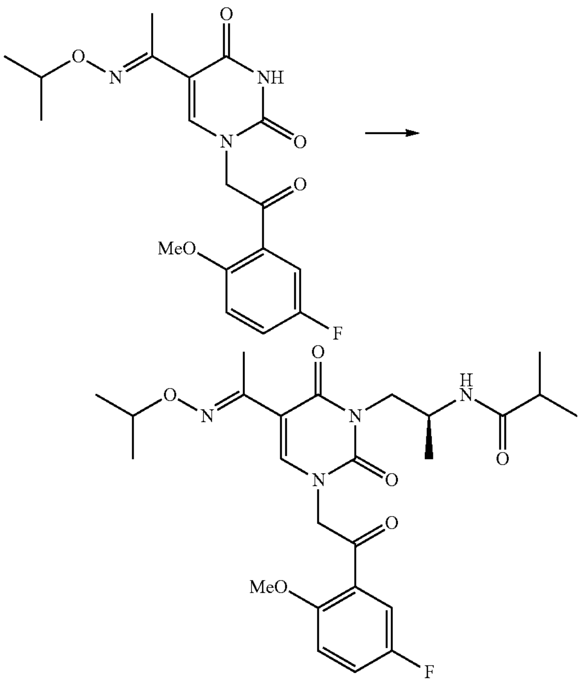

(E)-1-(2-(5-Fluoro-2-methoxyphenyl)-2-oxoethyl)-5-(1-(isopropoxyimino)ethyl)pyrimidine-2,4 (1H,3H)-dione (0.56 g) was dissolved in tetrahydrofuran (7 ml), tert-butyl (S)-(1-hydroxypropan-2-yl)carbamate (0.38 g), triphenylphosphine (0.58 g), and bis(2-methoxyethyl) azodicarboxylate (0.52 g) were added, and the resulting mixture was stirred at room temperature for 2 hours.

The reaction solution was purified by silica gel column chromatography (eluent: hexane/ethyl acetate), the obtained product was dissolved in 1,4-dioxane (7 ml), a 4 N hydrogen chloride/1,4-dioxane solution (7 ml) was added, and the resulting mixture was stirred at room temperature for 4 hours. The reaction solution was concentrated, the obtained residue was dissolved in methylene chloride (7 ml), triethylamine (3 ml) and isobutanoyl chloride (0.1 ml) were added under ice cooling, and the resulting mixture was stirred for 30 minutes. The reaction solution was concentrated under reduced pressure, and the obtained residue was purified by silica gel column chromatography (eluent: chloroform/ethyl acetate) to obtain 0.45 g of the target compound. Yield: 60%

$^1$H-NMR of the target product obtained is shown below. $^1$H-NMR ($CDCl_3$) δ: 7.62-6.99 (3H, m), 7.30 (1H, s), 6.08-2.20 (8H, m), 3.98 (3H, s), 2.15 (3H, s), 1.25-1.03 (15H, m)

Step 4

Synthesis of N-((2S)-1-(3-(2-(5-fluoro-2-methoxyphenyl)-2-hydroxyethyl)-5-((E)-1-(isopropoxyimino)ethyl)-2,6-dioxo-3,6-dihydropyrimidin-1(2H)-yl)propan-2-yl)isobutyramide (Compound Numbers A-74 and A-75)

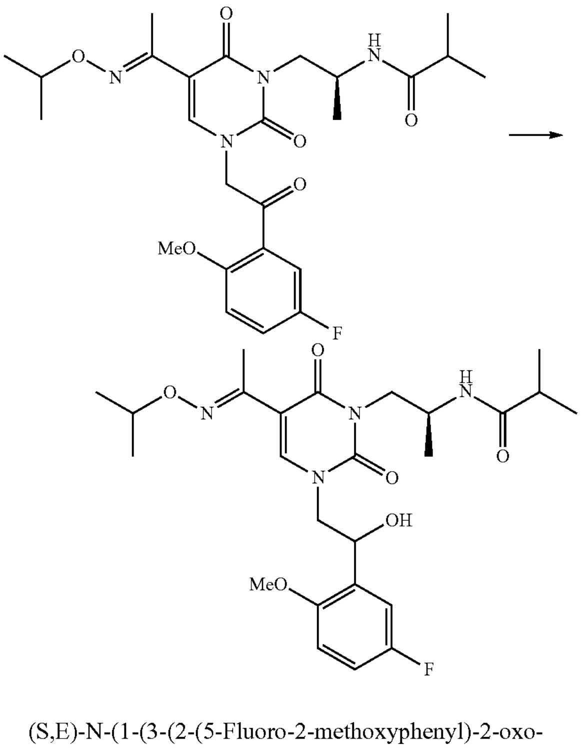

(S,E)-N-(1-(3-(2-(5-Fluoro-2-methoxyphenyl)-2-oxoethyl)-5-(1-(isopropoxyimino)ethyl)-2,6-dioxo-3,6-dihydropyrimidin-1(2H)-yl)propan-2-yl)isobutyramide (0.25 g) was dissolved in methanol (2 ml) and tetrahydrofuran (2 ml), sodium borohydride (18 mg) was added under ice cooling, and the resulting mixture was stirred for 20 minutes.

A saturated ammonium chloride aqueous solution was added to the reaction solution. The solution was extracted with ethyl acetate, washed with water and saturated brine, and then dried with anhydrous sodium sulfate. The solvent was removed by vacuum distillation, and the obtained residue was purified by silica gel column chromatography (eluent: n-hexane/ethyl acetate) to obtained target compounds A-74 (0.11 g) and A-75 (0.11 g). Yield: 44% each $^1$H-NMR of the target products obtained is shown below.

Compound number A-75: $^1$H-NMR ($CDCl_3$) δ: 7.38 (1H, s), 7.36-6.79 (3H, m), 5.64-4.22 (7H, m), 3.84 (3H, s), 3.80-3.11 (2H, m), 2.25-2.16 (1H, m), 2.12 (3H, s), 1.24-1.02 (15H, m)

Compound number A-74: $^1$H-NMR ($CDCl_3$) δ: 7.42 (1H, s), 7.39-6.79 (3H, m), 5.72-2.16 (10H, m), 3.84 (3H, s), 2.14 (3H, s), 1.27-1.02 (15H, m)

Example 4

Synthesis of N-((2S)-1-(3-(2-hydroxy-2-(2-(trifluoromethoxy)phenyl)ethyl)-5-((E)-1-(isopropoxyimino)ethyl)-2,6-dioxo-3,6-dihydropyrimidin-1(2H)-yl)propan-2-yl)isobutyramide (Compound Numbers C-193 and C-194)

Step 1

Synthesis of (E)-5-(1-(isopropoxyimino)ethyl)-1-(methoxymethyl)pyrimidine-2,4(1H,3H)-dione

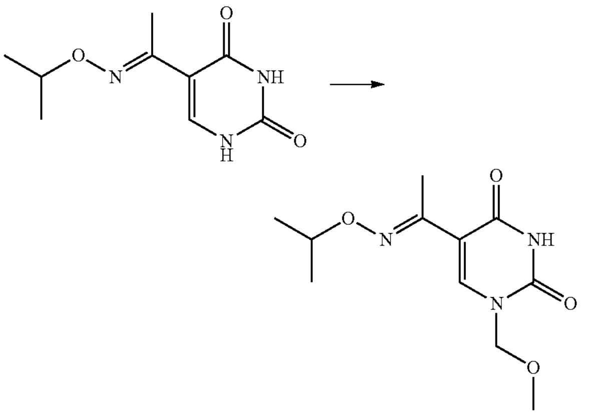

(E)-5-(1-(Isopropoxyimino)ethyl)pyrimidine-2,4(1H,3H)-dione (2.50 g) was dissolved in methylene chloride (140 ml), N,O-bis(trimethylsilyl)acetamide (10 ml) was added, and the resulting mixture was stirred at room temperature for an hour. Thereafter, chloromethyl methyl ether (1.3 ml) was added, and the resulting mixture was stirred at room temperature overnight.

The reaction solution was purified by silica gel chromatography (eluent: hexane-ethyl acetate) to obtain 3.00 g of the target product. Yield: 99%

$^1$H-NMR of the target product obtained is shown below. $^1$H-NMR ($CDCl_3$) δ: 8.32 (1H, s), 7.53 (1H, s), 5.15 (2H, s), 4.40-4.34 (1H, m), 3.44 (3H, s), 2.16 (3H, s), 1.27 (6H, d, J=15.2 Hz).

Step 2

Synthesis of (S,E)-N-(1-(5-(1-(isopropoxyimino)ethyl)-3-(methoxymethyl)-2,6-dioxo-3,6-dihydropyrimidin-1(2H)-yl)propan-2-yl)isobutyramide (production intermediate 10)

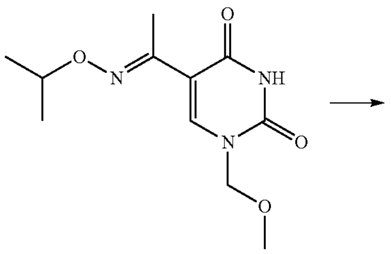

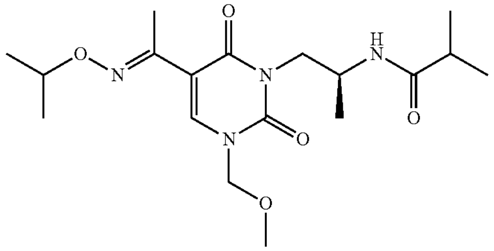

(E)-5-(1-(Isopropoxyimino)ethyl)-1-(methoxymethyl)pyrimidine-2,4(1H,3H)-dione (2.50 g) was dissolved in tetrahydrofuran (25 ml), tert-butyl (S)-(1-hydroxypropan-2-yl) carbamate (2.50 g), triphenylphosphine (3.80 g), and bis(2-methoxyethyl) azodicarboxylate (3.40 g) were added, and the resulting mixture was stirred at room temperature for 7 hours.

The reaction solution was purified by silica gel column chromatography (eluent: hexane/ethyl acetate), the obtained product was dissolved in 1,4-dioxane (20 ml), a 4 N hydrogen chloride/1,4-dioxane solution (12 ml) was added, and the resulting mixture was stirred at room temperature for 3 hours. The reaction solution was concentrated, the obtained residue was dissolved in methylene chloride (40 ml), triethylamine (3 ml) and isobutanoyl chloride (1.3 ml) were added under ice cooling, and the resulting mixture was stirred for 30 minutes. The reaction solution was concentrated under reduced pressure, and the obtained residue was purified by silica gel column chromatography (eluent: chloroform/ethyl acetate) to obtain 2.90 g of the target compound. Yield: 77%

$^1$H-NMR of the target product obtained is shown below. $^1$H-NMR ($CDCl_3$) δ: 7.49 (1H, s), 5.93 (1H, d, J=8.2 Hz), 5.19-5.13 (2H, m), 4.42-4.32 (2H, m), 4.15-3.87 (2H, m), 3.43 (3H, s), 2.30-2.18 (1H, m), 2.14 (3H, s), 1.37-0.93 (15H, m).

Step 3

Synthesis of (S,E)-N-(1-(5-(1-(isopropoxyimino)ethyl)-2,6-dioxo-3,6-dihydropyrimidin-1(2H)-yl)propan-2-yl)isobutyramide (production intermediate 9)

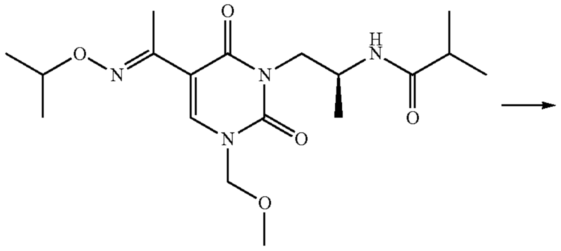

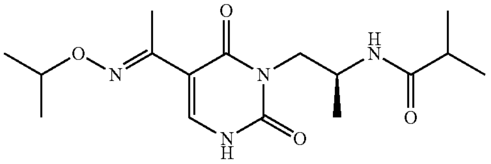

(S,E)-N-(1-(5-(1-(Isopropoxyimino)ethyl)-3-(methoxymethyl)-2,6-dioxo-3,6-dihydropyrimidin-1(2H)-yl)propan-2-yl)isobutyramide (0.50 g) was dissolved in methylene chloride (15 ml), under ice cooling, a solution of 17% boron tribromide in methylene chloride (1.5 ml) was added, and the resulting mixture was stirred overnight. A saturated sodium hydrogen carbonate aqueous solution was added to the reaction solution. The solution was extracted with methylene chloride and then dried with anhydrous sodium sulfate.

The solvent was removed by vacuum distillation, and the obtained residue was purified by silica gel chromatography (eluent: hexane-ethyl acetate) to obtain 0.32 g of the target product. Yield: 72%

$^1$H-NMR of the target product obtained is shown below. $^1$H-NMR ($CDCl_3$) δ: 9.33 (1H, d, J=6.3 Hz), 7.42 (1H, d, J=6.3 Hz), 5.94 (1H, d, J=8.2 Hz), 4.48-3.84 (4H, m), 2.25-2.21 (1H, m), 2.12 (3H, s), 1.26-1.01 (15H, m).

Step 4

Synthesis of (S,E)-N-(1-(5-(1-(isopropoxyimino)ethyl)-2,6-dioxo-3-(2-oxo-2-(2-(trifluoromethoxy)phenyl)ethyl)-3,6-dihydropyrimidin-1(2H)-yl)propan-2-yl)isobutyramide (Compound Number C-195)

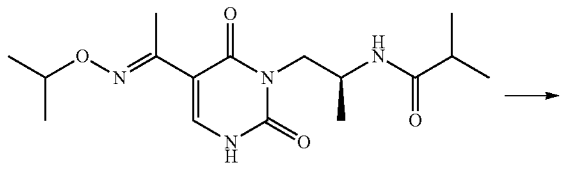

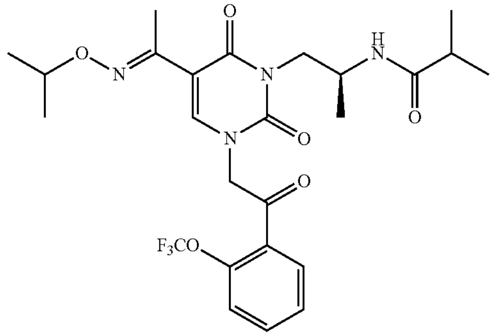

(S,E)-N-(1-(5-(1-(Isopropoxyimino)ethyl)-2,6-dioxo-3,6-dihydropyrimidin-1(2H)-yl)propan-2-yl)isobutyramide (0.20 g) was dissolved in N,N-dimethylformamide (3 ml), 2-bromo-1-(2-(trifluoromethoxy)phenyl)ethan-1-one (0.25 g) and potassium carbonate (0.10 g) were added under ice cooling, and the resulting mixture was stirred overnight.

Water was added to the reaction solution. The solution was extracted with ethyl acetate and then dried with anhydrous sodium sulfate. The solvent was removed by vacuum distillation, and the obtained residue was purified by silica gel chromatography (eluent: hexane-ethyl acetate) to obtain 0.23 g of the target product. Yield: 72%

$^1$H-NMR of the target product obtained is shown below. $^1$H-NMR ($CDCl_3$) δ: 7.98-7.36 (4H, m), 7.33 (1H, s), 6.07-3.90 (7H, m), 2.28-2.21 (1H, m), 2.17 (3H, s), 1.26-1.05 (15H, m).

Step 5

Synthesis of N-((2S)-1-(3-(2-hydroxy-2-(2-(trifluoromethoxy)phenyl)ethyl)-5-((E)-1-(isopropoxyimino)ethyl)-2,6-dioxo-3,6-dihydropyrimidin-1(2H)-yl)propan-2-yl)isobutyramide (Compound Numbers C-193 and C-194)

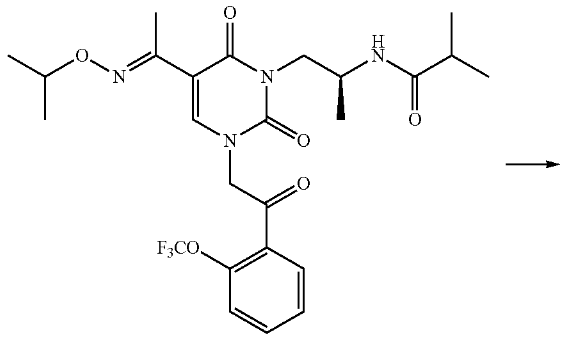

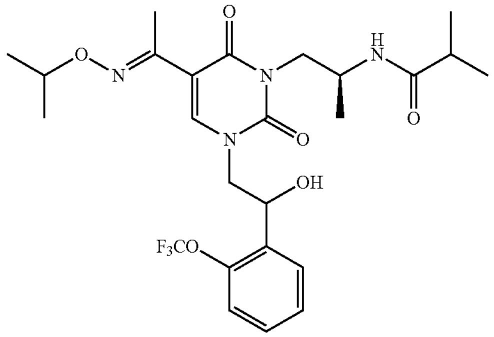

(S,E)-N-(1-(5-(1-(Isopropoxyimino)ethyl)-2,6-dioxo-3-(2-oxo-2-(2-(trifluoromethoxy)phenyl)ethyl)-3,6-dihydropyrimidin-1(2H)-yl)propan-2-yl)isobutyramide (0.19 g) was dissolved in methanol (2 ml) and tetrahydrofuran (2 ml), sodium borohydride (15 mg) was added under ice cooling, and the resulting mixture was stirred for 40 minutes. A saturated ammonium chloride aqueous solution was added to the reaction solution. The solution was extracted with ethyl acetate, washed with water and saturated brine, and then dried with anhydrous sodium sulfate. The solvent was removed by vacuum distillation, and the obtained residue was purified by silica gel column chromatography (eluent: n-hexane/ethyl acetate) to obtain target compounds C-193 (0.90 g) and C-194 (0.90 g). Yield: 47% each $^1$H-NMR of the target products obtained is shown below.

Compound number C-194: $^1$H-NMR ($CDCl_3$) δ: 7.76-7.27 (4H, m), 7.41 (1H, s), 5.75-5.43 (3H, m), 4.77-4.24 (4H, m), 3.81-3.13 (2H, m), 2.21-2.18 (1H, m), 2.12 (3H, s), 1.28-1.00 (15H, m).

Compound number C-193: $^1$H-NMR ($CDCl_3$) δ: 7.84-7.35 (4H, m), 7.42 (1H, s), 5.64-3.74 (9H, m), 2.25-2.18 (1H, m), 2.14 (3H, s), 1.28-1.01 (15H, m).

Some of the compounds of the present invention produced in the same manner as in Examples described above are shown in Table 2. In the table, the melting point (m.p.) is also shown as physical properties of each compound.

TABLE 2
| Compound number | Structural formula | Physical properties |
|---|---|---|
| A-1 | 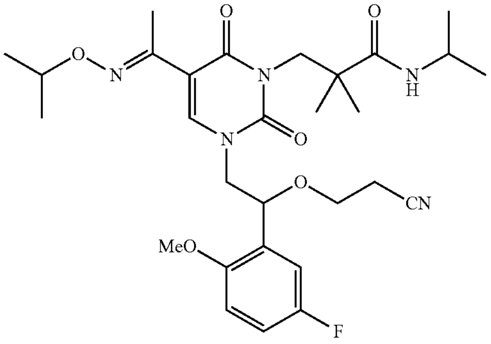 [SMILES: COc1ccc(F)cc1C(Cn1cc(/C(C)=N/OC(C)C)c(=O)n(CC(C)(C)C(=O)NC(C)C)c1=O)OCCC#N] | m.p. 151-152° C. |
| A-2 | 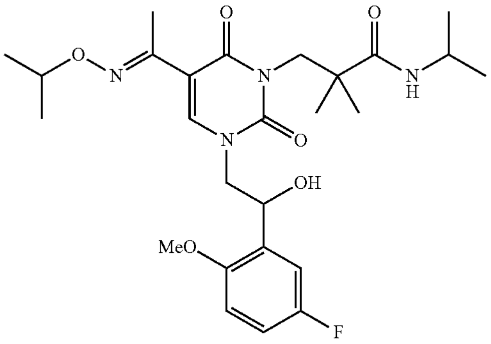 [SMILES: COc1ccc(F)cc1C(O)Cn1cc(/C(C)=N/OC(C)C)c(=O)n(CC(C)(C)C(=O)NC(C)C)c1=O] | m.p. 82-83° C. |
| A-3 | 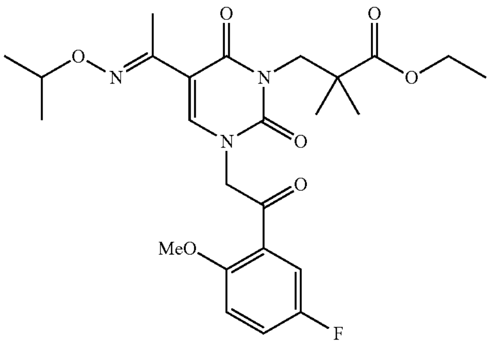 [SMILES: CCOC(=O)C(C)(C)Cn1c(=O)c(/C(C)=N/OC(C)C)cn(CC(=O)c2cc(F)ccc2OC)c1=O] | viscous oil |
| A-4 | 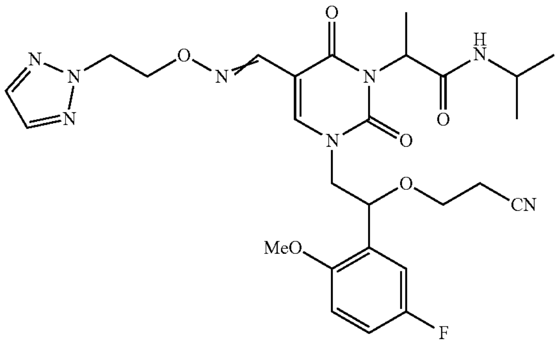 [SMILES: COc1ccc(F)cc1C(Cn1cc(C=NOCCn2nccn2)c(=O)n(C(C)C(=O)NC(C)C)c1=O)OCCC#N] | viscous oil |

TABLE 2-continued
| Compound number | Structural formula | Physical properties |
| --- | --- | --- |
| A-5 | 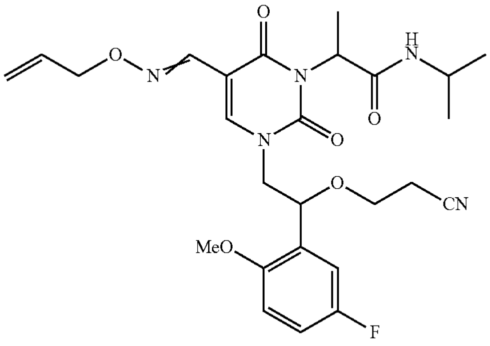 [SMILES: C=CCON=Cc1cn(CC(OCCC#N)c2cc(F)ccc2OC)c(=O)n(C(C)C(=O)NC(C)C)c1=O] | viscous oil |
| A-6 | 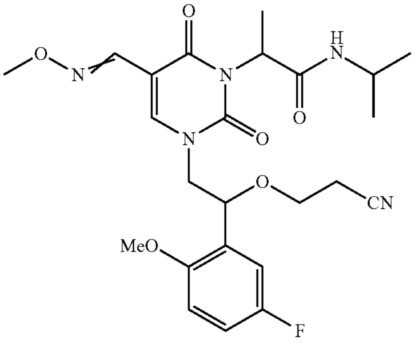 [SMILES: CON=Cc1cn(CC(OCCC#N)c2cc(F)ccc2OC)c(=O)n(C(C)C(=O)NC(C)C)c1=O] | viscous oil |
| A-7 | 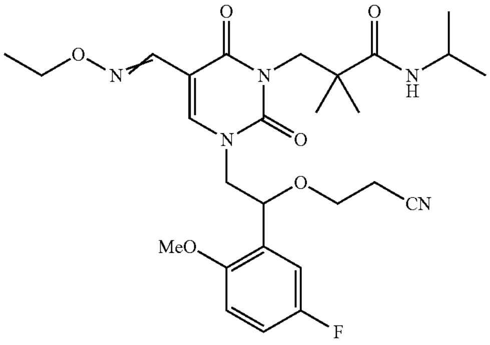 [SMILES: CCON=Cc1cn(CC(OCCC#N)c2cc(F)ccc2OC)c(=O)n(CC(C)(C)C(=O)NC(C)C)c1=O] | viscous oil |
| A-8 | 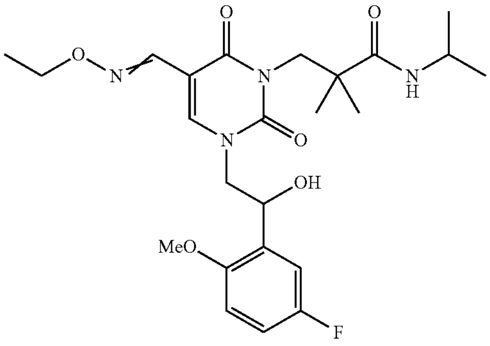 [SMILES: CCON=Cc1cn(CC(O)c2cc(F)ccc2OC)c(=O)n(CC(C)(C)C(=O)NC(C)C)c1=O] | m.p. 72-73° C. |

TABLE 2-continued
| Compound number | Structural formula | Physical properties |
|---|---|---|
| A-9 | 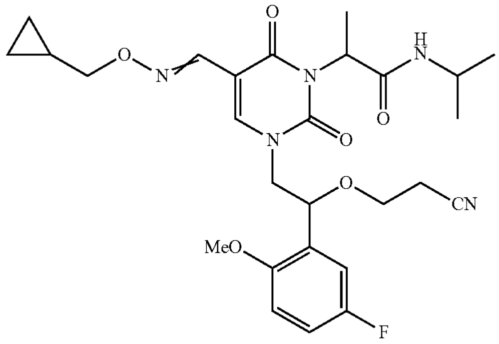 [SMILES: COc1ccc(F)cc1C(Cn1cc(C=NOCC2CC2)c(=O)n(C(C)C(=O)NC(C)C)c1=O)OCCC#N] | viscous oil |
| A-10 | 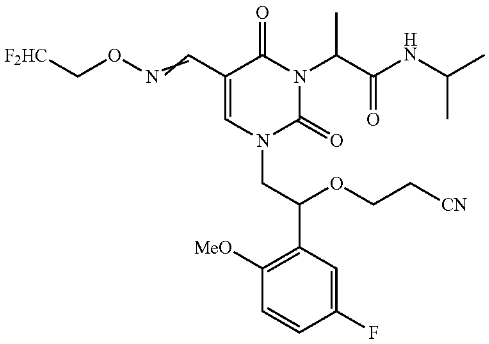 [SMILES: COc1ccc(F)cc1C(Cn1cc(C=NOCC(F)F)c(=O)n(C(C)C(=O)NC(C)C)c1=O)OCCC#N] | viscous oil |
| A-11 | 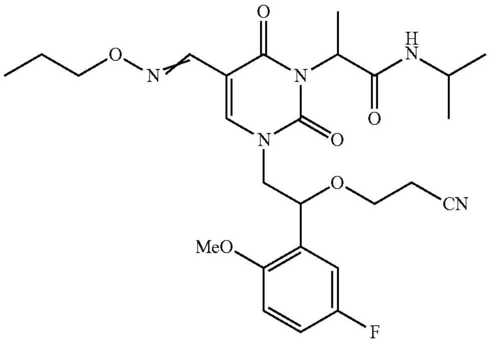 [SMILES: CCCON=Cc1cn(CC(OCCC#N)c2cc(F)ccc2OC)c(=O)n(C(C)C(=O)NC(C)C)c1=O] | viscous oil |
| A-12 | 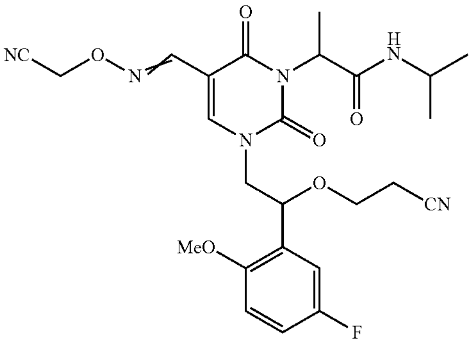 [SMILES: COc1ccc(F)cc1C(Cn1cc(C=NOCC#N)c(=O)n(C(C)C(=O)NC(C)C)c1=O)OCCC#N] | viscous oil |

TABLE 2-continued
| Compound number | Structural formula | Physical properties |
|---|---|---|
| A-13 | 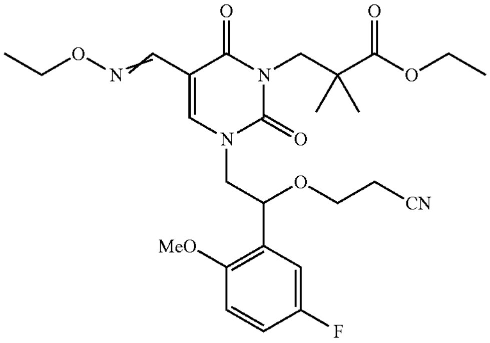 [SMILES: CCON=Cc1cn(CC(OCCC#N)c2cc(F)ccc2OC)c(=O)n(CC(C)(C)C(=O)OCC)c1=O] | viscous oil |
| A-14 | 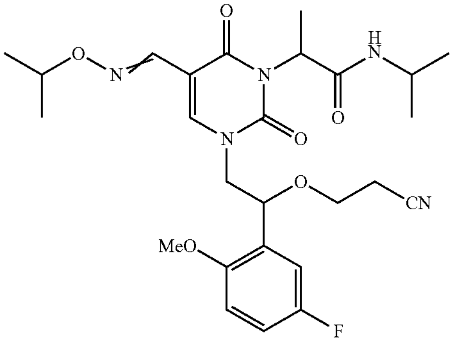 [SMILES: COc1ccc(F)cc1C(Cn1cc(C=NOC(C)C)c(=O)n(C(C)C(=O)NC(C)C)c1=O)OCCC#N] | viscous oil |
| A-15 | 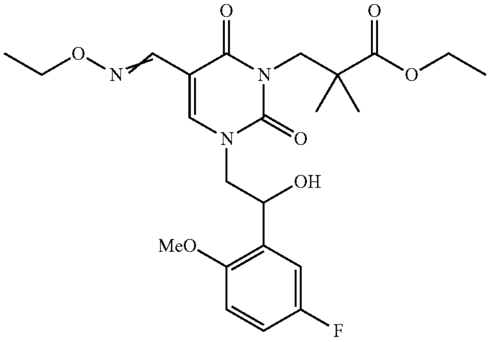 [SMILES: CCON=Cc1cn(CC(O)c2cc(F)ccc2OC)c(=O)n(CC(C)(C)C(=O)OCC)c1=O] | m.p. 120-121° C. |
| A-16 | 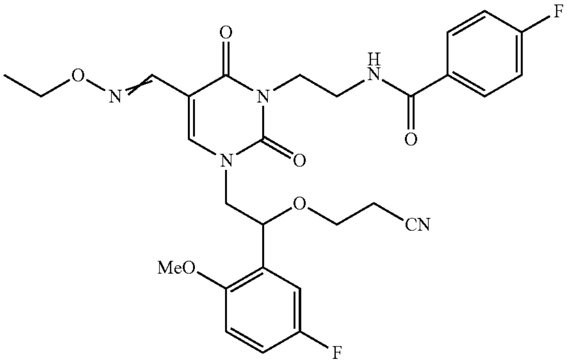 [SMILES: CCON=Cc1cn(CC(OCCC#N)c2cc(F)ccc2OC)c(=O)n(CCNC(=O)c2ccc(F)cc2)c1=O] | viscous oil |

TABLE 2-continued
| Compound number | Structural formula | Physical properties |
| --- | --- | --- |
| A-17 | 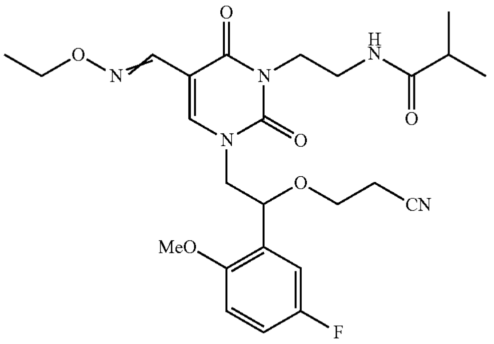 [SMILES: CCON=Cc1cn(CC(OCCC#N)c2cc(F)ccc2OC)c(=O)n(CCNC(=O)C(C)C)c1=O] | m.p. 52-53° C. |
| A-18 | 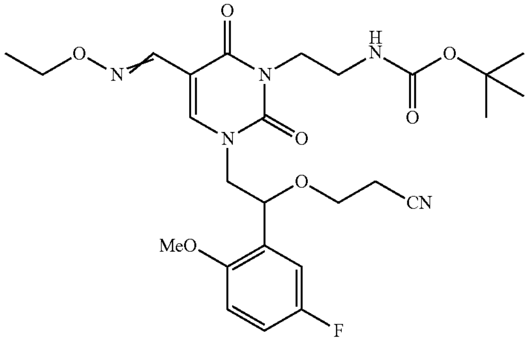 [SMILES: CCON=Cc1cn(CC(OCCC#N)c2cc(F)ccc2OC)c(=O)n(CCNC(=O)OC(C)(C)C)c1=O] | viscous oil |
| A-19 | 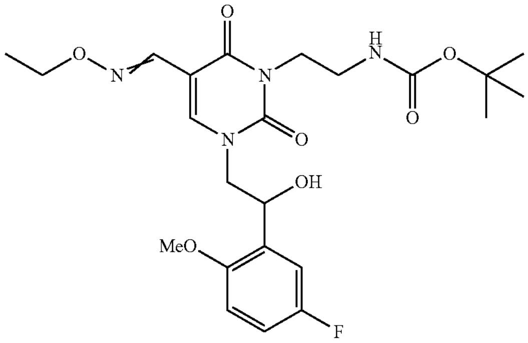 [SMILES: CCON=Cc1cn(CC(O)c2cc(F)ccc2OC)c(=O)n(CCNC(=O)OC(C)(C)C)c1=O] | m.p. 128-129° C. |
| A-20 | 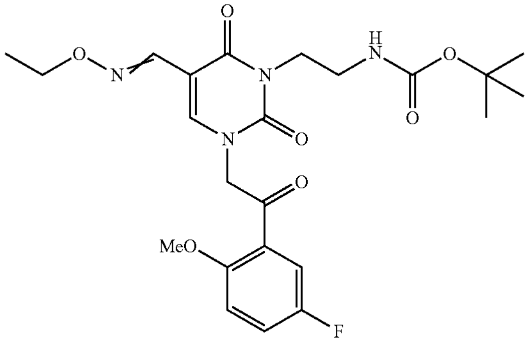 [SMILES: CCON=Cc1cn(CC(=O)c2cc(F)ccc2OC)c(=O)n(CCNC(=O)OC(C)(C)C)c1=O] | m.p. 82-83° C. |

TABLE 2-continued
| Compound number | Structural formula | Physical properties |
|---|---|---|
| A-21 | 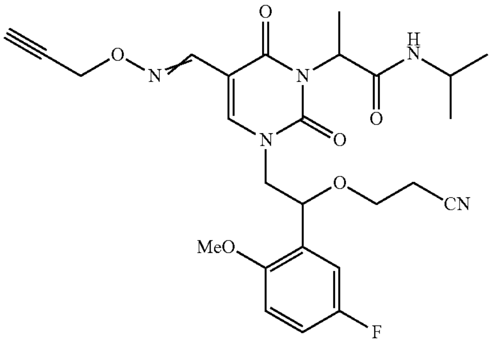 [SMILES: C#CCON=Cc1cn(CC(OCCC#N)c2cc(F)ccc2OC)c(=O)n(C(C)C(=O)NC(C)C)c1=O] | viscous oil |
| A-22 | 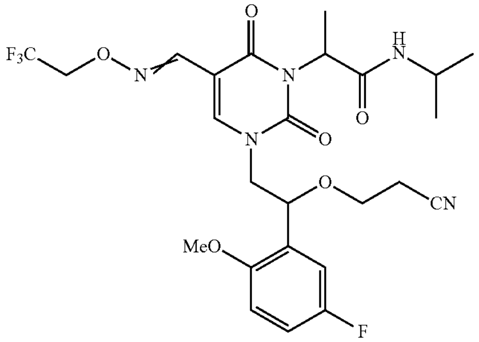 [SMILES: COc1ccc(F)cc1C(Cn1cc(C=NOCC(F)(F)F)c(=O)n(C(C)C(=O)NC(C)C)c1=O)OCCC#N] | viscous oil |
| A-23 | 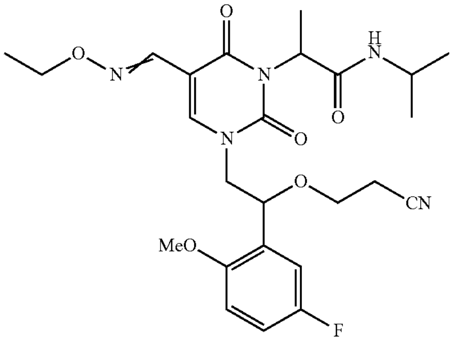 [SMILES: CCON=Cc1cn(CC(OCCC#N)c2cc(F)ccc2OC)c(=O)n(C(C)C(=O)NC(C)C)c1=O] | viscous oil |
| A-24 | 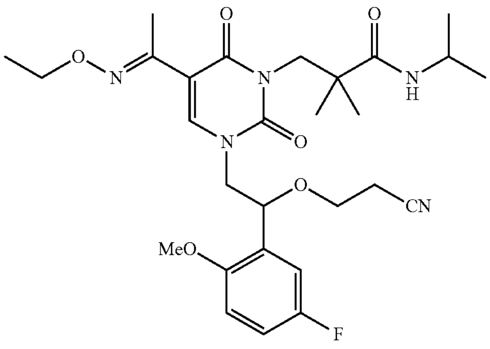 [SMILES: CCO/N=C(\C)c1cn(CC(OCCC#N)c2cc(F)ccc2OC)c(=O)n(CC(C)(C)C(=O)NC(C)C)c1=O] | viscous oil |

TABLE 2-continued
| Compound number | Structural formula | Physical properties |
|---|---|---|
| A-25 | 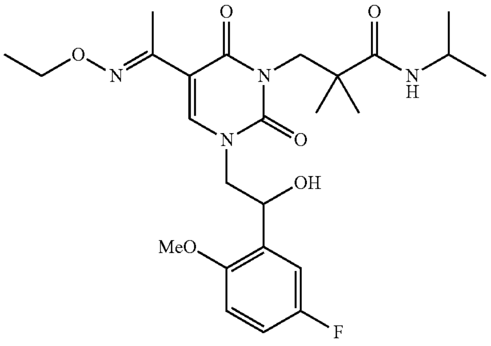 [SMILES: CCO/N=C(\C)c1cn(CC(O)c2cc(F)ccc2OC)c(=O)n(CC(C)(C)C(=O)NC(C)C)c1=O] | viscous oil |
| A-26 | 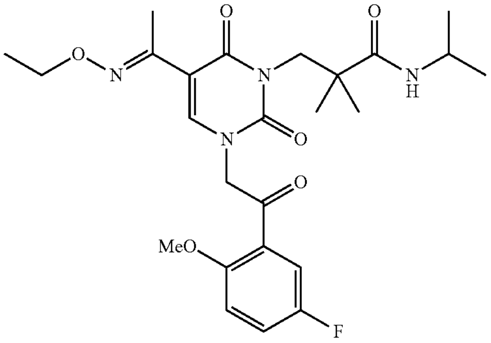 [SMILES: CCO/N=C(\C)c1cn(CC(=O)c2cc(F)ccc2OC)c(=O)n(CC(C)(C)C(=O)NC(C)C)c1=O] | m.p. 182-183° C. |
| A-27 | 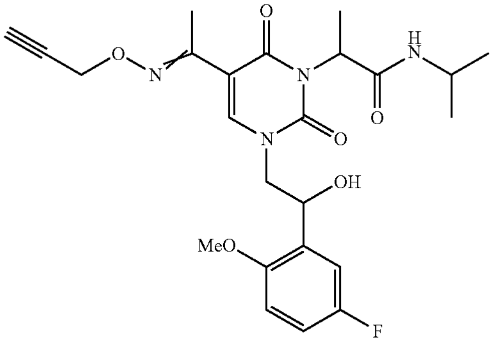 [SMILES: C#CCON=C(C)c1cn(CC(O)c2cc(F)ccc2OC)c(=O)n(C(C)C(=O)NC(C)C)c1=O] | m.p. 79-80° C. |
| A-28 | 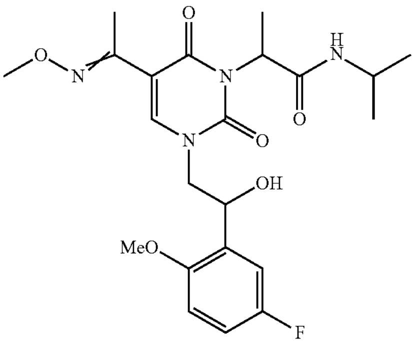 [SMILES: CON=C(C)c1cn(CC(O)c2cc(F)ccc2OC)c(=O)n(C(C)C(=O)NC(C)C)c1=O] | viscous oil |

TABLE 2-continued
| Compound number | Structural formula | Physical properties |
|---|---|---|
| A-29 | 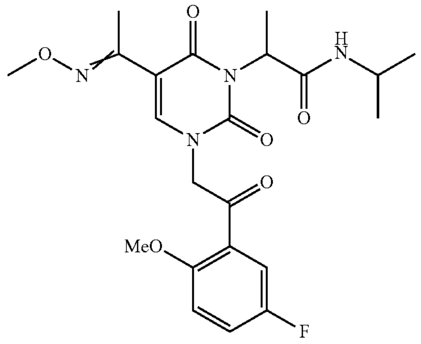 [SMILES: CON=C(C)c1cn(CC(=O)c2cc(F)ccc2OC)c(=O)n(C(C)C(=O)NC(C)C)c1=O] | m.p. 91-92° C. |
| A-30 | 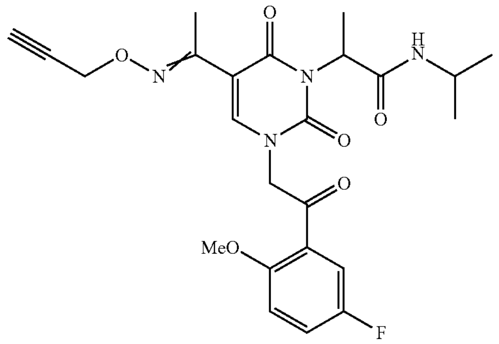 [SMILES: C#CCON=C(C)c1cn(CC(=O)c2cc(F)ccc2OC)c(=O)n(C(C)C(=O)NC(C)C)c1=O] | m.p. 138-139° C. |
| A-31 | 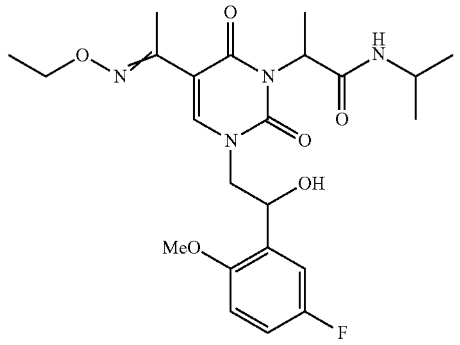 [SMILES: CCON=C(C)c1cn(CC(O)c2cc(F)ccc2OC)c(=O)n(C(C)C(=O)NC(C)C)c1=O] | viscous oil |
| A-32 | 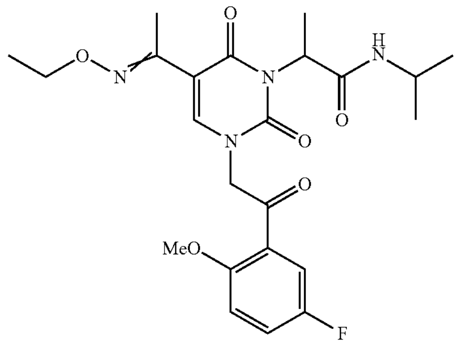 [SMILES: CCON=C(C)c1cn(CC(=O)c2cc(F)ccc2OC)c(=O)n(C(C)C(=O)NC(C)C)c1=O] | m.p. 105-106° C. |

TABLE 2-continued
| Compound number | Structural formula | Physical properties |
| --- | --- | --- |
| A-33 | 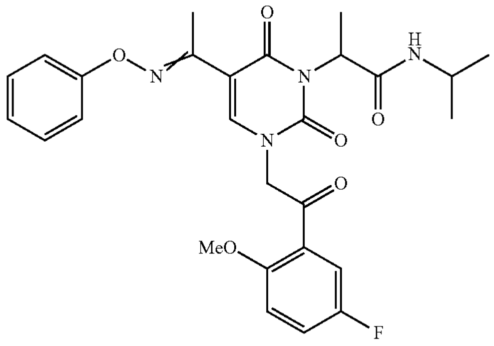 [SMILES: COc1ccc(F)cc1C(=O)Cn1cc(C(C)=NOc2ccccc2)c(=O)n(C(C)C(=O)NC(C)C)c1=O] | m.p. 102-103° C. |
| A-34 | 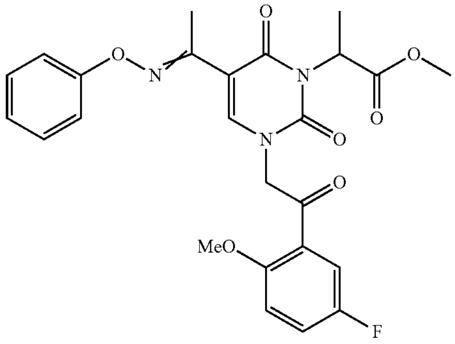 [SMILES: COC(=O)C(C)n1c(=O)c(C(C)=NOc2ccccc2)cn(CC(=O)c2cc(F)ccc2OC)c1=O] | m.p. 177-178° C. |
| A-35 | 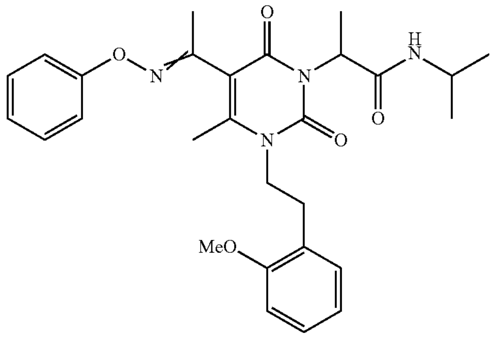 [SMILES: COc1ccccc1CCn1c(C)c(C(C)=NOc2ccccc2)c(=O)n(C(C)C(=O)NC(C)C)c1=O] | m.p. 145-146° C. |
| A-36 | 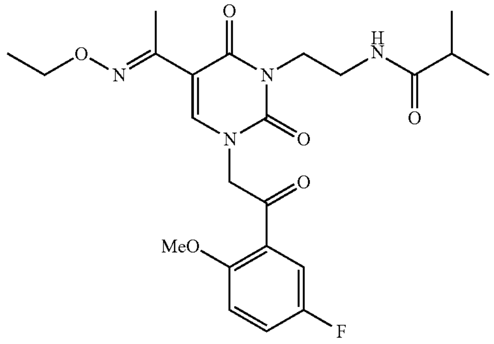 [SMILES: CCO/N=C(\C)c1cn(CC(=O)c2cc(F)ccc2OC)c(=O)n(CCNC(=O)C(C)C)c1=O] | m.p. 146-147° C. |

TABLE 2-continued

| Compound number | Structural formula | Physical properties |
|---|---|---|
| A-37 | 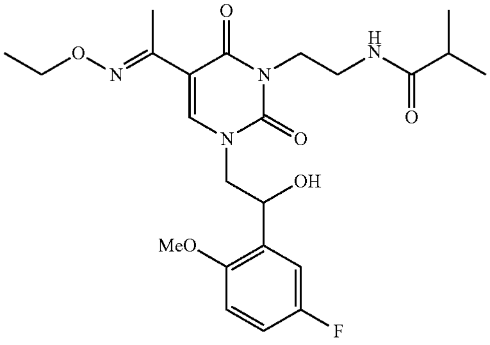 [SMILES: CCO/N=C(\C)c1cn(CC(O)c2cc(F)ccc2OC)c(=O)n(CCNC(=O)C(C)C)c1=O] | m.p. 148-149° C. |
| A-38 | 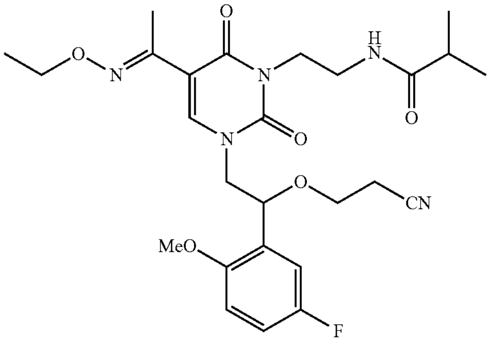 [SMILES: CCO/N=C(\C)c1cn(CC(OCCC#N)c2cc(F)ccc2OC)c(=O)n(CCNC(=O)C(C)C)c1=O] | m.p. 105-106° C. |

Further, some of the compounds of the present invention produced in the same manner as in Examples described above are shown in Table 3. In the table, the melting point (m.p.) is also shown as physical properties of each compound. When the compound is a stereoisomer, it is indicated in the remarks.

TABLE 3

| Compound number | Structural formula | Physical properties | Remarks |
|---|---|---|---|
| A-39 | 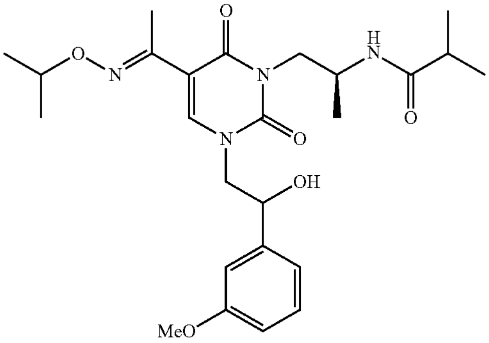 [SMILES: COc1cccc(C(O)Cn2cc(/C(C)=N/OC(C)C)c(=O)n(C[C@H](C)NC(=O)C(C)C)c2=O)c1] | m.p. 100-103° C. | |

TABLE 3-continued
| Compound number | Structural formula | Physical properties | Remarks |
|---|---|---|---|
| A-40 | 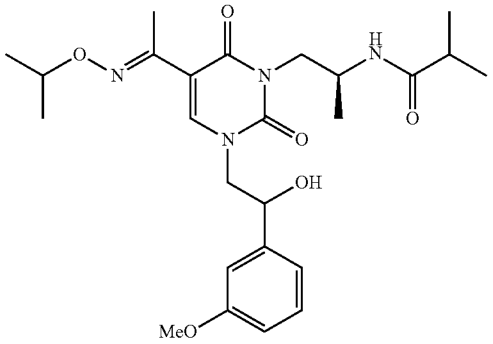 [SMILES: COc1cccc(C(O)Cn2cc(/C(C)=N/OC(C)C)c(=O)n(C[C@H](C)NC(=O)C(C)C)c2=O)c1] | m.p. 74-79° C. | Isomer of A-39 |
| A-41 | 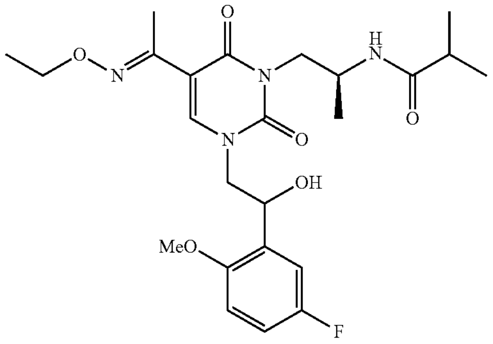 [SMILES: CCO/N=C(\C)c1cn(CC(O)c2cc(F)ccc2OC)c(=O)n(C[C@H](C)NC(=O)C(C)C)c1=O] | m.p. 80-84° C. | |
| A-42 | 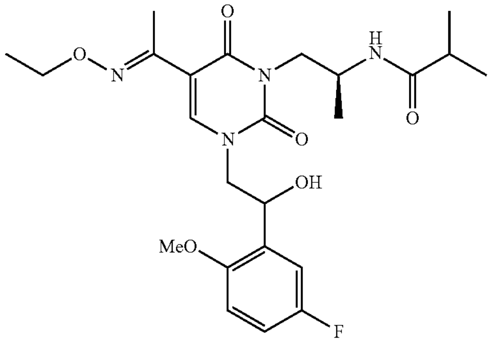 [SMILES: CCO/N=C(\C)c1cn(CC(O)c2cc(F)ccc2OC)c(=O)n(C[C@H](C)NC(=O)C(C)C)c1=O] | m.p. 141-142° C. | Isomer of A-41 |
| A-43 | 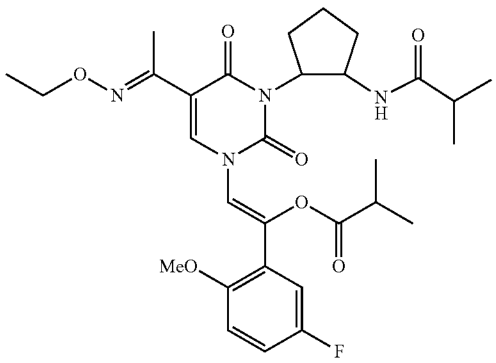 [SMILES: CCO/N=C(\C)c1cn(/C=C(\OC(=O)C(C)C)c2cc(F)ccc2OC)c(=O)n(C2CCCC2NC(=O)C(C)C)c1=O] | viscous oil | |

TABLE 3-continued
| Compound number | Structural formula | Physical properties | Remarks |
|---|---|---|---|
| A-44 | 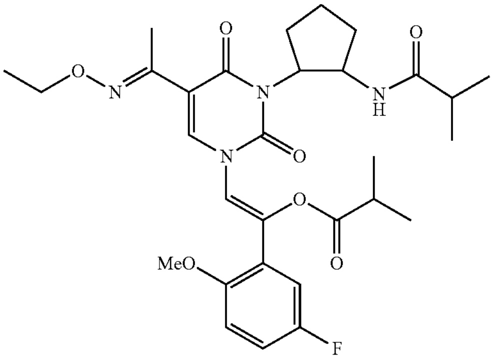 [SMILES: CCO/N=C(\C)c1cn(/C=C(\OC(=O)C(C)C)c2cc(F)ccc2OC)c(=O)n(C2CCCC2NC(=O)C(C)C)c1=O] | viscous oil | Isomer of A-43 |
| A-45 | 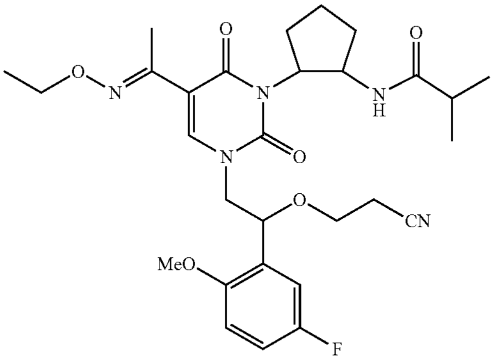 [SMILES: CCO/N=C(\C)c1cn(CC(OCCC#N)c2cc(F)ccc2OC)c(=O)n(C2CCCC2NC(=O)C(C)C)c1=O] | viscous oil | |
| A-46 | 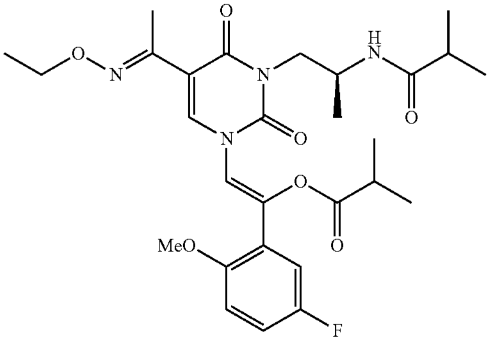 [SMILES: CCO/N=C(\C)c1cn(/C=C(\OC(=O)C(C)C)c2cc(F)ccc2OC)c(=O)n(C[C@H](C)NC(=O)C(C)C)c1=O] | viscous oil | |
| A-47 | 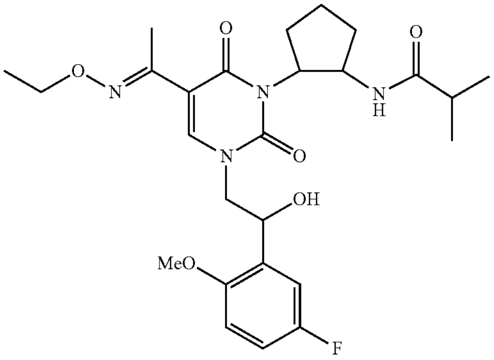 [SMILES: CCO/N=C(\C)c1cn(CC(O)c2cc(F)ccc2OC)c(=O)n(C2CCCC2NC(=O)C(C)C)c1=O] | viscous oil | |

TABLE 3-continued
| Compound number | Structural formula | Physical properties | Remarks |
|---|---|---|---|
| A-48 | 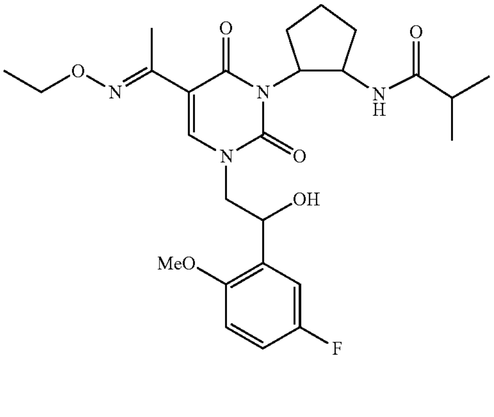 [SMILES: CCO/N=C(\C)c1cn(CC(O)c2cc(F)ccc2OC)c(=O)n(C2CCCC2NC(=O)C(C)C)c1=O] | viscous oil | Isomer of A-47 |
| A-49 | 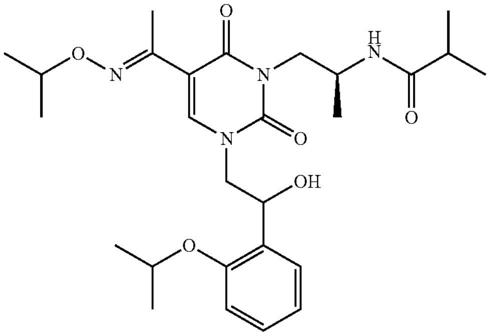 [SMILES: C/C(=N\OC(C)C)c1cn(CC(O)c2ccccc2OC(C)C)c(=O)n(C[C@H](C)NC(=O)C(C)C)c1=O] | m.p. 61-64° C. | |
| A-50 | 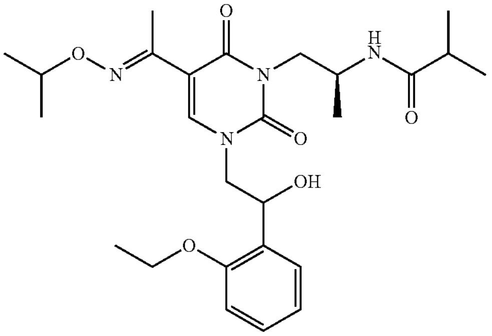 [SMILES: CCOc1ccccc1C(O)Cn1cc(/C(C)=N/OC(C)C)c(=O)n(C[C@H](C)NC(=O)C(C)C)c1=O] | m.p. 153-154° C. | |
| A-51 | 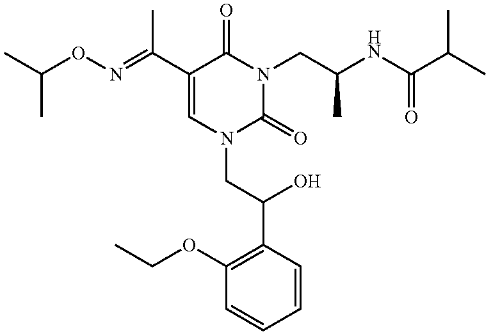 [SMILES: CCOc1ccccc1C(O)Cn1cc(/C(C)=N/OC(C)C)c(=O)n(C[C@H](C)NC(=O)C(C)C)c1=O] | m.p. 104-106° C. | Isomer of A-50 |

TABLE 3-continued
| Compound number | Structural formula | Physical properties | Remarks |
|---|---|---|---|
| A-52 | 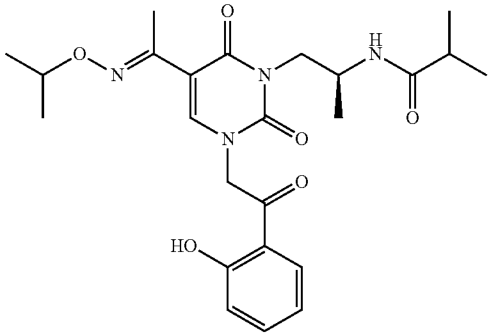 [SMILES: C/C(=N\OC(C)C)c1cn(CC(=O)c2ccccc2O)c(=O)n(C[C@H](C)NC(=O)C(C)C)c1=O] | m.p. 93-96° C. | |
| A-53 | 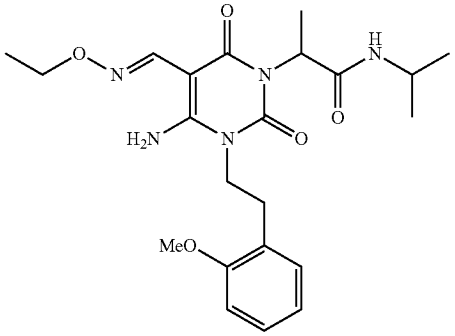 [SMILES: CCO/N=C/c1c(N)n(CCc2ccccc2OC)c(=O)n(C(C)C(=O)NC(C)C)c1=O] | amorphous | |
| A-54 | 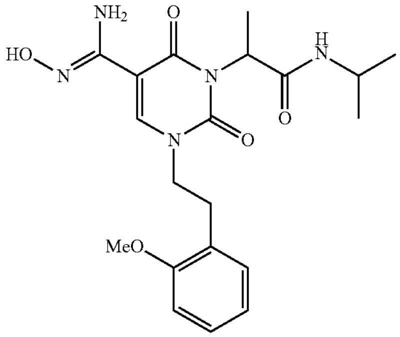 [SMILES: COc1ccccc1CCn1cc(/C(N)=N/O)c(=O)n(C(C)C(=O)NC(C)C)c1=O] | m.p. 217-219° C. | |
| A-55 | 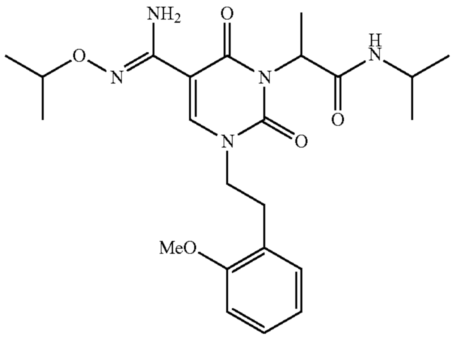 [SMILES: COc1ccccc1CCn1cc(/C(N)=N/OC(C)C)c(=O)n(C(C)C(=O)NC(C)C)c1=O] | m.p. 87-90° C. | |

TABLE 3-continued
| Compound number | Structural formula | Physical properties | Remarks |
| --- | --- | --- | --- |
| A-56 | 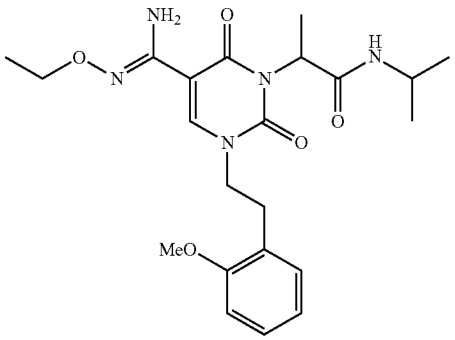 [SMILES: CCO/N=C(\N)c1cn(CCc2ccccc2OC)c(=O)n(C(C)C(=O)NC(C)C)c1=O] | m.p. 130-132° C. | |
| A-57 | 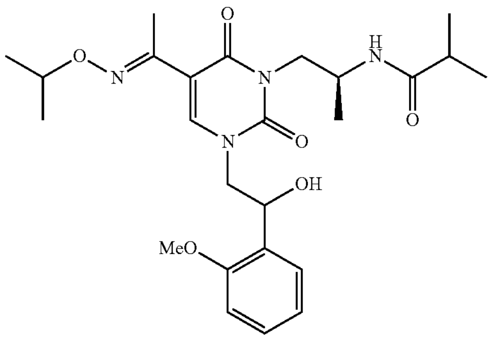 [SMILES: COc1ccccc1C(O)Cn1cc(/C(C)=N/OC(C)C)c(=O)n(C[C@H](C)NC(=O)C(C)C)c1=O] | m.p. 112-114° C. | |
| A-58 | 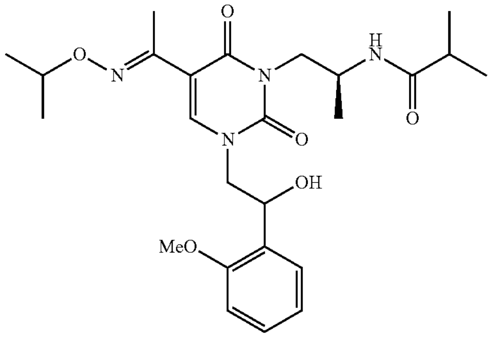 [SMILES: COc1ccccc1C(O)Cn1cc(/C(C)=N/OC(C)C)c(=O)n(C[C@H](C)NC(=O)C(C)C)c1=O] | m.p. 73-77° C. | Isomer of A-57 |
| A-59 | 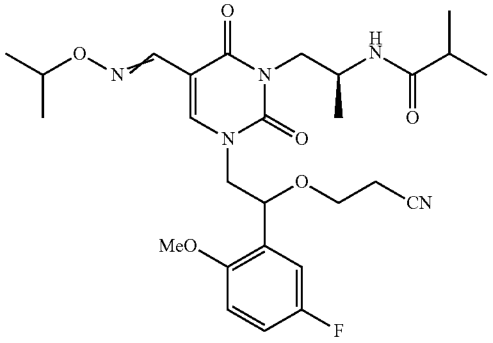 [SMILES: COc1ccc(F)cc1C(Cn1cc(C=NOC(C)C)c(=O)n(C[C@H](C)NC(=O)C(C)C)c1=O)OCCC#N] | m.p. 59-62° C. | |

TABLE 3-continued
| Compound number | Structural formula | Physical properties | Remarks |
|---|---|---|---|
| A-60 | 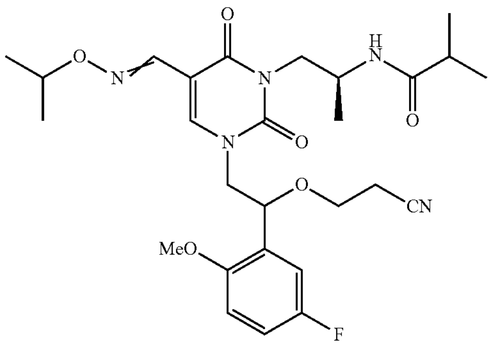 [SMILES: COc1ccc(F)cc1C(Cn1cc(C=NOC(C)C)c(=O)n(C[C@H](C)NC(=O)C(C)C)c1=O)OCCC#N] | m.p. 63-68° C. | Isomer of A-59 |
| A-61 | 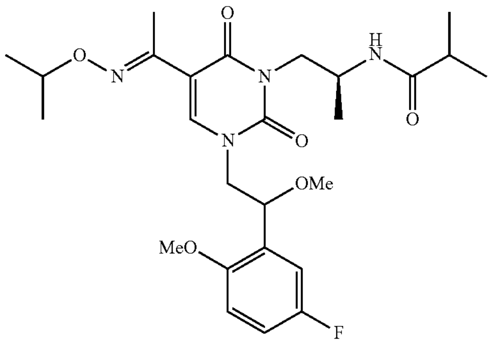 [SMILES: COc1ccc(F)cc1C(Cn1cc(/C(C)=N/OC(C)C)c(=O)n(C[C@H](C)NC(=O)C(C)C)c1=O)OC] | m.p. 42-51° C. | |
| A-62 | 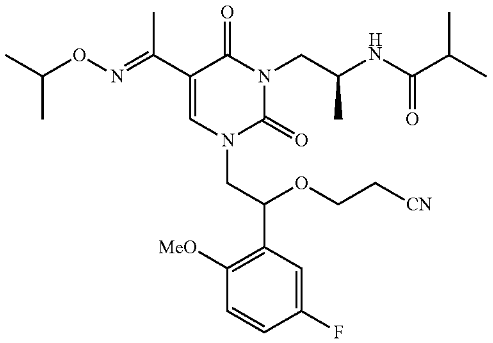 [SMILES: COc1ccc(F)cc1C(Cn1cc(/C(C)=N/OC(C)C)c(=O)n(C[C@H](C)NC(=O)C(C)C)c1=O)OCCC#N] | m.p. 53-54° C. | |
| A-63 | 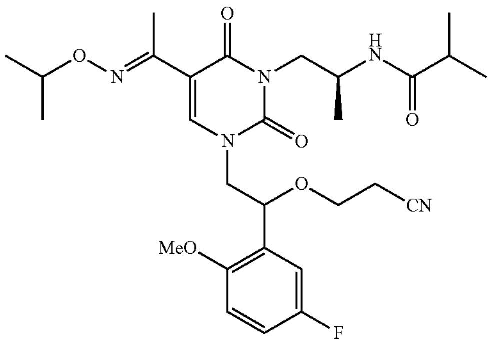 [SMILES: COc1ccc(F)cc1C(Cn1cc(/C(C)=N/OC(C)C)c(=O)n(C[C@H](C)NC(=O)C(C)C)c1=O)OCCC#N] | m.p. 53-54° C. | Isomer of A-62 |

TABLE 3-continued
| Compound number | Structural formula | Physical properties | Remarks |
| --- | --- | --- | --- |
| A-64 | 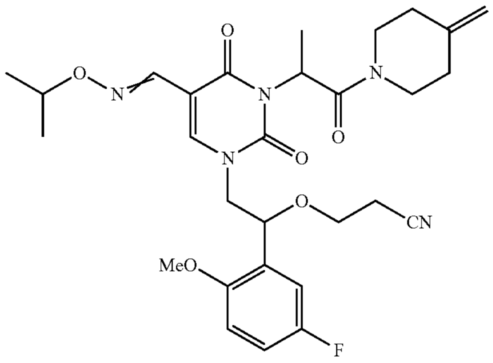 [SMILES: C=C1CCN(C(=O)C(C)n2c(=O)c(C=NOC(C)C)cn(CC(OCCC#N)c3cc(F)ccc3OC)c2=O)CC1] | m.p. 38-40° C. | |
| A-65 | 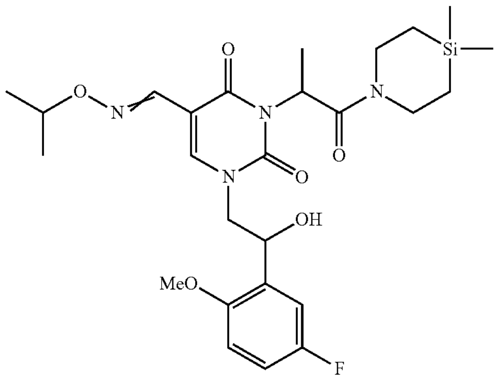 [SMILES: COc1ccc(F)cc1C(O)Cn1cc(C=NOC(C)C)c(=O)n(C(C)C(=O)N2CC[Si](C)(C)CC2)c1=O] | viscous oil | |
| A-66 | 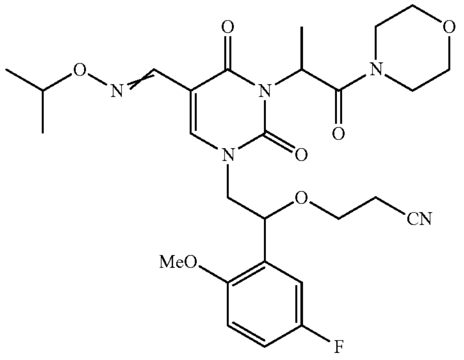 [SMILES: COc1ccc(F)cc1C(Cn1cc(C=NOC(C)C)c(=O)n(C(C)C(=O)N2CCOCC2)c1=O)OCCC#N] | m.p. 67-70° C. | |
| A-67 | 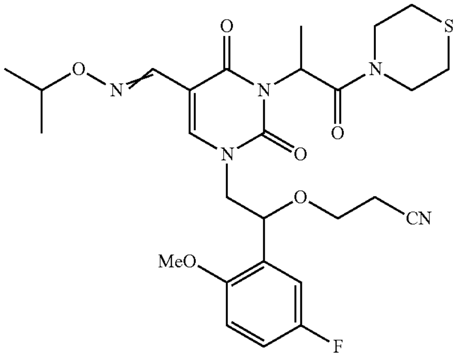 [SMILES: COc1ccc(F)cc1C(Cn1cc(C=NOC(C)C)c(=O)n(C(C)C(=O)N2CCSCC2)c1=O)OCCC#N] | m.p. 50-52° C. | |

TABLE 3-continued
| Compound number | Structural formula | Physical properties | Remarks |
| --- | --- | --- | --- |
| A-68 | 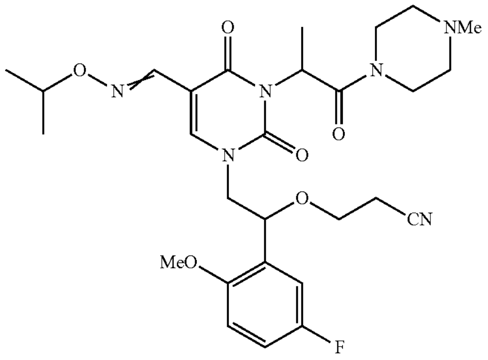 [SMILES: COc1ccc(F)cc1C(Cn1cc(C=NOC(C)C)c(=O)n(C(C)C(=O)N2CCN(C)CC2)c1=O)OCCC#N] | m.p. 66-69° C. | |
| A-69 | 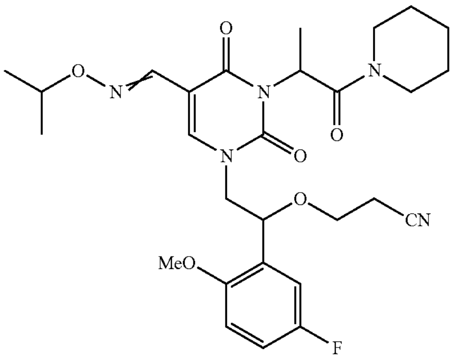 [SMILES: COc1ccc(F)cc1C(Cn1cc(C=NOC(C)C)c(=O)n(C(C)C(=O)N2CCCCC2)c1=O)OCCC#N] | m.p. 66-71° C. | |
| A-70 | 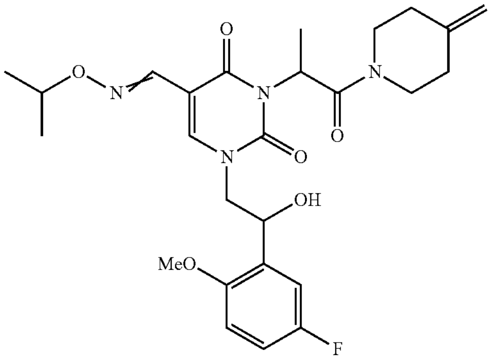 [SMILES: C=C1CCN(C(=O)C(C)n2c(=O)c(C=NOC(C)C)cn(CC(O)c3cc(F)ccc3OC)c2=O)CC1] | m.p. 80-82° C. | |
| A-71 | 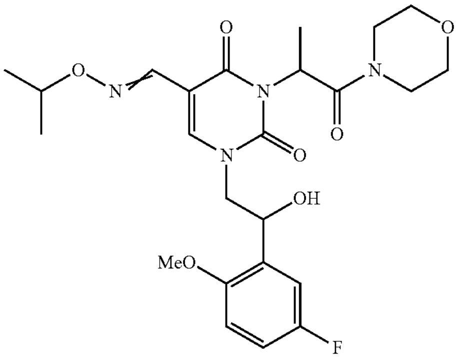 [SMILES: COc1ccc(F)cc1C(O)Cn1cc(C=NOC(C)C)c(=O)n(C(C)C(=O)N2CCOCC2)c1=O] | m.p. 84-87° C. | |

TABLE 3-continued
| Compound number | Structural formula | Physical properties | Remarks |
| --- | --- | --- | --- |
| A-72 | 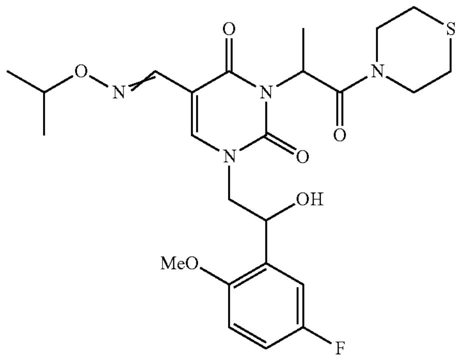 [SMILES: COc1ccc(F)cc1C(O)Cn1cc(C=NOC(C)C)c(=O)n(C(C)C(=O)N2CCSCC2)c1=O] | m.p. 83-85° C. | |
| A-73 | 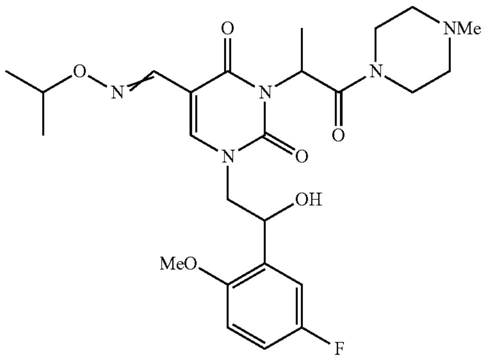 [SMILES: COc1ccc(F)cc1C(O)Cn1cc(C=NOC(C)C)c(=O)n(C(C)C(=O)N2CCN(C)CC2)c1=O] | m.p. 84-86° C. | |
| A-74 | 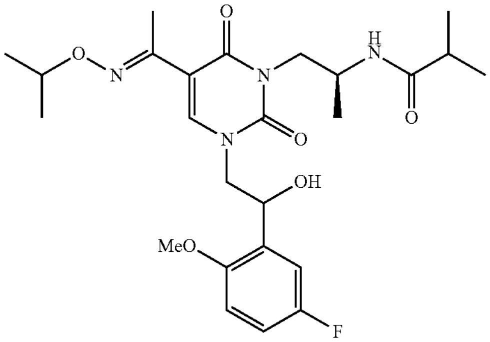 [SMILES: COc1ccc(F)cc1C(O)Cn1cc(/C(C)=N/OC(C)C)c(=O)n(C[C@H](C)NC(=O)C(C)C)c1=O] | m.p. 65-68° C. | |
| A-75 | 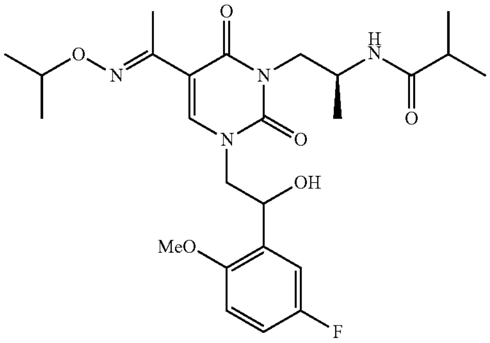 [SMILES: COc1ccc(F)cc1C(O)Cn1cc(/C(C)=N/OC(C)C)c(=O)n(C[C@H](C)NC(=O)C(C)C)c1=O] | m.p. 121-124° C. | Isomer of A-74 |

TABLE 3-continued
| Compound number | Structural formula | Physical properties | Remarks |
|---|---|---|---|
| A-76 | 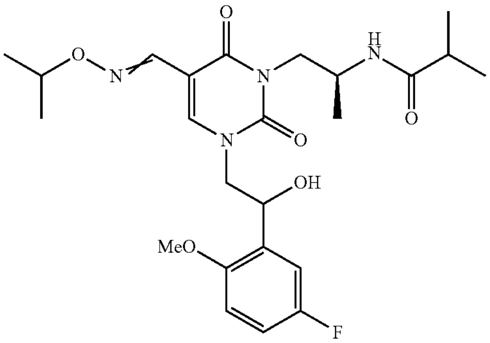 [SMILES: COc1ccc(F)cc1C(O)Cn1cc(C=NOC(C)C)c(=O)n(C[C@H](C)NC(=O)C(C)C)c1=O] | m.p. 70-76° C. | |
| A-77 | 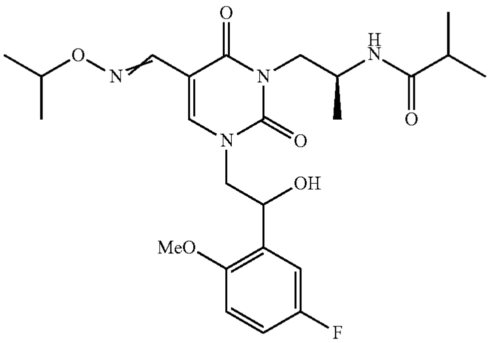 [SMILES: COc1ccc(F)cc1C(O)Cn1cc(C=NOC(C)C)c(=O)n(C[C@H](C)NC(=O)C(C)C)c1=O] | m.p. 73-74° C. | Isomer of A-76 |
| A-78 | 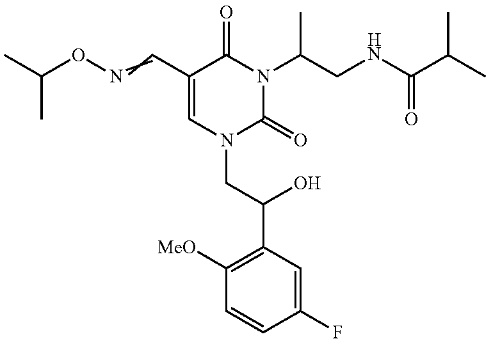 [SMILES: COc1ccc(F)cc1C(O)Cn1cc(C=NOC(C)C)c(=O)n(C(C)CNC(=O)C(C)C)c1=O] | m.p. 63-70° C. | |
| A-79 | 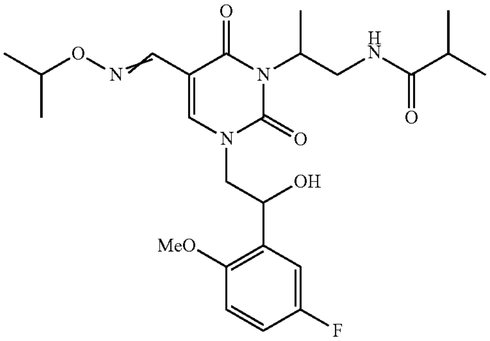 [SMILES: COc1ccc(F)cc1C(O)Cn1cc(C=NOC(C)C)c(=O)n(C(C)CNC(=O)C(C)C)c1=O] | m.p. 60-67° C. | Isomer of A-78 |

TABLE 3-continued
| Compound number | Structural formula | Physical properties | Remarks |
|---|---|---|---|
| A-80 | 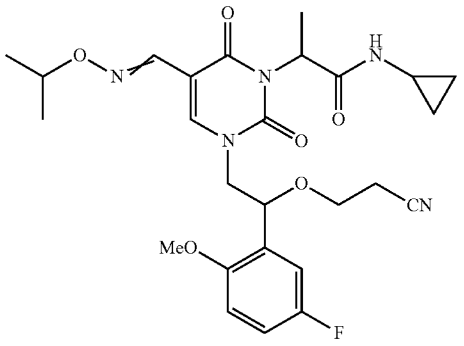 [SMILES: COc1ccc(F)cc1C(Cn1cc(C=NOC(C)C)c(=O)n(C(C)C(=O)NC2CC2)c1=O)OCCC#N] | m.p. 55-56° C. | |
| A-81 | 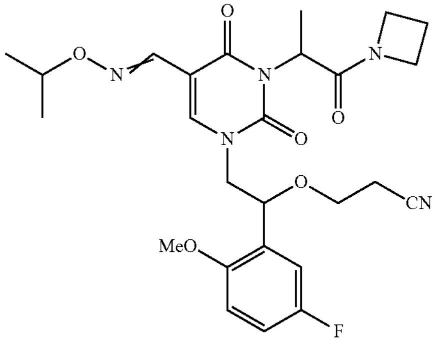 [SMILES: COc1ccc(F)cc1C(Cn1cc(C=NOC(C)C)c(=O)n(C(C)C(=O)N2CCC2)c1=O)OCCC#N] | m.p. 76-78° C. | |
| A-82 | 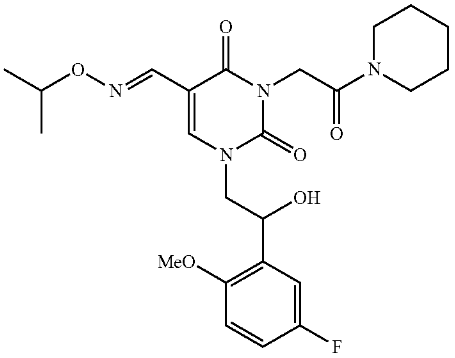 [SMILES: COc1ccc(F)cc1C(O)Cn1cc(/C=N/OC(C)C)c(=O)n(CC(=O)N2CCCCC2)c1=O] | viscous oil | |
| A-83 | 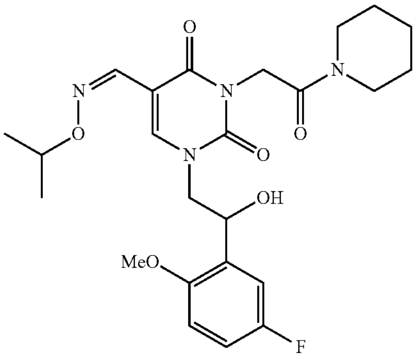 [SMILES: COc1ccc(F)cc1C(O)Cn1cc(/C=N\OC(C)C)c(=O)n(CC(=O)N2CCCCC2)c1=O] | viscous oil | |

TABLE 3-continued
| Compound number | Structural formula | Physical properties | Remarks |
|---|---|---|---|
| A-84 | 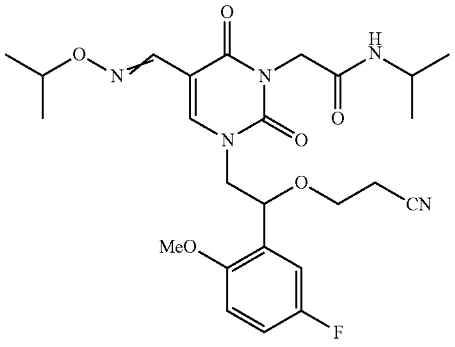 [SMILES: COc1ccc(F)cc1C(Cn1cc(C=NOC(C)C)c(=O)n(CC(=O)NC(C)C)c1=O)OCCC#N] | m.p. 125-126° C. | |
| A-85 | 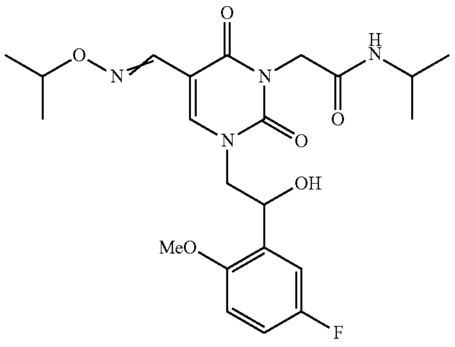 [SMILES: COc1ccc(F)cc1C(O)Cn1cc(C=NOC(C)C)c(=O)n(CC(=O)NC(C)C)c1=O] | m.p. 108-109° C. | |
| A-86 | 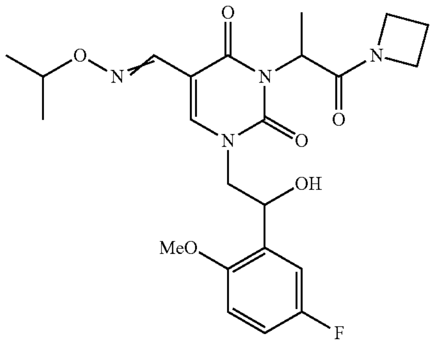 [SMILES: COc1ccc(F)cc1C(O)Cn1cc(C=NOC(C)C)c(=O)n(C(C)C(=O)N2CCC2)c1=O] | m.p. 84-85° C. | |
| A-87 | 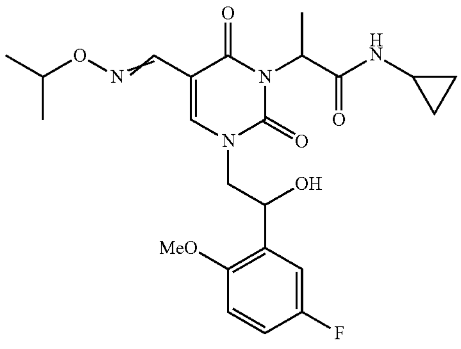 [SMILES: COc1ccc(F)cc1C(O)Cn1cc(C=NOC(C)C)c(=O)n(C(C)C(=O)NC2CC2)c1=O] | m.p. 84-89° C. | |

TABLE 3-continued
| Compound number | Structural formula | Physical properties | Remarks |
|---|---|---|---|
| A-88 | 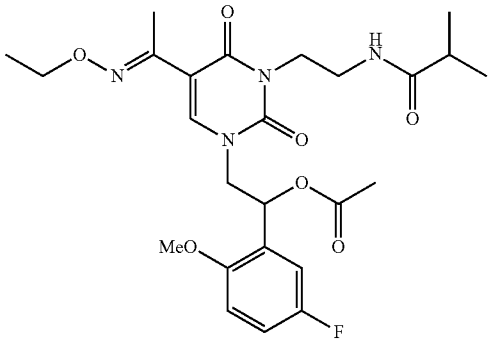 [SMILES: CCO/N=C(\C)c1cn(CC(OC(C)=O)c2cc(F)ccc2OC)c(=O)n(CCNC(=O)C(C)C)c1=O] | m.p. 174-175° C. | |
| A-89 | 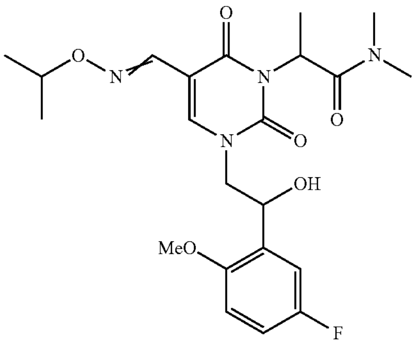 [SMILES: COc1ccc(F)cc1C(O)Cn1cc(C=NOC(C)C)c(=O)n(C(C)C(=O)N(C)C)c1=O] | viscous oil | |
| A-90 | 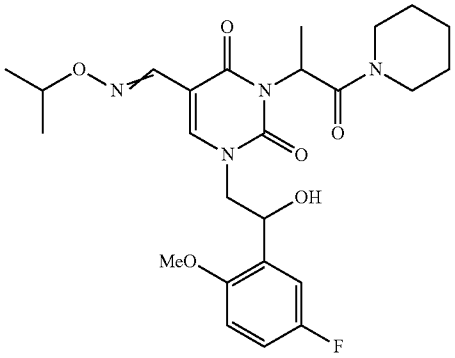 [SMILES: COc1ccc(F)cc1C(O)Cn1cc(C=NOC(C)C)c(=O)n(C(C)C(=O)N2CCCCC2)c1=O] | amorphous | |
| A-91 | 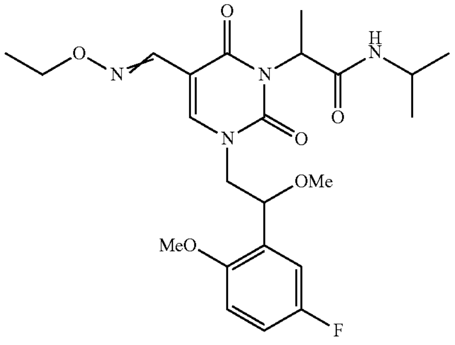 [SMILES: CCON=Cc1cn(CC(OC)c2cc(F)ccc2OC)c(=O)n(C(C)C(=O)NC(C)C)c1=O] | viscous oil | |

TABLE 3-continued
| Compound number | Structural formula | Physical properties | Remarks |
|---|---|---|---|
| A-92 | 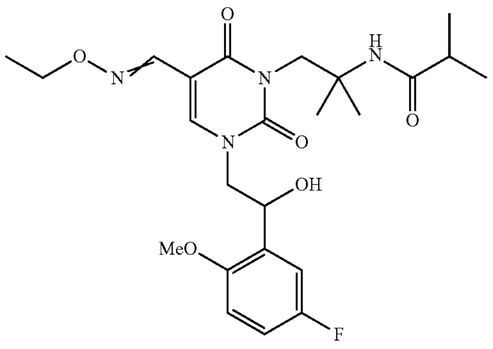 [SMILES: CCON=Cc1cn(CC(O)c2cc(F)ccc2OC)c(=O)n(CC(C)(C)NC(=O)C(C)C)c1=O] | amorphous | |
| A-93 | 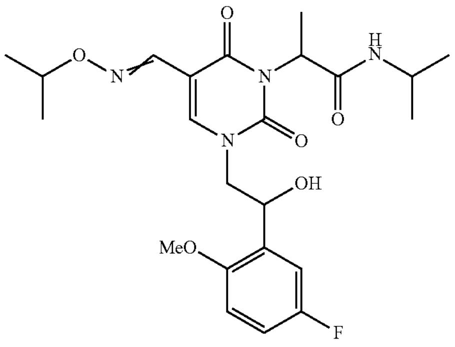 [SMILES: COc1ccc(F)cc1C(O)Cn1cc(C=NOC(C)C)c(=O)n(C(C)C(=O)NC(C)C)c1=O] | m.p. 91-92° C. | |
| A-94 | 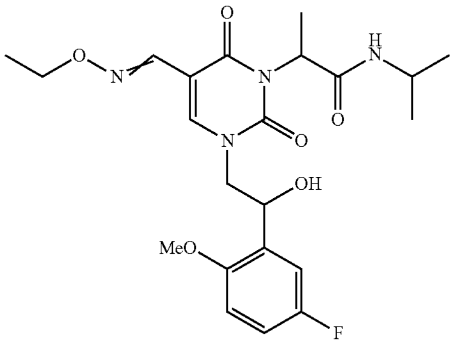 [SMILES: CCON=Cc1cn(CC(O)c2cc(F)ccc2OC)c(=O)n(C(C)C(=O)NC(C)C)c1=O] | m.p. 89-90° C. | |
| A-95 | 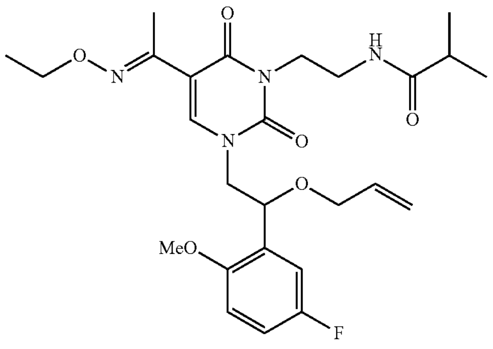 [SMILES: C=CCOC(Cn1cc(/C(C)=N/OCC)c(=O)n(CCNC(=O)C(C)C)c1=O)c1cc(F)ccc1OC] | m.p. 118-119° C. | |

TABLE 3-continued
| Compound number | Structural formula | Physical properties | Remarks |
|---|---|---|---|
| A-96 | 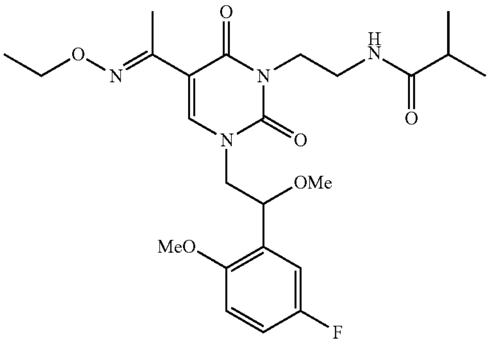 | m.p. 107-108° C. | |
| A-97 | 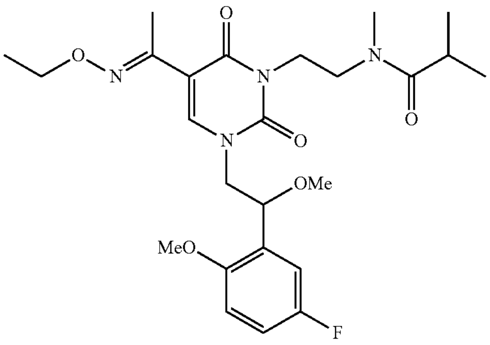 [SMILES: CCO/N=C(\C)c1cn(CC(OC)c2cc(F)ccc2OC)c(=O)n(CCN(C)C(=O)C(C)C)c1=O] | viscous oil | |
| A-98 | 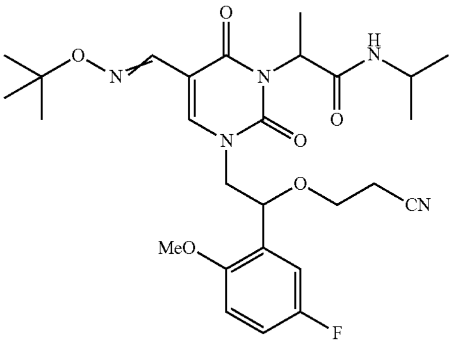 [SMILES: COc1ccc(F)cc1C(Cn1cc(C=NOC(C)(C)C)c(=O)n(C(C)C(=O)NC(C)C)c1=O)OCCC#N] | viscous oil | |
| A-99 | 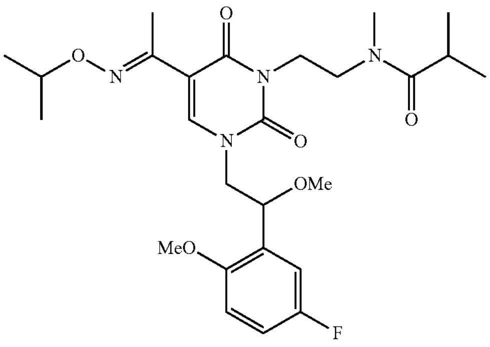 [SMILES: COc1ccc(F)cc1C(Cn1cc(/C(C)=N/OC(C)C)c(=O)n(CCN(C)C(=O)C(C)C)c1=O)OC] | viscous oil | |

TABLE 3-continued
| Compound number | Structural formula | Physical properties | Remarks |
|---|---|---|---|
| A-100 | 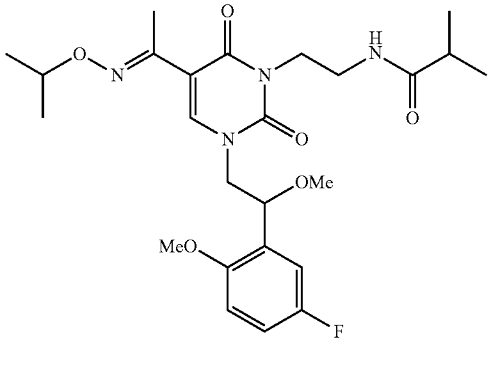 [SMILES: COc1ccc(F)cc1C(Cn1cc(/C(C)=N/OC(C)C)c(=O)n(CCNC(=O)C(C)C)c1=O)OC] | viscous oil | |
| A-101 | 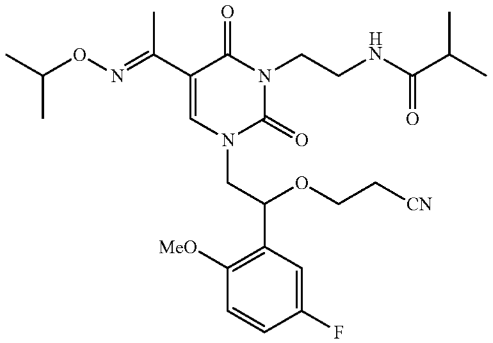 [SMILES: COc1ccc(F)cc1C(Cn1cc(/C(C)=N/OC(C)C)c(=O)n(CCNC(=O)C(C)C)c1=O)OCCC#N] | viscous oil | |
| A-102 | 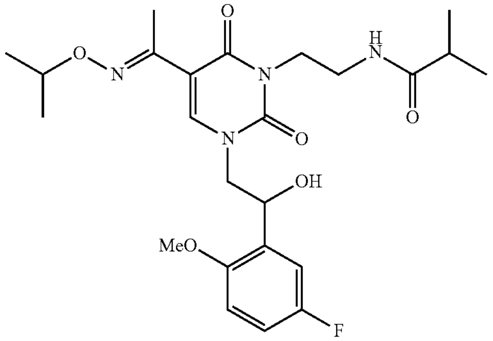 [SMILES: COc1ccc(F)cc1C(O)Cn1cc(/C(C)=N/OC(C)C)c(=O)n(CCNC(=O)C(C)C)c1=O] | m.p. 73-74° C. | |
| A-103 | 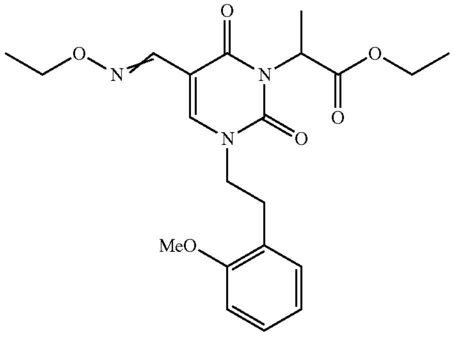 [SMILES: CCON=Cc1cn(CCc2ccccc2OC)c(=O)n(C(C)C(=O)OCC)c1=O] | viscous oil | |

TABLE 3-continued

| Compound number | Structural formula | Physical properties | Remarks |
|---|---|---|---|
| A-104 | 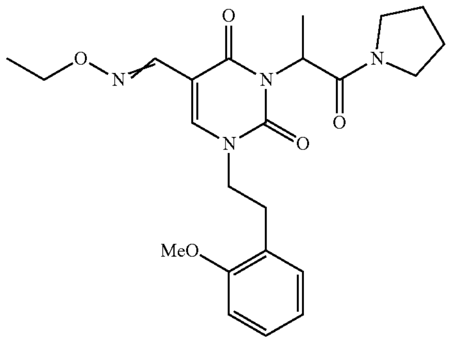 [SMILES: CCON=Cc1cn(CCc2ccccc2OC)c(=O)n(C(C)C(=O)N2CCCC2)c1=O] | viscous oil | |
| A-105 | 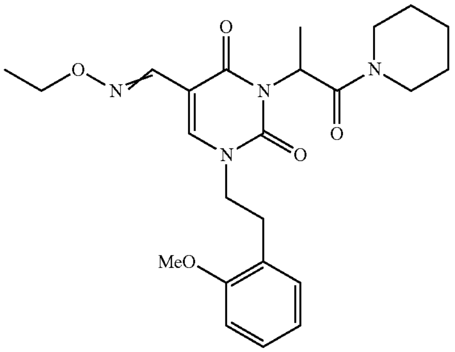 [SMILES: CCON=Cc1cn(CCc2ccccc2OC)c(=O)n(C(C)C(=O)N2CCCCC2)c1=O] | viscous oil | |
| A-106 | 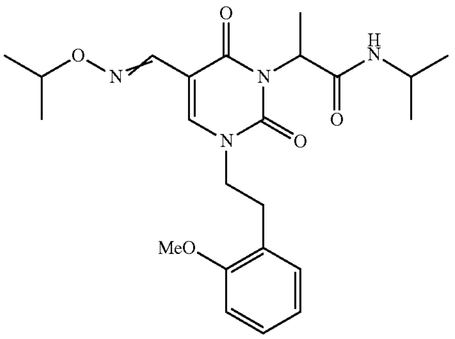 [SMILES: COc1ccccc1CCn1cc(C=NOC(C)C)c(=O)n(C(C)C(=O)NC(C)C)c1=O] | viscous oil | |
| A-107 | 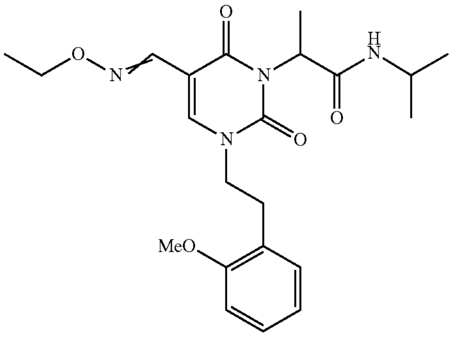 [SMILES: CCON=Cc1cn(CCc2ccccc2OC)c(=O)n(C(C)C(=O)NC(C)C)c1=O] | viscous oil | |

Further, some of the compounds of the present invention produced in the same manner as in Examples described above are shown in Table 4. In the table, the melting point (m.p.) is also shown as physical properties of each compound. When the compound is a stereoisomer, it is indicated in the remarks.

TABLE 4
| Compound number | Structural formula | Physical properties | Remarks |
|---|---|---|---|
| B-1 | 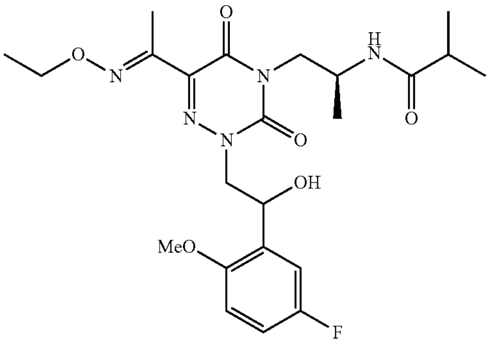 | viscous oil | |
| B-2 | 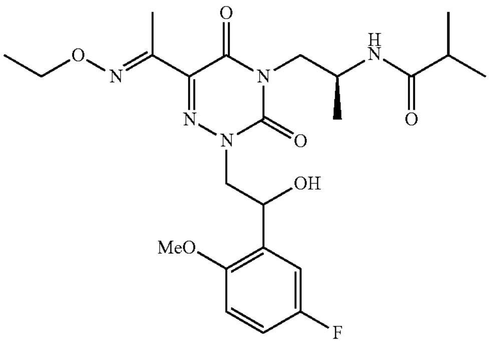 | viscous oil | Isomer of B-1 |
| B-3 | 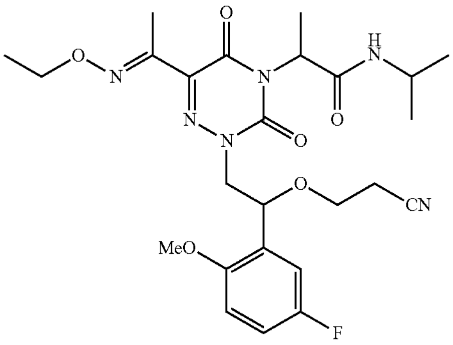 [SMILES: CCO/N=C(\C)c1nn(CC(OCCC#N)c2cc(F)ccc2OC)c(=O)n(C(C)C(=O)NC(C)C)c1=O] | amorphous | |
| B-4 | 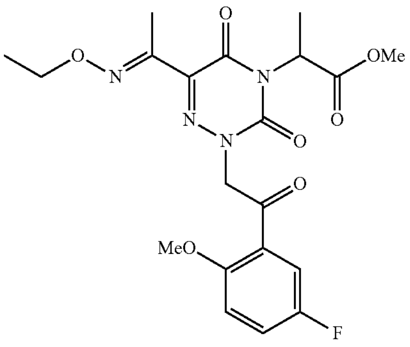 [SMILES: CCO/N=C(\C)c1nn(CC(=O)c2cc(F)ccc2OC)c(=O)n(C(C)C(=O)OC)c1=O] | viscous oil | |

TABLE 4-continued
| Compound number | Structural formula | Physical properties | Remarks |
| --- | --- | --- | --- |
| B-5 | 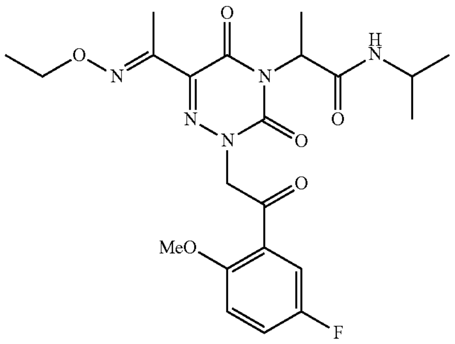 [SMILES: CCO/N=C(\C)c1nn(CC(=O)c2cc(F)ccc2OC)c(=O)n(C(C)C(=O)NC(C)C)c1=O] | m.p. 194-196° C. | |
| B-6 | 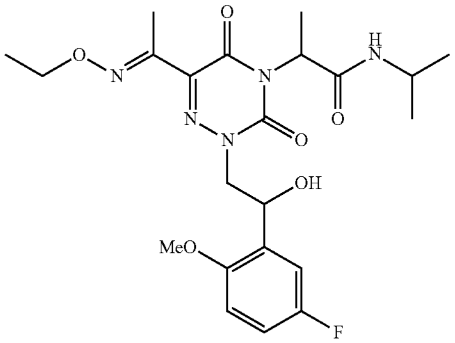 [SMILES: CCO/N=C(\C)c1nn(CC(O)c2cc(F)ccc2OC)c(=O)n(C(C)C(=O)NC(C)C)c1=O] | viscous oil | |
| B-7 | 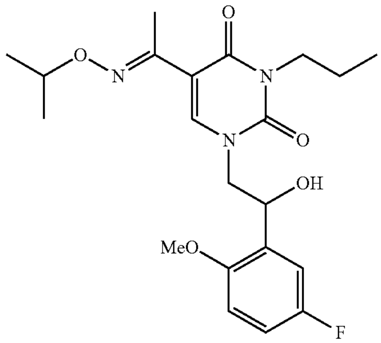 [SMILES: CCCn1c(=O)c(/C(C)=N/OC(C)C)cn(CC(O)c2cc(F)ccc2OC)c1=O] | m.p. 118-119° C. | |
| B-8 | 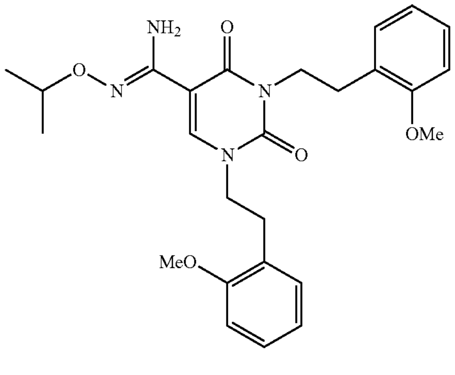 [SMILES: COc1ccccc1CCn1cc(/C(N)=N/OC(C)C)c(=O)n(CCc2ccccc2OC)c1=O] | viscous oil | |

TABLE 4-continued

| Compound number | Structural formula | Physical properties | Remarks |
| --- | --- | --- | --- |
| B-9 | 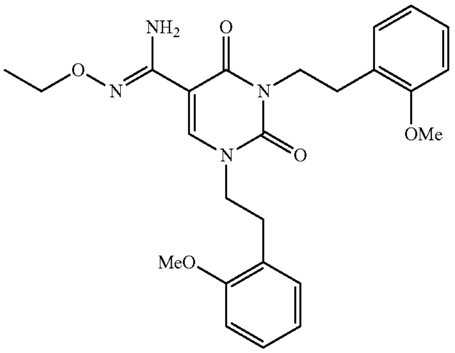 [SMILES: CCO/N=C(\N)c1cn(CCc2ccccc2OC)c(=O)n(CCc2ccccc2OC)c1=O] | viscous oil | |
| B-10 | 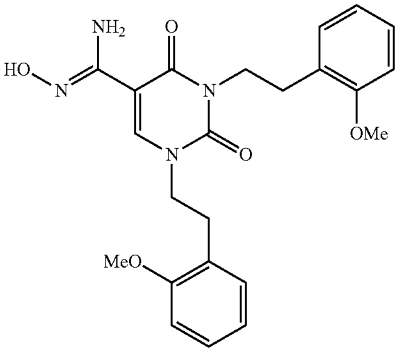 [SMILES: COc1ccccc1CCn1cc(/C(N)=N/O)c(=O)n(CCc2ccccc2OC)c1=O] | m.p. 138-140° C. | |

Among the compounds described in Tables 2 to 4, for a compound having an amorphous or viscous-oil property, the $^1$H-NMR data thereof are shown in Table 5 below.

TABLE 5

| Compound number | NMR data |
| --- | --- |
| A-3 | $^1$H-NMR ($CDCl_3$) δ: 7.64-6.97(4H, m), 5.09(2H, s), 4.38-3.96(8H, m), 2.16(3H, s), 1.28-1.21(15H, m). |
| A-4 | $^1$H-NMR ($CDCl_3$) δ: 8.64-7.50(2H, m) 7.61(2H, s)7.14-6.80(3H, m), 5.88-5.03 (3H, m), 4.74-2.51 (14H, m), 1.55(3H, d), 1.13(6H, d). |
| A-5 | $^1$H-NMR ($CDCl_3$) δ: 8.80-7.55(2H, m) 7.14-6.80(3H, m), 6.10-4.60 (8H, m), 4.40-3.41 (5H, m), 3.82 (3H, s), 2.65-2.51(2H, m), 1.55(3H, d), 1.13(6H, d). |
| A-6 | $^1$H-NMR ($CDCl_3$) δ: 8.71-7.51(2H, m) 7.14-6.80(3H, m), 5.85-5.07 (3H, m), 4.40-3.41 (5H, m), 3.93 (3H, s), 3.82 (3H, s), 2.65-2.51(2H, m), 1.55(3H, d), 1.13(6H, d). |
| A-7 | $^1$H-NMR ($CDCl_3$) δ: 8.71-7.51(2H, m) 7.14-6.80(3H, m), 6.08-2.55 (16H, m), 1.32-1.18 (15H, m). |
| A-9 | $^1$H-NMR ($CDCl_3$) δ: 8.90-7.51(2H, m) 7.14-6.80(3H, m), 5.85-5.07 (3H, m), 4.40-3.41 (7H, m), 3.82 (3H, s), 2.65-2.51(2H, m), 1.55(3H, d), 1.62-0.30(11H, m). |
| A-10 | $^1$H-NMR ($CDCl_3$) δ: 8.79-7.60(2H, m) 7.14-6.80(3H, m), 6.30-5.07 (4H, m), 4.40-3.41 (7H, m), 3.82 (3H, s), 2.65-2.51(2H, m), 1.55(3H, d), 1.13(6H, d). |
| A-11 | $^1$H-NMR ($CDCl_3$) δ: 8.80-7.51(2H, m) 7.14-6.80(3H, m), 5.85-5.07 (3H, m), 4.40-3.41 (7H, m), 3.82 (3H, s), 2.65-2.51(2H, m), 1.78-0.95(11H, m). |
| A-12 | $^1$H-NMR ($CDCl_3$) δ: 8.23-7.94(2H, m) 7.14-6.80(3H, m), 5.85-5.07 (3H, m), 4.74(2H, s), 4.40-3.41 (5H, m), 3.82 (3H, s), 2.65-2.51(2H, m), 1.55(3H, d), 1.13(6H, d). |

TABLE 5-continued

| Compound number | NMR data |
| --- | --- |
| A-13 | $^1$H-NMR ($CDCl_3$) δ: 8.67-7.48(2H, m) 7.15-6.80(3H, m), 5.08-2.53 (16H, m), 1.31-1.18 (12H, m). |
| A-14 | $^1$H-NMR ($CDCl_3$) δ: 8.84-7.51(2H, m) 7.14-6.80(3H, m), 5.85-5.07 (3H, m), 4.40-3.41 (6H, m), 3.82 (3H, s), 2.65-2.51(2H, m), 1.55(3H, d), 1.29-1.13(12H, m) |
| A-16 | $^1$H-NMR ($CDCl_3$) δ: 8.78-6.80(8H, m) 5.11-2.53(16H, m), 1.33(3H, t). |
| A-18 | $^1$H-NMR ($CDCl_3$) δ: 8.71-7.51(2H, m) 7.14-6.80(3H, m), 5.12-2.53 (17H, m), 1.39 (9H, s), 1.32 (3H, t). |
| A-21 | $^1$H-NMR ($CDCl_3$) δ: 8.77-7.51(2H, m) 7.14-6.80(3H, m), 5.85-5.07 (3H, m), 4.72-2.49 (10H, m), 3.82 (3H, s), 1.55(3H, d), 1.12(6H, d). |
| A-22 | $^1$H-NMR ($CDCl_3$) δ: 8.23-7.84(2H, m) 7.14-6.80(3H, m), 5.85-5.07 (3H, m), 4.40-3.41 (7H, m), 3.82 (3H, s), 2.65-2.51(2H, m), 1.55(3H, d), 1.13(6H, d). |
| A-23 | $^1$H-NMR ($CDCl_3$) δ: 8.80-7.51(2H, m) 7.14-6.80(3H, m), 5.85-5.07 (3H, m), 4.37-3.41 (7H, m), 3.82 (3H, s), 2.65-2.51(2H, m), 1.56-1.11(12H, m). |
| A-24 | $^1$H-NMR ($CDCl_3$) δ: 7.41(1H, s) 7.14-6.80(3H, m), 6.11(1H, d), 5.05-2.51(12H, m), 3.82 (3H, s), 2.14(3H, s), 1.31-1.13(15H, m). |
| A-25 | $^1$H-NMR ($CDCl_3$) δ: 7.30(1H, s) 7.20-6.77(3H, m), 5.91(1H, d), 5.24-3.81(9H, m), 3.85 (3H, s), 2.14(3H, s), 1.31-1.13(15H, m). |
| A-28 | $^1$H-NMR ($CDCl_3$) δ: 7.35(1H, s) 7.18-6.80(3H, m), 5.45-3.81(13H, m), 2.12 (3H, s), 1.52(3H, d), 1.15(6H, m). |
| A-31 | $^1$H-NMR ($CDCl_3$) δ: 7.33(1H, s) 7.18-6.80(3H, m), 5.45-3.81(12H, m), 2.14 (3H, s), 1.52(3H, d), 1.30-1.12(9H, m). |

TABLE 5-continued

| Compound number | NMR data |
|---|---|
| A-43 | $^1$H-NMR ($CDCl_3$) δ: 1.06-1.33(m, 15H), 1.69-2.30(m, 11H), 3.70-4.50(m, 5H), 4.78-5.23(m, 2H), 6.59-7.34(m, 4H), 8.21(s, 1H). |
| A-44 | $^1$H-NMR ($CDCl_3$) δ: 1.06-1.42(m, 15H), 1.69-2.30(m, 11H), 3.70-4.50(m, 5H), 4.78-5.23(m, 2H), 6.61-7.34(m, 4H), 7.27(s, 1H). |
| A-45 | $^1$H-NMR ($CDCl_3$) δ: 0.95-1.31(m, 9H), 1.69-2.30(m, 10H), 2.60-2.72(m, 2H), 3.48-4.52(m, 6H), 4.99-5.28(m, 2H), 6.82-7.31(m, 4H). |
| A-46 | $^1$H-NMR ($CDCl_3$) δ: 1.02-1.28(m, 18H), 2.13(s, 3H), 2.21-2.30(m, 1H), 2.75-2.82(m, 1H), 3.85(s, 3H), 3.93-4.40(m, 5H), 6.85-7.03(m, 3H), 7.17(s,1H), 7.59(s, 1H). |
| A-47 | $^1$H-NMR ($CDCl_3$) δ: 0.99-1.26(m, 9H), 1.48-2.70(m, 10H), 3.84(s, 3H), 4.05-4.55(m, 5H), 5.40-5.48(m, 2H), 6.77-6.95(m, 2H), 7.24-7.29(m, 2H). |
| A-48 | $^1$H-NMR ($CDCl_3$) δ: 1.05-1.30(m, 9H), 1.48-2.39(m, 10H), 3.22-4.53(m, H)s, 8H), 5.09-5.32(m, 2H), 6.77-6.98(m, 2H), 7.24-7.29(m, 2H). |
| A-53 | $^1$H-NMR ($CDCl_3$) δ: 1.26-1.30(m, 6H), 1.66(d, 3H), 2.93-2.98(m, 2H), 3.83(s, 3H), 4.10-4.22(m, 8H), 4.51-4.54(m, 1H), 6.81-7.24(m, 4H), 8.23(s, 1H). |
| A-65 | $^1$H-NMR ($CDCl_3$) δ: 8.80-7.51(2H, m) 7.14-6.80(3H, m) 5.57-3.13 (11H, m), 3.84 (3H, s), 1.55-1.23(13H, m), 0.09(6H, s). |
| A-82 | $^1$H-NMR ($CDCl_3$) δ: 8.82(1H, s), 7.51(1H, s), 7.25-6.80 (3H, m), 5.25-3.47 (11H, m), 3.79 (3H, s), 1.69-1.23(12H, m). |
| A-83 | $^1$H-NMR ($CDCl_3$) δ: 8.01(1H, s), 7.70(1H, s), 7.25-6.80 (3H, m), 5.25-3.45 (11H, m), 3.79 (3H, s), 1.69-1.23(12H, m). |
| A-89 | $^1$H-NMR ($CDCl_3$) δ: 8.83-8.74 (1H, m), 7.97-7.47 (1H, m), 7.09-7.07 (1H, m), 6.97-6.91 (1H, m), 6.80-6.78 (1H, m), 5.51-5.46 (1H, m), 5.24-5.16 (1H, m), 4.44-4.07 (3H, m), 3.87 (3H, s), 2.94-2.64 (6H, m), 1.50-1.46 (3H, m), 1.31-1.23 (6H, m). |
| A-90 | $^1$H-NMR ($CDCl_3$) δ: 8.83-7.62 (1H, m), 8.01-7.51 (1H, m), 7.16-7.11 (1H, m), 6.99-6.94 (1H, m), 6.83-6.80 (1H, m), 5.53-5.50 (1H, m), 5.21-5.18 (1H, m), 4.44-3.08 (7H, m), 3.865 (3H, s), 1.634-1.243 (15H, m). |
| A-91 | $^1$H-NMR ($CDCl_3$) δ: 8.74-7.49(2H, m) 7.11-6.80(3H, m), 5.50-4.83 (3H, m), 4.37-3.41 (5H, m), 3.82 (3H, s), 3.30 (3H, s), 1.56-1.11(12H, m). |
| A-92 | $^1$H-NMR ($CDCl_3$) δ: 8.76-8.09 (1H, m), 7.74-7.48 (1H, m), 7.23-7.19 (1H, m), 6.98-6.94 (1H, m), 6.83-6.78 (1H, m), 5.27-5.26 (1H, m), 4.32-4.04 (7H, m), 3.84 (3H, s), 2.23-2.16 (1H, m), 1.46-1.46 (6H, m), 1.33-1.26 (3H, m), 1.06-1.04 (6H, m). |
| A-97 | $^1$H-NMR ($CDCl_3$) δ: 7.40-6.79(4H, m), 4.90-2.69(10H, m), 3.82 (3H, s), 3.29 (3H, s), 3.05 (3H, s), 2.14 (3H, s), 1.30-1.01(9H, m) |
| A-98 | $^1$H-NMR ($CDCl_3$) δ: 8.87-7.51(2H, m) 7.14-6.80(3H, m), 5.85-5.07 (3H, m), 4.34-3.41 (5H, m), 3.82 (3H, s), 2.65-2.51(2H, m), 1.56-1.11(18H, m) |
| A-99 | $^1$H-NMR ($CDCl_3$) δ: 7.40-6.79(4H, m), 4.90-2.69(9H, m), 3.82 (3H, s), 3.29 (3H, s), 3.05 (3H, s), 2.14 (3H, s), 1.30-1.01(12H, m) |

TABLE 5-continued

| Compound number | NMR data |
|---|---|
| A-100 | $^1$H-NMR ($CDCl_3$) δ: 7.36(1H, s), 7.10-6.82(3H, m) 6.29-4.88(2H, m), 4.40-3.41(7H, m), 3.82 (3H, s), 3.29 (3H, s), 2.34-2.15(4H, m), 1.30-1.11(12H, m). |
| A-101 | $^1$H-NMR ($CDCl_3$) δ: 7.43(1H, s), 7.14-6.82(3H, m) 6.29-5.10(2H, m), 4.40-3.43(9H, m), 3.84 (3H, s), 2.63(2H, t), 2.34-2.15(4H, m), 1.30-1.11(12H, m). |
| A-103 | $^1$H-NMR ($CDCl_3$) δ: 1.18-1.26(m, 6H), 1.58(d, 3H), 2.98-3.04(m, 2H), 3.71-4.10(m, 9H), 5.46-5.51(m, 1H), 6.82-7.38(m, 5H), 7.95(s, 1H). |
| A-104 | $^1$H-NMR ($CDCl_3$) δ: 1.25-1.29(m, 3H), 1.62-1.95(m, 4H), 2.68-3.47(m, 6H), 3.81-4.18(m, 7H), 5.39-5.441(m, 1H), 6.82-7.54(m, 5H), 7.96(s, 1H). |
| A-105 | $^1$H-NMR ($CDCl_3$) δ: 1.18-1.62(m, 12H), 2.94-3.12(m, 4H), 3.40-3.62(m, 2H), 3.81-4.19(m, 7H), 5.45-5.51(m, 1H), 6.82-7.49(m, 5H), 7.97(s, 1H). |
| A-106 | $^1$H-NMR ($CDCl_3$) δ: 1H-NMR ($CDC_3$) δ: 8.50-6.85(6H, m) 5.50-5.38(2H, m), 4.35-3.94 (4H, m), 3.80 (3H, s), 3.15-2.91(2H, m), 1.56-1.14(15H, m). |
| A-107 | $^1$H-NMR ($CDCl_3$) δ: 8.43-6.85(6H, m) 5.50-5.38(2H, m), 4.18-3.98(5H, m), 3.80 (3H, s), 3.15-2.91(2H, m), 1.56-1.14(12H, m). |
| B-1 | $^1$H-NMR ($CDCl_3$) δ: 1.01-1.08(m, 6H), 1.23-1.29(m, 6H), 2.03-2.30(m, 4H), 3.63-3.85(m, 2H), 3.86(s, 3H), 4.05-4.40(m, 2H), 4.60-4.72(m, 2H), 5.44-5.56(m, 1H), 6.75-6.81(m, 1H), 6.89-6.95(m, 1H), 7.32-7.38(m, 1H). |
| B-2 | $^1$H-NMR ($CDCl_3$) δ: 1.04-1.09(m, 6H), 1.22-1.31(m, 6H), 2.02-2.25(m, 4H), 3.48-3.90(m, 5H), 4.11-4.28(m, 2H), 5.18-5.65(m, 2H), 6.75-6.81(m, 1H), 6.89-6.95(m, 1H), 7.32-7.38(m, 1H). |
| B-3 | $^1$H-NMR ($CDCl_3$) δ: 1.14-1.62(m, 12H), 2.15(s, 3H), 2.58-2.62(m, 2H), 3.47-4.43(m, 11H), 5.15-5.32(m, 2H), 6.89-6.93(m, 1H), 6.95-6.98(m, 1H), 7.19-7.24(m, 1H). |
| B-4 | $^1$H-NMR ($CDCl_3$) δ: 1.33(t, 3H), 1.72(d, 3H), 2.18(s, 3H), 3.68-3.77(m, 3H), 3.95(s, 3H), 4.25-4.31(m, 2H), 5.29-5.38(m, 2H), 6.96-6.99(m, 1H), 7.21-7.25(m, 1H), 7.62-7.65(m, 1H). |
| B-6 | $^1$H-NMR ($CDCl_3$) δ: 1.14-1.16(m, 6H), 1.30(t, 3H), 1.64(d, 3H), 2.13(s, 3H), 3.40-3.47(m, 1H), 3.89(s, 3H), 4.01-4.55(m, 5H), 5.05-5.19(m, 2H), 6.82-6.85(m, 1H), 6.91-6.98(m, 1H), 7.06-7.12(m, 1H). |
| B-8 | $^1$H-NMR ($CDCl_3$) δ: 1.20-1.28(m, 6H), 2.91-2.97(m, 4H), 3.80(s, 3H), 3.84(s, 3H), 3.94-4.20(m, 4H), 6.82-7.24(m, 8H), 7.60(s, 1H). |
| B-9 | $^1$H-NMR ($CDCl_3$) δ: 1.20-1.27(m, 3H), 2.91-2.96(m, 4H), 3.81(s, 3H), 3.84(s, 3H), 3.95-4.20(m, 4H), 6.82-7.24(m, 8H), 7.64(s, 1H). |

Further, some of the compounds of the present invention produced in the same manner as in Examples described above are shown in Table 6. In the table, the melting point (m.p.) is also shown as physical properties of each compound. When the compound is a stereoisomer, it is indicated in the remarks.

TABLE 6
| Compound number | Structural formula | Physical properties | Remarks |
|---|---|---|---|
| C-1 | 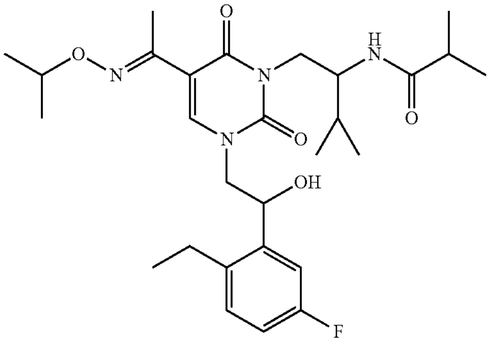 [SMILES: CCc1ccc(F)cc1C(O)Cn1cc(/C(C)=N/OC(C)C)c(=O)n(CC(NC(=O)C(C)C)C(C)C)c1=O] | m.p. 73-75° C. | |
| C-2 | 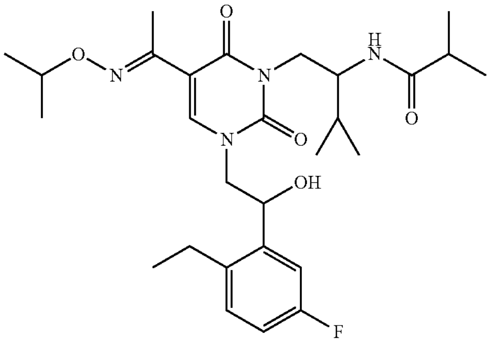 [SMILES: CCc1ccc(F)cc1C(O)Cn1cc(/C(C)=N/OC(C)C)c(=O)n(CC(NC(=O)C(C)C)C(C)C)c1=O] | m.p. 82-84° C. | Isomer of C-1 |
| C-3 | 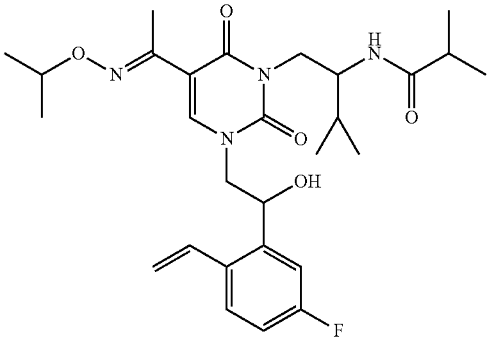 [SMILES: C=Cc1ccc(F)cc1C(O)Cn1cc(/C(C)=N/OC(C)C)c(=O)n(CC(NC(=O)C(C)C)C(C)C)c1=O] | viscous oil | |
| C-4 | 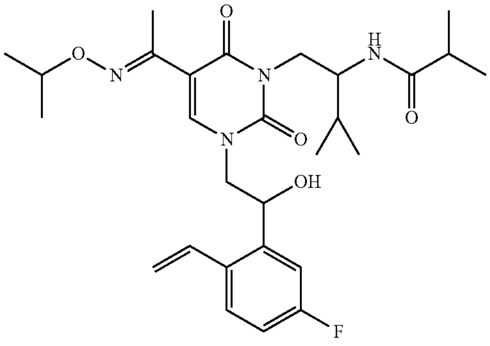 [SMILES: C=Cc1ccc(F)cc1C(O)Cn1cc(/C(C)=N/OC(C)C)c(=O)n(CC(NC(=O)C(C)C)C(C)C)c1=O] | viscous oil | Isomer of C-3 |

TABLE 6-continued
| Compound number | Structural formula | Physical properties | Remarks |
| --- | --- | --- | --- |
| C-5 | 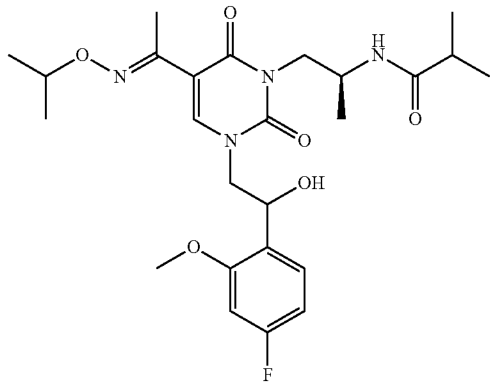 [SMILES: COc1cc(F)ccc1C(O)Cn1cc(/C(C)=N/OC(C)C)c(=O)n(C[C@H](C)NC(=O)C(C)C)c1=O] | amorphous | |
| C-6 | 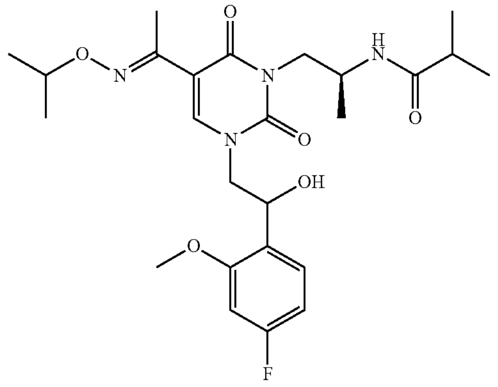 [SMILES: COc1cc(F)ccc1C(O)Cn1cc(/C(C)=N/OC(C)C)c(=O)n(C[C@H](C)NC(=O)C(C)C)c1=O] | m.p. 124-126° C. | Isomer of C-5 |
| C-7 | 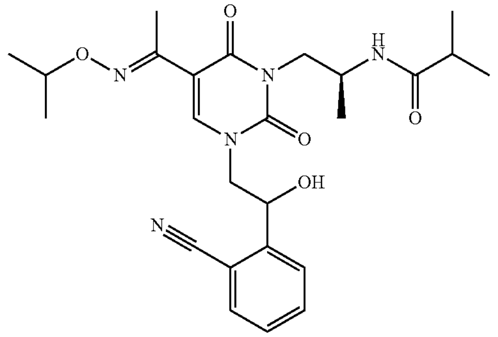 [SMILES: C/C(=N\OC(C)C)c1cn(CC(O)c2ccccc2C#N)c(=O)n(C[C@H](C)NC(=O)C(C)C)c1=O] | 182-185° C. | |
| C-8 | 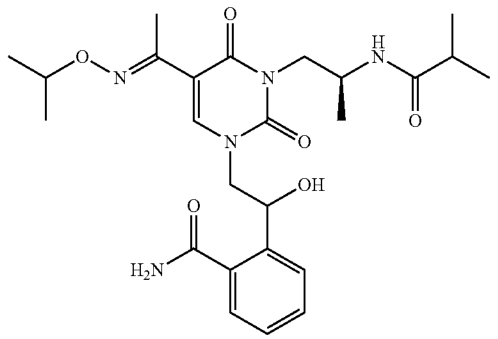 [SMILES: C/C(=N\OC(C)C)c1cn(CC(O)c2ccccc2C(N)=O)c(=O)n(C[C@H](C)NC(=O)C(C)C)c1=O] | viscous oil | |

TABLE 6-continued
| Compound number | Structural formula | Physical properties | Remarks |
|---|---|---|---|
| C-9 | 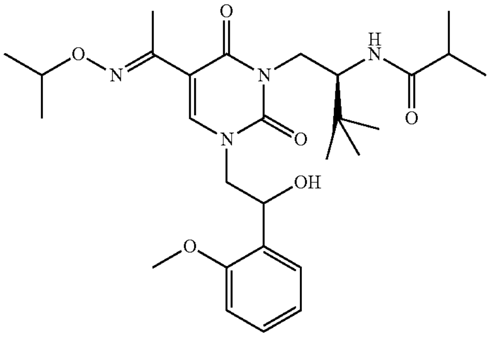 [SMILES: COc1ccccc1C(O)Cn1cc(/C(C)=N/OC(C)C)c(=O)n(C[C@@H](NC(=O)C(C)C)C(C)(C)C)c1=O] | m.p. 72-76° C. | |
| C-10 | 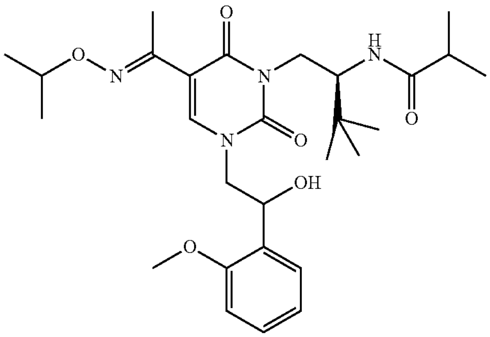 [SMILES: COc1ccccc1C(O)Cn1cc(/C(C)=N/OC(C)C)c(=O)n(C[C@@H](NC(=O)C(C)C)C(C)(C)C)c1=O] | m.p. 124-126° C. | Isomer of C-9 |
| C-11 | 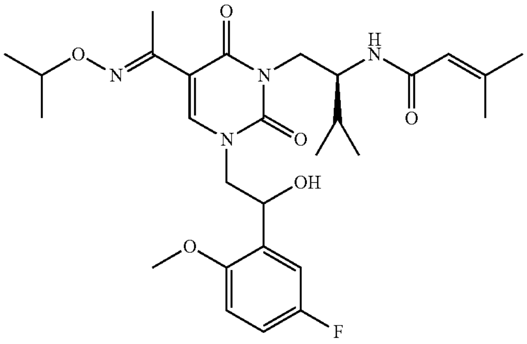 [SMILES: COc1ccc(F)cc1C(O)Cn1cc(/C(C)=N/OC(C)C)c(=O)n(C[C@@H](NC(=O)C=C(C)C)C(C)C)c1=O] | m.p. 68-69° C. | |
| C-12 | 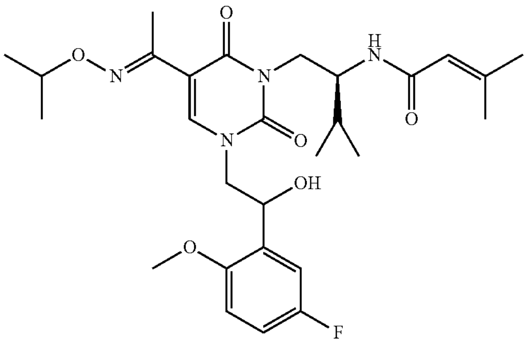 [SMILES: COc1ccc(F)cc1C(O)Cn1cc(/C(C)=N/OC(C)C)c(=O)n(C[C@@H](NC(=O)C=C(C)C)C(C)C)c1=O] | m.p. 150-153° C. | Isomer of C-11 |

TABLE 6-continued
| Compound number | Structural formula | Physical properties | Remarks |
|---|---|---|---|
| C-13 | 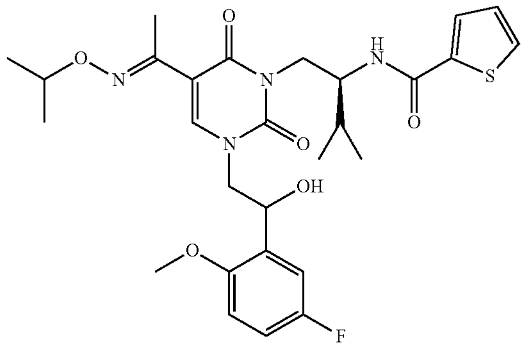 [SMILES: COc1ccc(F)cc1C(O)Cn1cc(/C(C)=N/OC(C)C)c(=O)n(C[C@@H](NC(=O)c2cccs2)C(C)C)c1=O] | m.p. 69-70° C. | |
| C-14 | 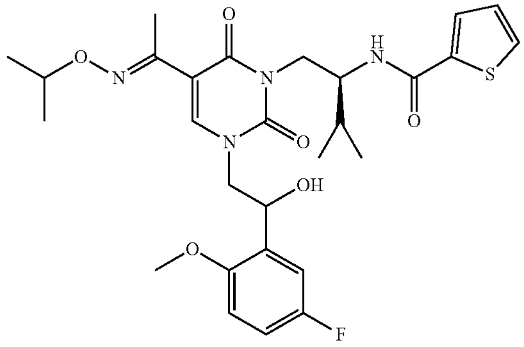 | m.p. 74-75° C. | Isomer of C-13 |
| C-15 | 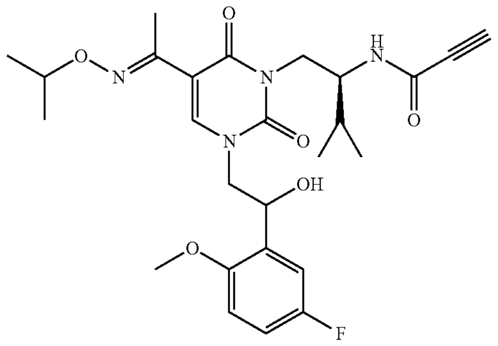 [SMILES: C#CC(=O)N[C@H](Cn1c(=O)c(/C(C)=N/OC(C)C)cn(CC(O)c2cc(F)ccc2OC)c1=O)C(C)C] | m.p. 49-50° C. | |
| C-16 | 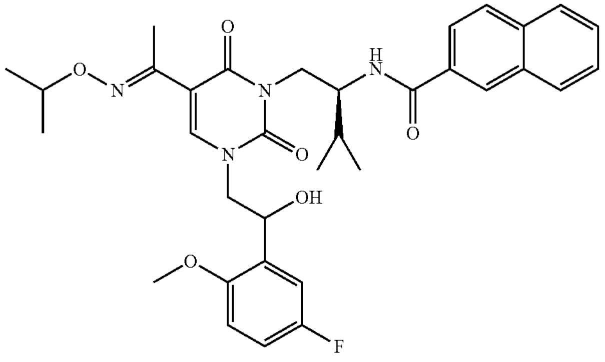 [SMILES: COc1ccc(F)cc1C(O)Cn1cc(/C(C)=N/OC(C)C)c(=O)n(C[C@@H](NC(=O)c2ccc3ccccc3c2)C(C)C)c1=O] | m.p. 77-78° C. | |

TABLE 6-continued
| Compound number | Structural formula | Physical properties | Remarks |
|---|---|---|---|
| C-17 | 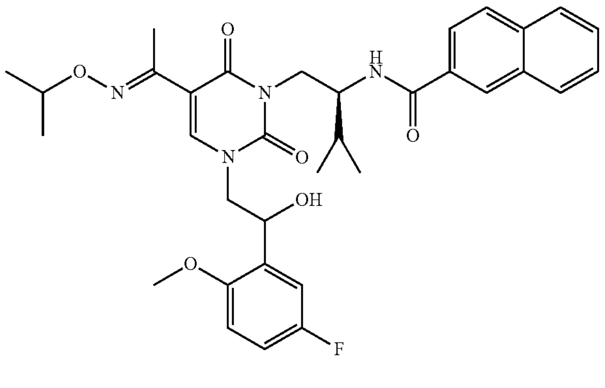 [SMILES: COc1ccc(F)cc1C(O)Cn1cc(/C(C)=N/OC(C)C)c(=O)n(C[C@@H](NC(=O)c2ccc3ccccc3c2)C(C)C)c1=O] | m.p. 88-89° C. | Isomer of C-16 |
| C-18 | 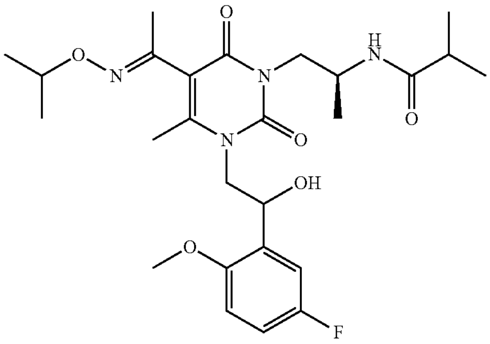 | viscous oil | |
| C-19 | 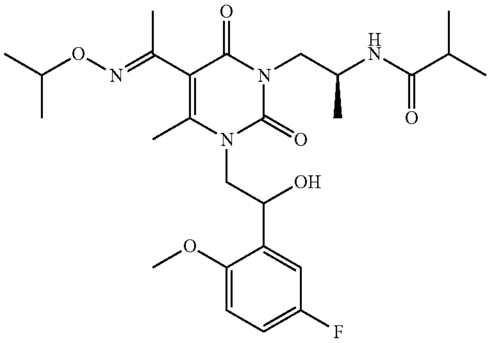 [SMILES: COc1ccc(F)cc1C(O)Cn1c(C)c(/C(C)=N/OC(C)C)c(=O)n(C[C@H](C)NC(=O)C(C)C)c1=O] | amorphous | Isomer of C-18 |
| C-20 | 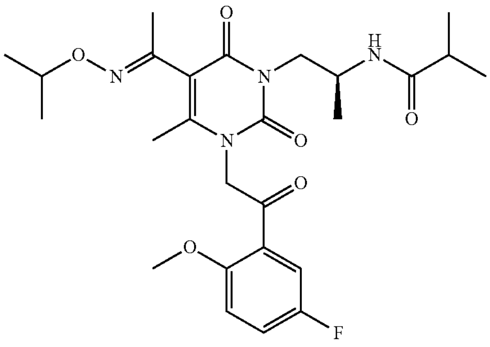 [SMILES: COc1ccc(F)cc1C(=O)Cn1c(C)c(/C(C)=N/OC(C)C)c(=O)n(C[C@H](C)NC(=O)C(C)C)c1=O] | m.p. 187-189° C. | |

TABLE 6-continued
| Compound number | Structural formula | Physical properties | Remarks |
|---|---|---|---|
| C-21 | 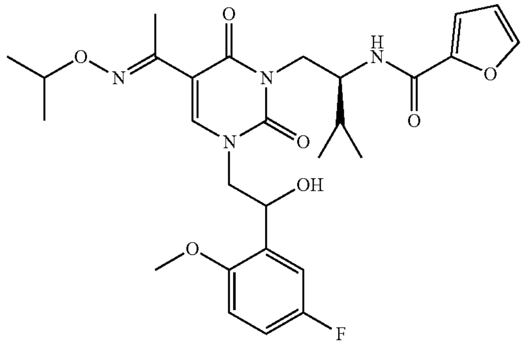 [SMILES: COc1ccc(F)cc1C(O)Cn1cc(/C(C)=N/OC(C)C)c(=O)n(C[C@@H](NC(=O)c2ccco2)C(C)C)c1=O] | m.p. 64-65° C. | |
| C-22 | 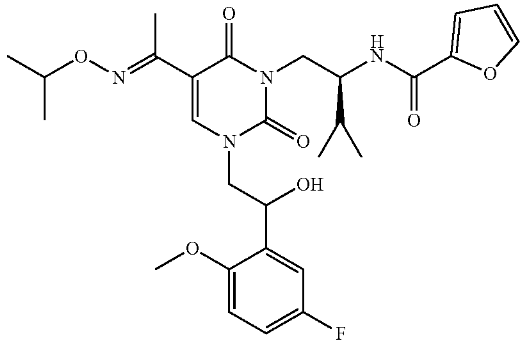 [SMILES: COc1ccc(F)cc1C(O)Cn1cc(/C(C)=N/OC(C)C)c(=O)n(C[C@@H](NC(=O)c2ccco2)C(C)C)c1=O] | m.p. 68-70° C. | Isomer of C-21 |
| C-23 | 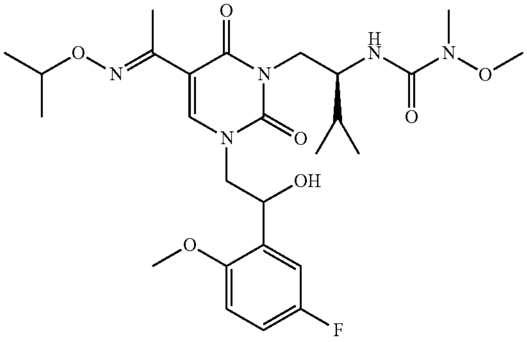 [SMILES: COc1ccc(F)cc1C(O)Cn1cc(/C(C)=N/OC(C)C)c(=O)n(C[C@@H](NC(=O)N(C)OC)C(C)C)c1=O] | m.p. 56-57° C. | |
| C-24 | 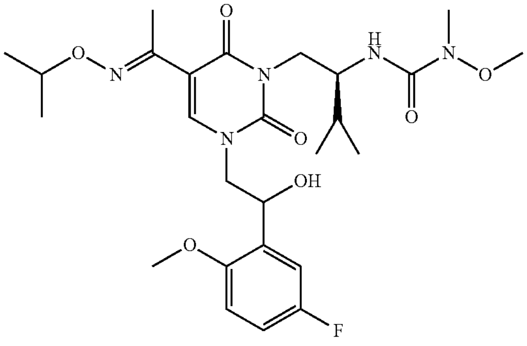 [SMILES: COc1ccc(F)cc1C(O)Cn1cc(/C(C)=N/OC(C)C)c(=O)n(C[C@@H](NC(=O)N(C)OC)C(C)C)c1=O] | m.p. 44-47° C. | Isomer of C-23 |

TABLE 6-continued
| Compound number | Structural formula | Physical properties | Remarks |
| --- | --- | --- | --- |
| C-25 | 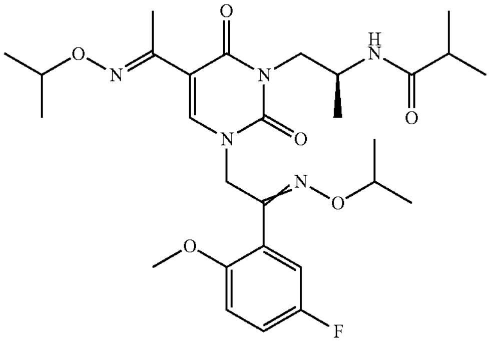 [SMILES: COc1ccc(F)cc1C(Cn1cc(/C(C)=N/OC(C)C)c(=O)n(C[C@H](C)NC(=O)C(C)C)c1=O)=NOC(C)C] | m.p. 146-147° C. | |
| C-26 | 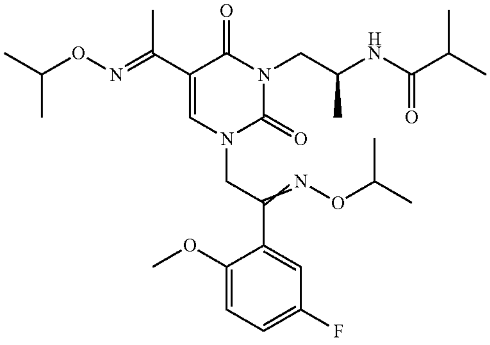 [SMILES: COc1ccc(F)cc1C(Cn1cc(/C(C)=N/OC(C)C)c(=O)n(C[C@H](C)NC(=O)C(C)C)c1=O)=NOC(C)C] | viscous oil | Isomer of C-25 |
| C-27 | 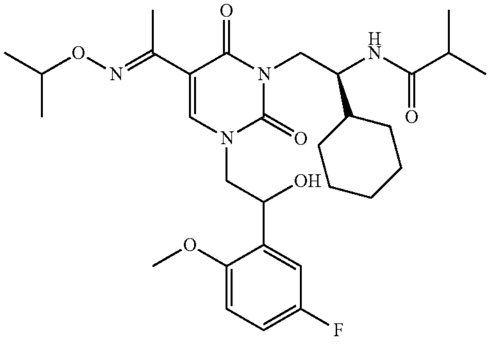 [SMILES: COc1ccc(F)cc1C(O)Cn1cc(/C(C)=N/OC(C)C)c(=O)n(C[C@@H](NC(=O)C(C)C)C2CCCCC2)c1=O] | m.p. 142-144° C. | |
| C-28 | 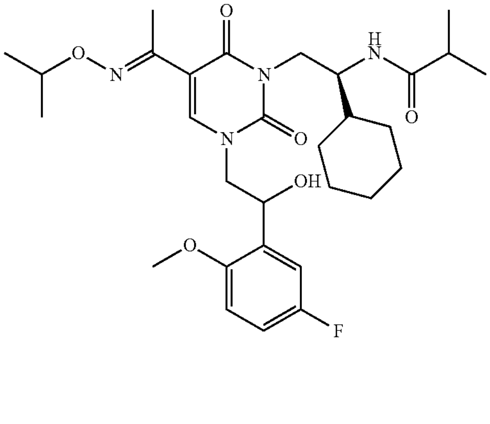 [SMILES: COc1ccc(F)cc1C(O)Cn1cc(/C(C)=N/OC(C)C)c(=O)n(C[C@@H](NC(=O)C(C)C)C2CCCCC2)c1=O] | m.p. 82-85° C. | Isomer of C-27 |

TABLE 6-continued
| Compound number | Structural formula | Physical properties | Remarks |
|---|---|---|---|
| C-29 | 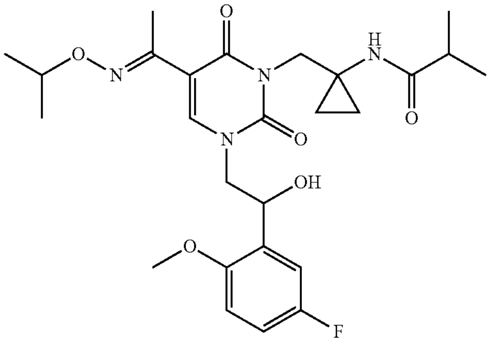 [SMILES: COc1ccc(F)cc1C(O)Cn1cc(/C(C)=N/OC(C)C)c(=O)n(CC2(NC(=O)C(C)C)CC2)c1=O] | m.p. 70-75° C. | |
| C-30 | 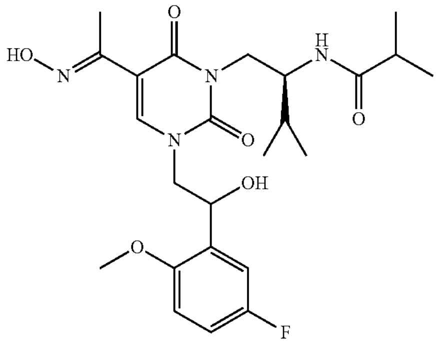 [SMILES: COc1ccc(F)cc1C(O)Cn1cc(/C(C)=N/O)c(=O)n(C[C@@H](NC(=O)C(C)C)C(C)C)c1=O] | m.p. 72-73° C. | |
| C-31 | 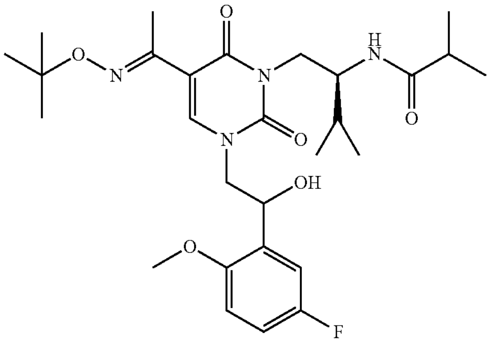 [SMILES: COc1ccc(F)cc1C(O)Cn1cc(/C(C)=N/OC(C)(C)C)c(=O)n(C[C@@H](NC(=O)C(C)C)C(C)C)c1=O] | m.p. 76-77° C. | |
| C-32 | 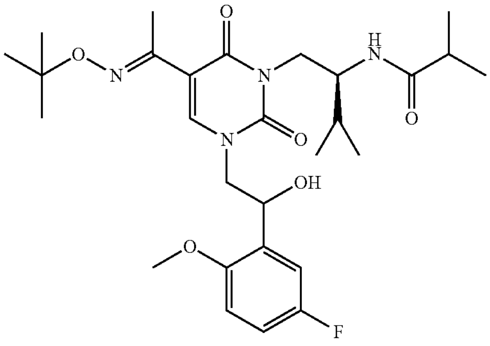 [SMILES: COc1ccc(F)cc1C(O)Cn1cc(/C(C)=N/OC(C)(C)C)c(=O)n(C[C@@H](NC(=O)C(C)C)C(C)C)c1=O] | m.p. 70-72° C. | Isomer of C-31 |

TABLE 6-continued
| Compound number | Structural formula | Physical properties | Remarks |
|---|---|---|---|
| C-33 | 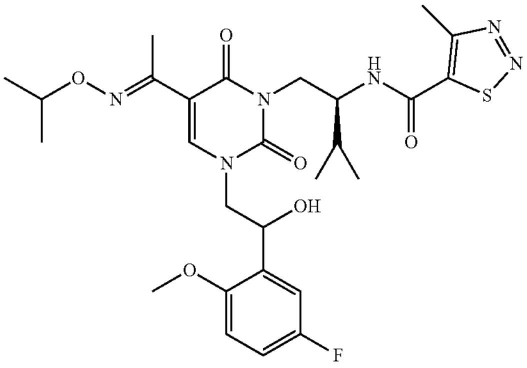 [SMILES: COc1ccc(F)cc1C(O)Cn1cc(/C(C)=N/OC(C)C)c(=O)n(C[C@@H](NC(=O)c2snnc2C)C(C)C)c1=O] | m.p. 76-77° C. | |
| C-34 | 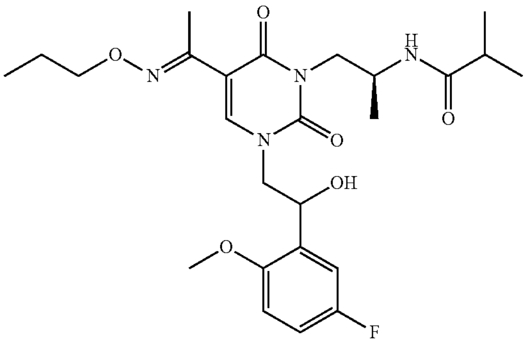 [SMILES: CCCO/N=C(\C)c1cn(CC(O)c2cc(F)ccc2OC)c(=O)n(C[C@H](C)NC(=O)C(C)C)c1=O] | m.p. 61-62° C. | |
| C-35 | 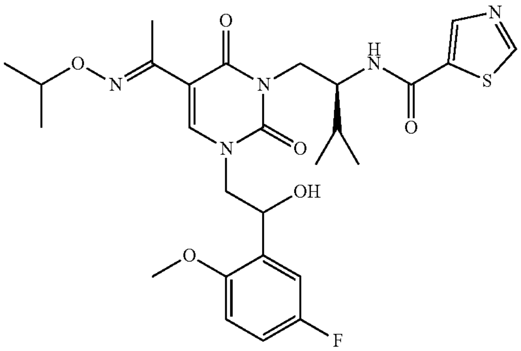 [SMILES: COc1ccc(F)cc1C(O)Cn1cc(/C(C)=N/OC(C)C)c(=O)n(C[C@@H](NC(=O)c2cncs2)C(C)C)c1=O] | m.p. 75-78° C. | |
| C-36 | 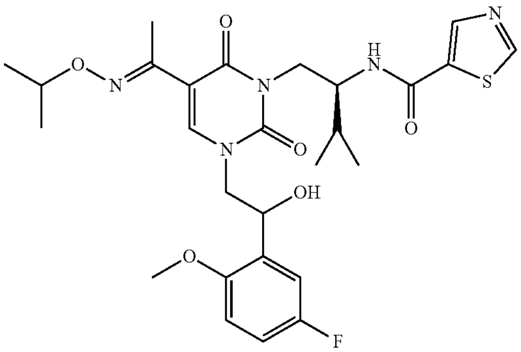 [SMILES: COc1ccc(F)cc1C(O)Cn1cc(/C(C)=N/OC(C)C)c(=O)n(C[C@@H](NC(=O)c2cncs2)C(C)C)c1=O] | m.p. 89-90° C. | Isomer of C-35 |

TABLE 6-continued
| Compound number | Structural formula | Physical properties | Remarks |
| --- | --- | --- | --- |
| C-37 | 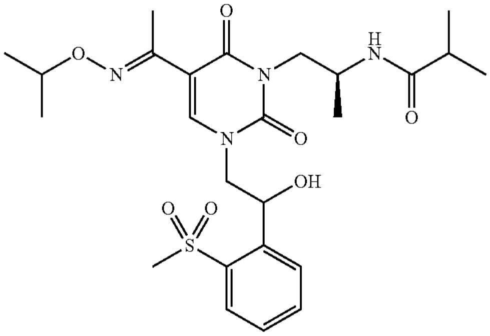 [SMILES: C/C(=N\OC(C)C)c1cn(CC(O)c2ccccc2S(C)(=O)=O)c(=O)n(C[C@H](C)NC(=O)C(C)C)c1=O] | viscous oil | |
| C-38 | 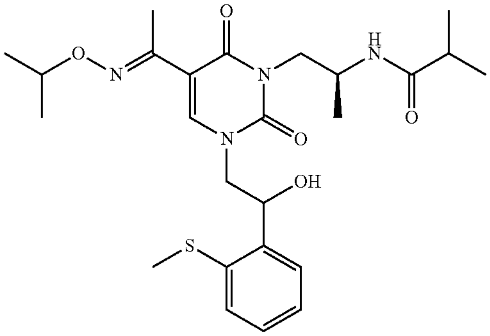 [SMILES: CSc1ccccc1C(O)Cn1cc(/C(C)=N/OC(C)C)c(=O)n(C[C@H](C)NC(=O)C(C)C)c1=O] | m.p. 109-111° C. | |
| C-39 | 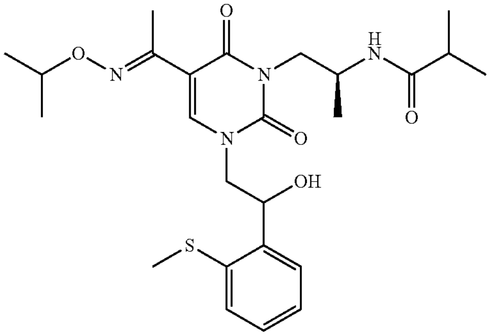 | m.p. 76-79° C. | Isomer of C-38 |
| C-40 | 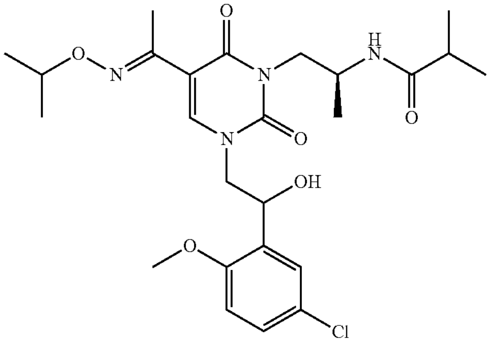 | amorphous | |

TABLE 6-continued
| Compound number | Structural formula | Physical properties | Remarks |
|---|---|---|---|
| C-41 | 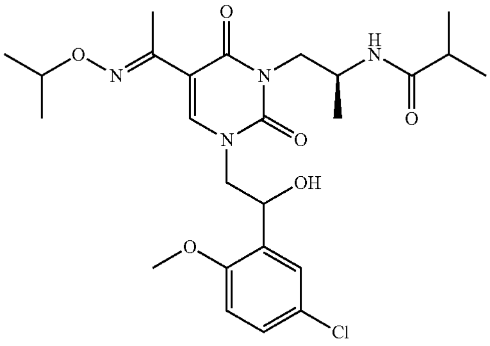 [SMILES: COc1ccc(Cl)cc1C(O)Cn1cc(/C(C)=N/OC(C)C)c(=O)n(C[C@H](C)NC(=O)C(C)C)c1=O] | m.p. 126-129° C. | Isomer of C-40 |
| C-42 | 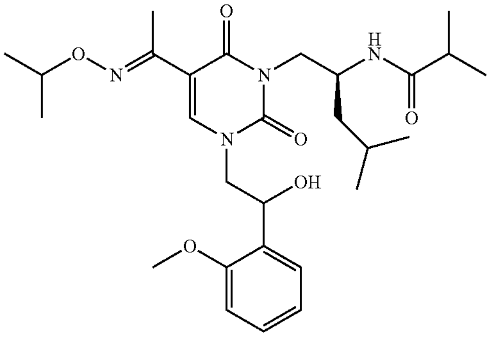 [SMILES: COc1ccccc1C(O)Cn1cc(/C(C)=N/OC(C)C)c(=O)n(C[C@H](CC(C)C)NC(=O)C(C)C)c1=O] | viscous oil | |
| C-43 | 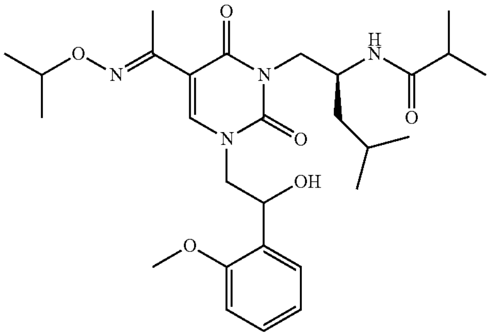 [SMILES: COc1ccccc1C(O)Cn1cc(/C(C)=N/OC(C)C)c(=O)n(C[C@H](CC(C)C)NC(=O)C(C)C)c1=O] | amorphous | Isomer of C-42 |
| C-44 | 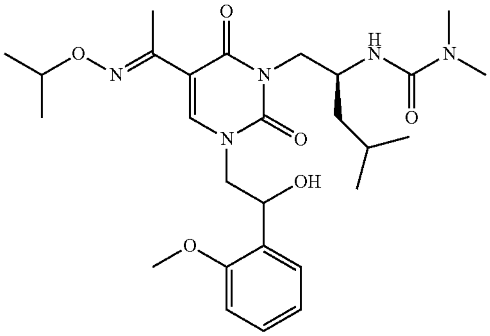 [SMILES: COc1ccccc1C(O)Cn1cc(/C(C)=N/OC(C)C)c(=O)n(C[C@H](CC(C)C)NC(=O)N(C)C)c1=O] | viscous oil | |

TABLE 6-continued
| Compound number | Structural formula | Physical properties | Remarks |
| --- | --- | --- | --- |
| C-45 | 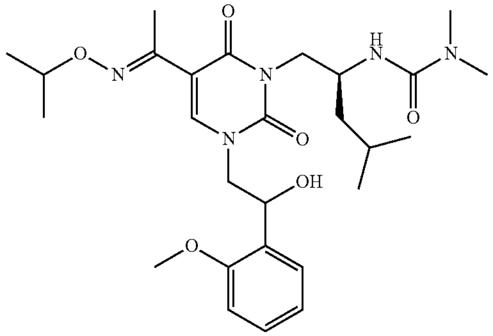 [SMILES: COc1ccccc1C(O)Cn1cc(/C(C)=N/OC(C)C)c(=O)n(C[C@H](CC(C)C)NC(=O)N(C)C)c1=O] | viscous oil | Isomer of C-44 |
| C-46 | 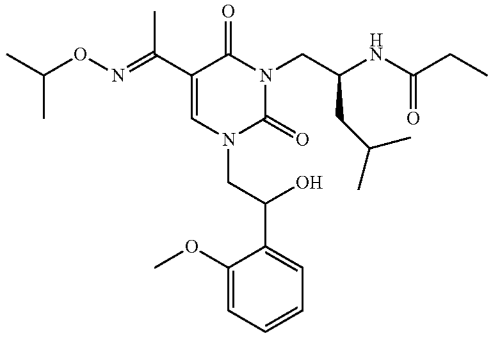 [SMILES: CCC(=O)N[C@@H](CC(C)C)Cn1c(=O)c(/C(C)=N/OC(C)C)cn(CC(O)c2ccccc2OC)c1=O] | amorphous | |
| C-47 | 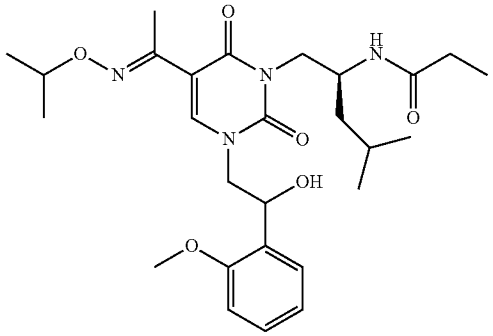 [SMILES: CCC(=O)N[C@@H](CC(C)C)Cn1c(=O)c(/C(C)=N/OC(C)C)cn(CC(O)c2ccccc2OC)c1=O] | m.p. 72-74° C. | Isomer of C-46 |
| C-48 | 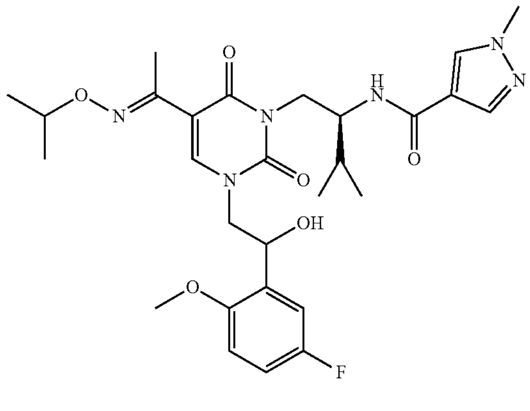 [SMILES: COc1ccc(F)cc1C(O)Cn1cc(/C(C)=N/OC(C)C)c(=O)n(C[C@@H](NC(=O)c2cnn(C)c2)C(C)C)c1=O] | m.p. 85-86° C. | |

TABLE 6-continued
| Compound number | Structural formula | Physical properties | Remarks |
|---|---|---|---|
| C-49 | 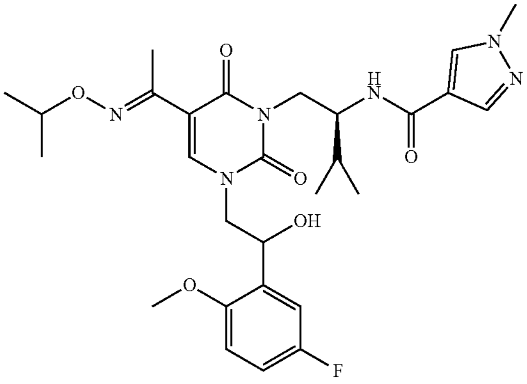 [SMILES: COc1ccc(F)cc1C(O)Cn1cc(/C(C)=N/OC(C)C)c(=O)n(C[C@@H](NC(=O)c2cnn(C)c2)C(C)C)c1=O] | m.p. 80-82° C. | Isomer of C-48 |
| C-50 | 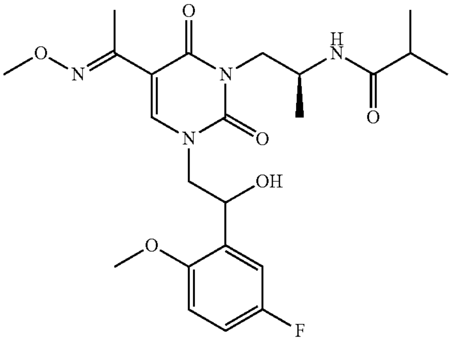 [SMILES: CO/N=C(\C)c1cn(CC(O)c2cc(F)ccc2OC)c(=O)n(C[C@H](C)NC(=O)C(C)C)c1=O] | m.p. 70-74° C. | |
| C-51 | 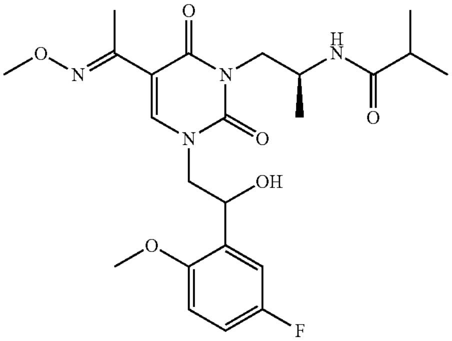 [SMILES: CO/N=C(\C)c1cn(CC(O)c2cc(F)ccc2OC)c(=O)n(C[C@H](C)NC(=O)C(C)C)c1=O] | m.p. 137-139° C. | Isomer of C-50 |
| C-52 | 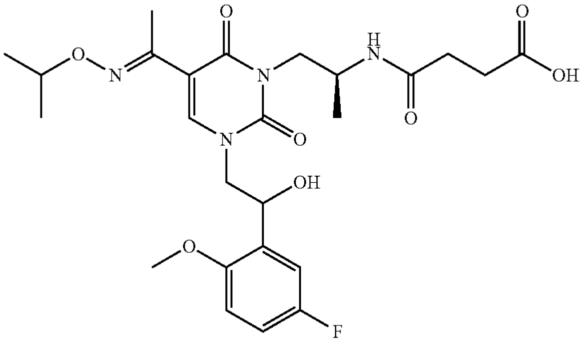 [SMILES: COc1ccc(F)cc1C(O)Cn1cc(/C(C)=N/OC(C)C)c(=O)n(C[C@H](C)NC(=O)CCC(=O)O)c1=O] | m.p. 178-179° C. | |

TABLE 6-continued
| Compound number | Structural formula | Physical properties | Remarks |
| --- | --- | --- | --- |
| C-53 | 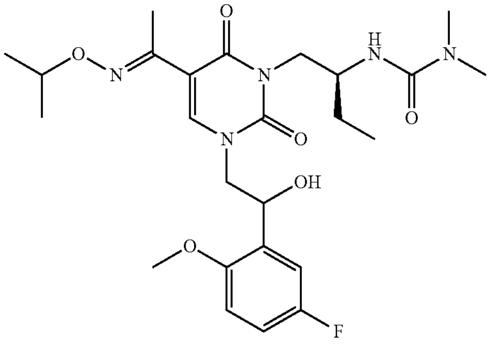 [SMILES: CC[C@@H](Cn1c(=O)c(/C(C)=N/OC(C)C)cn(CC(O)c2cc(F)ccc2OC)c1=O)NC(=O)N(C)C] | amorphous | |
| C-54 | 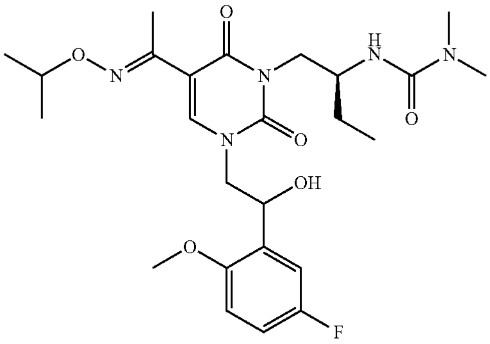 [SMILES: CC[C@@H](Cn1c(=O)c(/C(C)=N/OC(C)C)cn(CC(O)c2cc(F)ccc2OC)c1=O)NC(=O)N(C)C] | m.p. 83-85° C. | Isomer of C-53 |
| C-55 | 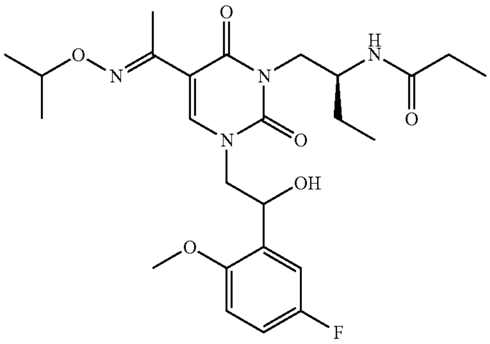 [SMILES: CCC(=O)N[C@@H](CC)Cn1c(=O)c(/C(C)=N/OC(C)C)cn(CC(O)c2cc(F)ccc2OC)c1=O] | viscous oil | |
| C-56 | 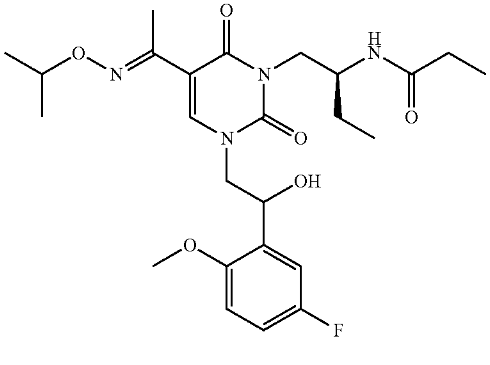 [SMILES: CCC(=O)N[C@@H](CC)Cn1c(=O)c(/C(C)=N/OC(C)C)cn(CC(O)c2cc(F)ccc2OC)c1=O] | m.p. 129-130° C. | Isomer of C-55 |

TABLE 6-continued
| Compound number | Structural formula | Physical properties | Remarks |
|---|---|---|---|
| C-57 | 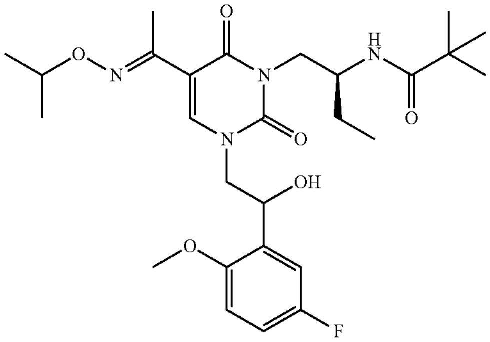 [SMILES: CC[C@@H](Cn1c(=O)c(/C(C)=N/OC(C)C)cn(CC(O)c2cc(F)ccc2OC)c1=O)NC(=O)C(C)(C)C] | m.p. 63-66° C. | |
| C-58 | 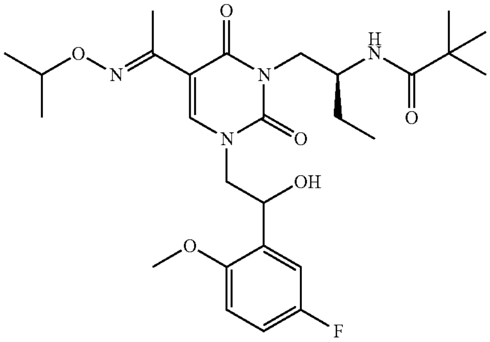 [SMILES: CC[C@@H](Cn1c(=O)c(/C(C)=N/OC(C)C)cn(CC(O)c2cc(F)ccc2OC)c1=O)NC(=O)C(C)(C)C] | m.p. 68-71° C. | Isomer of C-57 |
| C-59 | 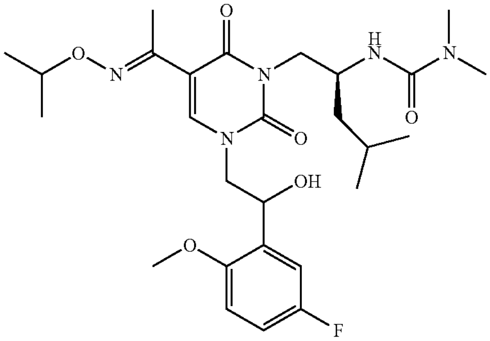 [SMILES: COc1ccc(F)cc1C(O)Cn1cc(/C(C)=N/OC(C)C)c(=O)n(C[C@H](CC(C)C)NC(=O)N(C)C)c1=O] | amorphous | |
| C-60 | 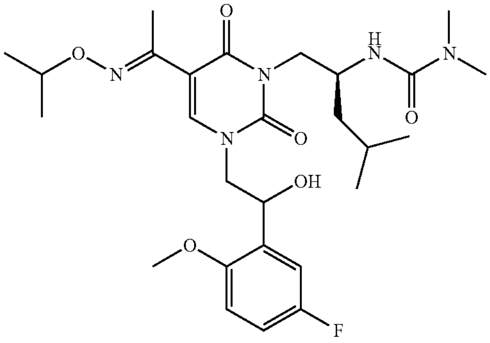 [SMILES: COc1ccc(F)cc1C(O)Cn1cc(/C(C)=N/OC(C)C)c(=O)n(C[C@H](CC(C)C)NC(=O)N(C)C)c1=O] | viscous oil | Isomer of C-59 |

TABLE 6-continued
| Compound number | Structural formula | Physical properties | Remarks |
|---|---|---|---|
| C-61 | 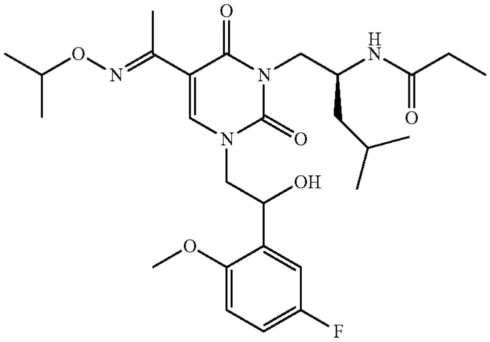 [SMILES: CCC(=O)N[C@@H](CC(C)C)Cn1c(=O)c(/C(C)=N/OC(C)C)cn(CC(O)c2cc(F)ccc2OC)c1=O] | amorphous | |
| C-62 | 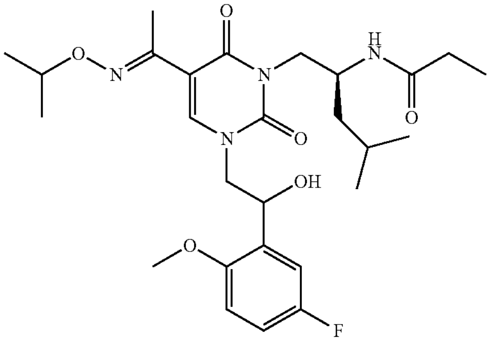 [SMILES: CCC(=O)N[C@@H](CC(C)C)Cn1c(=O)c(/C(C)=N/OC(C)C)cn(CC(O)c2cc(F)ccc2OC)c1=O] | m.p. 137-142° C. | Isomer of C-61 |
| C-63 | 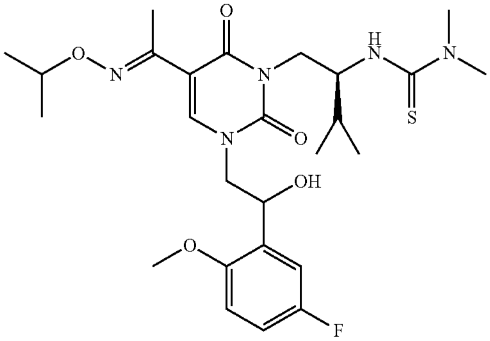 [SMILES: COc1ccc(F)cc1C(O)Cn1cc(/C(C)=N/OC(C)C)c(=O)n(C[C@@H](NC(=S)N(C)C)C(C)C)c1=O] | m.p. 56-57° C. | |
| C-64 | 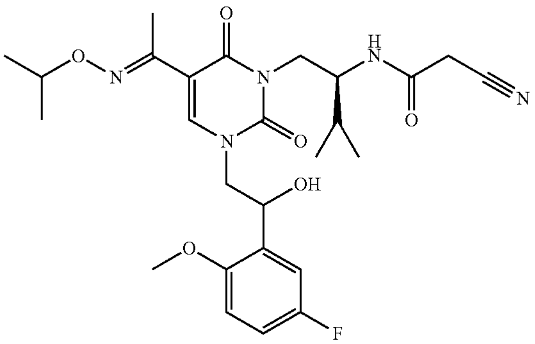 [SMILES: COc1ccc(F)cc1C(O)Cn1cc(/C(C)=N/OC(C)C)c(=O)n(C[C@@H](NC(=O)CC#N)C(C)C)c1=O] | m.p. 66-67° C. | |

TABLE 6-continued
| Compound number | Structural formula | Physical properties | Remarks |
|---|---|---|---|
| C-65 | 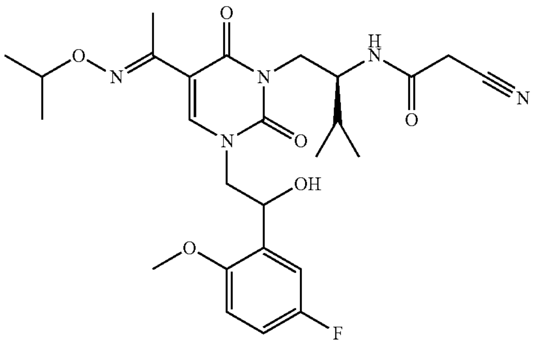 [SMILES: COc1ccc(F)cc1C(O)Cn1cc(/C(C)=N/OC(C)C)c(=O)n(C[C@@H](NC(=O)CC#N)C(C)C)c1=O] | m.p. 61-63° C. | Isomer of C-64 |
| C-66 | 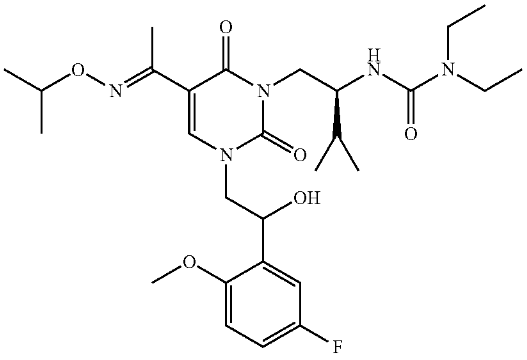 [SMILES: CCN(CC)C(=O)N[C@H](Cn1c(=O)c(/C(C)=N/OC(C)C)cn(CC(O)c2cc(F)ccc2OC)c1=O)C(C)C] | m.p. 70-78° C. | |
| C-67 | 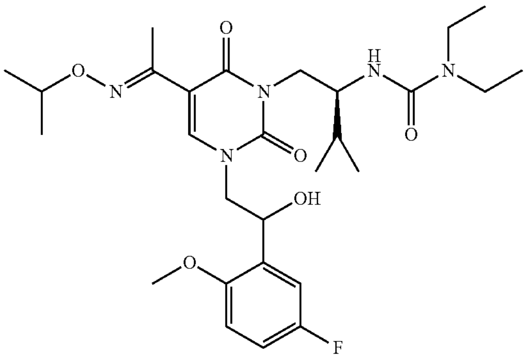 [SMILES: CCN(CC)C(=O)N[C@H](Cn1c(=O)c(/C(C)=N/OC(C)C)cn(CC(O)c2cc(F)ccc2OC)c1=O)C(C)C] | m.p. 105-106° C. | Isomer of C-66 |
| C-68 | 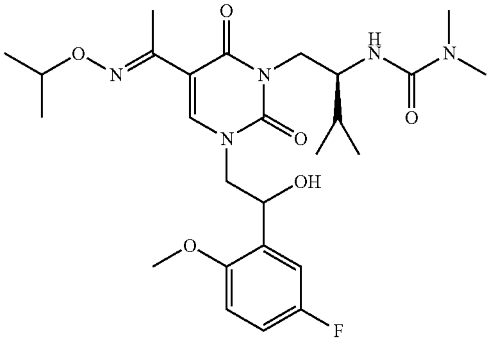 [SMILES: COc1ccc(F)cc1C(O)Cn1cc(/C(C)=N/OC(C)C)c(=O)n(C[C@@H](NC(=O)N(C)C)C(C)C)c1=O] | m.p. 80-81° C. | |

TABLE 6-continued
| Compound number | Structural formula | Physical properties | Remarks |
|---|---|---|---|
| C-69 | 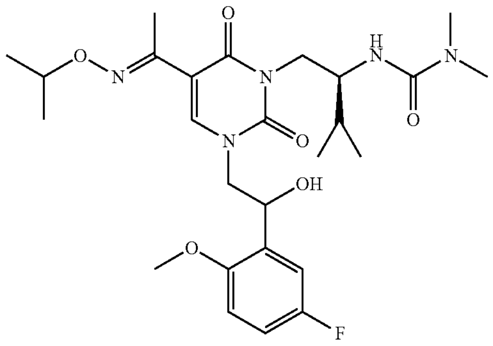 | m.p. 144-146° C. | Isomer of C-68 |
| C-70 | 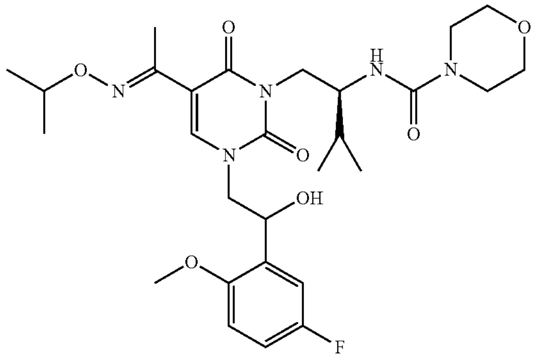 [SMILES: COc1ccc(F)cc1C(O)Cn1cc(/C(C)=N/OC(C)C)c(=O)n(C[C@@H](NC(=O)N2CCOCC2)C(C)C)c1=O] | m.p. 75-76° C. | |
| C-71 | 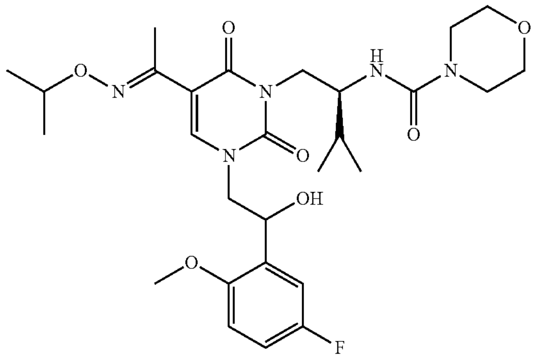 [SMILES: COc1ccc(F)cc1C(O)Cn1cc(/C(C)=N/OC(C)C)c(=O)n(C[C@@H](NC(=O)N2CCOCC2)C(C)C)c1=O] | m.p. 71-75° C. | Isomer of C-70 |
| C-72 | 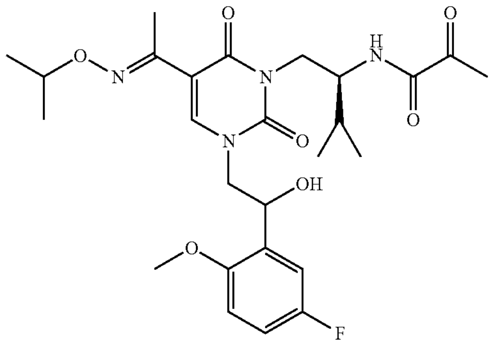 [SMILES: COc1ccc(F)cc1C(O)Cn1cc(/C(C)=N/OC(C)C)c(=O)n(C[C@@H](NC(=O)C(C)=O)C(C)C)c1=O] | m.p. 51-52° C. | |

TABLE 6-continued
| Compound number | Structural formula | Physical properties | Remarks |
|---|---|---|---|
| C-73 | 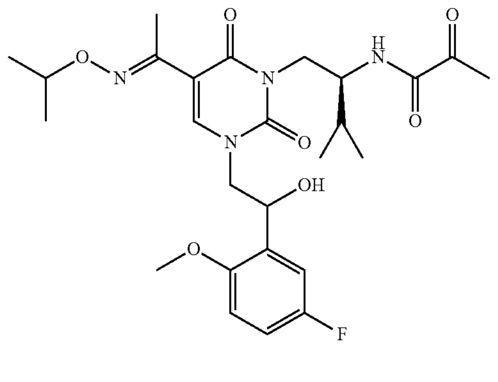 [SMILES: COc1ccc(F)cc1C(O)Cn1cc(/C(C)=N/OC(C)C)c(=O)n(C[C@@H](NC(=O)C(C)=O)C(C)C)c1=O] | m.p. 66-69° C. | Isomer of C-72 |
| C-74 | 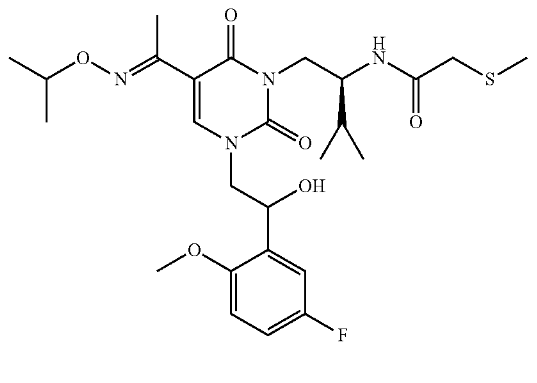 | m.p. 52-53° C. | |
| C-75 | 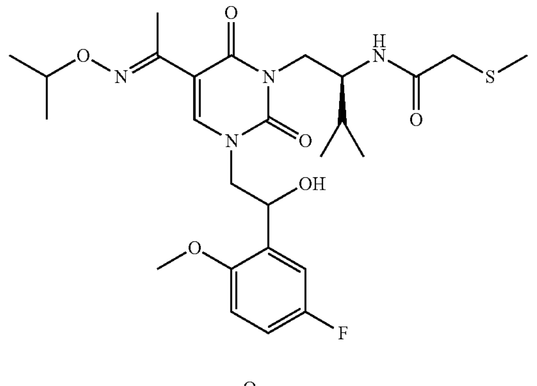 | m.p. 64-65° C. | Isomer of C-74 |
| C-76 | 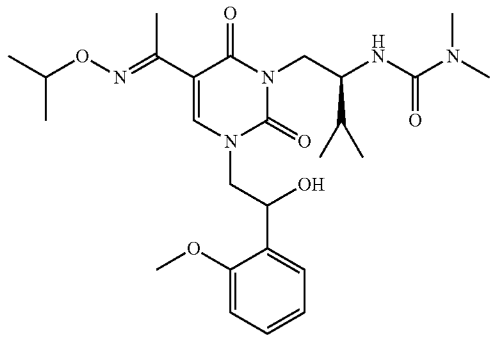 | viscous oil | |

TABLE 6-continued
| Compound number | Structural formula | Physical properties | Remarks |
|---|---|---|---|
| C-77 | 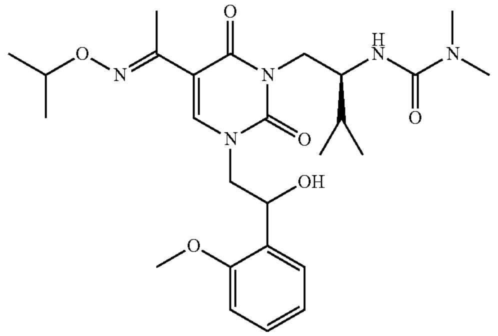 [SMILES: COc1ccccc1C(O)Cn1cc(/C(C)=N/OC(C)C)c(=O)n(C[C@@H](NC(=O)N(C)C)C(C)C)c1=O] | viscous oil | Isomer of C-76 |
| C-78 | 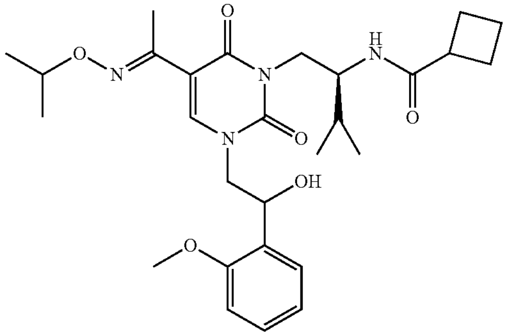 [SMILES: COc1ccccc1C(O)Cn1cc(/C(C)=N/OC(C)C)c(=O)n(C[C@@H](NC(=O)C2CCC2)C(C)C)c1=O] | amorphous | |
| C-79 | 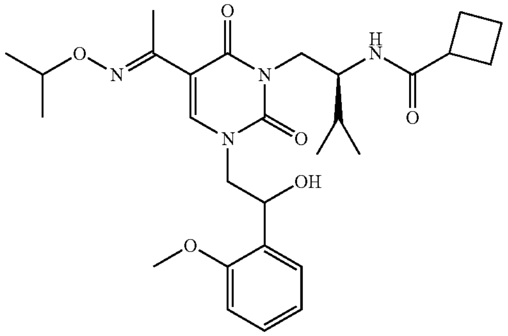 [SMILES: COc1ccccc1C(O)Cn1cc(/C(C)=N/OC(C)C)c(=O)n(C[C@@H](NC(=O)C2CCC2)C(C)C)c1=O] | m.p. 129-131° C. | Isomer of C-78 |
| C-80 | 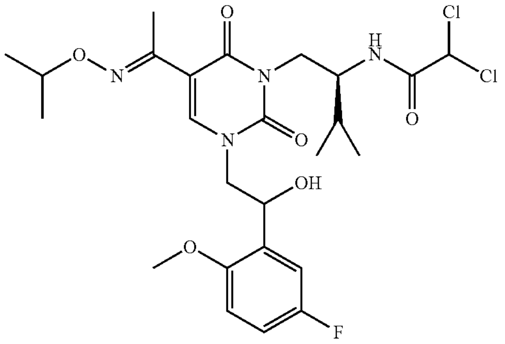 [SMILES: COc1ccc(F)cc1C(O)Cn1cc(/C(C)=N/OC(C)C)c(=O)n(C[C@@H](NC(=O)C(Cl)Cl)C(C)C)c1=O] | m.p. 60-63° C. | |

TABLE 6-continued
| Compound number | Structural formula | Physical properties | Remarks |
|---|---|---|---|
| C-81 | 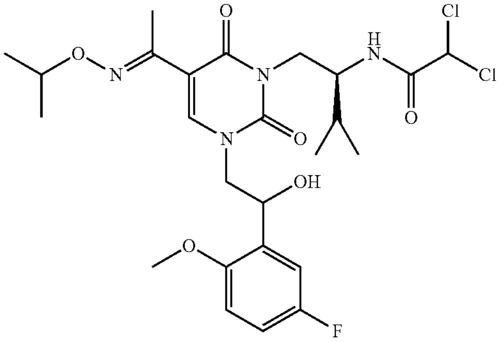 [SMILES: COc1ccc(F)cc1C(O)Cn1cc(/C(C)=N/OC(C)C)c(=O)n(C[C@@H](NC(=O)C(Cl)Cl)C(C)C)c1=O] | m.p. 64-67° C. | Isomer of C-80 |
| C-82 | 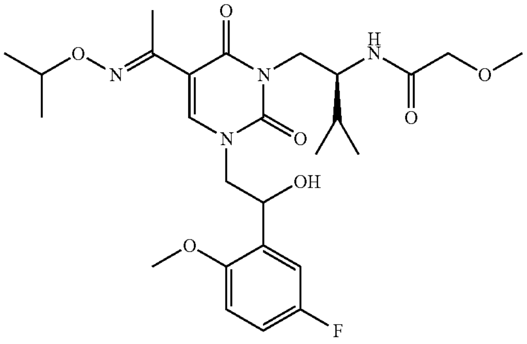 [SMILES: COCC(=O)N[C@H](Cn1c(=O)c(/C(C)=N/OC(C)C)cn(CC(O)c2cc(F)ccc2OC)c1=O)C(C)C] | m.p. 59-60° C. | |
| C-83 | 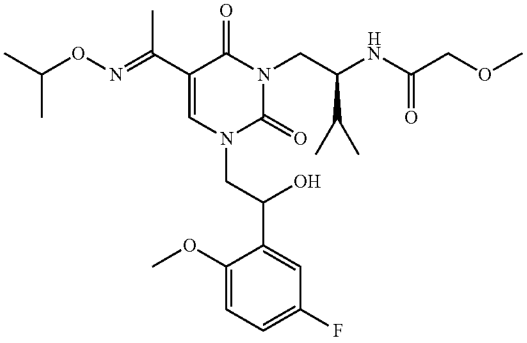 [SMILES: COCC(=O)N[C@H](Cn1c(=O)c(/C(C)=N/OC(C)C)cn(CC(O)c2cc(F)ccc2OC)c1=O)C(C)C] | m.p. 55-57° C. | Isomer of C-82 |
| C-84 | 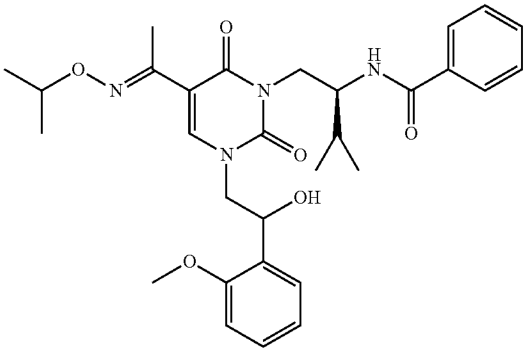 [SMILES: COc1ccccc1C(O)Cn1cc(/C(C)=N/OC(C)C)c(=O)n(C[C@@H](NC(=O)c2ccccc2)C(C)C)c1=O] | m.p. 160-162° C. | |

TABLE 6-continued
| Compound number | Structural formula | Physical properties | Remarks |
|---|---|---|---|
| C-85 | 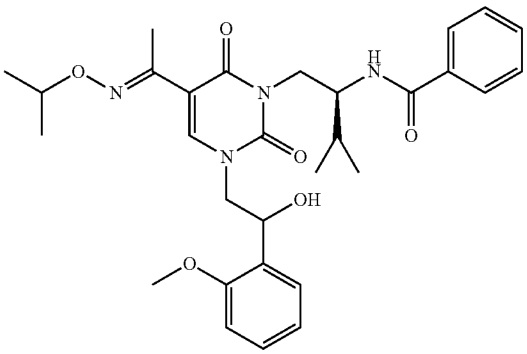 [SMILES: COc1ccccc1C(O)Cn1cc(/C(C)=N/OC(C)C)c(=O)n(C[C@@H](NC(=O)c2ccccc2)C(C)C)c1=O] | viscous oil | Isomer of C-84 |
| C-86 | 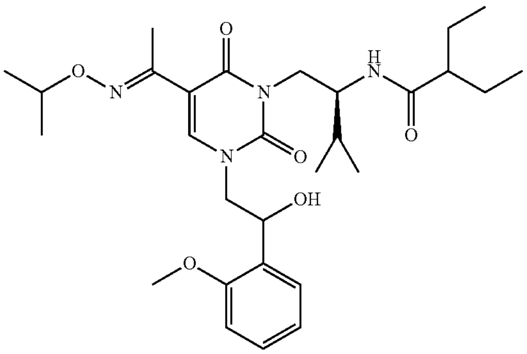 [SMILES: CCC(CC)C(=O)N[C@H](Cn1c(=O)c(/C(C)=N/OC(C)C)cn(CC(O)c2ccccc2OC)c1=O)C(C)C] | m.p. 165-167° C. | |
| C-87 | 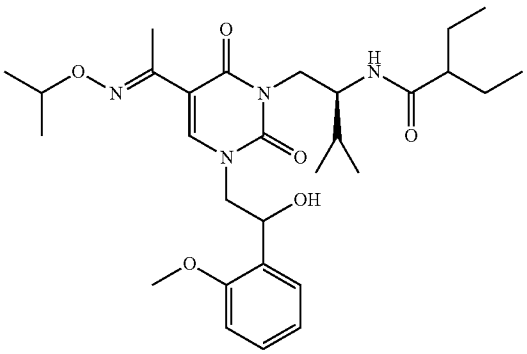 [SMILES: CCC(CC)C(=O)N[C@H](Cn1c(=O)c(/C(C)=N/OC(C)C)cn(CC(O)c2ccccc2OC)c1=O)C(C)C] | amorphous | Isomer of C-86 |
| C-88 | 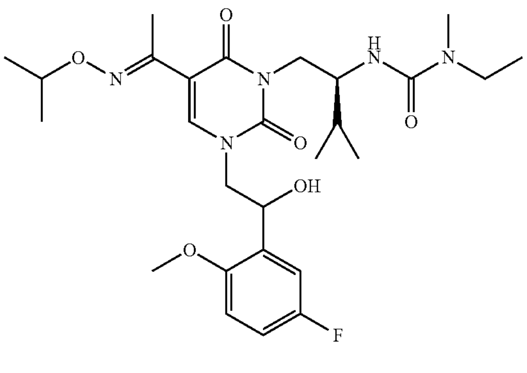 [SMILES: CCN(C)C(=O)N[C@H](Cn1c(=O)c(/C(C)=N/OC(C)C)cn(CC(O)c2cc(F)ccc2OC)c1=O)C(C)C] | m.p. 60-63° C. | |

TABLE 6-continued
| Compound number | Structural formula | Physical properties | Remarks |
|---|---|---|---|
| C-89 | 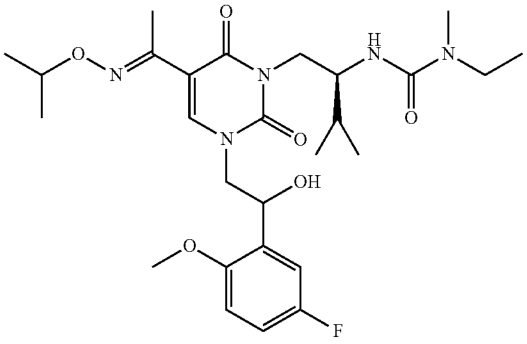 [SMILES: CCN(C)C(=O)N[C@H](Cn1c(=O)c(/C(C)=N/OC(C)C)cn(CC(O)c2cc(F)ccc2OC)c1=O)C(C)C] | m.p. 126-130° C. | Isomer of C-88 |
| C-90 | 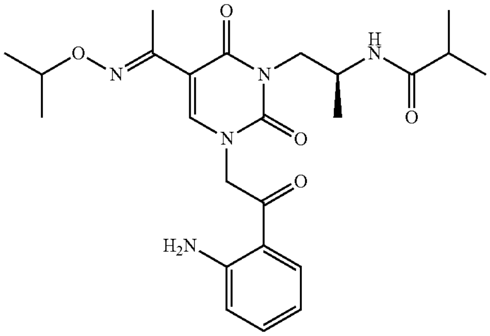 [SMILES: C/C(=N\OC(C)C)c1cn(CC(=O)c2ccccc2N)c(=O)n(C[C@H](C)NC(=O)C(C)C)c1=O] | m.p. 91-96° C. | |
| C-91 | 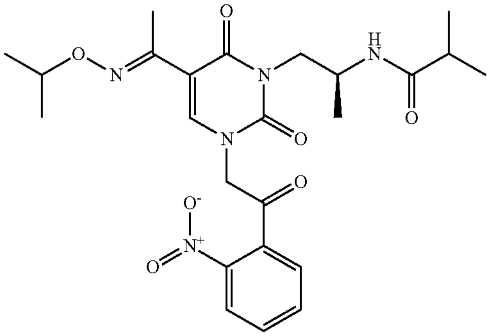 [SMILES: C/C(=N\OC(C)C)c1cn(CC(=O)c2ccccc2[N+](=O)[O-])c(=O)n(C[C@H](C)NC(=O)C(C)C)c1=O] | m.p. 202-203° C. | |
| C-92 | 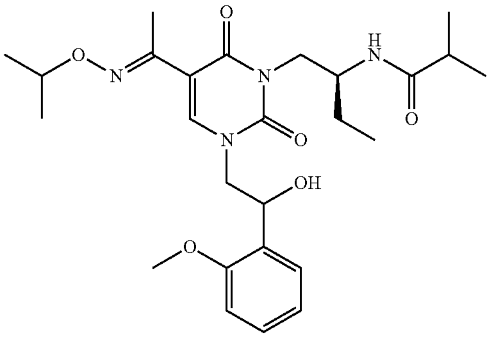 [SMILES: CC[C@@H](Cn1c(=O)c(/C(C)=N/OC(C)C)cn(CC(O)c2ccccc2OC)c1=O)NC(=O)C(C)C] | m.p. 121-122° C. | |

TABLE 6-continued
| Compound number | Structural formula | Physical properties | Remarks |
|---|---|---|---|
| C-93 | 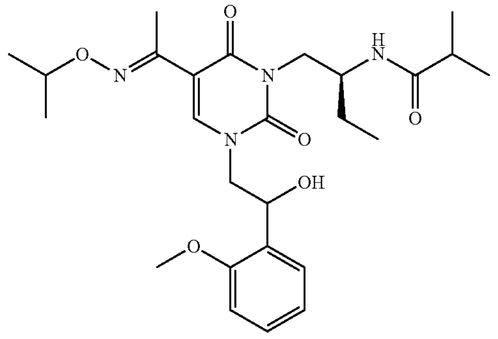 [SMILES: CC[C@@H](Cn1c(=O)c(/C(C)=N/OC(C)C)cn(CC(O)c2ccccc2OC)c1=O)NC(=O)C(C)C] | m.p. 130-131° C. | Isomer of C-92 |
| C-94 | 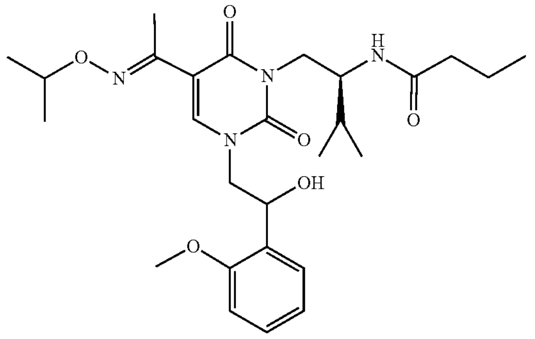 [SMILES: CCCC(=O)N[C@H](Cn1c(=O)c(/C(C)=N/OC(C)C)cn(CC(O)c2ccccc2OC)c1=O)C(C)C] | viscous oil | |
| C-95 | 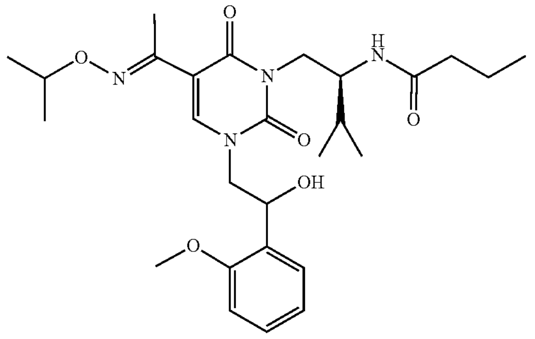 [SMILES: CCCC(=O)N[C@H](Cn1c(=O)c(/C(C)=N/OC(C)C)cn(CC(O)c2ccccc2OC)c1=O)C(C)C] | viscous oil | Isomer of C-94 |
| C-96 | 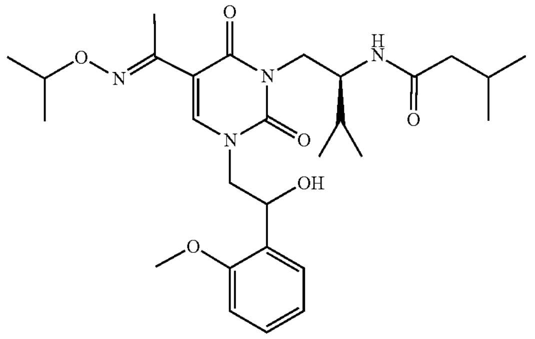 [SMILES: COc1ccccc1C(O)Cn1cc(/C(C)=N/OC(C)C)c(=O)n(C[C@@H](NC(=O)CC(C)C)C(C)C)c1=O] | m.p. 133-135° C. | |

TABLE 6-continued
| Compound number | Structural formula | Physical properties | Remarks |
| --- | --- | --- | --- |
| C-97 | 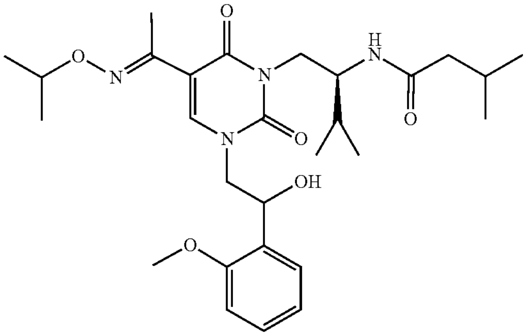 [SMILES: COc1ccccc1C(O)Cn1cc(/C(C)=N/OC(C)C)c(=O)n(C[C@@H](NC(=O)CC(C)C)C(C)C)c1=O] | amorphous | Isomer of C-96 |
| C-98 | 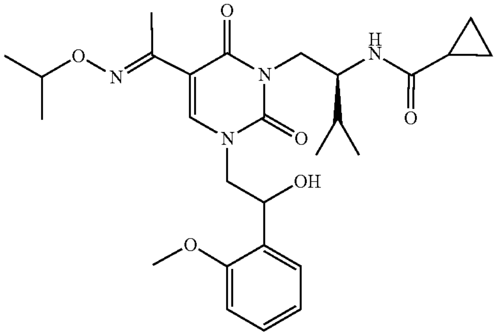 [SMILES: COc1ccccc1C(O)Cn1cc(/C(C)=N/OC(C)C)c(=O)n(C[C@@H](NC(=O)C2CC2)C(C)C)c1=O] | m.p. 139-141° C. | |
| C-99 | 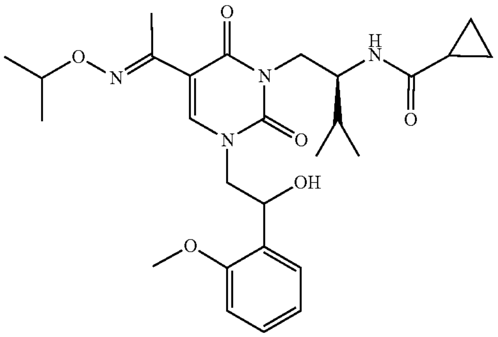 [SMILES: COc1ccccc1C(O)Cn1cc(/C(C)=N/OC(C)C)c(=O)n(C[C@@H](NC(=O)C2CC2)C(C)C)c1=O] | m.p. 132-134° C. | Isomer of C-98 |
| C-100 | 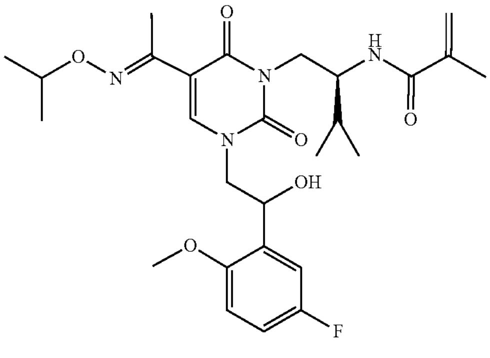 [SMILES: C=C(C)C(=O)N[C@H](Cn1c(=O)c(/C(C)=N/OC(C)C)cn(CC(O)c2cc(F)ccc2OC)c1=O)C(C)C] | m.p. 70-72° C. | |

TABLE 6-continued
| Compound number | Structural formula | Physical properties | Remarks |
|---|---|---|---|
| C-101 | 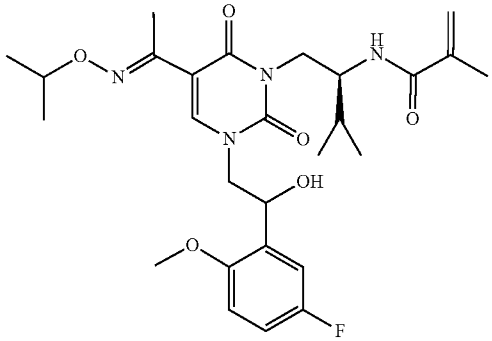 [SMILES: C=C(C)C(=O)N[C@H](Cn1c(=O)c(/C(C)=N/OC(C)C)cn(CC(O)c2cc(F)ccc2OC)c1=O)C(C)C] | m.p. 129-130° C. | Isomer of C-100 |
| C-102 | 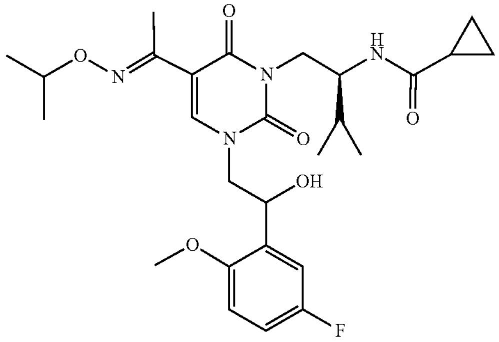 [SMILES: COc1ccc(F)cc1C(O)Cn1cc(/C(C)=N/OC(C)C)c(=O)n(C[C@@H](NC(=O)C2CC2)C(C)C)c1=O] | m.p. 82-83° C. | |
| C-103 | 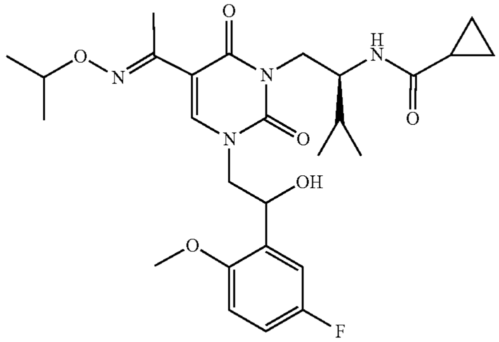 [SMILES: COc1ccc(F)cc1C(O)Cn1cc(/C(C)=N/OC(C)C)c(=O)n(C[C@@H](NC(=O)C2CC2)C(C)C)c1=O] | m.p. 84-86° C. | Isomer of C-102 |
| C-104 | 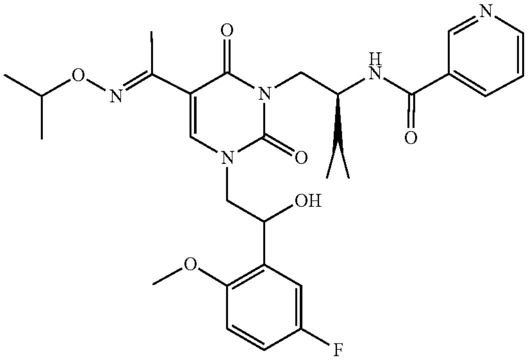 [SMILES: COc1ccc(F)cc1C(O)Cn1cc(/C(C)=N/OC(C)C)c(=O)n(C[C@@H](NC(=O)c2cccnc2)C(C)C)c1=O] | m.p. 77-79° C. | |

TABLE 6-continued
| Compound number | Structural formula | Physical properties | Remarks |
|---|---|---|---|
| C-105 | 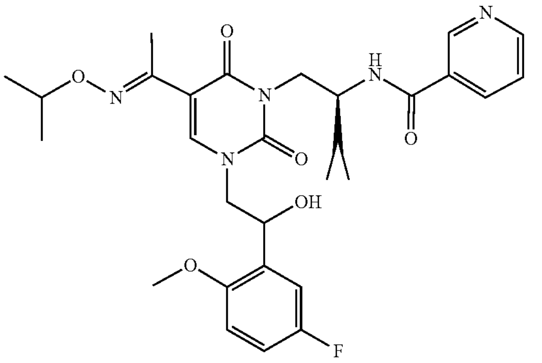 [SMILES: COc1ccc(F)cc1C(O)Cn1cc(/C(C)=N/OC(C)C)c(=O)n(C[C@@H](NC(=O)c2cccnc2)C(C)C)c1=O] | m.p. 77-78° C. | Isomer of C-104 |
| C-106 | 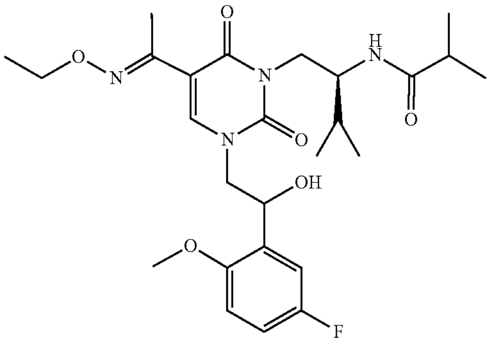 [SMILES: CCO/N=C(\C)c1cn(CC(O)c2cc(F)ccc2OC)c(=O)n(C[C@@H](NC(=O)C(C)C)C(C)C)c1=O] | m.p. 71-73° C. | |
| C-107 | 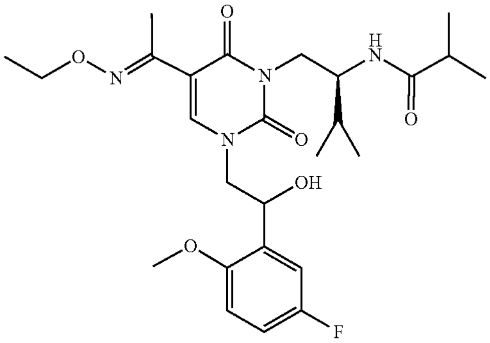 [SMILES: CCO/N=C(\C)c1cn(CC(O)c2cc(F)ccc2OC)c(=O)n(C[C@@H](NC(=O)C(C)C)C(C)C)c1=O] | m.p. 67-68° C. | Isomer of C-106 |
| C-108 | 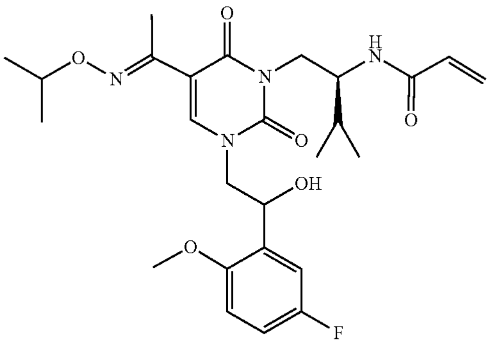 [SMILES: C=CC(=O)N[C@H](Cn1c(=O)c(/C(C)=N/OC(C)C)cn(CC(O)c2cc(F)ccc2OC)c1=O)C(C)C] | m.p. 85-86° C. | |

TABLE 6-continued
| Compound number | Structural formula | Physical properties | Remarks |
| --- | --- | --- | --- |
| C-109 | 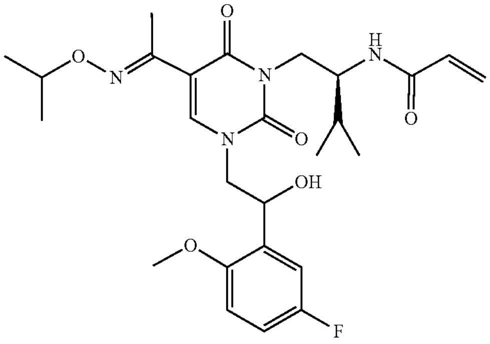 [SMILES: C=CC(=O)N[C@H](Cn1c(=O)c(/C(C)=N/OC(C)C)cn(CC(O)c2cc(F)ccc2OC)c1=O)C(C)C] | m.p. 88-89° C. | Isomer of C-108 |
| C-110 | 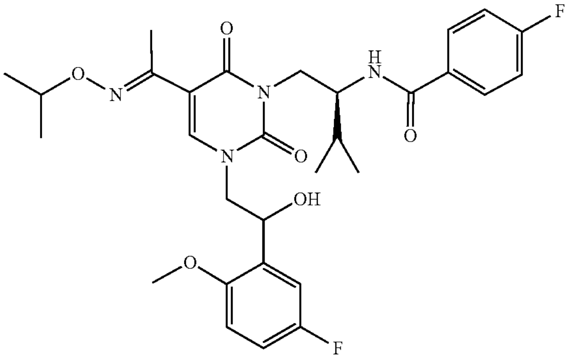 [SMILES: COc1ccc(F)cc1C(O)Cn1cc(/C(C)=N/OC(C)C)c(=O)n(C[C@@H](NC(=O)c2ccc(F)cc2)C(C)C)c1=O] | m.p. 75-76° C. | |
| C-111 | 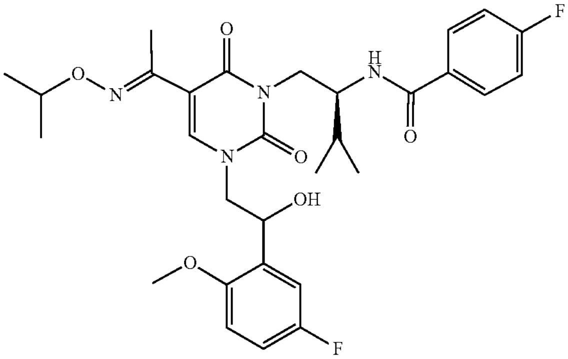 [SMILES: COc1ccc(F)cc1C(O)Cn1cc(/C(C)=N/OC(C)C)c(=O)n(C[C@@H](NC(=O)c2ccc(F)cc2)C(C)C)c1=O] | m.p. 80-81° C. | Isomer of C-110 |
| C-112 | 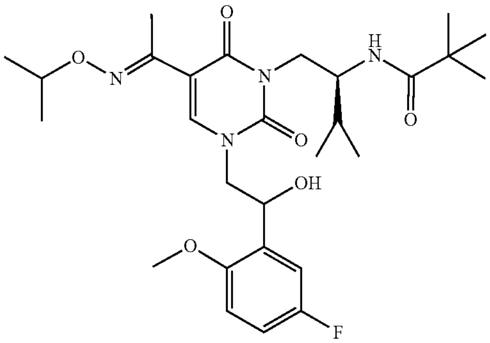 [SMILES: COc1ccc(F)cc1C(O)Cn1cc(/C(C)=N/OC(C)C)c(=O)n(C[C@@H](NC(=O)C(C)(C)C)C(C)C)c1=O] | m.p. 69-70° C. | |

TABLE 6-continued
| Compound number | Structural formula | Physical properties | Remarks |
|---|---|---|---|
| C-113 | 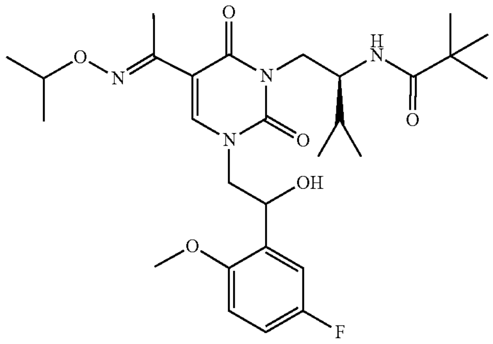 [SMILES: COc1ccc(F)cc1C(O)Cn1cc(/C(C)=N/OC(C)C)c(=O)n(C[C@@H](NC(=O)C(C)(C)C)C(C)C)c1=O] | m.p. 70-73° C. | Isomer of C-112 |
| C-114 | 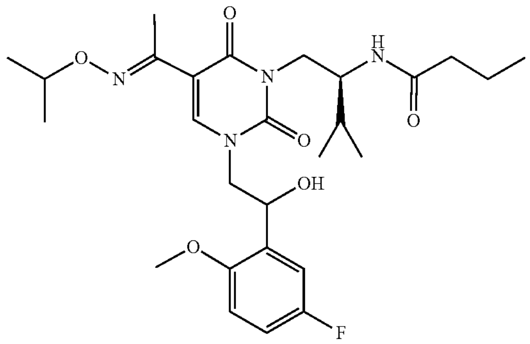 [SMILES: CCCC(=O)N[C@H](Cn1c(=O)c(/C(C)=N/OC(C)C)cn(CC(O)c2cc(F)ccc2OC)c1=O)C(C)C] | m.p. 56-57° C. | |
| C-115 | 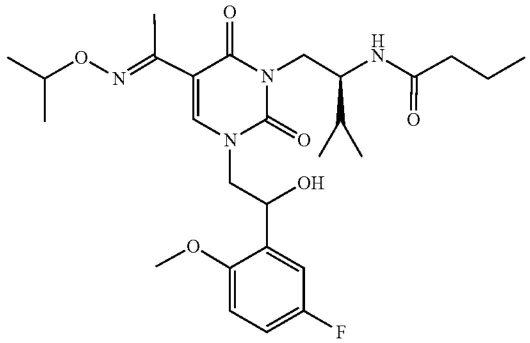 [SMILES: CCCC(=O)N[C@H](Cn1c(=O)c(/C(C)=N/OC(C)C)cn(CC(O)c2cc(F)ccc2OC)c1=O)C(C)C] | m.p. 128-129° C. | Isomer of C-114 |
| C-116 | 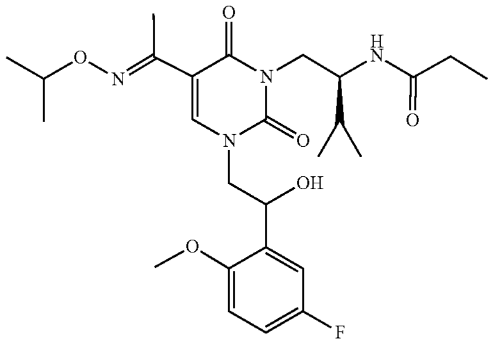 [SMILES: CCC(=O)N[C@H](Cn1c(=O)c(/C(C)=N/OC(C)C)cn(CC(O)c2cc(F)ccc2OC)c1=O)C(C)C] | m.p. 62-63° C. | |

TABLE 6-continued
| Compound number | Structural formula | Physical properties | Remarks |
|---|---|---|---|
| C-117 | 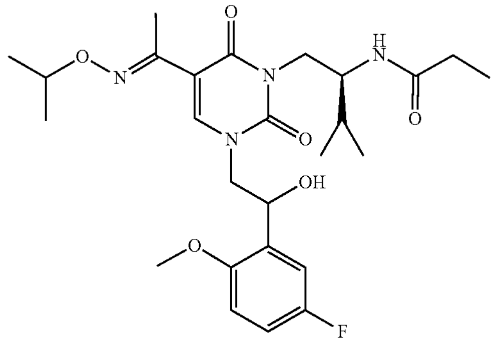 [SMILES: CCC(=O)N[C@H](Cn1c(=O)c(/C(C)=N/OC(C)C)cn(CC(O)c2cc(F)ccc2OC)c1=O)C(C)C] | m.p. 76-77° C. | Isomer of C-116 |
| C-118 | 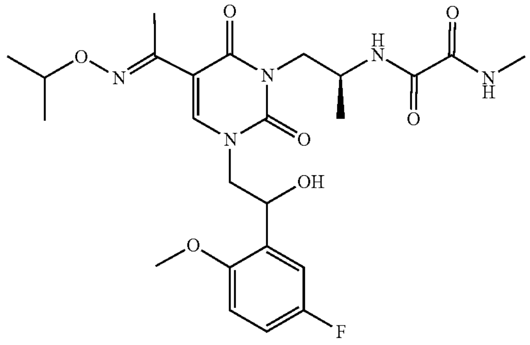 [SMILES: CNC(=O)C(=O)N[C@@H](C)Cn1c(=O)c(/C(C)=N/OC(C)C)cn(CC(O)c2cc(F)ccc2OC)c1=O] | m.p. 91-92° C. | |
| C-119 | 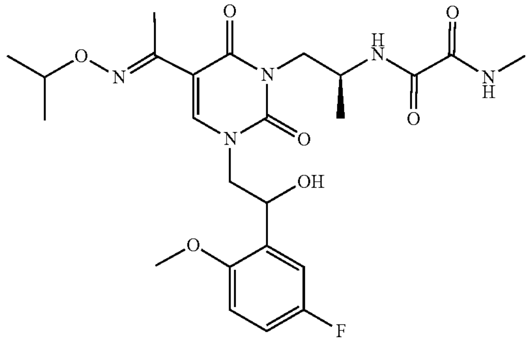 [SMILES: CNC(=O)C(=O)N[C@@H](C)Cn1c(=O)c(/C(C)=N/OC(C)C)cn(CC(O)c2cc(F)ccc2OC)c1=O] | m.p. 171-172° C. | |
| C-120 | 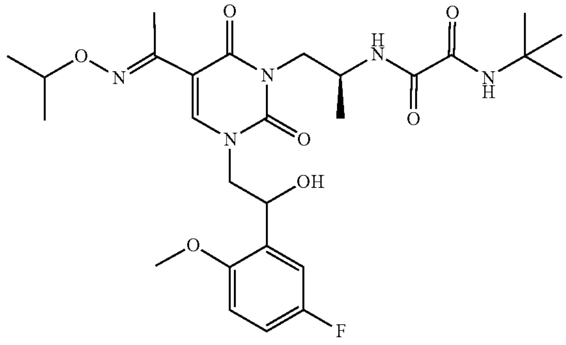 [SMILES: COc1ccc(F)cc1C(O)Cn1cc(/C(C)=N/OC(C)C)c(=O)n(C[C@H](C)NC(=O)C(=O)NC(C)(C)C)c1=O] | m.p. 72-73° C. | |

TABLE 6-continued
| Compound number | Structural formula | Physical properties | Remarks |
|---|---|---|---|
| C-121 | 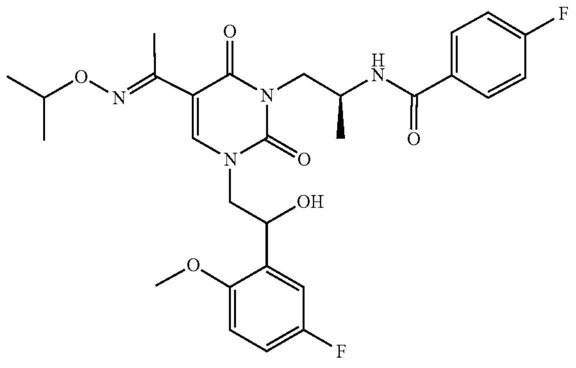 [SMILES: COc1ccc(F)cc1C(O)Cn1cc(/C(C)=N/OC(C)C)c(=O)n(C[C@H](C)NC(=O)c2ccc(F)cc2)c1=O] | m.p. 73-75° C. | |
| C-122 | 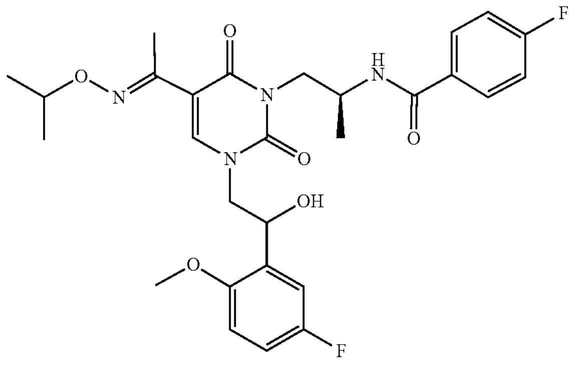 [SMILES: COc1ccc(F)cc1C(O)Cn1cc(/C(C)=N/OC(C)C)c(=O)n(C[C@H](C)NC(=O)c2ccc(F)cc2)c1=O] | m.p. 92-93° C. | Isomer of C-121 |
| C-123 | 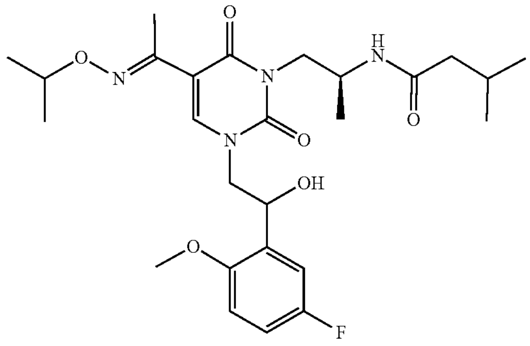 [SMILES: COc1ccc(F)cc1C(O)Cn1cc(/C(C)=N/OC(C)C)c(=O)n(C[C@H](C)NC(=O)CC(C)C)c1=O] | m.p. 65-68° C. | |
| C-124 | 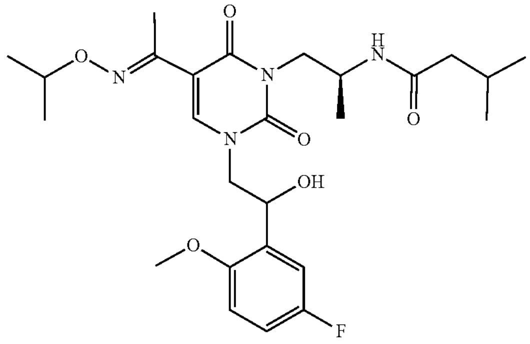 [SMILES: COc1ccc(F)cc1C(O)Cn1cc(/C(C)=N/OC(C)C)c(=O)n(C[C@H](C)NC(=O)CC(C)C)c1=O] | m.p. 69-71° C. | Isomer of C-123 |

TABLE 6-continued
| Compound number | Structural formula | Physical properties | Remarks |
|---|---|---|---|
| C-125 | 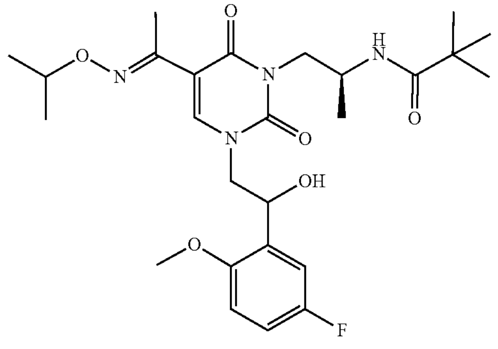 [SMILES: COc1ccc(F)cc1C(O)Cn1cc(/C(C)=N/OC(C)C)c(=O)n(C[C@H](C)NC(=O)C(C)(C)C)c1=O] | m.p. 81-82° C. | |
| C-126 | 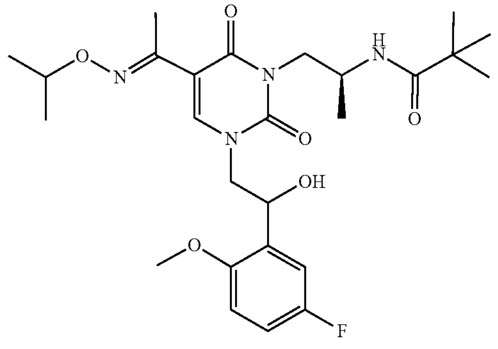 [SMILES: COc1ccc(F)cc1C(O)Cn1cc(/C(C)=N/OC(C)C)c(=O)n(C[C@H](C)NC(=O)C(C)(C)C)c1=O] | m.p. 83-84° C. | Isomer of C-125 |
| C-127 | 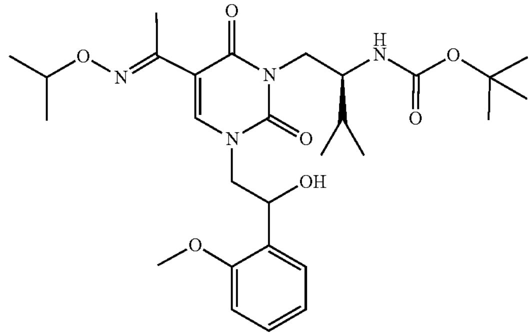 [SMILES: COc1ccccc1C(O)Cn1cc(/C(C)=N/OC(C)C)c(=O)n(C[C@@H](NC(=O)OC(C)(C)C)C(C)C)c1=O] | amorphous | |
| C-128 | 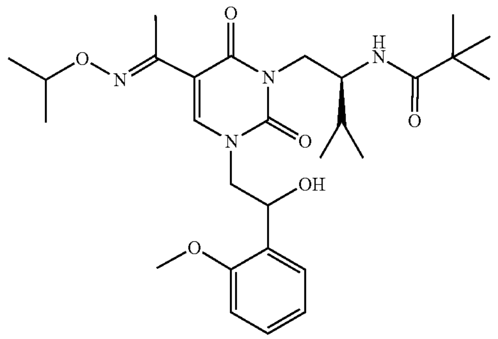 [SMILES: COc1ccccc1C(O)Cn1cc(/C(C)=N/OC(C)C)c(=O)n(C[C@@H](NC(=O)C(C)(C)C)C(C)C)c1=O] | viscous oil | |

TABLE 6-continued
| Compound number | Structural formula | Physical properties | Remarks |
|---|---|---|---|
| C-129 | 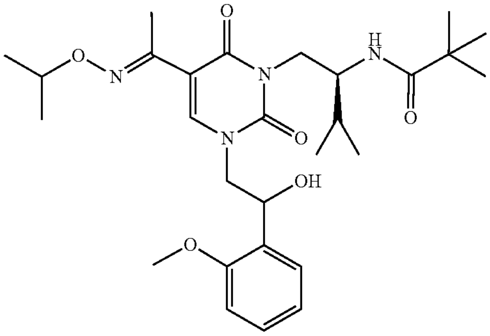 [SMILES: COc1ccccc1C(O)Cn1cc(/C(C)=N/OC(C)C)c(=O)n(C[C@@H](NC(=O)C(C)(C)C)C(C)C)c1=O] | viscous oil | Isomer of C-128 |
| C-130 | 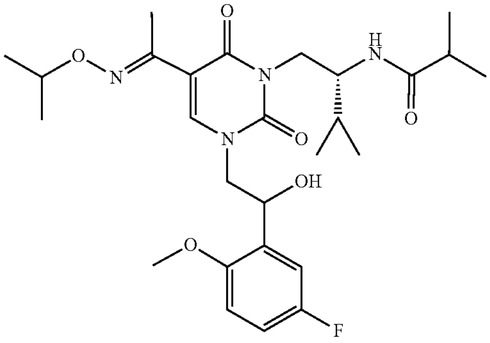 [SMILES: COc1ccc(F)cc1C(O)Cn1cc(/C(C)=N/OC(C)C)c(=O)n(C[C@H](NC(=O)C(C)C)C(C)C)c1=O] | amorphous | |
| C-131 | 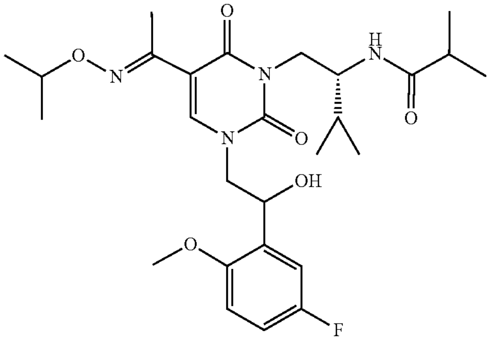 [SMILES: COc1ccc(F)cc1C(O)Cn1cc(/C(C)=N/OC(C)C)c(=O)n(C[C@H](NC(=O)C(C)C)C(C)C)c1=O] | viscous oil | Isomer of C-130 |
| C-132 | 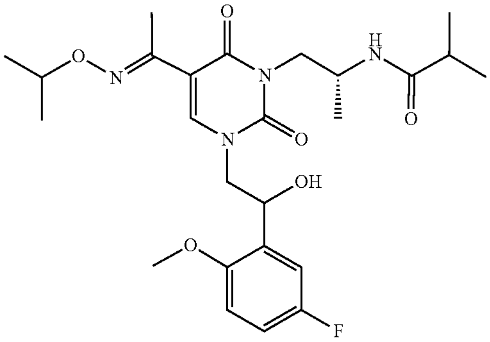 [SMILES: COc1ccc(F)cc1C(O)Cn1cc(/C(C)=N/OC(C)C)c(=O)n(C[C@@H](C)NC(=O)C(C)C)c1=O] | viscous oil | |

TABLE 6-continued
| Compound number | Structural formula | Physical properties | Remarks |
|---|---|---|---|
| C-133 | 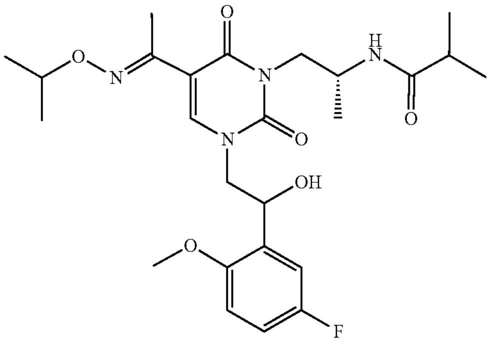 [SMILES: COc1ccc(F)cc1C(O)Cn1cc(/C(C)=N/OC(C)C)c(=O)n(C[C@@H](C)NC(=O)C(C)C)c1=O] | viscous oil | Isomer of C-132 |
| C-134 | 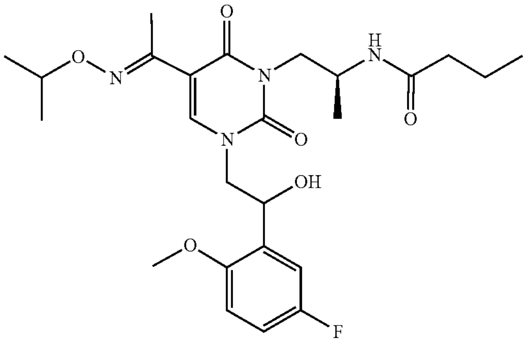 [SMILES: CCCC(=O)N[C@@H](C)Cn1c(=O)c(/C(C)=N/OC(C)C)cn(CC(O)c2cc(F)ccc2OC)c1=O] | m.p. 83-86° C. | |
| C-135 | 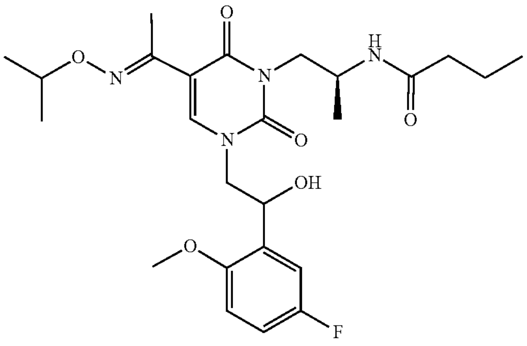 [SMILES: CCCC(=O)N[C@@H](C)Cn1c(=O)c(/C(C)=N/OC(C)C)cn(CC(O)c2cc(F)ccc2OC)c1=O] | m.p. 126-129° C. | Isomer of C-134 |
| C-136 | 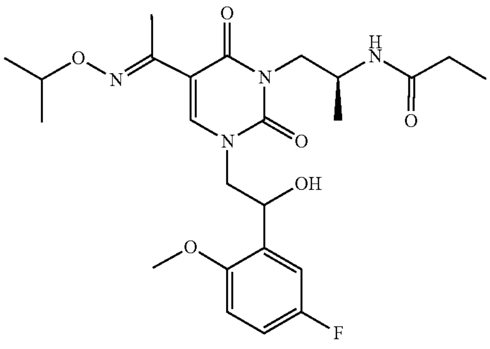 [SMILES: CCC(=O)N[C@@H](C)Cn1c(=O)c(/C(C)=N/OC(C)C)cn(CC(O)c2cc(F)ccc2OC)c1=O] | viscous oil | |

TABLE 6-continued
| Compound number | Structural formula | Physical properties | Remarks |
|---|---|---|---|
| C-137 | 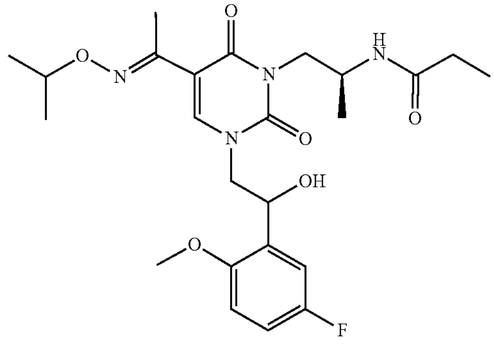 [SMILES: CCC(=O)N[C@@H](C)Cn1c(=O)c(/C(C)=N/OC(C)C)cn(CC(O)c2cc(F)ccc2OC)c1=O] | m.p. 140-141° C. | Isomer of C-136 |
| C-138 | 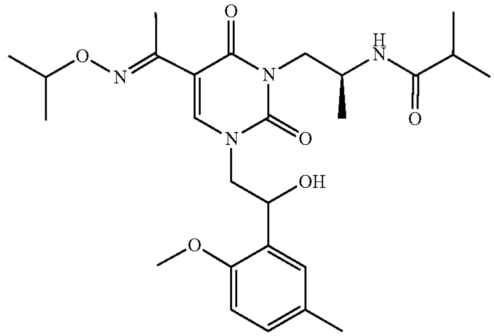 [SMILES: COc1ccc(C)cc1C(O)Cn1cc(/C(C)=N/OC(C)C)c(=O)n(C[C@H](C)NC(=O)C(C)C)c1=O] | m.p. 76-79° C. | |
| C-139 | 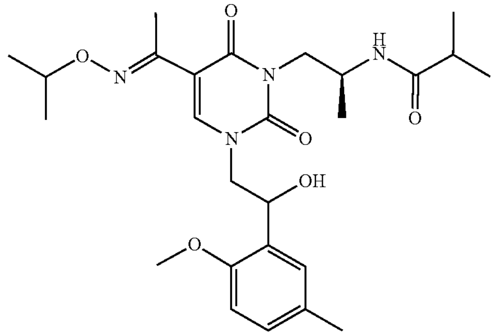 [SMILES: COc1ccc(C)cc1C(O)Cn1cc(/C(C)=N/OC(C)C)c(=O)n(C[C@H](C)NC(=O)C(C)C)c1=O] | m.p. 81-83° C. | Isomer of C-138 |
| C-140 | 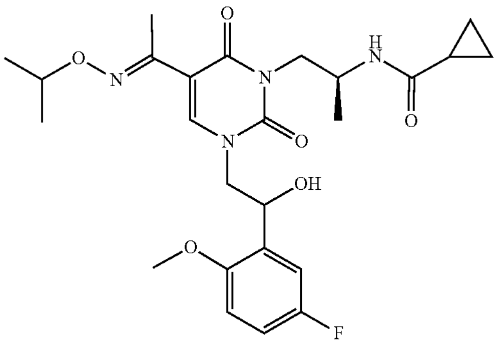 [SMILES: COc1ccc(F)cc1C(O)Cn1cc(/C(C)=N/OC(C)C)c(=O)n(C[C@H](C)NC(=O)C2CC2)c1=O] | m.p. 81-84° C. | |

TABLE 6-continued
| Compound number | Structural formula | Physical properties | Remarks |
|---|---|---|---|
| C-141 | 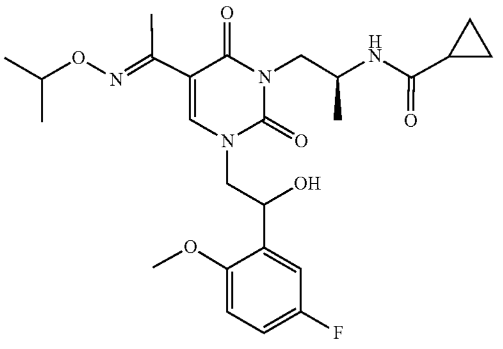 [SMILES: COc1ccc(F)cc1C(O)Cn1cc(/C(C)=N/OC(C)C)c(=O)n(C[C@H](C)NC(=O)C2CC2)c1=O] | m.p. 131-132° C. | Isomer of C-140 |
| C-142 | 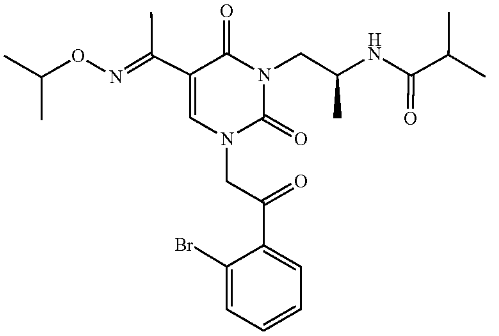 [SMILES: C/C(=N\OC(C)C)c1cn(CC(=O)c2ccccc2Br)c(=O)n(C[C@H](C)NC(=O)C(C)C)c1=O] | m.p. 163-164° C. | |
| C-143 | 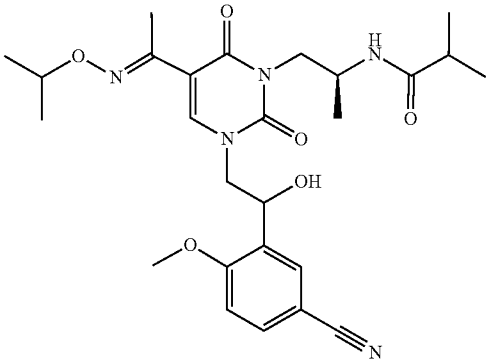 [SMILES: COc1ccc(C#N)cc1C(O)Cn1cc(/C(C)=N/OC(C)C)c(=O)n(C[C@H](C)NC(=O)C(C)C)c1=O] | m.p. 113-117° C. | |
| C-144 | 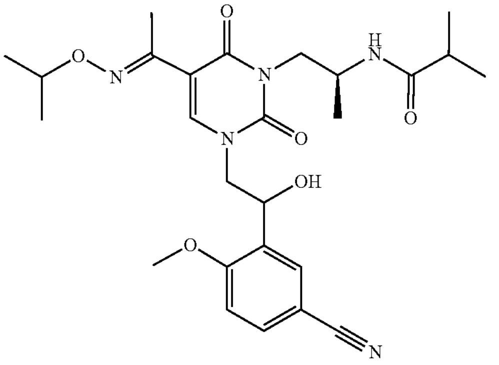 [SMILES: COc1ccc(C#N)cc1C(O)Cn1cc(/C(C)=N/OC(C)C)c(=O)n(C[C@H](C)NC(=O)C(C)C)c1=O] | m.p. 148-149° C. | Isomer of C-143 |

TABLE 6-continued
| Compound number | Structural formula | Physical properties | Remarks |
|---|---|---|---|
| C-145 | 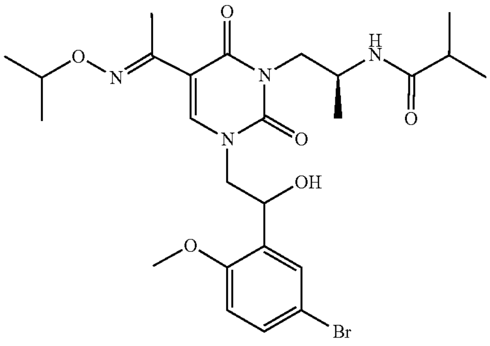 [SMILES: COc1ccc(Br)cc1C(O)Cn1cc(/C(C)=N/OC(C)C)c(=O)n(C[C@H](C)NC(=O)C(C)C)c1=O] | m.p. 82-83° C. | |
| C-146 | 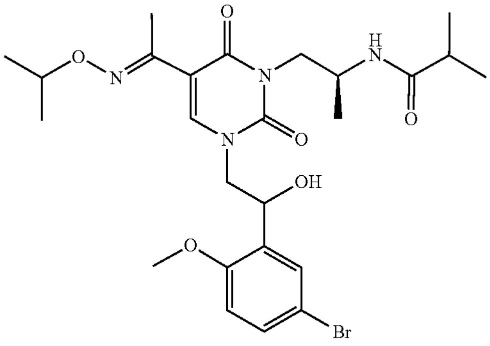 [SMILES: COc1ccc(Br)cc1C(O)Cn1cc(/C(C)=N/OC(C)C)c(=O)n(C[C@H](C)NC(=O)C(C)C)c1=O] | m.p. 129-130° C. | Isomer of C-145 |
| C-147 | 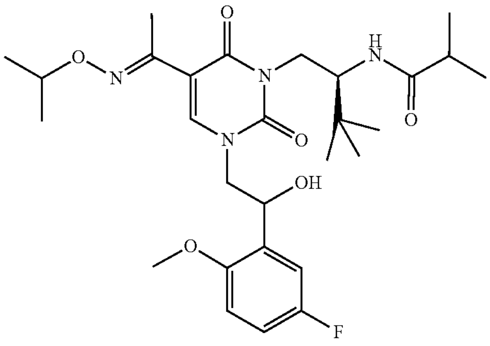 [SMILES: COc1ccc(F)cc1C(O)Cn1cc(/C(C)=N/OC(C)C)c(=O)n(C[C@@H](NC(=O)C(C)C)C(C)(C)C)c1=O] | m.p. 70-71° C. | |
| C-148 | 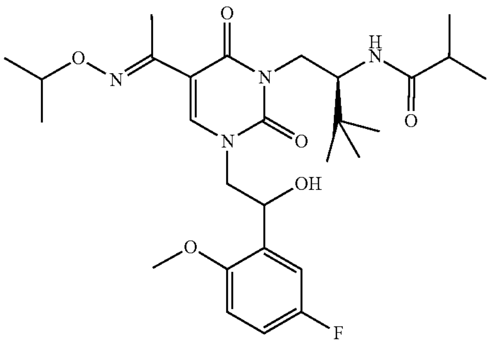 [SMILES: COc1ccc(F)cc1C(O)Cn1cc(/C(C)=N/OC(C)C)c(=O)n(C[C@@H](NC(=O)C(C)C)C(C)(C)C)c1=O] | m.p. 111-112° C. | Isomer of C-147 |

TABLE 6-continued
| Compound number | Structural formula | Physical properties | Remarks |
| --- | --- | --- | --- |
| C-149 | 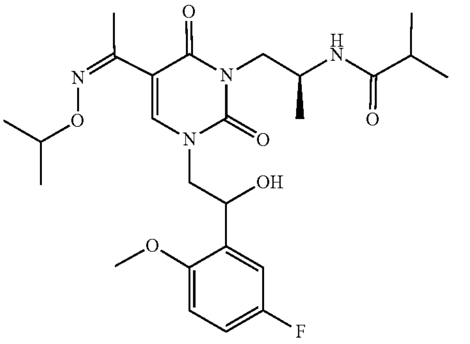 [SMILES: COc1ccc(F)cc1C(O)Cn1cc(/C(C)=N\OC(C)C)c(=O)n(C[C@H](C)NC(=O)C(C)C)c1=O] | viscous oil | |
| C-150 | 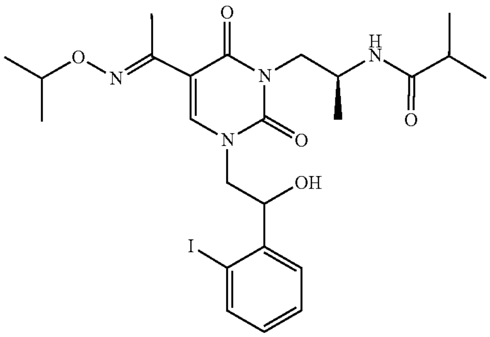 [SMILES: C/C(=N\OC(C)C)c1cn(CC(O)c2ccccc2I)c(=O)n(C[C@H](C)NC(=O)C(C)C)c1=O] | m.p. 120-121° C. | |
| C-151 | 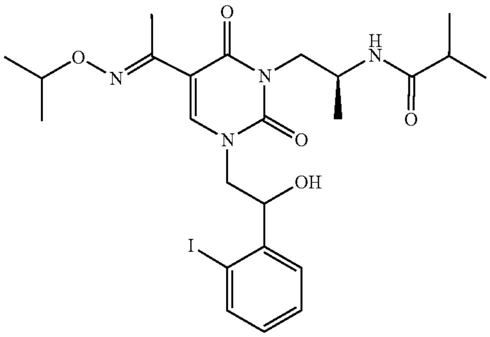 [SMILES: C/C(=N\OC(C)C)c1cn(CC(O)c2ccccc2I)c(=O)n(C[C@H](C)NC(=O)C(C)C)c1=O] | m.p. 100-101° C. | Isomer of C-150 |
| C-152 | 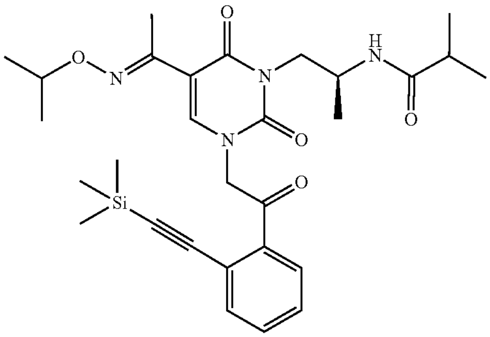 [SMILES: C/C(=N\OC(C)C)c1cn(CC(=O)c2ccccc2C#C[Si](C)(C)C)c(=O)n(C[C@H](C)NC(=O)C(C)C)c1=O] | m.p. 72-73° C. | |

TABLE 6-continued
| Compound number | Structural formula | Physical properties | Remarks |
|---|---|---|---|
| C-153 | 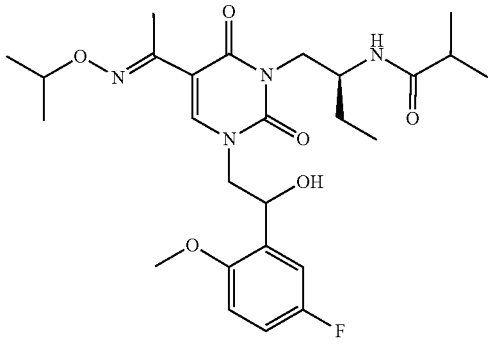 [SMILES: CC[C@@H](Cn1c(=O)c(/C(C)=N/OC(C)C)cn(CC(O)c2cc(F)ccc2OC)c1=O)NC(=O)C(C)C] | viscous oil | |
| C-154 | 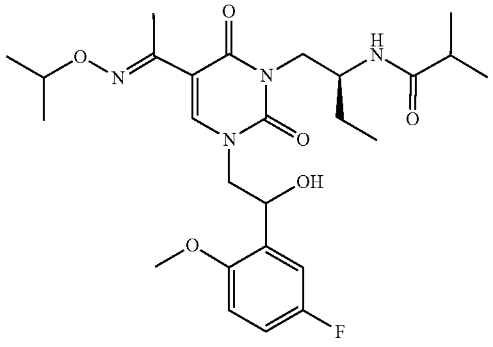 [SMILES: CC[C@@H](Cn1c(=O)c(/C(C)=N/OC(C)C)cn(CC(O)c2cc(F)ccc2OC)c1=O)NC(=O)C(C)C] | m.p. 120-121° C. | Isomer of C-153 |
| C-155 | 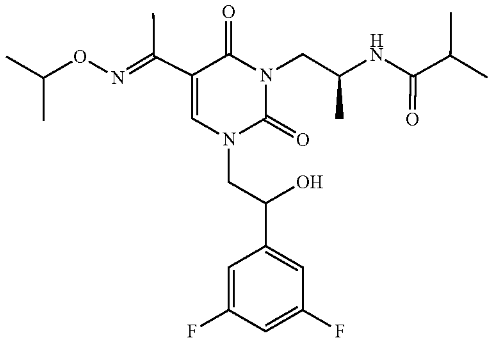 [SMILES: C/C(=N\OC(C)C)c1cn(CC(O)c2cc(F)cc(F)c2)c(=O)n(C[C@H](C)NC(=O)C(C)C)c1=O] | m.p. 154-155° C. | |
| C-156 | 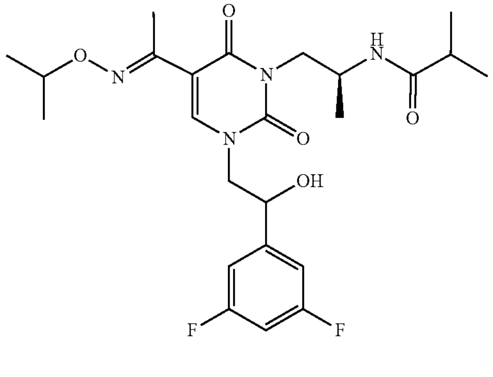 [SMILES: C/C(=N\OC(C)C)c1cn(CC(O)c2cc(F)cc(F)c2)c(=O)n(C[C@H](C)NC(=O)C(C)C)c1=O] | m.p. 93-94° C. | Isomer of C-155 |

TABLE 6-continued
| Compound number | Structural formula | Physical properties | Remarks |
| --- | --- | --- | --- |
| C-157 | 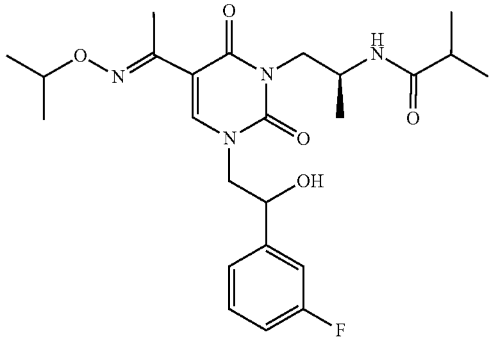 [SMILES: C/C(=N\OC(C)C)c1cn(CC(O)c2cccc(F)c2)c(=O)n(C[C@H](C)NC(=O)C(C)C)c1=O] | m.p. 156-157° C. | |
| C-158 | 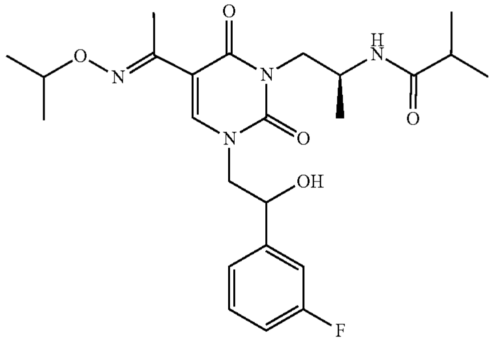 [SMILES: C/C(=N\OC(C)C)c1cn(CC(O)c2cccc(F)c2)c(=O)n(C[C@H](C)NC(=O)C(C)C)c1=O] | m.p. 97-98° C. | Isomer of C-157 |
| C-159 | 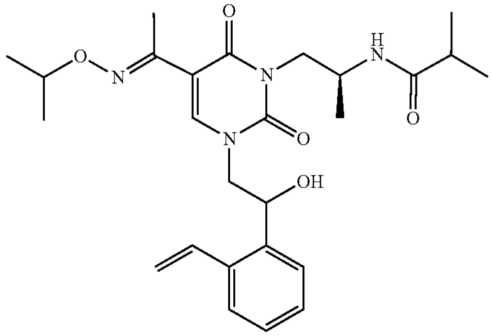 [SMILES: C=Cc1ccccc1C(O)Cn1cc(/C(C)=N/OC(C)C)c(=O)n(C[C@H](C)NC(=O)C(C)C)c1=O] | m.p. 157-158° C. | |
| C-160 | 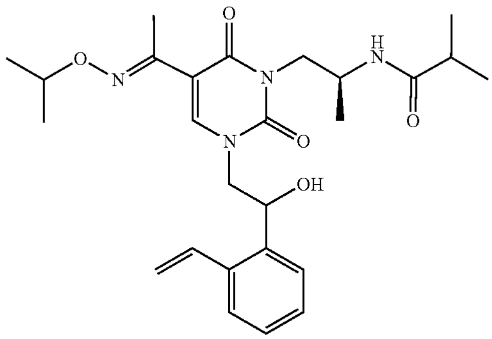 [SMILES: C=Cc1ccccc1C(O)Cn1cc(/C(C)=N/OC(C)C)c(=O)n(C[C@H](C)NC(=O)C(C)C)c1=O] | m.p. 134-135° C. | Isomer of C-159 |

TABLE 6-continued
| Compound number | Structural formula | Physical properties | Remarks |
|---|---|---|---|
| C-161 | 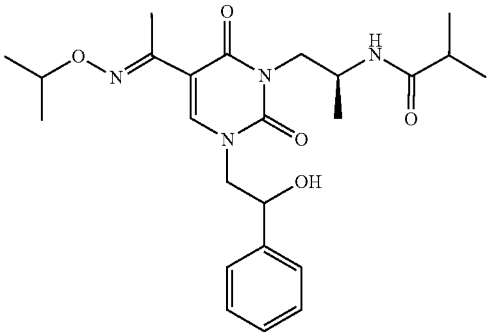 [SMILES: C/C(=N\OC(C)C)c1cn(CC(O)c2ccccc2)c(=O)n(C[C@H](C)NC(=O)C(C)C)c1=O] | m.p. 161-162° C. | |
| C-162 | 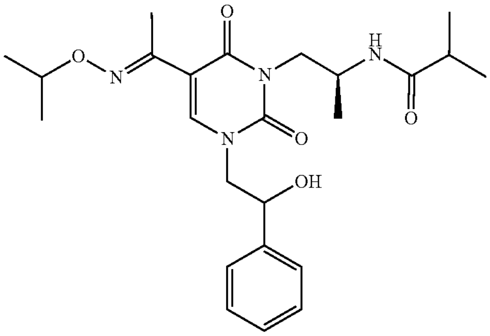 [SMILES: C/C(=N\OC(C)C)c1cn(CC(O)c2ccccc2)c(=O)n(C[C@H](C)NC(=O)C(C)C)c1=O] | m.p. 120-122° C. | Isomer of C-161 |
| C-163 | 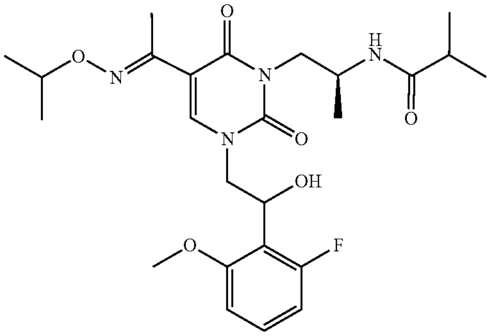 [SMILES: COc1cccc(F)c1C(O)Cn1cc(/C(C)=N/OC(C)C)c(=O)n(C[C@H](C)NC(=O)C(C)C)c1=O] | viscous oil | |
| C-164 | 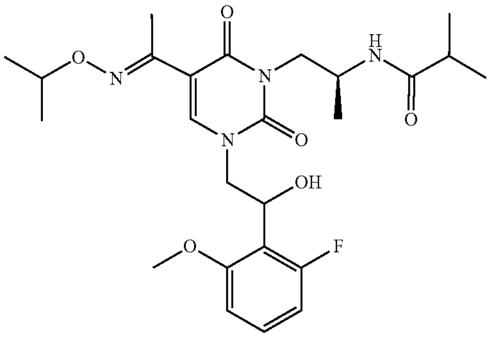 [SMILES: COc1cccc(F)c1C(O)Cn1cc(/C(C)=N/OC(C)C)c(=O)n(C[C@H](C)NC(=O)C(C)C)c1=O] | viscous oil | Isomer of C-163 |

TABLE 6-continued
| Compound number | Structural formula | Physical properties | Remarks |
| --- | --- | --- | --- |
| C-165 | 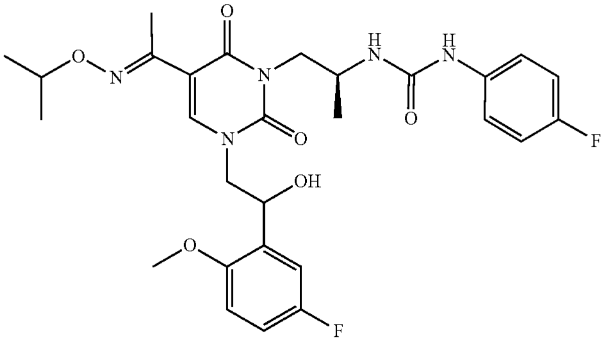 [SMILES: COc1ccc(F)cc1C(O)Cn1cc(/C(C)=N/OC(C)C)c(=O)n(C[C@H](C)NC(=O)Nc2ccc(F)cc2)c1=O] | m.p. 97-99° C. | |
| C-166 | 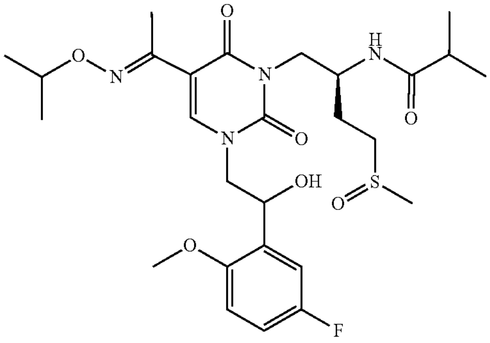 [SMILES: COc1ccc(F)cc1C(O)Cn1cc(/C(C)=N/OC(C)C)c(=O)n(C[C@H](CCS(C)=O)NC(=O)C(C)C)c1=O] | m.p. 123-125° C. | |
| C-167 | 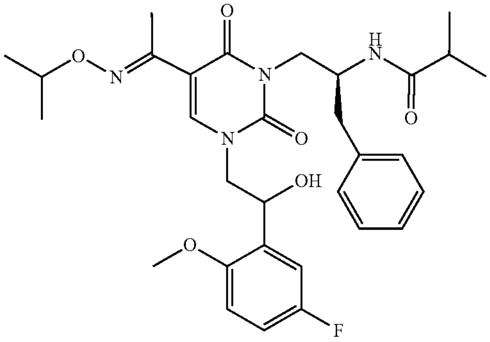 [SMILES: COc1ccc(F)cc1C(O)Cn1cc(/C(C)=N/OC(C)C)c(=O)n(C[C@H](Cc2ccccc2)NC(=O)C(C)C)c1=O] | m.p. 78-81° C. | |
| C-168 | 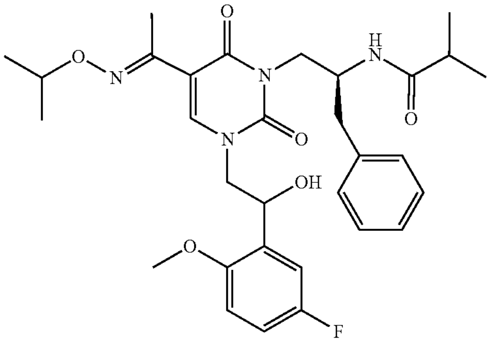 [SMILES: COc1ccc(F)cc1C(O)Cn1cc(/C(C)=N/OC(C)C)c(=O)n(C[C@H](Cc2ccccc2)NC(=O)C(C)C)c1=O] | m.p. 96-100° C. | Isomer of C-167 |

TABLE 6-continued
| Compound number | Structural formula | Physical properties | Remarks |
|---|---|---|---|
| C-169 | 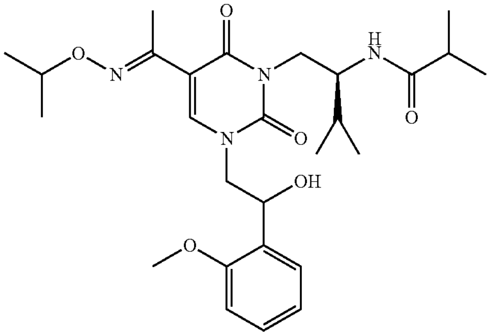 [SMILES: COc1ccccc1C(O)Cn1cc(/C(C)=N/OC(C)C)c(=O)n(C[C@@H](NC(=O)C(C)C)C(C)C)c1=O] | m.p. 145-146° C. | |
| C-170 | 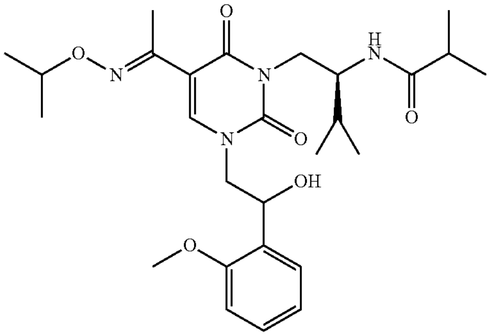 [SMILES: COc1ccccc1C(O)Cn1cc(/C(C)=N/OC(C)C)c(=O)n(C[C@@H](NC(=O)C(C)C)C(C)C)c1=O] | m.p. 86-88° C. | Isomer of C-169 |
| C-171 | 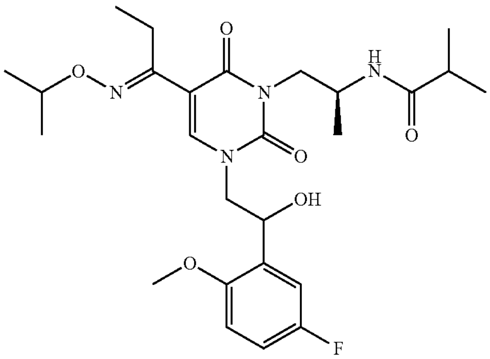 [SMILES: CC/C(=N\OC(C)C)c1cn(CC(O)c2cc(F)ccc2OC)c(=O)n(C[C@H](C)NC(=O)C(C)C)c1=O] | m.p. 70-71° C. | |
| C-172 | 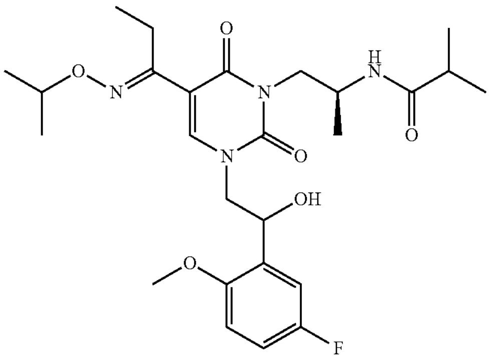 [SMILES: CC/C(=N\OC(C)C)c1cn(CC(O)c2cc(F)ccc2OC)c(=O)n(C[C@H](C)NC(=O)C(C)C)c1=O] | m.p. 69-70° C. | Isomer of C-171 |

TABLE 6-continued
| Compound number | Structural formula | Physical properties | Remarks |
|---|---|---|---|
| C-173 | 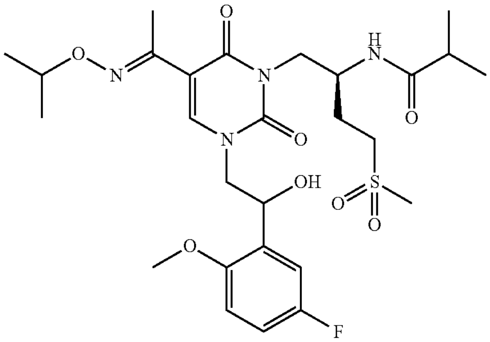 [SMILES: COc1ccc(F)cc1C(O)Cn1cc(/C(C)=N/OC(C)C)c(=O)n(C[C@H](CCS(C)(=O)=O)NC(=O)C(C)C)c1=O] | m.p. 82-85° C. | |
| C-174 | 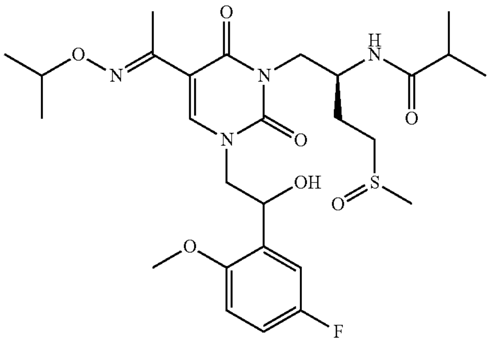 [SMILES: COc1ccc(F)cc1C(O)Cn1cc(/C(C)=N/OC(C)C)c(=O)n(C[C@H](CCS(C)=O)NC(=O)C(C)C)c1=O] | m.p. 78-81° C. | |
| C-175 | 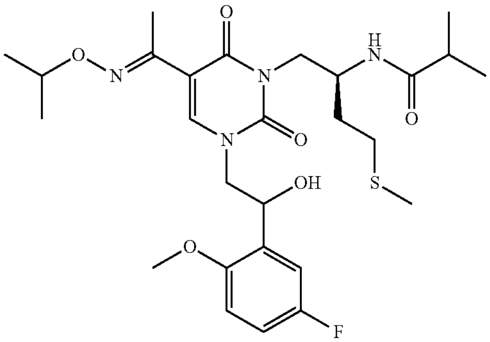 [SMILES: COc1ccc(F)cc1C(O)Cn1cc(/C(C)=N/OC(C)C)c(=O)n(C[C@H](CCSC)NC(=O)C(C)C)c1=O] | m.p. 119-120° C. | |
| C-176 | 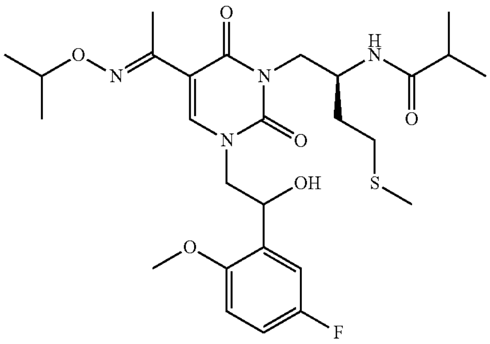 [SMILES: COc1ccc(F)cc1C(O)Cn1cc(/C(C)=N/OC(C)C)c(=O)n(C[C@H](CCSC)NC(=O)C(C)C)c1=O] | m.p. 104-108° C. | Isomer of C-175 |

TABLE 6-continued
| Compound number | Structural formula | Physical properties | Remarks |
|---|---|---|---|
| C-177 | 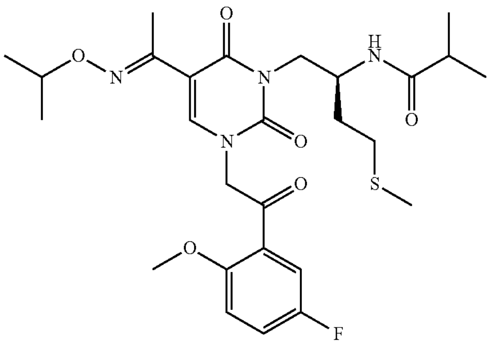 [SMILES: COc1ccc(F)cc1C(=O)Cn1cc(/C(C)=N/OC(C)C)c(=O)n(C[C@H](CCSC)NC(=O)C(C)C)c1=O] | m.p. 100-101° C. | |
| C-178 | 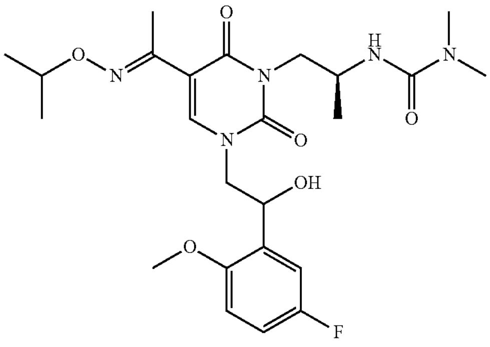 [SMILES: COc1ccc(F)cc1C(O)Cn1cc(/C(C)=N/OC(C)C)c(=O)n(C[C@H](C)NC(=O)N(C)C)c1=O] | m.p. 71-72° C. | |
| C-179 | 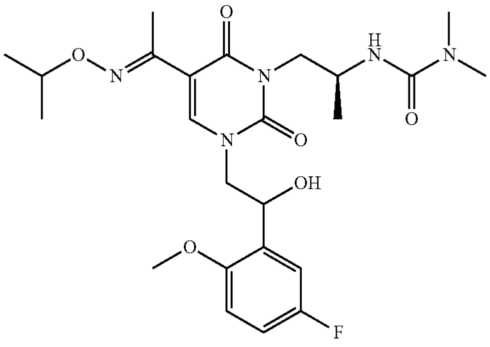 [SMILES: COc1ccc(F)cc1C(O)Cn1cc(/C(C)=N/OC(C)C)c(=O)n(C[C@H](C)NC(=O)N(C)C)c1=O] | m.p. 83-84° C. | Isomer of C-178 |
| C-180 | 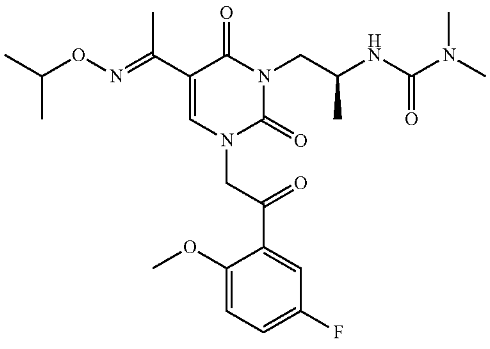 [SMILES: COc1ccc(F)cc1C(=O)Cn1cc(/C(C)=N/OC(C)C)c(=O)n(C[C@H](C)NC(=O)N(C)C)c1=O] | m.p. 73-74° C. | |

TABLE 6-continued
| Compound number | Structural formula | Physical properties | Remarks |
|---|---|---|---|
| C-181 | 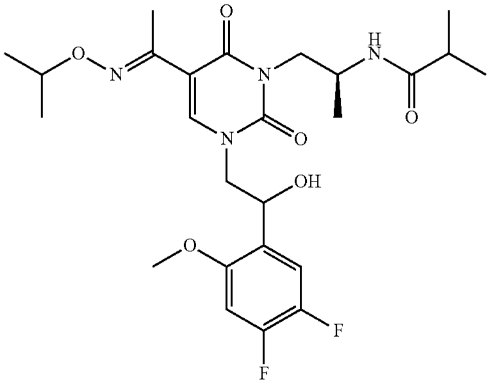 [SMILES: COc1cc(F)c(F)cc1C(O)Cn1cc(/C(C)=N/OC(C)C)c(=O)n(C[C@H](C)NC(=O)C(C)C)c1=O] | m.p. 72-73° C. | |
| C-182 | 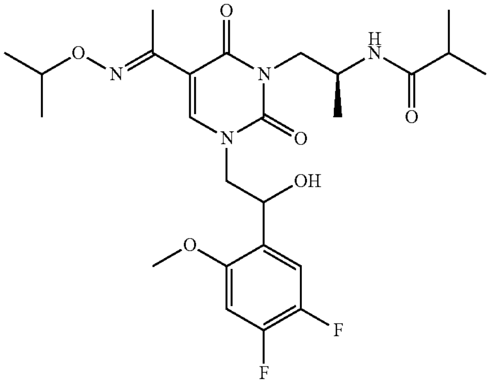 [SMILES: COc1cc(F)c(F)cc1C(O)Cn1cc(/C(C)=N/OC(C)C)c(=O)n(C[C@H](C)NC(=O)C(C)C)c1=O] | m.p. 81-82° C. | Isomer of C-181 |
| C-183 | 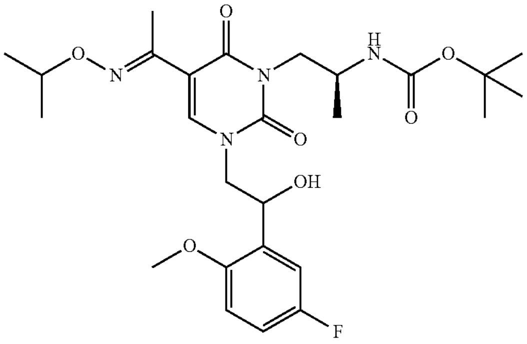 [SMILES: COc1ccc(F)cc1C(O)Cn1cc(/C(C)=N/OC(C)C)c(=O)n(C[C@H](C)NC(=O)OC(C)(C)C)c1=O] | viscous oil | |
| C-184 | 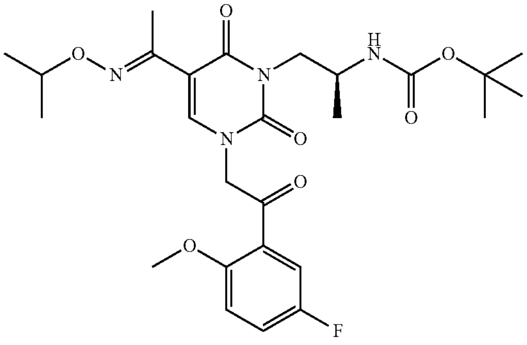 [SMILES: COc1ccc(F)cc1C(=O)Cn1cc(/C(C)=N/OC(C)C)c(=O)n(C[C@H](C)NC(=O)OC(C)(C)C)c1=O] | m.p. 138-139° C. | |

TABLE 6-continued
| Compound number | Structural formula | Physical properties | Remarks |
|---|---|---|---|
| C-185 | 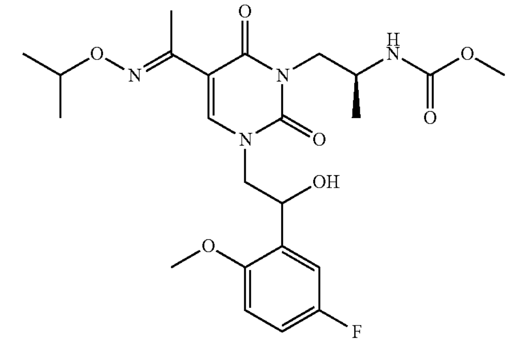 [SMILES: COC(=O)N[C@@H](C)Cn1c(=O)c(/C(C)=N/OC(C)C)cn(CC(O)c2cc(F)ccc2OC)c1=O] | viscous oil | |
| C-186 | 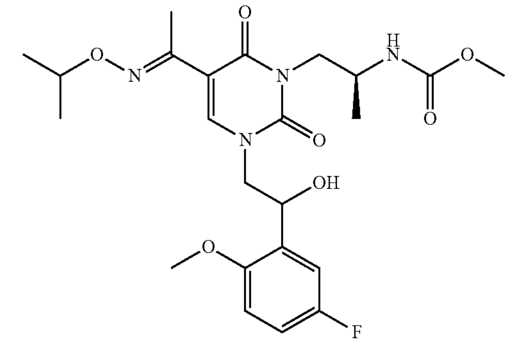 [SMILES: COC(=O)N[C@@H](C)Cn1c(=O)c(/C(C)=N/OC(C)C)cn(CC(O)c2cc(F)ccc2OC)c1=O] | m.p. 117-118° C. | Isomer of C-185 |
| C-187 | 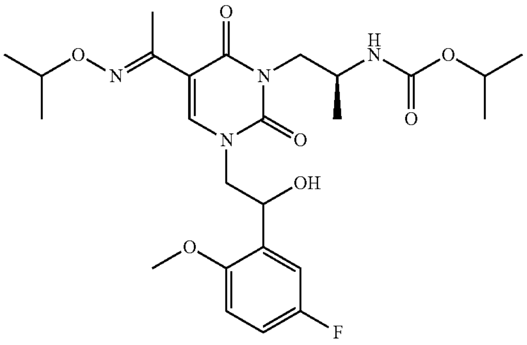 [SMILES: COc1ccc(F)cc1C(O)Cn1cc(/C(C)=N/OC(C)C)c(=O)n(C[C@H](C)NC(=O)OC(C)C)c1=O] | viscous oil | |
| C-188 | 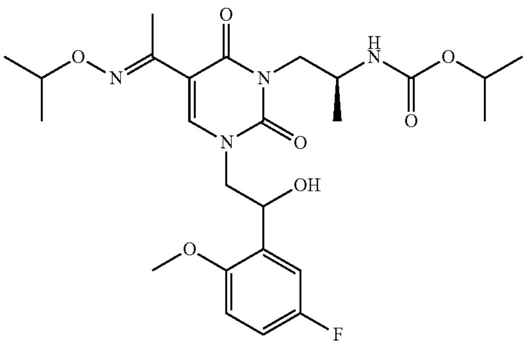 [SMILES: COc1ccc(F)cc1C(O)Cn1cc(/C(C)=N/OC(C)C)c(=O)n(C[C@H](C)NC(=O)OC(C)C)c1=O] | viscous oil | Isomer of C-187 |

TABLE 6-continued
| Compound number | Structural formula | Physical properties | Remarks |
|---|---|---|---|
| C-189 | 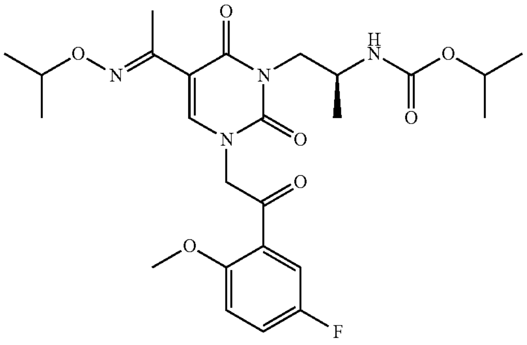 [SMILES: COc1ccc(F)cc1C(=O)Cn1cc(/C(C)=N/OC(C)C)c(=O)n(C[C@H](C)NC(=O)OC(C)C)c1=O] | m.p. 118-119° C. | |
| C-190 | 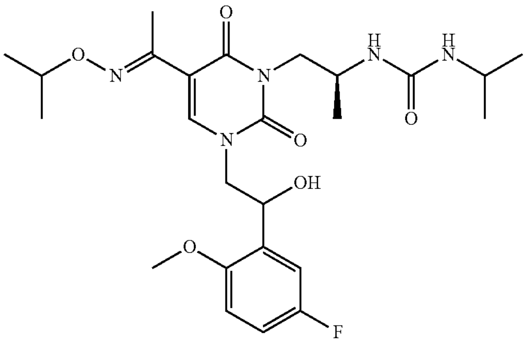 [SMILES: COc1ccc(F)cc1C(O)Cn1cc(/C(C)=N/OC(C)C)c(=O)n(C[C@H](C)NC(=O)NC(C)C)c1=O] | m.p. 89-90° C. | |
| C-191 | 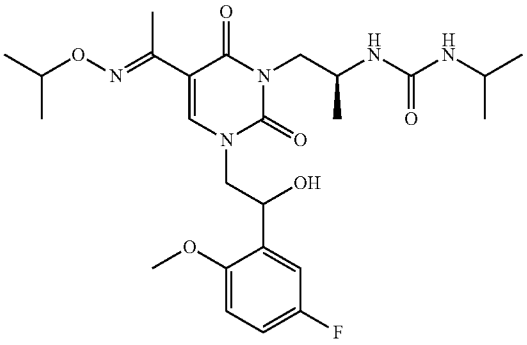 [SMILES: COc1ccc(F)cc1C(O)Cn1cc(/C(C)=N/OC(C)C)c(=O)n(C[C@H](C)NC(=O)NC(C)C)c1=O] | m.p. 176-177° C. | Isomer of C-190 |
| C-192 | 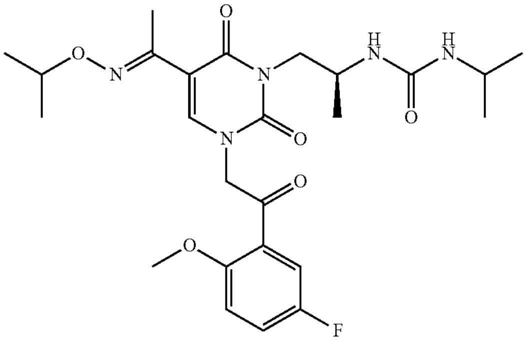 [SMILES: COc1ccc(F)cc1C(=O)Cn1cc(/C(C)=N/OC(C)C)c(=O)n(C[C@H](C)NC(=O)NC(C)C)c1=O] | m.p. 162-163° C. | |

TABLE 6-continued
| Compound number | Structural formula | Physical properties | Remarks |
| --- | --- | --- | --- |
| C-193 | 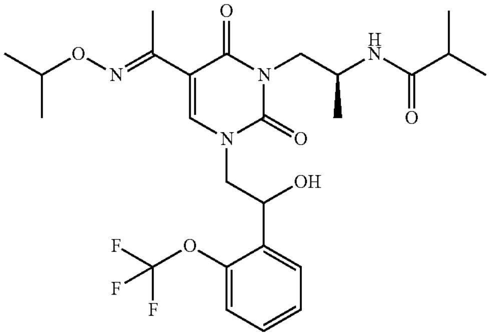 [SMILES: C/C(=N\OC(C)C)c1cn(CC(O)c2ccccc2OC(F)(F)F)c(=O)n(C[C@H](C)NC(=O)C(C)C)c1=O] | viscous oil | |
| C-194 | 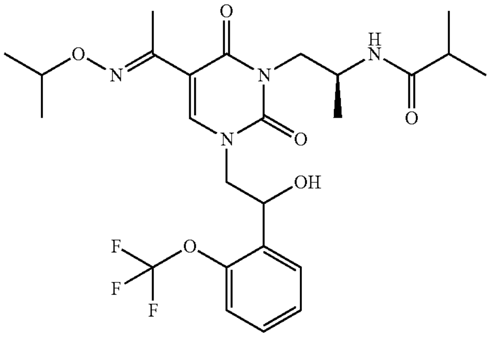 [SMILES: C/C(=N\OC(C)C)c1cn(CC(O)c2ccccc2OC(F)(F)F)c(=O)n(C[C@H](C)NC(=O)C(C)C)c1=O] | m.p. 105-110° C. | Isomer of C-193 |
| C-195 | 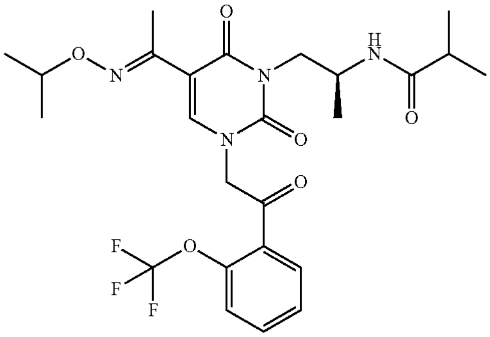 [SMILES: C/C(=N\OC(C)C)c1cn(CC(=O)c2ccccc2OC(F)(F)F)c(=O)n(C[C@H](C)NC(=O)C(C)C)c1=O] | m.p. 159-160° C. | |
| C-196 | 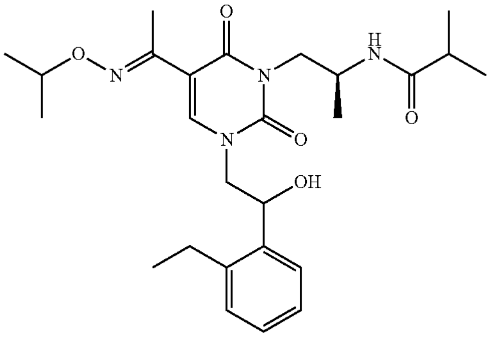 [SMILES: CCc1ccccc1C(O)Cn1cc(/C(C)=N/OC(C)C)c(=O)n(C[C@H](C)NC(=O)C(C)C)c1=O] | m.p. 147-148° C. | |

TABLE 6-continued
| Compound number | Structural formula | Physical properties | Remarks |
|---|---|---|---|
| C-197 | 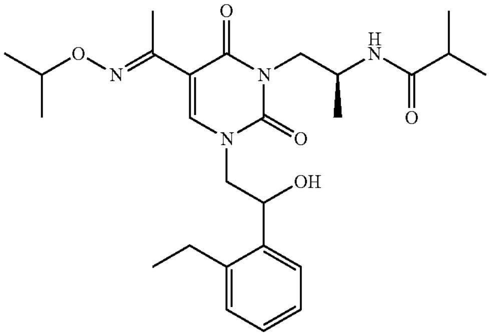 [SMILES: CCc1ccccc1C(O)Cn1cc(/C(C)=N/OC(C)C)c(=O)n(C[C@H](C)NC(=O)C(C)C)c1=O] | viscous oil | Isomer of C-196 |
| C-198 | 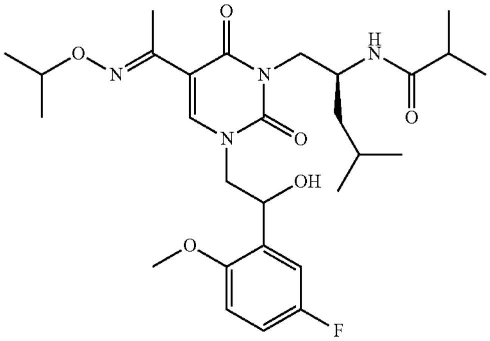 [SMILES: COc1ccc(F)cc1C(O)Cn1cc(/C(C)=N/OC(C)C)c(=O)n(C[C@H](CC(C)C)NC(=O)C(C)C)c1=O] | viscous oil | |
| C-199 | 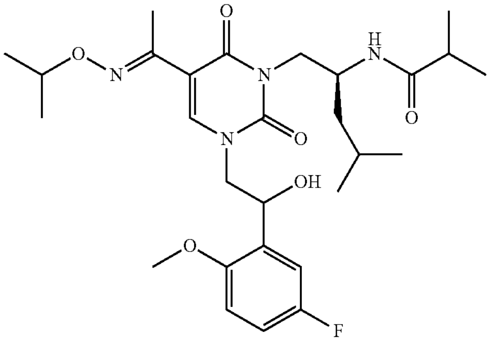 [SMILES: COc1ccc(F)cc1C(O)Cn1cc(/C(C)=N/OC(C)C)c(=O)n(C[C@H](CC(C)C)NC(=O)C(C)C)c1=O] | viscous oil | Isomer of C-198 |
| C-200 | 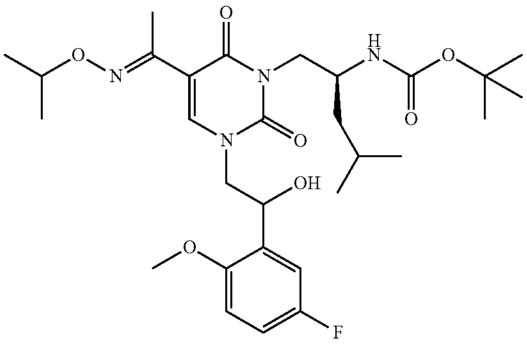 [SMILES: COc1ccc(F)cc1C(O)Cn1cc(/C(C)=N/OC(C)C)c(=O)n(C[C@H](CC(C)C)NC(=O)OC(C)(C)C)c1=O] | viscous oil | |

TABLE 6-continued
| Compound number | Structural formula | Physical properties | Remarks |
|---|---|---|---|
| C-201 | 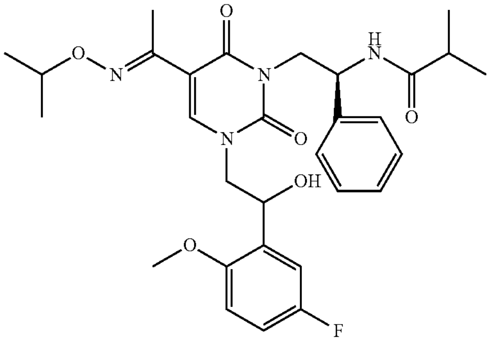 [SMILES: COc1ccc(F)cc1C(O)Cn1cc(/C(C)=N/OC(C)C)c(=O)n(C[C@@H](NC(=O)C(C)C)c2ccccc2)c1=O] | m.p. 81-85° C. | |
| C-202 | 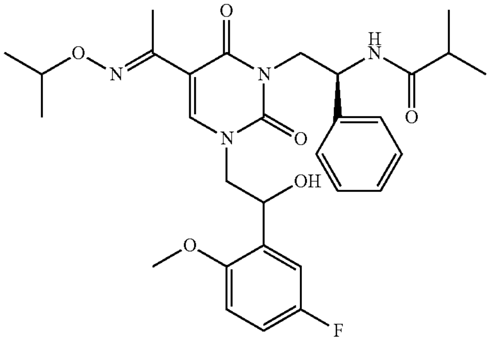 [SMILES: COc1ccc(F)cc1C(O)Cn1cc(/C(C)=N/OC(C)C)c(=O)n(C[C@@H](NC(=O)C(C)C)c2ccccc2)c1=O] | m.p. 161-162° C. | Isomer of C-201 |
| C-203 | 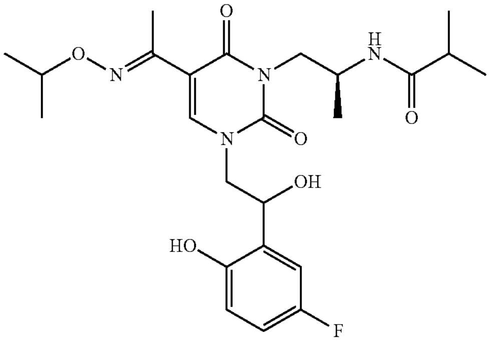 [SMILES: C/C(=N\OC(C)C)c1cn(CC(O)c2cc(F)ccc2O)c(=O)n(C[C@H](C)NC(=O)C(C)C)c1=O] | m.p. 101-102° C. | |
| C-204 | 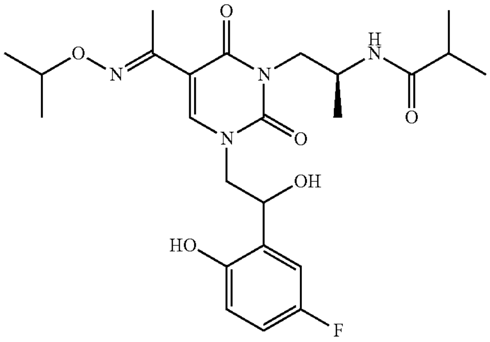 [SMILES: C/C(=N\OC(C)C)c1cn(CC(O)c2cc(F)ccc2O)c(=O)n(C[C@H](C)NC(=O)C(C)C)c1=O] | viscous oil | Isomer of C-203 |

TABLE 6-continued
| Compound number | Structural formula | Physical properties | Remarks |
|---|---|---|---|
| C-205 | 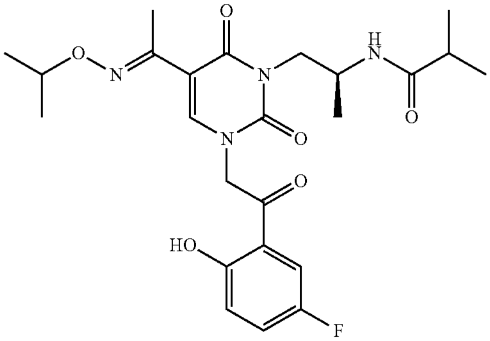 [SMILES: C/C(=N\OC(C)C)c1cn(CC(=O)c2cc(F)ccc2O)c(=O)n(C[C@H](C)NC(=O)C(C)C)c1=O] | m.p. 95-99° C. | |
| C-206 | 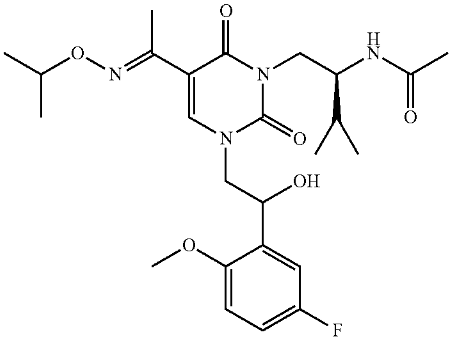 [SMILES: COc1ccc(F)cc1C(O)Cn1cc(/C(C)=N/OC(C)C)c(=O)n(C[C@@H](NC(C)=O)C(C)C)c1=O] | viscous oil | |
| C-207 | 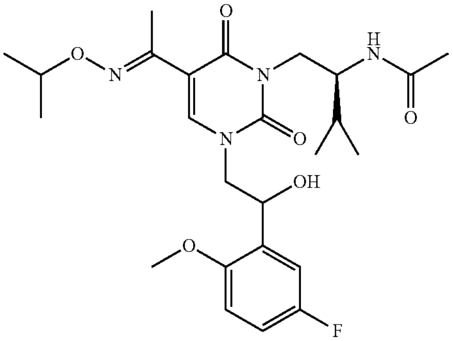 [SMILES: COc1ccc(F)cc1C(O)Cn1cc(/C(C)=N/OC(C)C)c(=O)n(C[C@@H](NC(C)=O)C(C)C)c1=O] | m.p. 73-74° C. | Isomer of C-206 |
| C-208 | 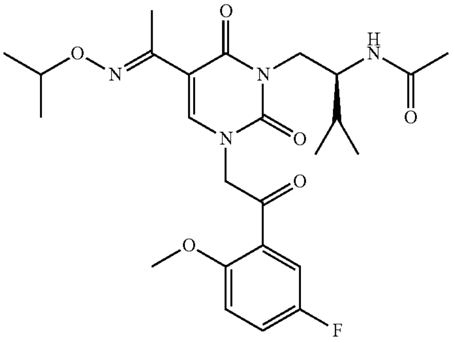 [SMILES: COc1ccc(F)cc1C(=O)Cn1cc(/C(C)=N/OC(C)C)c(=O)n(C[C@@H](NC(C)=O)C(C)C)c1=O] | m.p. 147-148° C. | |

TABLE 6-continued
| Compound number | Structural formula | Physical properties | Remarks |
|---|---|---|---|
| C-209 | 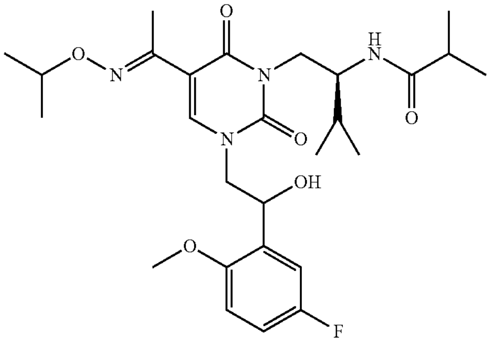 [SMILES: COc1ccc(F)cc1C(O)Cn1cc(/C(C)=N/OC(C)C)c(=O)n(C[C@@H](NC(=O)C(C)C)C(C)C)c1=O] | viscous oil | |
| C-210 | 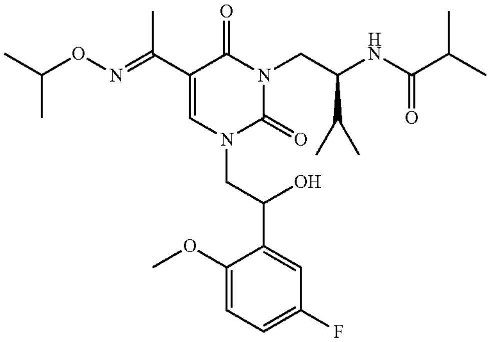 [SMILES: COc1ccc(F)cc1C(O)Cn1cc(/C(C)=N/OC(C)C)c(=O)n(C[C@@H](NC(=O)C(C)C)C(C)C)c1=O] | m.p. 91-92° C. | Isomer of C-209 |
| C-211 | 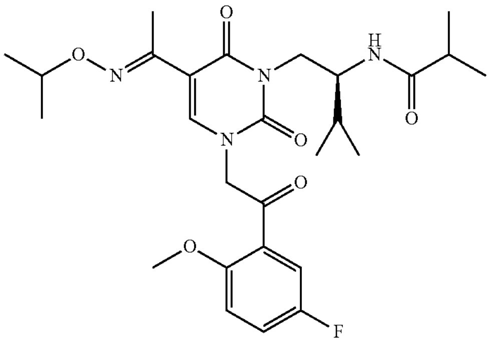 [SMILES: COc1ccc(F)cc1C(=O)Cn1cc(/C(C)=N/OC(C)C)c(=O)n(C[C@@H](NC(=O)C(C)C)C(C)C)c1=O] | m.p. 131-132° C. | |
| C-212 | 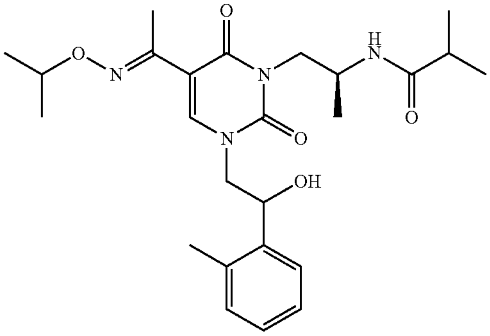 [SMILES: C/C(=N\OC(C)C)c1cn(CC(O)c2ccccc2C)c(=O)n(C[C@H](C)NC(=O)C(C)C)c1=O] | m.p. 176-177° C. | |

TABLE 6-continued
| Compound number | Structural formula | Physical properties | Remarks |
|---|---|---|---|
| C-213 | 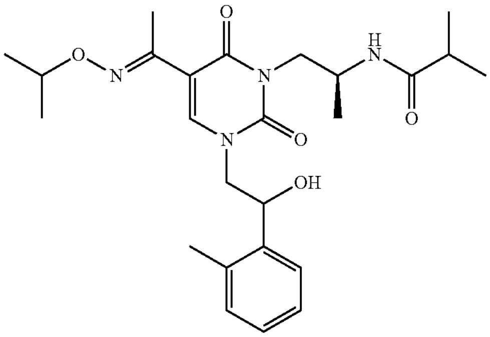 [SMILES: C/C(=N\OC(C)C)c1cn(CC(O)c2ccccc2C)c(=O)n(C[C@H](C)NC(=O)C(C)C)c1=O] | m.p. 89-90° C. | Isomer of C-212 |
| C-214 | 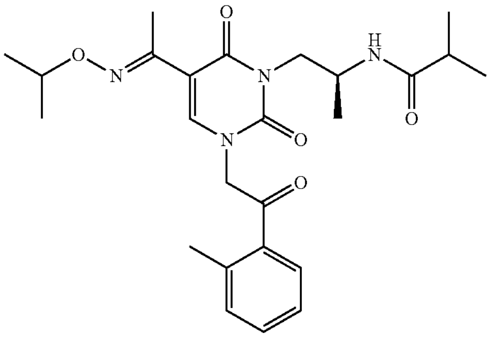 [SMILES: C/C(=N\OC(C)C)c1cn(CC(=O)c2ccccc2C)c(=O)n(C[C@H](C)NC(=O)C(C)C)c1=O] | m.p. 150-151° C. | |
| C-215 | 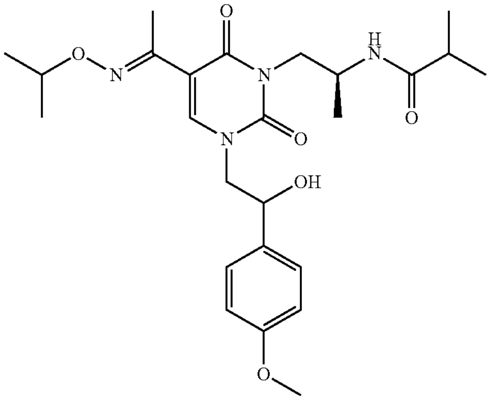 [SMILES: COc1ccc(C(O)Cn2cc(/C(C)=N/OC(C)C)c(=O)n(C[C@H](C)NC(=O)C(C)C)c2=O)cc1] | m.p. 117-118° C. | |
| C-216 | 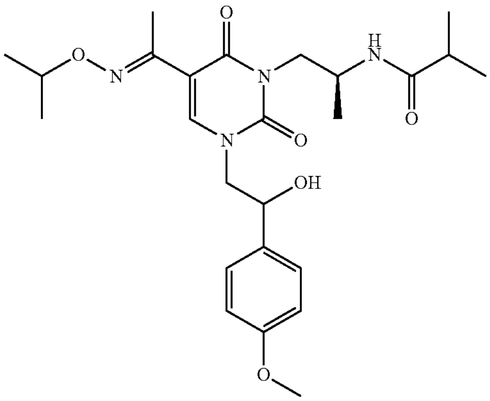 [SMILES: COc1ccc(C(O)Cn2cc(/C(C)=N/OC(C)C)c(=O)n(C[C@H](C)NC(=O)C(C)C)c2=O)cc1] | m.p. 75-76° C. | Isomer of C-215 |

TABLE 6-continued
| Compound number | Structural formula | Physical properties | Remarks |
| --- | --- | --- | --- |
| C-217 | 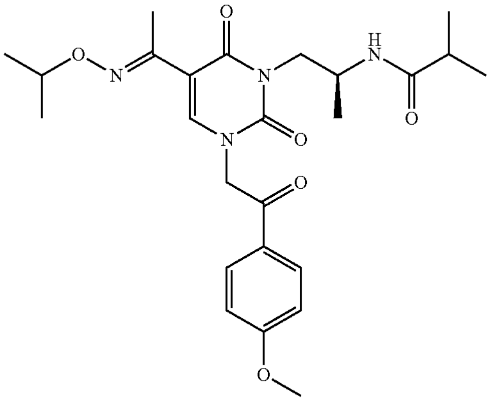 [SMILES: COc1ccc(C(=O)Cn2cc(/C(C)=N/OC(C)C)c(=O)n(C[C@H](C)NC(=O)C(C)C)c2=O)cc1] | m.p. 68-70° C. | |
| C-218 | 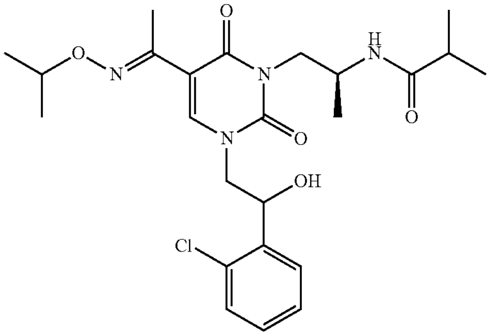 [SMILES: C/C(=N\OC(C)C)c1cn(CC(O)c2ccccc2Cl)c(=O)n(C[C@H](C)NC(=O)C(C)C)c1=O] | m.p. 176-177° C. | |
| C-219 | 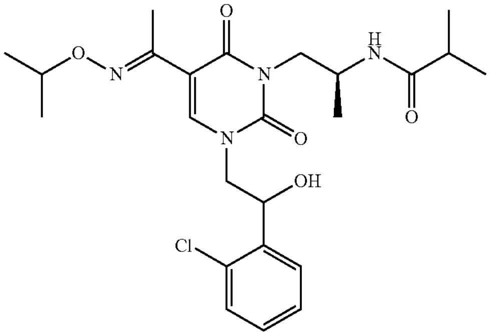 [SMILES: C/C(=N\OC(C)C)c1cn(CC(O)c2ccccc2Cl)c(=O)n(C[C@H](C)NC(=O)C(C)C)c1=O] | m.p. 123-124° C. | Isomer of C-218 |
| C-220 | 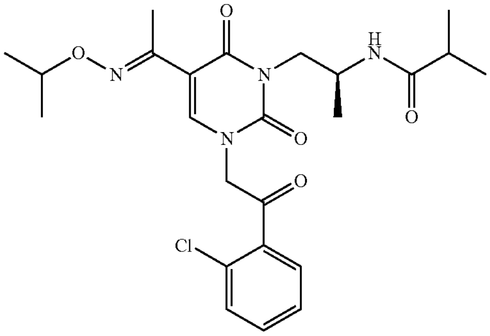 [SMILES: C/C(=N\OC(C)C)c1cn(CC(=O)c2ccccc2Cl)c(=O)n(C[C@H](C)NC(=O)C(C)C)c1=O] | m.p. 142-143° C. | |

TABLE 6-continued
| Compound number | Structural formula | Physical properties | Remarks |
|---|---|---|---|
| C-221 | 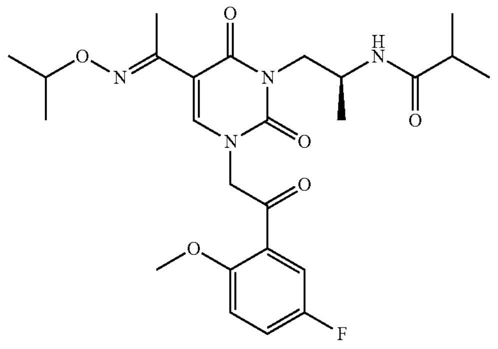 [SMILES: COc1ccc(F)cc1C(=O)Cn1cc(/C(C)=N/OC(C)C)c(=O)n(C[C@H](C)NC(=O)C(C)C)c1=O] | m.p. 129-130° C. | |
| C-222 | 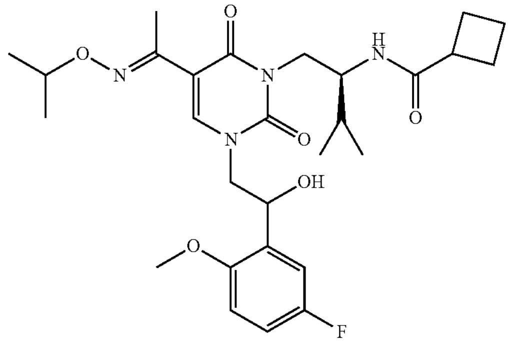 [SMILES: COc1ccc(F)cc1C(O)Cn1cc(/C(C)=N/OC(C)C)c(=O)n(C[C@@H](NC(=O)C2CCC2)C(C)C)c1=O] | m.p. 66-67° C. | |
| C-223 | 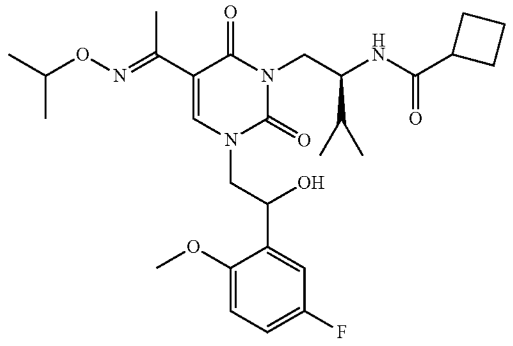 [SMILES: COc1ccc(F)cc1C(O)Cn1cc(/C(C)=N/OC(C)C)c(=O)n(C[C@@H](NC(=O)C2CCC2)C(C)C)c1=O] | m.p. 70-71° C. | Isomer of C-222 |
| C-224 | 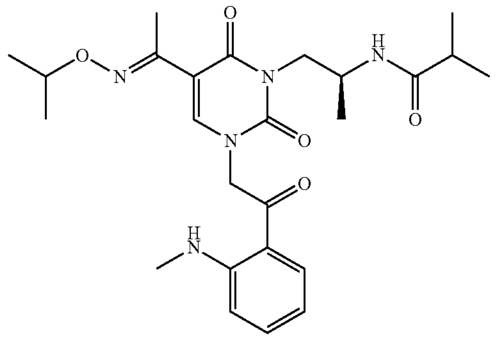 [SMILES: CNc1ccccc1C(=O)Cn1cc(/C(C)=N/OC(C)C)c(=O)n(C[C@H](C)NC(=O)C(C)C)c1=O] | m.p. 197-201° C. | |

TABLE 6-continued
| Compound number | Structural formula | Physical properties | Remarks |
|---|---|---|---|
| C-225 | 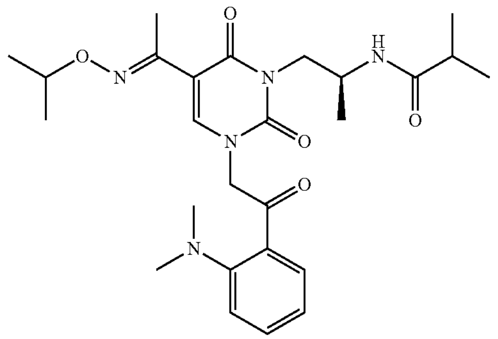 [SMILES: C/C(=N\OC(C)C)c1cn(CC(=O)c2ccccc2N(C)C)c(=O)n(C[C@H](C)NC(=O)C(C)C)c1=O] | m.p. 157-163° C. | |
| C-226 | 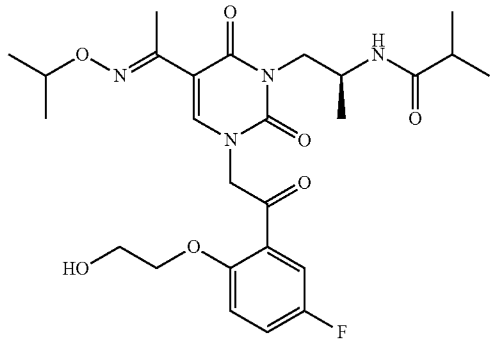 [SMILES: C/C(=N\OC(C)C)c1cn(CC(=O)c2cc(F)ccc2OCCO)c(=O)n(C[C@H](C)NC(=O)C(C)C)c1=O] | m.p. 78-80° C. | |
| C-227 | 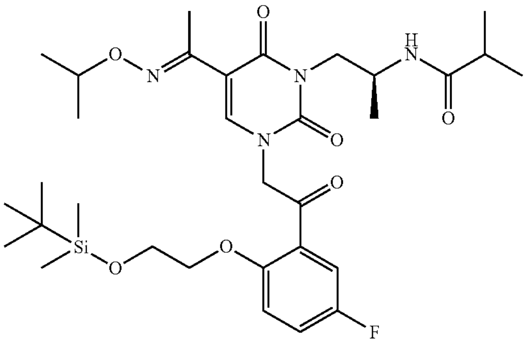 [SMILES: C/C(=N\OC(C)C)c1cn(CC(=O)c2cc(F)ccc2OCCO[Si](C)(C)C(C)(C)C)c(=O)n(C[C@H](C)NC(=O)C(C)C)c1=O] | m.p. 53-56° C. | |
| C-228 | 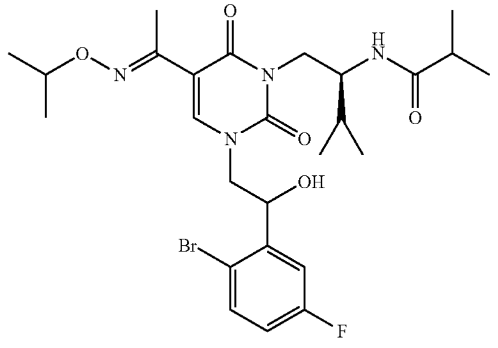 [SMILES: C/C(=N\OC(C)C)c1cn(CC(O)c2cc(F)ccc2Br)c(=O)n(C[C@@H](NC(=O)C(C)C)C(C)C)c1=O] | m.p. 88-90° C. | |

TABLE 6-continued
| Compound number | Structural formula | Physical properties | Remarks |
|---|---|---|---|
| C-229 | 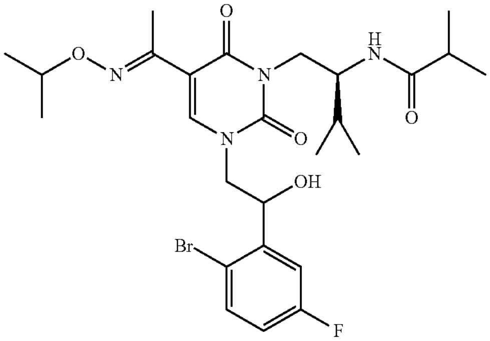 [SMILES: C/C(=N\OC(C)C)c1cn(CC(O)c2cc(F)ccc2Br)c(=O)n(C[C@@H](NC(=O)C(C)C)C(C)C)c1=O] | m.p. 92-94° C. | Isomer of C-228 |
| C-230 | 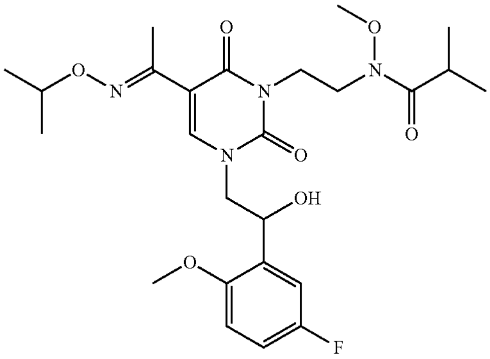 [SMILES: COc1ccc(F)cc1C(O)Cn1cc(/C(C)=N/OC(C)C)c(=O)n(CCN(OC)C(=O)C(C)C)c1=O] | m.p. 57-58° C. | |
| C-231 | 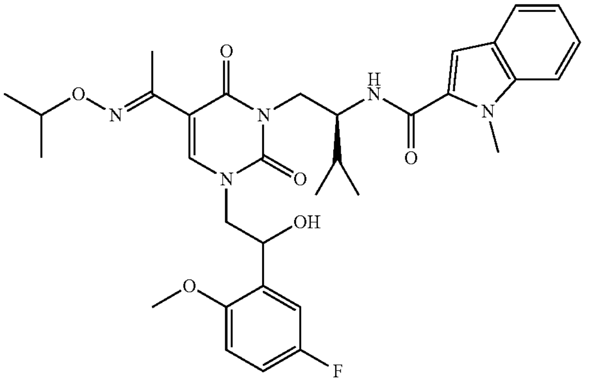 [SMILES: COc1ccc(F)cc1C(O)Cn1cc(/C(C)=N/OC(C)C)c(=O)n(C[C@@H](NC(=O)c2cc3ccccc3n2C)C(C)C)c1=O] | m.p. 127-128° C. | |
| C-232 | 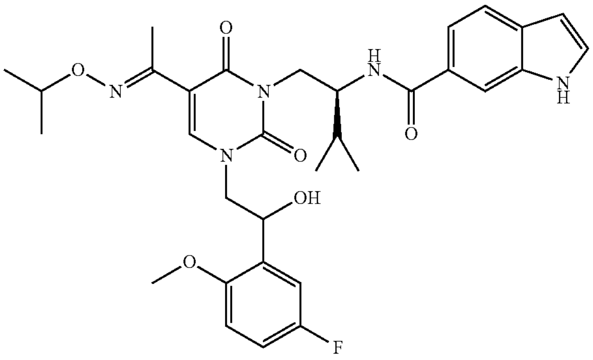 [SMILES: COc1ccc(F)cc1C(O)Cn1cc(/C(C)=N/OC(C)C)c(=O)n(C[C@@H](NC(=O)c2ccc3cc[nH]c3c2)C(C)C)c1=O] | m.p. 97-98° C. | |

TABLE 6-continued
| Compound number | Structural formula | Physical properties | Remarks |
|---|---|---|---|
| C-233 | 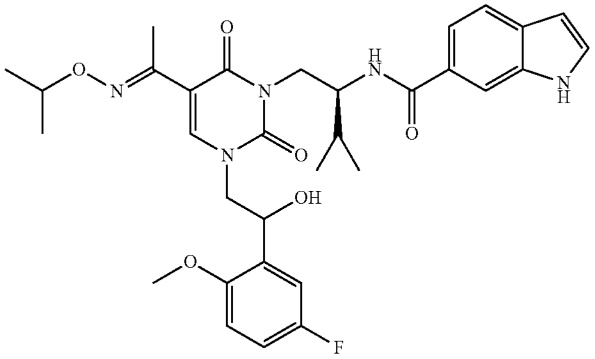 [SMILES: COc1ccc(F)cc1C(O)Cn1cc(/C(C)=N/OC(C)C)c(=O)n(C[C@@H](NC(=O)c2ccc3cc[nH]c3c2)C(C)C)c1=O] | m.p. 90-92° C. | Isomer of C-232 |
| C-234 | 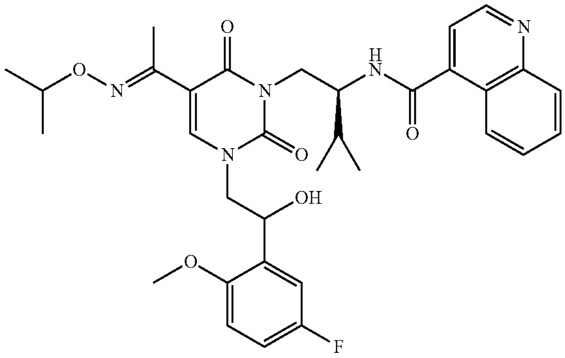 [SMILES: COc1ccc(F)cc1C(O)Cn1cc(/C(C)=N/OC(C)C)c(=O)n(C[C@@H](NC(=O)c2ccnc3ccccc23)C(C)C)c1=O] | m.p. 120-122° C. | |
| C-235 | 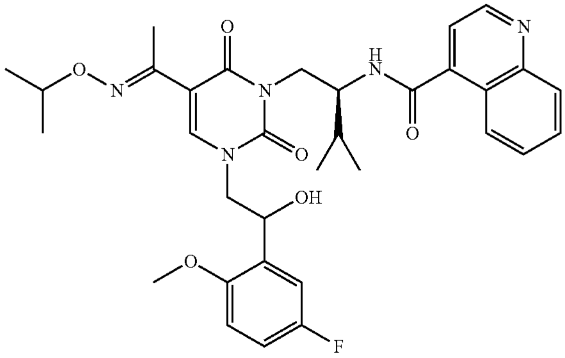 [SMILES: COc1ccc(F)cc1C(O)Cn1cc(/C(C)=N/OC(C)C)c(=O)n(C[C@@H](NC(=O)c2ccnc3ccccc23)C(C)C)c1=O] | m.p. 101-102° C. | Isomer of C-234 |
| C-236 | 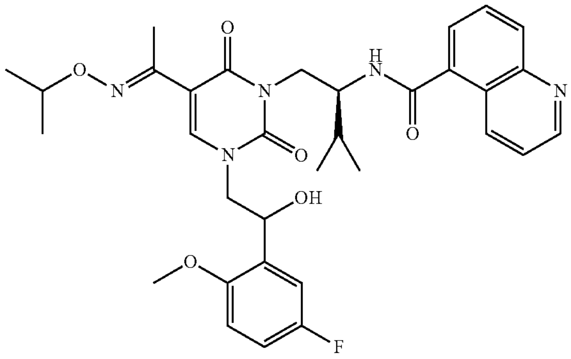 [SMILES: COc1ccc(F)cc1C(O)Cn1cc(/C(C)=N/OC(C)C)c(=O)n(C[C@@H](NC(=O)c2cccc3ncccc23)C(C)C)c1=O] | m.p. 124-125° C. | |

TABLE 6-continued
| Compound number | Structural formula | Physical properties | Remarks |
|---|---|---|---|
| C-237 | 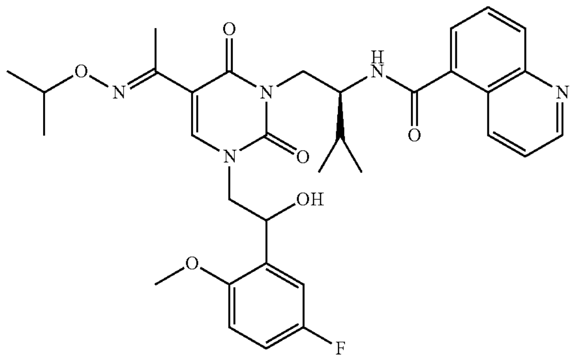 [SMILES: COc1ccc(F)cc1C(O)Cn1cc(/C(C)=N/OC(C)C)c(=O)n(C[C@@H](NC(=O)c2cccc3ncccc23)C(C)C)c1=O] | m.p. 116-117° C. | Isomer of C-236 |
| C-238 | 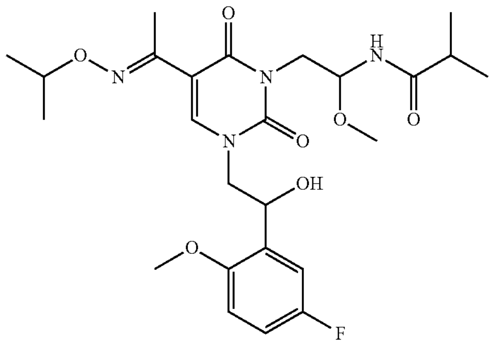 [SMILES: COc1ccc(F)cc1C(O)Cn1cc(/C(C)=N/OC(C)C)c(=O)n(CC(NC(=O)C(C)C)OC)c1=O] | m.p. 97-100° C. | |
| C-239 | 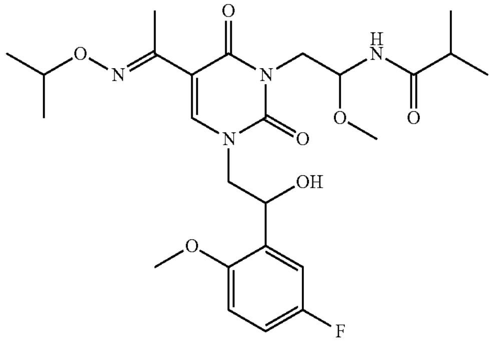 [SMILES: COc1ccc(F)cc1C(O)Cn1cc(/C(C)=N/OC(C)C)c(=O)n(CC(NC(=O)C(C)C)OC)c1=O] | m.p. 89-91° C. | Isomer of C-238 |
| C-240 | 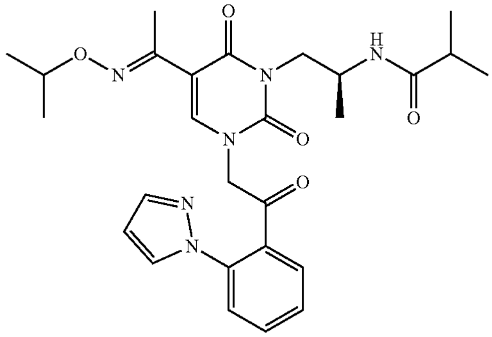 [SMILES: C/C(=N\OC(C)C)c1cn(CC(=O)c2ccccc2-n2cccn2)c(=O)n(C[C@H](C)NC(=O)C(C)C)c1=O] | m.p. 206-210° C. | |

TABLE 6-continued

| Compound number | Structural formula | Physical properties | Remarks |
|---|---|---|---|
| C-241 | 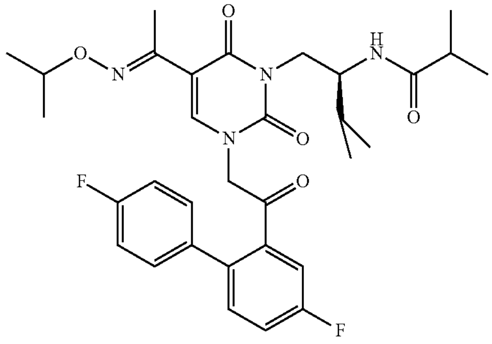 [SMILES: C/C(=N\OC(C)C)c1cn(CC(=O)c2cc(F)ccc2-c2ccc(F)cc2)c(=O)n(C[C@@H](NC(=O)C(C)C)C(C)C)c1=O] | m.p. 179-180° C. | |
| C-242 | 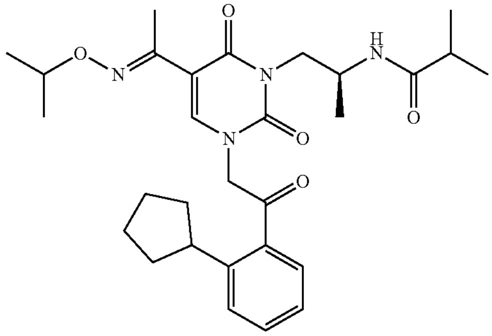 [SMILES: C/C(=N\OC(C)C)c1cn(CC(=O)c2ccccc2C2CCCC2)c(=O)n(C[C@H](C)NC(=O)C(C)C)c1=O] | viscous oil | |
| C-243 | 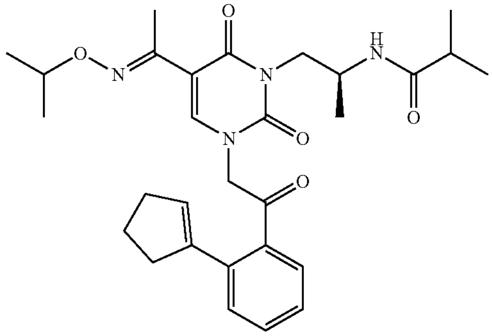 [SMILES: C/C(=N\OC(C)C)c1cn(CC(=O)c2ccccc2C2=CCCC2)c(=O)n(C[C@H](C)NC(=O)C(C)C)c1=O] | viscous oil | |

Further, some of the compounds of the present invention produced in the same manner as in Examples described above are shown in Table 7. In the table, the melting point (m.p.) is also shown as physical properties of each compound. When the compound is a stereoisomer, it is indicated in the remarks.

TABLE 7
| Compound number | Structural formula | Physical properties | Remarks |
|---|---|---|---|
| D-1 | 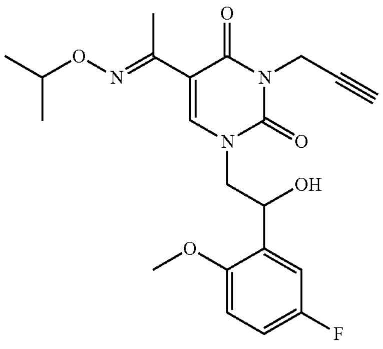 [SMILES: C#CCn1c(=O)c(/C(C)=N/OC(C)C)cn(CC(O)c2cc(F)ccc2OC)c1=O] | m.p. 127-131° C. | |
| D-2 | 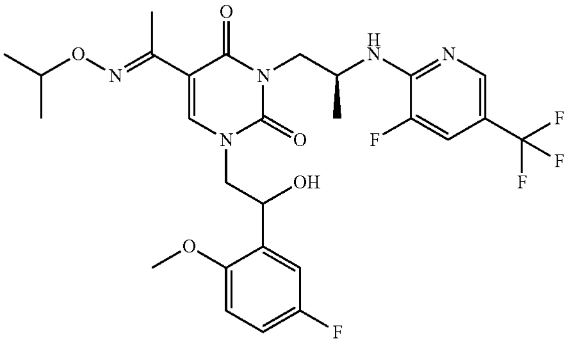 [SMILES: COc1ccc(F)cc1C(O)Cn1cc(/C(C)=N/OC(C)C)c(=O)n(C[C@H](C)Nc2ncc(C(F)(F)F)cc2F)c1=O] | viscous oil | |
| D-3 | 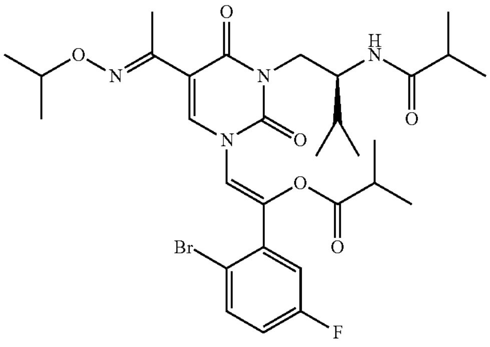 [SMILES: C/C(=N\OC(C)C)c1cn(/C=C(\OC(=O)C(C)C)c2cc(F)ccc2Br)c(=O)n(C[C@@H](NC(=O)C(C)C)C(C)C)c1=O] | viscous oil | |
| D-4 | 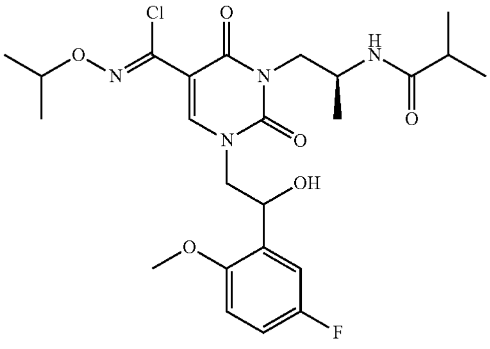 | m.p. 69-74° C. | |

TABLE 7-continued
| Compound number | Structural formula | Physical properties | Remarks |
| --- | --- | --- | --- |
| D-5 | 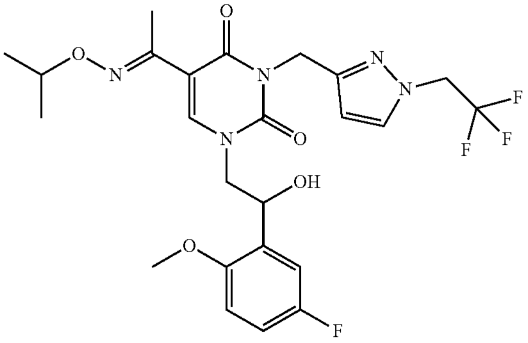 [SMILES: COc1ccc(F)cc1C(O)Cn1cc(/C(C)=N/OC(C)C)c(=O)n(Cc2ccn(CC(F)(F)F)n2)c1=O] | amorphous | |
| D-6 | 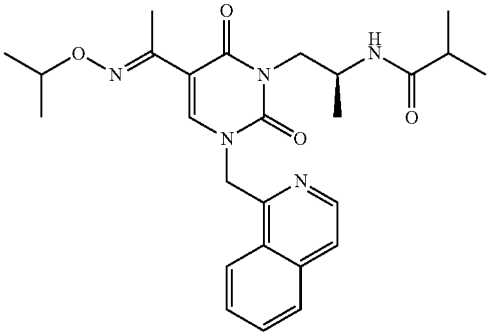 [SMILES: C/C(=N\OC(C)C)c1cn(Cc2nccc3ccccc23)c(=O)n(C[C@H](C)NC(=O)C(C)C)c1=O] | m.p. 174-175° C. | |
| D-7 | 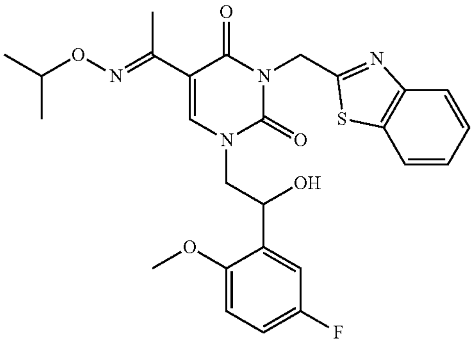 [SMILES: COc1ccc(F)cc1C(O)Cn1cc(/C(C)=N/OC(C)C)c(=O)n(Cc2nc3ccccc3s2)c1=O] | m.p. 97-99° C. | |
| D-8 | 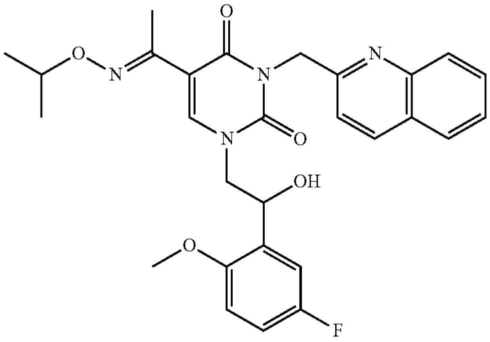 [SMILES: COc1ccc(F)cc1C(O)Cn1cc(/C(C)=N/OC(C)C)c(=O)n(Cc2ccc3ccccc3n2)c1=O] | m.p. 93-95° C. | |

TABLE 7-continued
| Compound number | Structural formula | Physical properties | Remarks |
|---|---|---|---|
| D-9 | 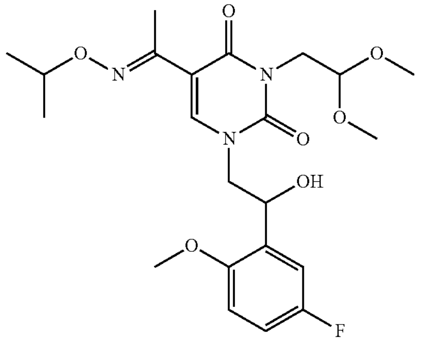 [SMILES: COc1ccc(F)cc1C(O)Cn1cc(/C(C)=N/OC(C)C)c(=O)n(CC(OC)OC)c1=O] | viscous oil | |
| D-10 | 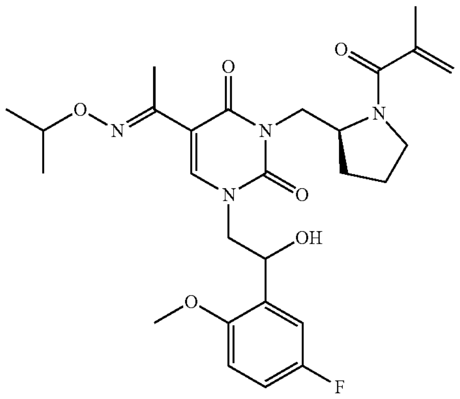 [SMILES: C=C(C)C(=O)N1CCC[C@H]1Cn1c(=O)c(/C(C)=N/OC(C)C)cn(CC(O)c2cc(F)ccc2OC)c1=O] | m.p. 53-56° C. | |
| D-11 | 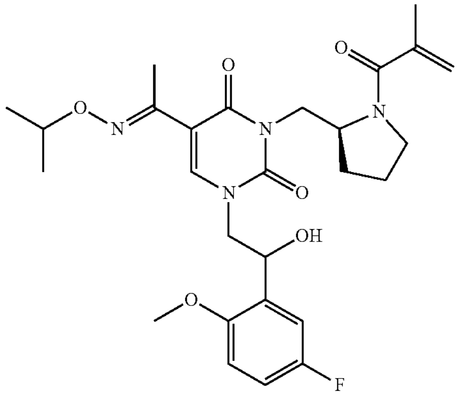 [SMILES: C=C(C)C(=O)N1CCC[C@H]1Cn1c(=O)c(/C(C)=N/OC(C)C)cn(CC(O)c2cc(F)ccc2OC)c1=O] | m.p. 62-63° C. | Isomer of D-10 |
| D-12 | 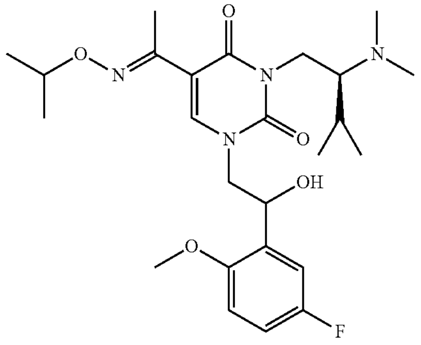 [SMILES: COc1ccc(F)cc1C(O)Cn1cc(/C(C)=N/OC(C)C)c(=O)n(C[C@H](C(C)C)N(C)C)c1=O] | amorphous | |

TABLE 7-continued
| Compound number | Structural formula | Physical properties | Remarks |
|---|---|---|---|
| D-13 | 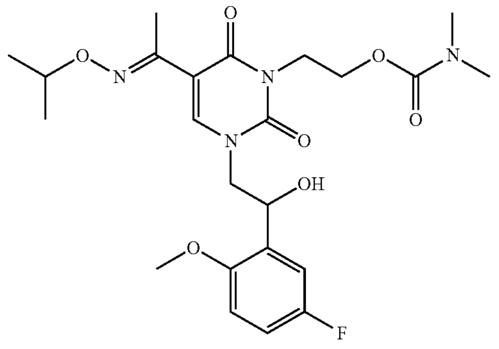 [SMILES: COc1ccc(F)cc1C(O)Cn1cc(/C(C)=N/OC(C)C)c(=O)n(CCOC(=O)N(C)C)c1=O] | visous oil | |
| D-14 | 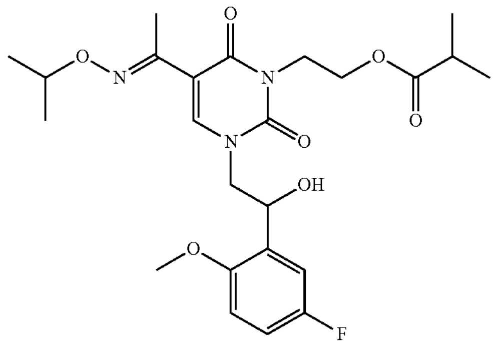 [SMILES: COc1ccc(F)cc1C(O)Cn1cc(/C(C)=N/OC(C)C)c(=O)n(CCOC(=O)C(C)C)c1=O] | viscous oil | |
| D-15 | 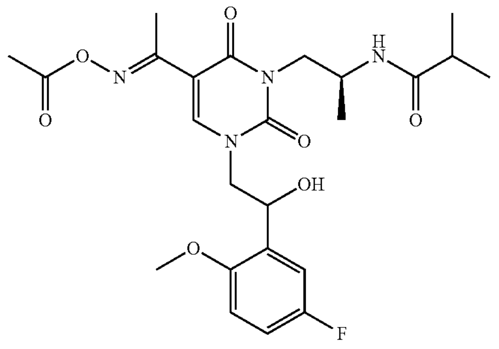 [SMILES: COc1ccc(F)cc1C(O)Cn1cc(/C(C)=N/OC(C)=O)c(=O)n(C[C@H](C)NC(=O)C(C)C)c1=O] | m.p. 87-88° C. | |
| D-16 | 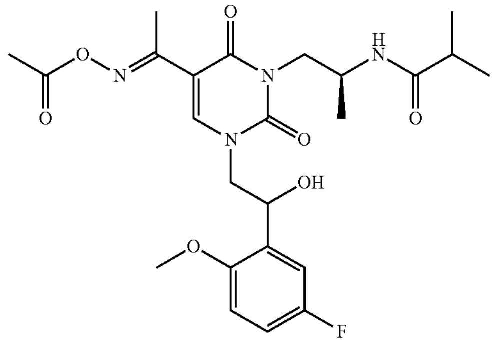 [SMILES: COc1ccc(F)cc1C(O)Cn1cc(/C(C)=N/OC(C)=O)c(=O)n(C[C@H](C)NC(=O)C(C)C)c1=O] | m.p. 90-91° C. | Isomer of D-15 |

TABLE 7-continued
| Compound number | Structural formula | Physical properties | Remarks |
|---|---|---|---|
| D-17 | 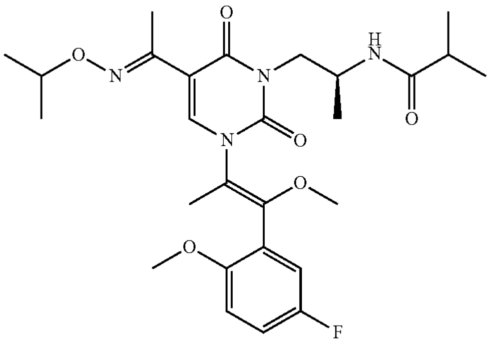 [SMILES: CO/C(=C(/C)n1cc(/C(C)=N/OC(C)C)c(=O)n(C[C@H](C)NC(=O)C(C)C)c1=O)c1cc(F)ccc1OC] | m.p. 60-61° C. | |
| D-18 | 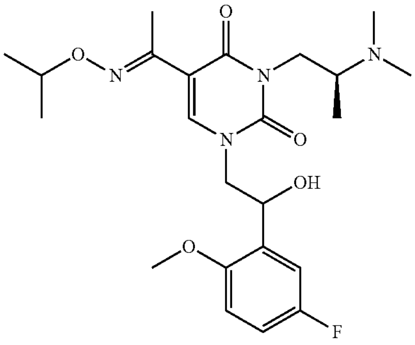 [SMILES: COc1ccc(F)cc1C(O)Cn1cc(/C(C)=N/OC(C)C)c(=O)n(C[C@H](C)N(C)C)c1=O] | amorphous | |
| D-19 | 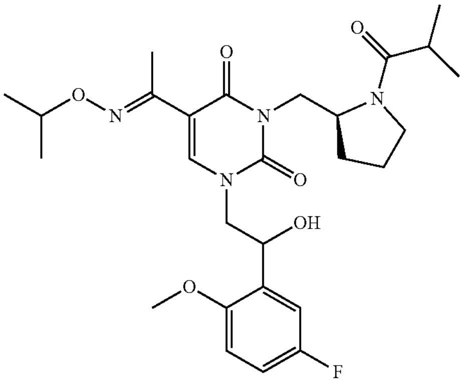 [SMILES: COc1ccc(F)cc1C(O)Cn1cc(/C(C)=N/OC(C)C)c(=O)n(C[C@@H]2CCCN2C(=O)C(C)C)c1=O] | amorphous | |
| D-20 | 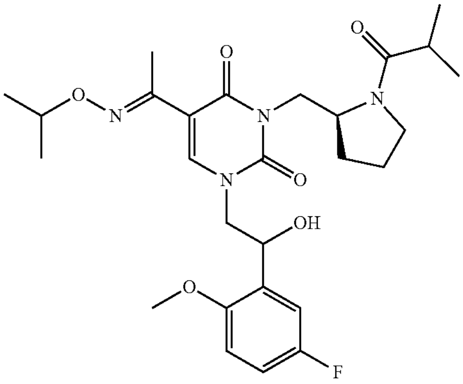 [SMILES: COc1ccc(F)cc1C(O)Cn1cc(/C(C)=N/OC(C)C)c(=O)n(C[C@@H]2CCCN2C(=O)C(C)C)c1=O] | amorphous | Isomer of D-19 |

TABLE 7-continued
| Compound number | Structural formula | Physical properties | Remarks |
| --- | --- | --- | --- |
| D-21 | 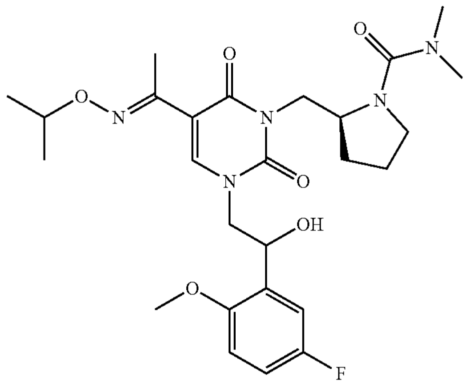 [SMILES: COc1ccc(F)cc1C(O)Cn1cc(/C(C)=N/OC(C)C)c(=O)n(C[C@@H]2CCCN2C(=O)N(C)C)c1=O] | m.p. 65-66° C. | |
| D-22 | 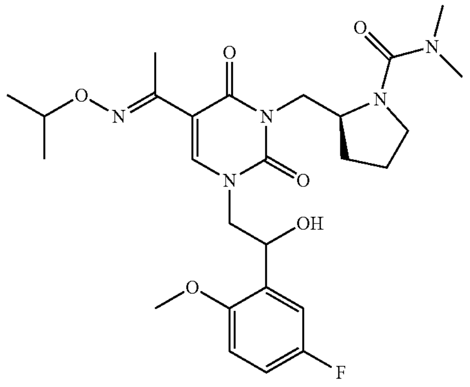 [SMILES: COc1ccc(F)cc1C(O)Cn1cc(/C(C)=N/OC(C)C)c(=O)n(C[C@@H]2CCCN2C(=O)N(C)C)c1=O] | m.p. 69-70° C. | Isomer of D-21 |
| D-23 | 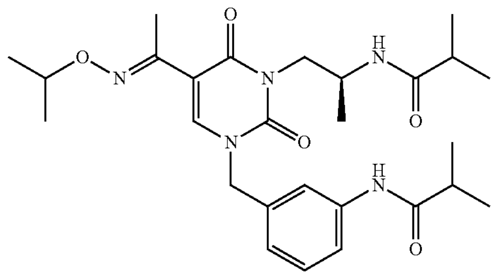 [SMILES: C/C(=N\OC(C)C)c1cn(Cc2cccc(NC(=O)C(C)C)c2)c(=O)n(C[C@H](C)NC(=O)C(C)C)c1=O] | m.p. 190-191° C. | |
| D-24 | 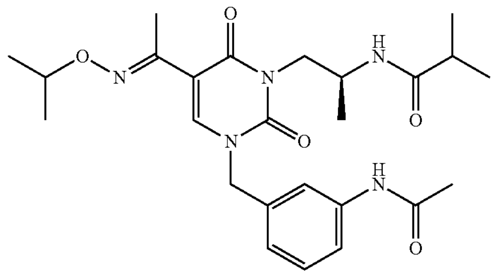 [SMILES: CC(=O)Nc1cccc(Cn2cc(/C(C)=N/OC(C)C)c(=O)n(C[C@H](C)NC(=O)C(C)C)c2=O)c1] | m.p. 117-119° C. | |

TABLE 7-continued
| Compound number | Structural formula | Physical properties | Remarks |
|---|---|---|---|
| D-25 | 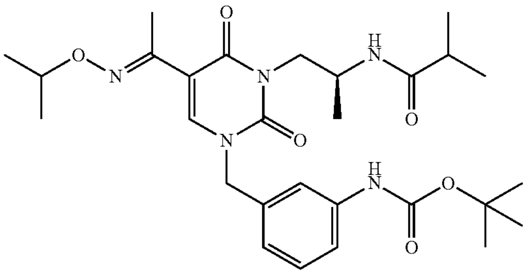 [SMILES: C/C(=N\OC(C)C)c1cn(Cc2cccc(NC(=O)OC(C)(C)C)c2)c(=O)n(C[C@H](C)NC(=O)C(C)C)c1=O] | m.p. 125-126° C. | |
| D-26 | 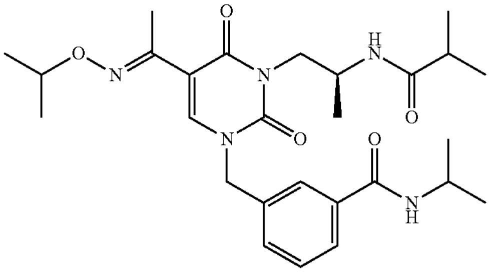 [SMILES: C/C(=N\OC(C)C)c1cn(Cc2cccc(C(=O)NC(C)C)c2)c(=O)n(C[C@H](C)NC(=O)C(C)C)c1=O] | m.p. 219-220° C. | |
| D-27 | 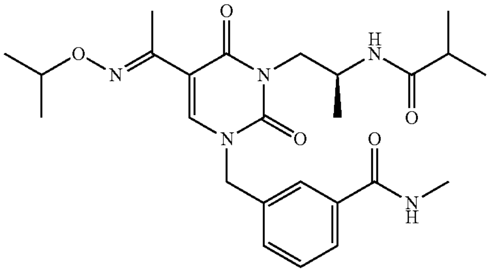 [SMILES: CNC(=O)c1cccc(Cn2cc(/C(C)=N/OC(C)C)c(=O)n(C[C@H](C)NC(=O)C(C)C)c2=O)c1] | m.p. 106-113° C. | |
| D-28 | 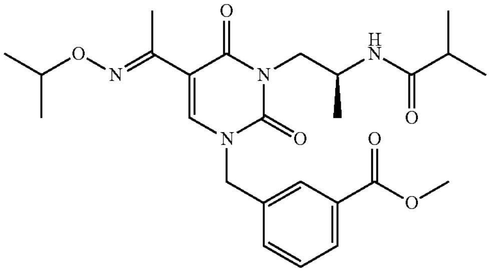 [SMILES: COC(=O)c1cccc(Cn2cc(/C(C)=N/OC(C)C)c(=O)n(C[C@H](C)NC(=O)C(C)C)c2=O)c1] | m.p. 151-152° C. | |
| D-29 | 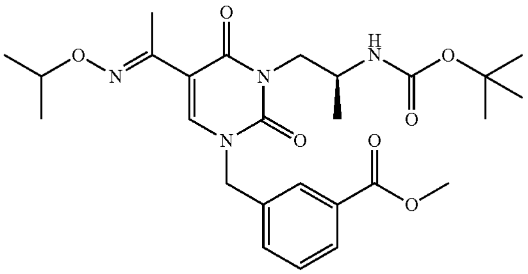 [SMILES: COC(=O)c1cccc(Cn2cc(/C(C)=N/OC(C)C)c(=O)n(C[C@H](C)NC(=O)OC(C)(C)C)c2=O)c1] | viscous oil | |

TABLE 7-continued
| Compound number | Structural formula | Physical properties | Remarks |
|---|---|---|---|
| D-30 | 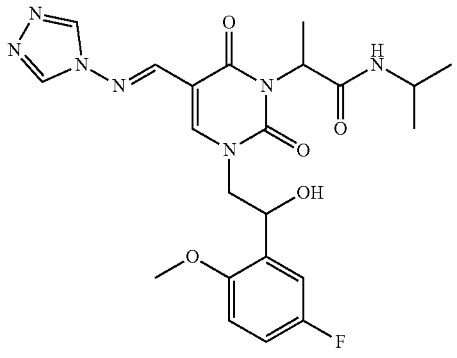 [SMILES: COc1ccc(F)cc1C(O)Cn1cc(/C=N/n2cnnc2)c(=O)n(C(C)C(=O)NC(C)C)c1=O] | m.p. 274-275° C. | |
| D-31 | 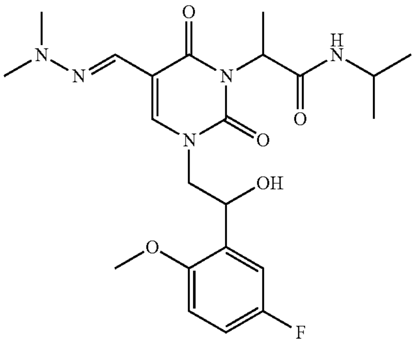 [SMILES: COc1ccc(F)cc1C(O)Cn1cc(/C=N/N(C)C)c(=O)n(C(C)C(=O)NC(C)C)c1=O] | m.p. 67-68° C. | |
| D-32 | 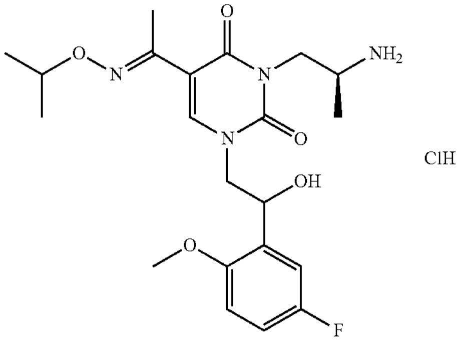 [SMILES: COc1ccc(F)cc1C(O)Cn1cc(/C(C)=N/OC(C)C)c(=O)n(C[C@H](C)N)c1=O ; Cl] | m.p. 191-192° C. | |
| D-33 | 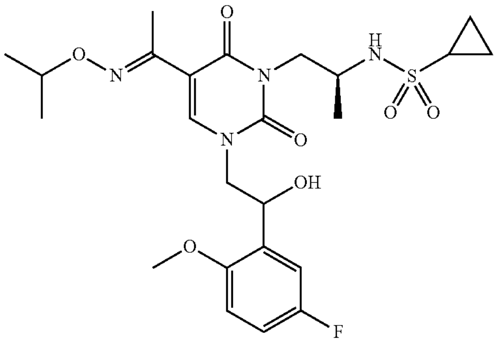 [SMILES: COc1ccc(F)cc1C(O)Cn1cc(/C(C)=N/OC(C)C)c(=O)n(C[C@H](C)NS(=O)(=O)C2CC2)c1=O] | m.p. 69-73° C. | |

TABLE 7-continued
| Compound number | Structural formula | Physical properties | Remarks |
|---|---|---|---|
| D-34 | 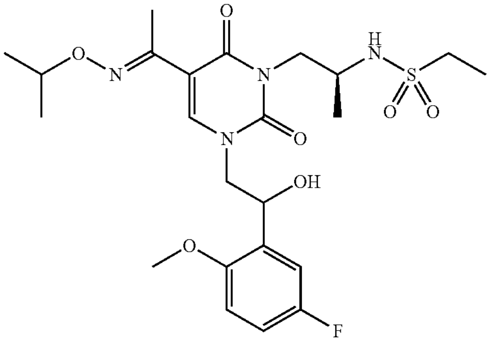 [SMILES: CCS(=O)(=O)N[C@@H](C)Cn1c(=O)c(/C(C)=N/OC(C)C)cn(CC(O)c2cc(F)ccc2OC)c1=O] | m.p. 62-65° C. | |
| D-35 | 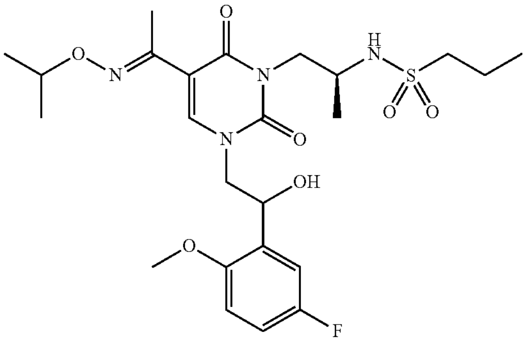 [SMILES: CCCS(=O)(=O)N[C@@H](C)Cn1c(=O)c(/C(C)=N/OC(C)C)cn(CC(O)c2cc(F)ccc2OC)c1=O] | viscous oil | |
| D-36 | 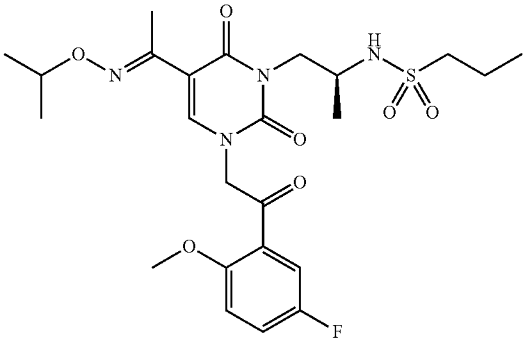 [SMILES: CCCS(=O)(=O)N[C@@H](C)Cn1c(=O)c(/C(C)=N/OC(C)C)cn(CC(=O)c2cc(F)ccc2OC)c1=O] | m.p. 97-98° C. | |
| D-37 | 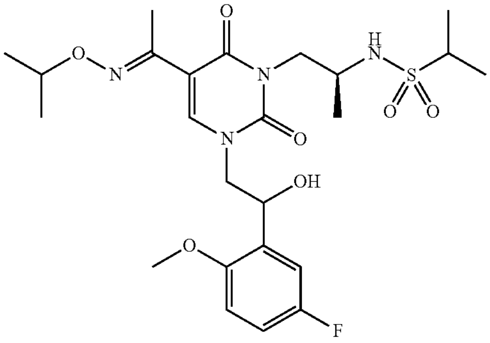 [SMILES: COc1ccc(F)cc1C(O)Cn1cc(/C(C)=N/OC(C)C)c(=O)n(C[C@H](C)NS(=O)(=O)C(C)C)c1=O] | viscous oil | |

TABLE 7-continued
| Compound number | Structural formula | Physical properties | Remarks |
|---|---|---|---|
| D-38 | 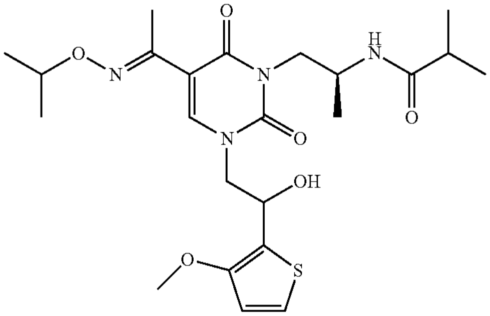 [SMILES: COc1ccsc1C(O)Cn1cc(/C(C)=N/OC(C)C)c(=O)n(C[C@H](C)NC(=O)C(C)C)c1=O] | m.p. 71-72° C. | |
| D-39 | 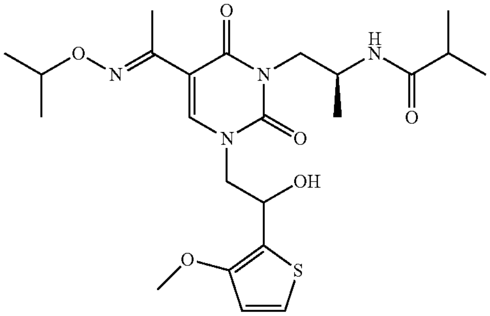 [SMILES: COc1ccsc1C(O)Cn1cc(/C(C)=N/OC(C)C)c(=O)n(C[C@H](C)NC(=O)C(C)C)c1=O] | m.p. 77-78° C. | Isomer of D-38 |
| D-40 | 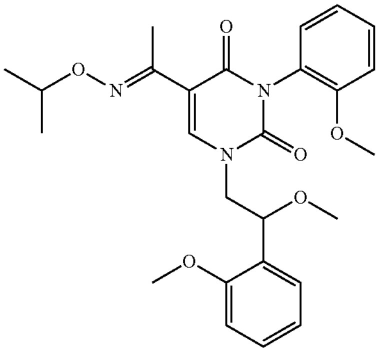 [SMILES: COc1ccccc1C(Cn1cc(/C(C)=N/OC(C)C)c(=O)n(-c2ccccc2OC)c1=O)OC] | amorphous | |
| D-41 | 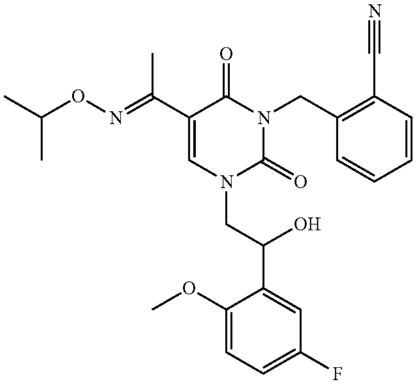 [SMILES: COc1ccc(F)cc1C(O)Cn1cc(/C(C)=N/OC(C)C)c(=O)n(Cc2ccccc2C#N)c1=O] | m.p. 153-154° C. | |

TABLE 7-continued
| Compound number | Structural formula | Physical properties | Remarks |
| --- | --- | --- | --- |
| D-42 | 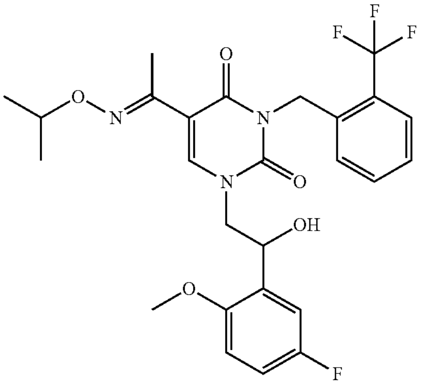 [SMILES: COc1ccc(F)cc1C(O)Cn1cc(/C(C)=N/OC(C)C)c(=O)n(Cc2ccccc2C(F)(F)F)c1=O] | m.p. 162-163° C. | |
| D-43 | 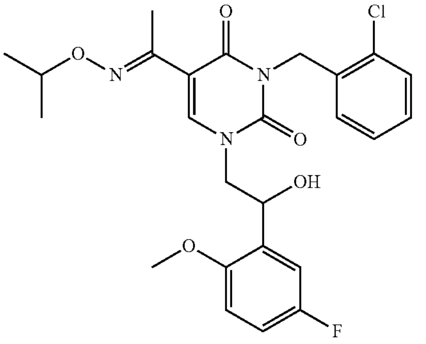 [SMILES: COc1ccc(F)cc1C(O)Cn1cc(/C(C)=N/OC(C)C)c(=O)n(Cc2ccccc2Cl)c1=O] | m.p. 155-156° C. | |
| D-44 | 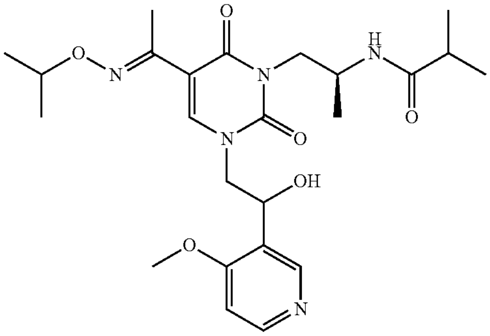 [SMILES: COc1ccncc1C(O)Cn1cc(/C(C)=N/OC(C)C)c(=O)n(C[C@H](C)NC(=O)C(C)C)c1=O] | m.p. 86-92° C. | |
| D-45 | 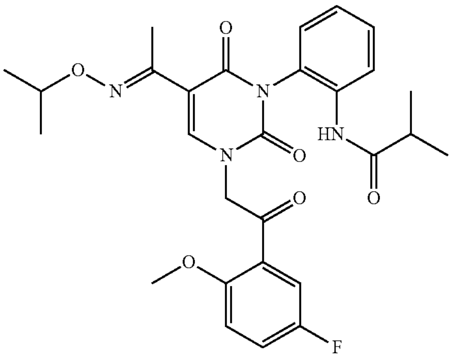 [SMILES: COc1ccc(F)cc1C(=O)Cn1cc(/C(C)=N/OC(C)C)c(=O)n(-c2ccccc2NC(=O)C(C)C)c1=O] | m.p. 63-65° C. | |

TABLE 7-continued
| Compound number | Structural formula | Physical properties | Remarks |
|---|---|---|---|
| D-46 | 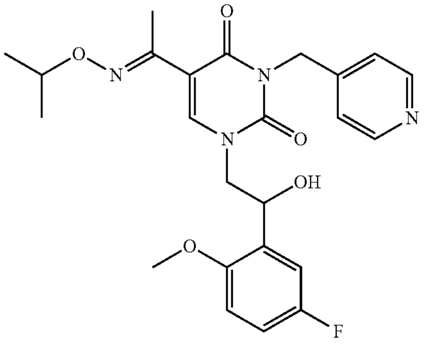 [SMILES: COc1ccc(F)cc1C(O)Cn1cc(/C(C)=N/OC(C)C)c(=O)n(Cc2ccncc2)c1=O] | m.p. 102-103° C. | |
| D-47 | 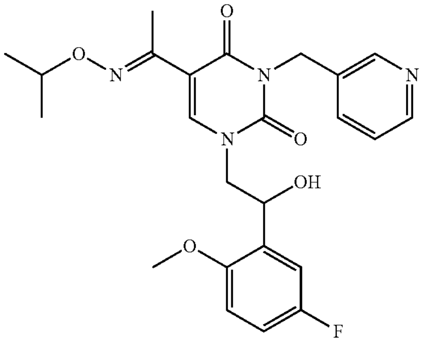 [SMILES: COc1ccc(F)cc1C(O)Cn1cc(/C(C)=N/OC(C)C)c(=O)n(Cc2cccnc2)c1=O] | viscous oil | |
| D-48 | 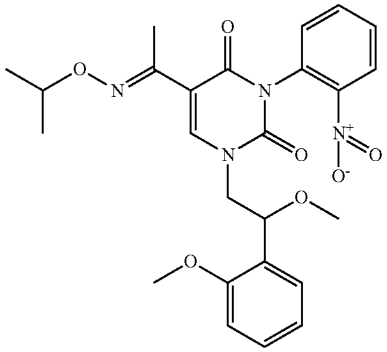 [SMILES: COc1ccccc1C(Cn1cc(/C(C)=N/OC(C)C)c(=O)n(-c2ccccc2[N+](=O)[O-])c1=O)OC] | m.p. 69-70° C. | |
| D-49 | 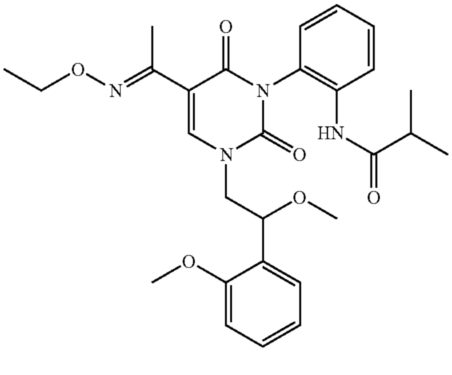 [SMILES: CCO/N=C(\C)c1cn(CC(OC)c2ccccc2OC)c(=O)n(-c2ccccc2NC(=O)C(C)C)c1=O] | m.p. 157-159° C. | |

TABLE 7-continued
| Compound number | Structural formula | Physical properties | Remarks |
| --- | --- | --- | --- |
| D-50 | 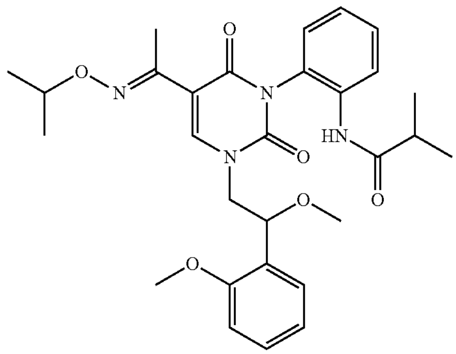 [SMILES: COc1ccccc1C(Cn1cc(/C(C)=N/OC(C)C)c(=O)n(-c2ccccc2NC(=O)C(C)C)c1=O)OC] | m.p. 142-143° C. | |
| D-51 | 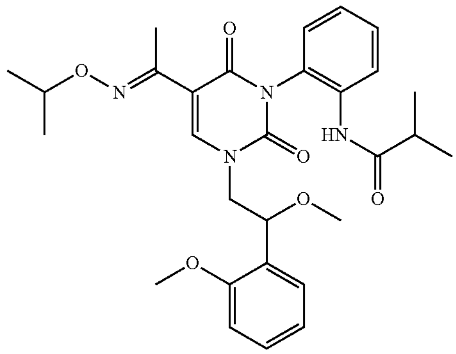 [SMILES: COc1ccccc1C(Cn1cc(/C(C)=N/OC(C)C)c(=O)n(-c2ccccc2NC(=O)C(C)C)c1=O)OC] | m.p. 149-150° C. | Isomer of D-50 |
| D-52 | 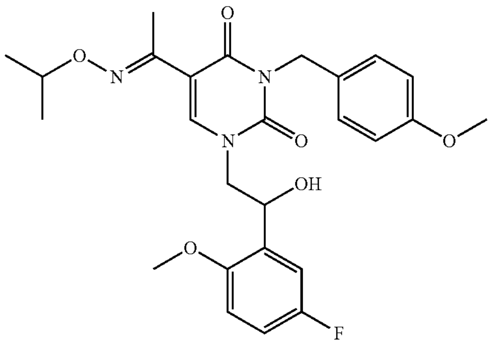 [SMILES: COc1ccc(Cn2c(=O)c(/C(C)=N/OC(C)C)cn(CC(O)c3cc(F)ccc3OC)c2=O)cc1] | viscous oil | |
| D-53 | 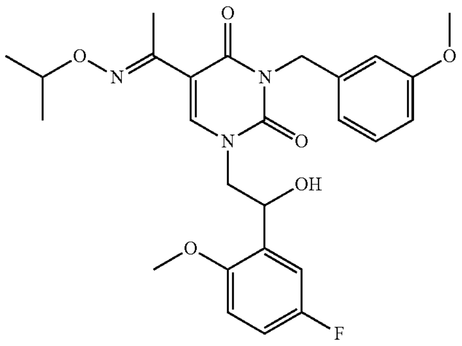 [SMILES: COc1cccc(Cn2c(=O)c(/C(C)=N/OC(C)C)cn(CC(O)c3cc(F)ccc3OC)c2=O)c1] | m.p. 87-89° C. | |

TABLE 7-continued
| Compound number | Structural formula | Physical properties | Remarks |
| --- | --- | --- | --- |
| D-54 | 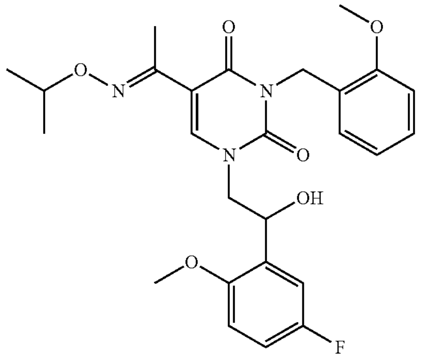 [SMILES: COc1ccccc1Cn1c(=O)c(/C(C)=N/OC(C)C)cn(CC(O)c2cc(F)ccc2OC)c1=O] | m.p. 132-133° C. | |
| D-55 | 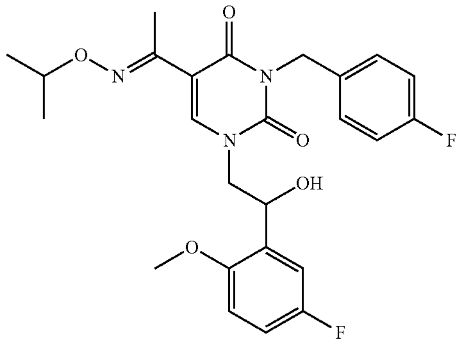 [SMILES: COc1ccc(F)cc1C(O)Cn1cc(/C(C)=N/OC(C)C)c(=O)n(Cc2ccc(F)cc2)c1=O] | m.p. 112-113° C. | |
| D-56 | 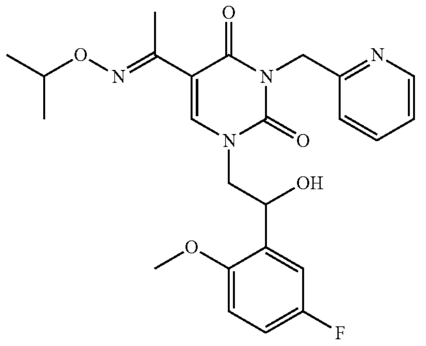 [SMILES: COc1ccc(F)cc1C(O)Cn1cc(/C(C)=N/OC(C)C)c(=O)n(Cc2ccccn2)c1=O] | m.p. 162-163° C. | |
| D-57 | 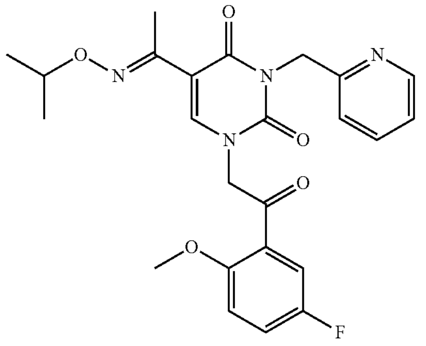 [SMILES: COc1ccc(F)cc1C(=O)Cn1cc(/C(C)=N/OC(C)C)c(=O)n(Cc2ccccn2)c1=O] | viscous oil | |

TABLE 7-continued
| Compound number | Structural formula | Physical properties | Remarks |
|---|---|---|---|
| D-58 | 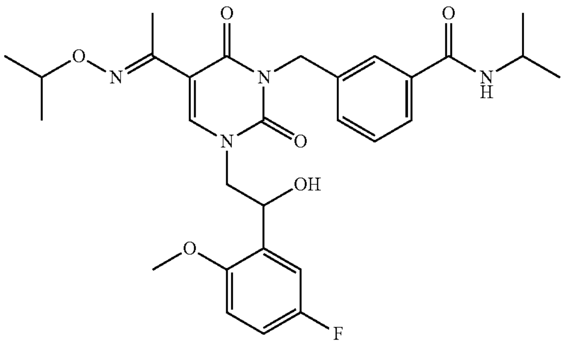 [SMILES: COc1ccc(F)cc1C(O)Cn1cc(/C(C)=N/OC(C)C)c(=O)n(Cc2cccc(C(=O)NC(C)C)c2)c1=O] | m.p. 81-82° C. | |
| D-59 | 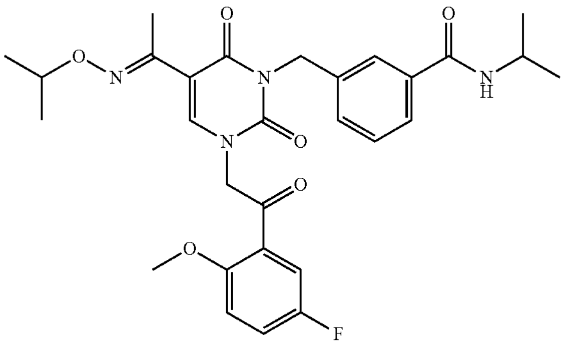 [SMILES: COc1ccc(F)cc1C(=O)Cn1cc(/C(C)=N/OC(C)C)c(=O)n(Cc2cccc(C(=O)NC(C)C)c2)c1=O] | m.p. 105-106° C. | |
| D-60 | 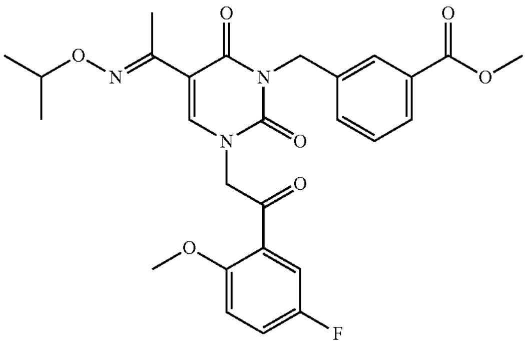 [SMILES: COC(=O)c1cccc(Cn2c(=O)c(/C(C)=N/OC(C)C)cn(CC(=O)c3cc(F)ccc3OC)c2=O)c1] | m.p. 67-70° C. | |
| D-61 | 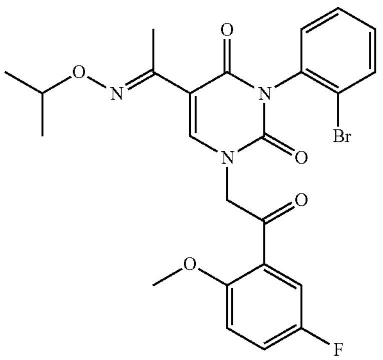 [SMILES: COc1ccc(F)cc1C(=O)Cn1cc(/C(C)=N/OC(C)C)c(=O)n(-c2ccccc2Br)c1=O] | m.p. 69-73° C. | |

TABLE 7-continued
| Compound number | Structural formula | Physical properties | Remarks |
|---|---|---|---|
| D-62 | 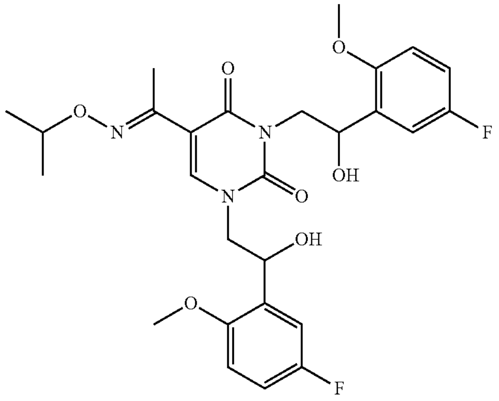 [SMILES: COc1ccc(F)cc1C(O)Cn1cc(/C(C)=N/OC(C)C)c(=O)n(CC(O)c2cc(F)ccc2OC)c1=O] | m.p. 60-65° C. | |
| D-63 | 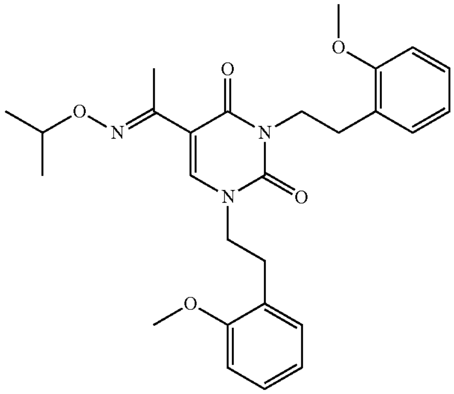 [SMILES: COc1ccccc1CCn1cc(/C(C)=N/OC(C)C)c(=O)n(CCc2ccccc2OC)c1=O] | viscous oil | |
| D-64 | 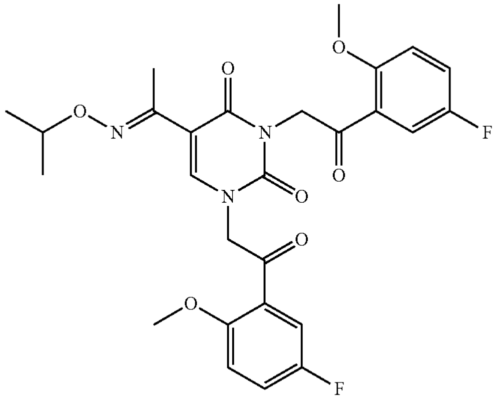 [SMILES: COc1ccc(F)cc1C(=O)Cn1cc(/C(C)=N/OC(C)C)c(=O)n(CC(=O)c2cc(F)ccc2OC)c1=O] | m.p. 83-84° C. | |
| D-65 | 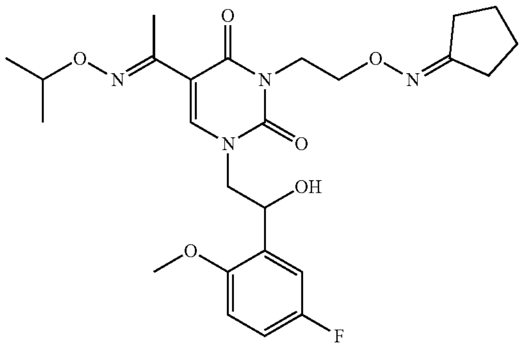 [SMILES: COc1ccc(F)cc1C(O)Cn1cc(/C(C)=N/OC(C)C)c(=O)n(CCON=C2CCCC2)c1=O] | viscous oil | |

TABLE 7-continued
| Compound number | Structural formula | Physical properties | Remarks |
|---|---|---|---|
| D-66 | 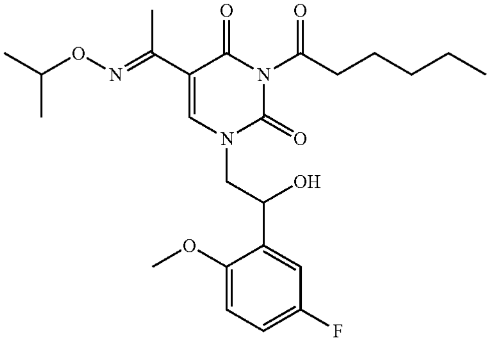 [SMILES: CCCCCC(=O)n1c(=O)c(/C(C)=N/OC(C)C)cn(CC(O)c2cc(F)ccc2OC)c1=O] | viscous oil | |
| D-67 | 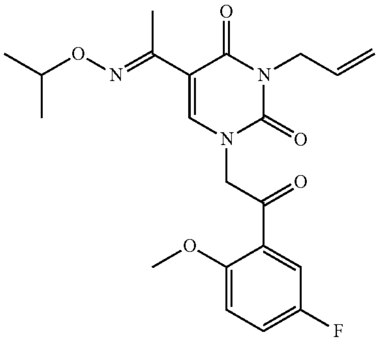 [SMILES: C=CCn1c(=O)c(/C(C)=N/OC(C)C)cn(CC(=O)c2cc(F)ccc2OC)c1=O] | m.p. 63-66° C. | |
| D-68 | 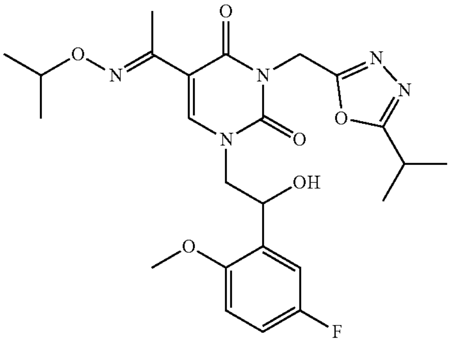 [SMILES: COc1ccc(F)cc1C(O)Cn1cc(/C(C)=N/OC(C)C)c(=O)n(Cc2nnc(C(C)C)o2)c1=O] | m.p. 40-45° C. | |
| D-69 | 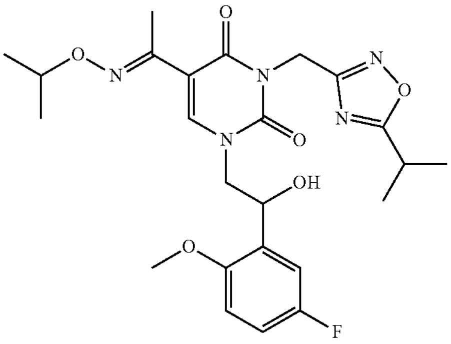 [SMILES: COc1ccc(F)cc1C(O)Cn1cc(/C(C)=N/OC(C)C)c(=O)n(Cc2noc(C(C)C)n2)c1=O] | m.p. 53-58° C. | |

TABLE 7-continued
| Compound number | Structural formula | Physical properties | Remarks |
| --- | --- | --- | --- |
| D-70 | 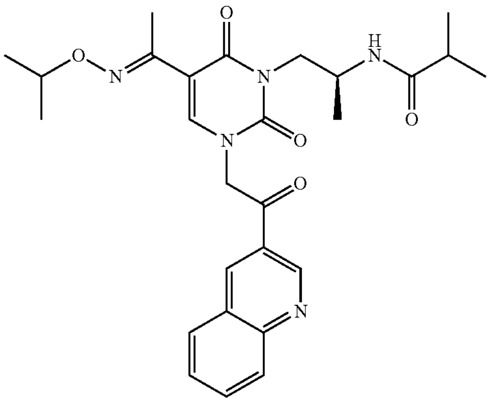 [SMILES: C/C(=N\OC(C)C)c1cn(CC(=O)c2cnc3ccccc3c2)c(=O)n(C[C@H](C)NC(=O)C(C)C)c1=O] | m.p. 85-90° C. | |
| D-71 | 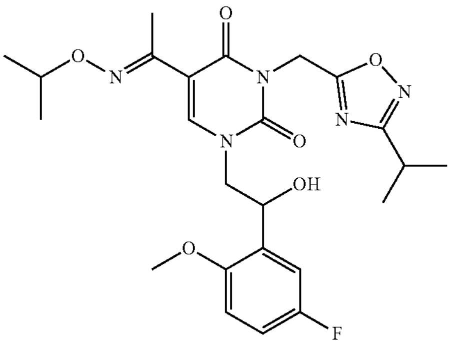 [SMILES: COc1ccc(F)cc1C(O)Cn1cc(/C(C)=N/OC(C)C)c(=O)n(Cc2nc(C(C)C)no2)c1=O] | m.p. 150-151° C. | |
| D-72 | 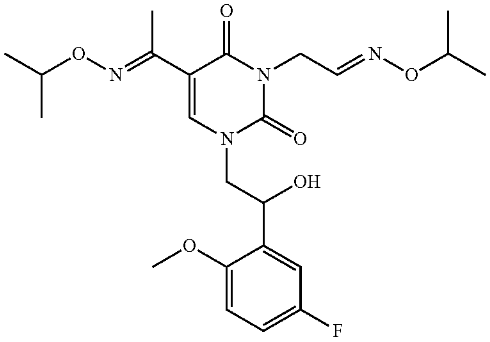 [SMILES: COc1ccc(F)cc1C(O)Cn1cc(/C(C)=N/OC(C)C)c(=O)n(C/C=N/OC(C)C)c1=O] | m.p. 127-129° C. | |
| D-73 | 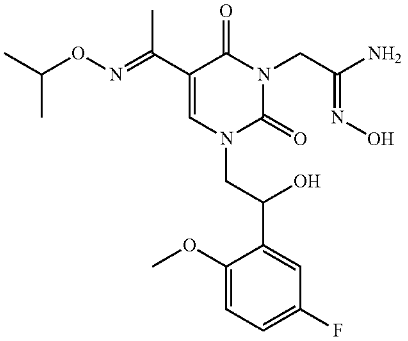 [SMILES: COc1ccc(F)cc1C(O)Cn1cc(/C(C)=N/OC(C)C)c(=O)n(C/C(N)=N/O)c1=O] | m.p. 192-196° C. | |

TABLE 7-continued
| Compound number | Structural formula | Physical properties | Remarks |
|---|---|---|---|
| D-74 | 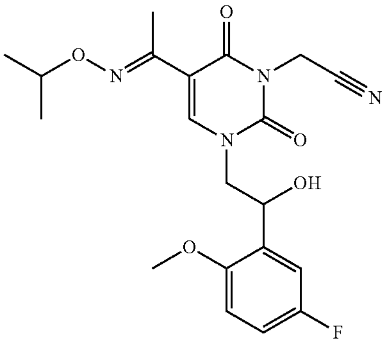 [SMILES: COc1ccc(F)cc1C(O)Cn1cc(/C(C)=N/OC(C)C)c(=O)n(CC#N)c1=O] | viscous oil | |
| D-75 | 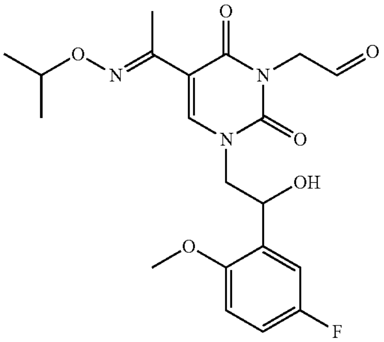 [SMILES: COc1ccc(F)cc1C(O)Cn1cc(/C(C)=N/OC(C)C)c(=O)n(CC=O)c1=O] | m.p. 108-110° C. | |
| D-76 | 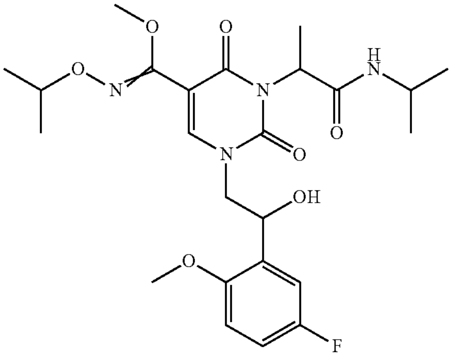 [SMILES: COC(=NOC(C)C)c1cn(CC(O)c2cc(F)ccc2OC)c(=O)n(C(C)C(=O)NC(C)C)c1=O] | m.p. 84-85° C. | |
| D-77 | 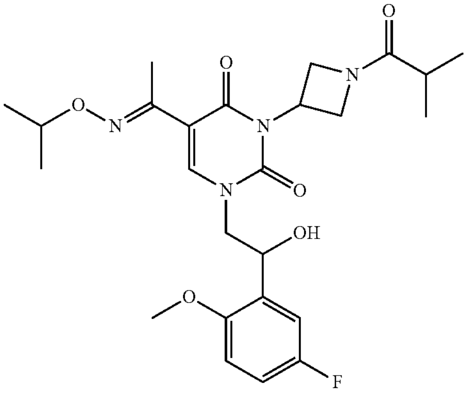 [SMILES: COc1ccc(F)cc1C(O)Cn1cc(/C(C)=N/OC(C)C)c(=O)n(C2CN(C(=O)C(C)C)C2)c1=O] | m.p. 75-76° C. | |

TABLE 7-continued
| Compound number | Structural formula | Physical properties | Remarks |
|---|---|---|---|
| D-78 | 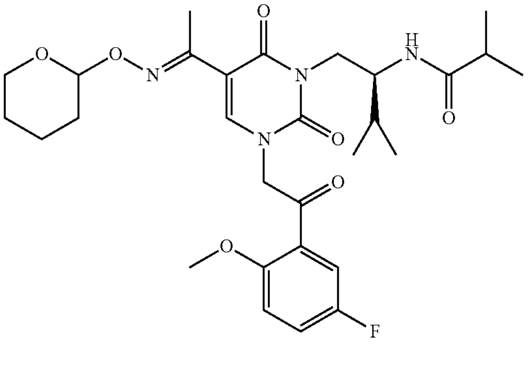 [SMILES: COc1ccc(F)cc1C(=O)Cn1cc(/C(C)=N/OC2CCCCO2)c(=O)n(C[C@@H](NC(=O)C(C)C)C(C)C)c1=O] | m.p. 84-85° C. | |
| D-79 | 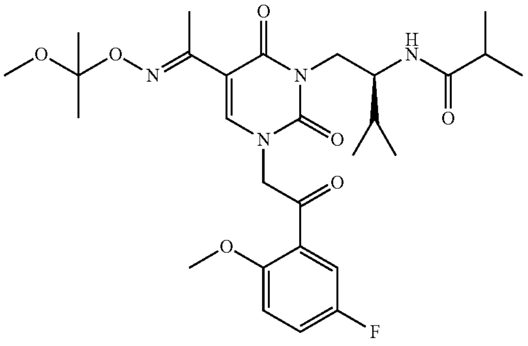 [SMILES: COc1ccc(F)cc1C(=O)Cn1cc(/C(C)=N/OC(C)(C)OC)c(=O)n(C[C@@H](NC(=O)C(C)C)C(C)C)c1=O] | m.p. 87-88° C. | |
| D-80 | 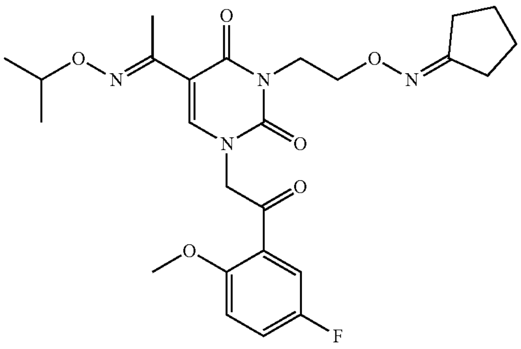 [SMILES: COc1ccc(F)cc1C(=O)Cn1cc(/C(C)=N/OC(C)C)c(=O)n(CCON=C2CCCC2)c1=O] | viscous oil | |
| D-81 | 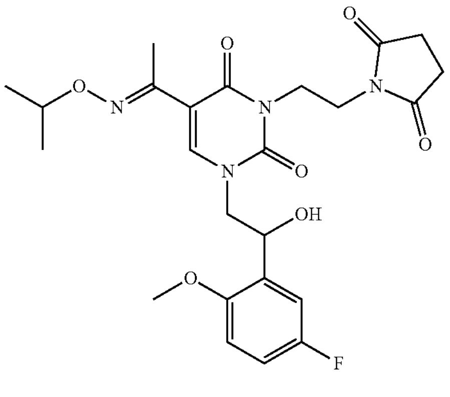 [SMILES: COc1ccc(F)cc1C(O)Cn1cc(/C(C)=N/OC(C)C)c(=O)n(CCN2C(=O)CCC2=O)c1=O] | m.p. 200-202° C. | |

TABLE 7-continued
| Compound number | Structural formula | Physical properties | Remarks |
|---|---|---|---|
| D-82 | 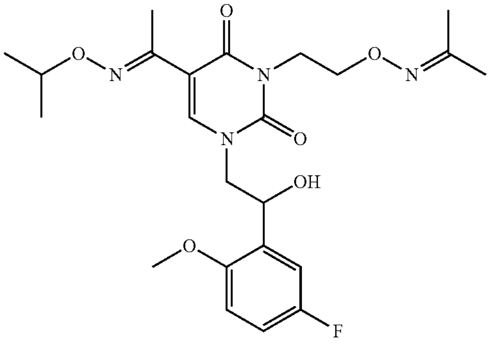 [SMILES: COc1ccc(F)cc1C(O)Cn1cc(/C(C)=N/OC(C)C)c(=O)n(CCON=C(C)C)c1=O] | m.p. 110-114° C. | |
| D-83 | 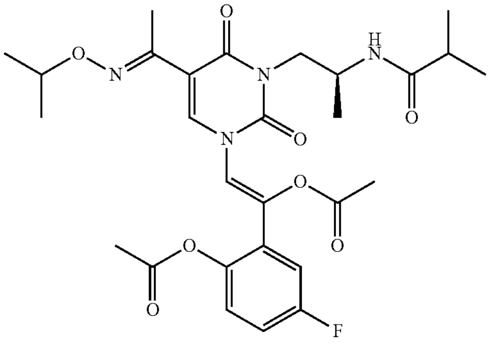 [SMILES: CC(=O)O/C(=C\n1cc(/C(C)=N/OC(C)C)c(=O)n(C[C@H](C)NC(=O)C(C)C)c1=O)c1cc(F)ccc1OC(C)=O] | viscous oil | |
| D-84 | 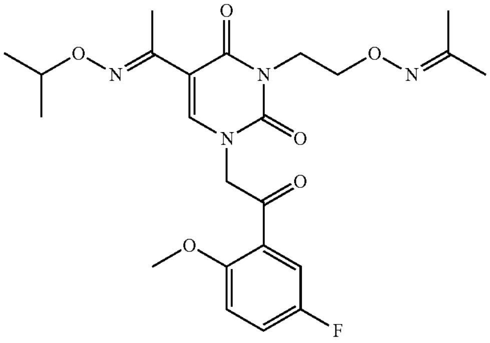 [SMILES: COc1ccc(F)cc1C(=O)Cn1cc(/C(C)=N/OC(C)C)c(=O)n(CCON=C(C)C)c1=O] | viscous oil | |
| D-85 | 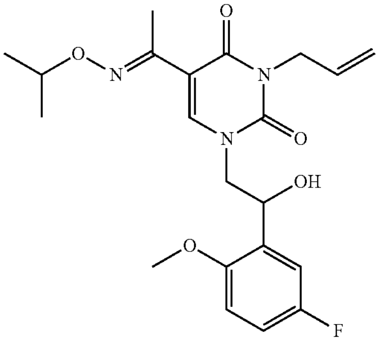 [SMILES: C=CCn1c(=O)c(/C(C)=N/OC(C)C)cn(CC(O)c2cc(F)ccc2OC)c1=O] | viscous oil | |

TABLE 7-continued
| Compound number | Structural formula | Physical properties | Remarks |
|---|---|---|---|
| D-86 | 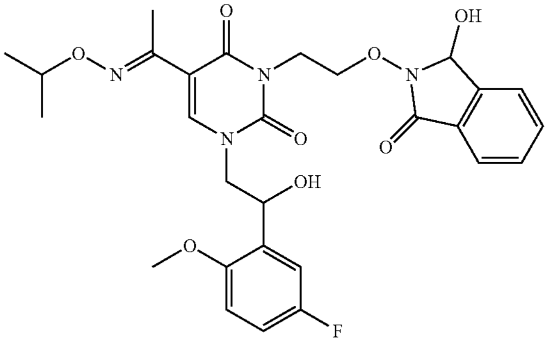 [SMILES: COc1ccc(F)cc1C(O)Cn1cc(/C(C)=N/OC(C)C)c(=O)n(CCON2C(=O)c3ccccc3C2O)c1=O] | viscous oil | |
| D-87 | 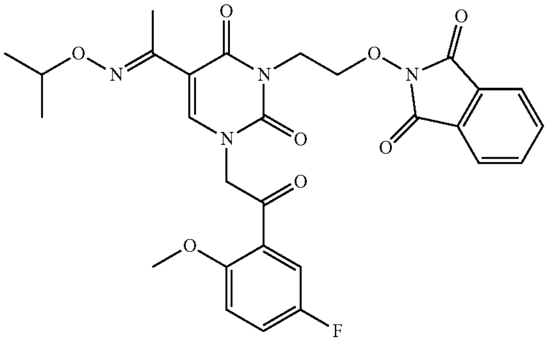 [SMILES: COc1ccc(F)cc1C(=O)Cn1cc(/C(C)=N/OC(C)C)c(=O)n(CCON2C(=O)c3ccccc3C2=O)c1=O] | amorphous | |
| D-88 | 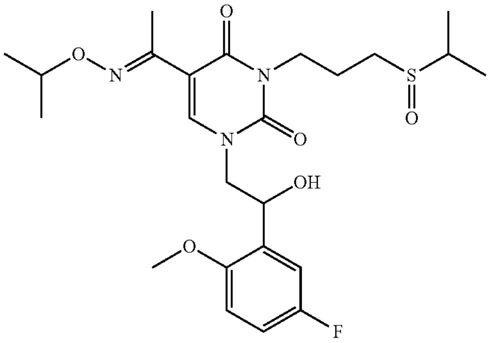 [SMILES: COc1ccc(F)cc1C(O)Cn1cc(/C(C)=N/OC(C)C)c(=O)n(CCCS(=O)C(C)C)c1=O] | viscous oil | |
| D-89 | 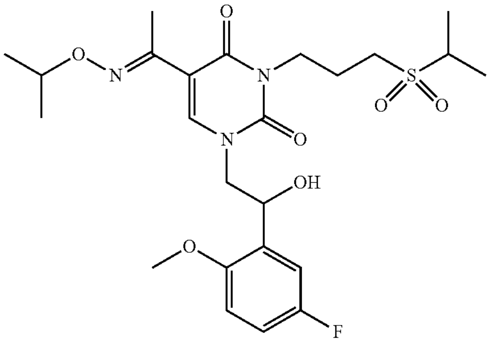 [SMILES: COc1ccc(F)cc1C(O)Cn1cc(/C(C)=N/OC(C)C)c(=O)n(CCCS(=O)(=O)C(C)C)c1=O] | viscous oil | |

TABLE 7-continued

| Compound number | Structural formula | Physical properties | Remarks |
|---|---|---|---|
| D-90 | 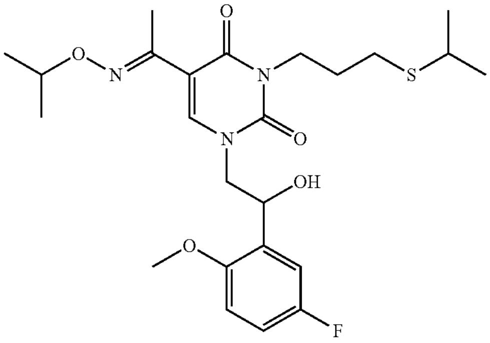 [SMILES: COc1ccc(F)cc1C(O)Cn1cc(/C(C)=N/OC(C)C)c(=O)n(CCCSC(C)C)c1=O] | viscous oil | |
| D-91 | 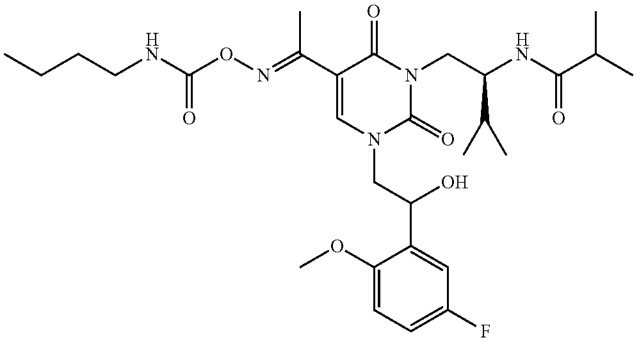 [SMILES: CCCCNC(=O)O/N=C(\C)c1cn(CC(O)c2cc(F)ccc2OC)c(=O)n(C[C@@H](NC(=O)C(C)C)C(C)C)c1=O] | m.p. 68-69° C. | |

Among the compounds described in Tables 6 and 7, for a compound having an amorphous or viscous-oil property, the $^1$H-NMR data thereof are shown in Table 8 below.

TABLE 8

| Compound number | NMR |
|---|---|
| C-3 | $^1$H-NMR ($CDCl_3$) δ: 7.46-6.96(5H, m), 5.68-1.82(14H, m), 2.12(3H, s), 1.32-1.03(18H, m). |
| C-4 | $^1$H-NMR ($CDCl_3$) δ: 7.53-6.96(4H, m), 7.41(1H, s), 5.75-1.82(14H, m), 2.12(3H, s), 1.32-1.00(18H, m). |
| C-5 | $^1$H-NMR ($CDCl_3$) δ: 7.54 (1H, dd, J = 8.2, 6.9 Hz), 7.40 (1H, s), 6.71 (1H, td, J = 8.4, 2.4 Hz), 6.62 (1H, dd, J = 10.5, 2.3 Hz), 5.77 (1H, d, J = 8.7 Hz), 5.18-5.14 (1H, m), 4.57-4.47 (2H, m), 4.38-4.32 (1H, m), 4.18 (1H, dd, J = 13.3, 11.0 Hz), 4.14-4.08 (1H, m), 3.90 (1H, dd, J = 14.0, 2.5 Hz), 3.86 (3H, s), 3.84 (1H, dd, J = 8.7, 3.2 Hz), 2.21 (1H, td, J = 13.5, 6.6 Hz), 2.14 (3H, s), 1.27 (6H, dd, J = 6.2, 1.6 Hz), 1.23 (3H, d, J = 6.9 Hz), 1.04 (6H, dd, J = 13.1, 7.1 Hz). |
| C-8 | $^1$H-NMR ($CDCl_3$) δ: 7.63 (2H, t, J = 7.3 Hz), 7.52-7.48 (2H, m), 7.38 (1H, dd, J = 8.7, 7.3 Hz), 6.65-6.62 (1H, m), 5.85-5.81 (1H, m), 5.63-5.54 (3H, m), 4.69-4.60 (1H, m), 4.51 (1H, dd, J = 13.7, 3.2 Hz), 4.36 (1H, t, J = 6.2 Hz), 4.22 (1H, dd, J = 12.8, 11.4 Hz), 3.80 (1H, dd, J = 13.3, 3.7 Hz), 3.65 (1H, dd, J = 13.7, 9.6 Hz), 2.20 (1H, td, J = 13.7, 6.9 Hz), 2.12 (3H, s), 1.26 (9H, dd, J = 6.2, 1.1 Hz), 1.01 (6H, dd, J = 16.0, 6.9 Hz). |
| C-18 | $^1$H-NMR ($CDCl_3$) δ: 7.44 (1H, dd, J = 9.2, 3.2 Hz), 7.02-6.92 (1H, m), 6.81 (1H, dd, J = 9.2, 4.1 Hz), 5.85 (1H, d, J = 8.7 Hz), 5.24 (1H, d, J = 9.2 Hz), 4.62 (1H, s), 4.55-4.45 (1H, m), 4.41-4.28 (2H, m), 4.21-4.14 (1H, m), 3.96 (1H, dd, J = 14.7, 2.3 Hz), 3.87 (1H, dd, J = 13.3, 3.2 Hz), 3.83 (3H, s), 2.37 (3H, s), 2.27-2.21 (1H, m), 2.05 (3H, s), 1.29-1.20 (9H, m), 1.06 (6H, dd, J = 8.5, 7.1 Hz). |

TABLE 8-continued

| Compound number | NMR |
|---|---|
| C-19 | $^1$H-NMR (DMSO-$D_6$) δ: 7.69 (1H, d, J = 8.7 Hz), 7.26 (1H, dd, J = 9.6, 3.2 Hz), 7.08 (1H, td, J = 8.5, 3.2 Hz), 6.96 (1H, dd, J = 9.2, 4.6 Hz), 5.76 (1H, d, J = 5.0 Hz), 5.35-5.22 (1H, m), 4.40-4.16 (2H, m), 4.11-3.92 (2H, m), 3.91-3.63 (2H, m), 3.71 (3H, s), 2.32-2.16 (1H, m), 2.11 (3H, s), 1.89 (3H, s), 1.19 (6H, dd, J = 6.2, 5.7 Hz), 1.06 (3H, d, J = 6.9 Hz), 0.90 (6H, dd, J = 7.8, 7.3 Hz). |
| C-26 | $^1$H-NMR ($CDCl_3$) δ: 7.51(1H, s), 7.26-6.08(4H, m), 4.98-2.19(8H, m), 3.79(3H, s), 2.12(3H, s), 1.33-1.00(21H, m). |
| C-37 | $^1$H-NMR ($CDCl_3$) δ: 8.12 (1H, dd, J = 7.8, 0.9 Hz), 7.87 (1H, dd, J = 7.8, 0.9 Hz), 7.70 (1H, td, J = 7.7, 1.2 Hz), 7.54 (1H, s), 7.54-7.49 (1H, m), 6.02-5.98 (1H, m), 5.74 (1H, d, J = 5.0 Hz), 5.59 (1H, d, J = 7.3 Hz), 4.76-4.68 (1H, m), 4.49 (1H, dd, J = 13.7, 2.7 Hz), 4.40-4.34 (1H, m), 4.25 (1H, dd, J = 13.3, 11.4 Hz), 3.82 (1H, dd, J = 13.3, 3.7 Hz), 3.58 (1H, dd, J = 13.3, 10.1 Hz), 3.30 (3H, s), 2.25-2.17 (1H, m), 2.13 (3H, s), 1.28-1.24 (9H, m), 1.02 (6H, dd, J = 14.7, 6.9 Hz). |
| C-40 | $^1$H-NMR ($CDCl_3$) δ: 7.62 (1H, d, J = 2.7 Hz), 7.44 (1H, s), 7.24 (1H, dd, J = 8.9, 2.5 Hz), 6.81 (1H, d, J = 8.7 Hz), 5.75 (1H, d, J = 8.7 Hz), 5.17 (1H, dd, J = 5.7, 3.4 Hz), 4.70 (1H, s), 4.57-4.51 (1H, m), 4.39-4.33 (1H, m), 4.19 (1H, dd, J = 13.3, 11.0 Hz), 4.11-4.07 (1H, m), 3.90 (1H, dd, J = 13.7, 2.3 Hz), 3.86 (3H, s), 3.84-3.83 (1H, m), 2.21 (1H, td, J = 13.6, 6.7 Hz), 2.14 (3H, s), 1.27 (6H, d, J = 6.9 Hz), 1.23 (3H, d, J = 6.4 Hz), 1.04 (6H, dd, J = 13.5, 7.1 Hz). |
| C-42 | $^1$H-NMR ($CDCl_3$) δ: 7.60 (1H, d, J = 7.7 Hz), 7.45 (1H, s), 7.31-7.26 (1H, m), 7.02 (1H, t, J = 7.5 Hz), 6.89 (1H, d, J = 8.6 Hz), 5.53 (1H, d, J = 9.1 Hz), 5.20-5.17 (1H, m), 4.65 (1H, d, J = 4.5 Hz), 4.54-4.52 (1H, m), 4.39-4.32 (1H, m), 4.20-4.09 (2H, m), 3.93-3.85 (2H, m), 3.88 (3H, s), 2.25-2.18 (1H, m), 2.14 (3H, s), 1.74-1.65 (1H, m), 1.40 (2H, t, J = 7.2 Hz), 1.27 (6H, dd, J = 6.3, 1.4 Hz), 1.03 (6H, dd, J = 17.7, 6.8 Hz), 0.96 (6H, dd, J = 19.5, 6.3 Hz). |
| C-43 | $^1$H-NMR ($CDCl_3$) δ: 7.59 (1H, dd, J = 7.6, 1.6 Hz), 7.41 (1H, s), 7.29-7.25 (1H, m), 7.00 (1H, td, J = 7.4, 1.1 Hz), 6.89 (1H, d, J = 7.8 Hz), 5.66-5.61 (1H, m), 5.42 (1H, d, J = 9.2 Hz), 5.14 (1H, d, J = 5.0 Hz), 4.72-4.60 (1H, m), 4.57 (1H, dd, J = 13.3, 3.2 Hz), 4.38-4.32 (1H, m), 4.21 (1H, dd, J = 13.1, 11.2 Hz), 3.90 (3H, s), 3.83 (1H, dd, J = 12.8, 3.7 Hz), 3.25 (1H, dd, J = 13.3, 10.1 Hz), 2.21 (1H, td, J = 13.5, 6.6 Hz), 2.11 (3H, s), 1.74-1.67 (1H, m), 1.44-1.40 (2H, m), 1.25 (6H, d, J = 6.4 Hz), 1.03 (6H, dd, J = 16.7, 7.1 Hz), 0.96 (6H, dd, J = 23.1, 7.1 Hz). |
| C-44 | $^1$H-NMR ($CDCl_3$) δ: 7.67 (1H, d, J = 7.8 Hz), 7.49 (1H, s), 7.31-7.26 (1H, m), 7.03 (1H, t, J = 7.6 Hz), 6.89 (1H, d, J = 8.2 Hz), 5.25 (1H, s), 5.17 (1H, d, J = 8.7 Hz), 4.41-4.35 (3H, m), 4.13-4.07 (2H, m), 3.94-3.86 (2H, m), 3.88 (3H, s), 2.79 (6H, s), 2.15 (3H, s), 1.82-1.72 (1H, m), 1.41 (2H, dt, J = 14.5, 5.6 Hz), 1.29 (6H, dd, J = 6.4, 3.2 Hz), 0.96 (6H, dd, J = 18.1, 6.6 Hz). |
| C-45 | $^1$H-NMR ($CDCl_3$) δ: 7.57 (1H, dd, J = 7.6, 1.6 Hz), 7.42 (1H, s), 7.29-7.24 (1H, m), 6.99 (1H, t, J = 7.1 Hz), 6.88 (1H, d, J = 7.8 Hz), 5.66-5.59 (2H, m), 4.58 (1H, dd, J = 13.5, 3.0 Hz), 4.51-4.46 (1H, m), 4.39-4.33 (1H, m), 4.26-4.15 (2H, m), 3.89 (3H, s), 3.87 (1H, dd, J = 13.1, 3.9 Hz), 3.18 (1H, dd, J = 13.1, 9.8 Hz), 2.79 (6H, s), 2.11 (3H, s), 1.80-1.73 (1H, m), 1.41 (2H, t, J = 7.3 Hz), 1.27 (6H, dd, J = 6.4, 4.6 Hz), 0.97 (6H, dd, J = 18.5, 6.6 Hz). |
| C-46 | $^1$H-NMR ($CDCl_3$) δ: 7.58 (1H, d, J = 7.2 Hz), 7.44 (1H, s), 7.30-7.27 (1H, m), 7.02 (1H, t, J = 7.5 Hz), 6.89 (1H, d, J = 8.2 Hz), 5.52 (1H, d, J = 9.5 Hz), 5.19 (1H, d, J = 8.2 Hz), 4.59-4.49 (2H, m), 4.39-4.31 (1H, m), 4.15-3.98 (3H, m), 3.91-3.89 (1H, m), 3.88 (3H, s), 2.14 (3H, s), 2.13-2.05 (2H, m), 1.40 (2H, t, J = 7.2 Hz), 1.27 (6H, d, J = 6.3 Hz), 1.03 (3H, t, J = 7.5 Hz), 0.96 (6H, dd, J = 17.2, 6.8 Hz). |

TABLE 8-continued

| Compound number | NMR |
|---|---|
| C-53 | $^1$H-NMR ($CDCl_3$) δ: 7.47 (1H, s), 7.45 (1H, dd, J = 9.2, 3.2 Hz), 6.95 (1H, td, J = 8.2, 3.2 Hz), 6.80 (1H, dd, J = 9.2, 4.1 Hz), 5.42 (1H, br s), 5.14 (1H, d, J = 9.2 Hz), 4.44-4.08 (5H, m), 3.93 (1H, dd, J = 12.8, 3.2 Hz), 3.86 (3H, s), 3.81 (1H, d, J = 12.8 Hz), 2.79 (6H, s), 2.15 (3H, s), 1.71-1.58 (1H, m), 1.57-1.44 (1H, m), 1.29 (6H, dd, J = 6.4, 3.7 Hz), 1.02 (3H, t, J = 7.6 Hz). |
| C-55 | $^1$H-NMR ($CDCl_3$) δ: 7.41 (1H, s), 7.37 (1H, dd, J = 9.4, 3.0 Hz), 6.99-6.90 (1H, m), 6.79 (1H, dd, J = 8.9, 4.4 Hz), 5.51 (1H, d, J = 9.2 Hz), 5.16 (1H, d, J = 8.7 Hz), 4.76 (1H, br s), 4.41-4.29 (2H, m), 4.20-4.00 (2H, m), 3.96-3.86 (2H, m), 3.85 (3H, s), 2.13 (3H, s), 2.12-2.06 (2H, m), 1.70-1.61 (1H, m), 1.54-1.40 (1H, m), 1.26 (6H, d, J = 6.0 Hz), 1.05-0.98 (6H, m). |
| C-59 | $^1$H-NMR ($CDCl_3$) δ: 7.48 (1H, s), 7.46-7.45 (1H, m), 6.95 (1H, td, J = 8.5, 3.2 Hz), 6.80 (1H, dd, J = 8.9, 4.4 Hz), 5.53 (1H, s), 5.13 (1H, d, J = 9.2 Hz), 4.45-4.43 (1H, m), 4.41-4.35 (1H, m), 4.32-4.17 (2H, m), 4.13-4.10 (1H, m), 3.91-3.88 (1H, m), 3.86 (3H, s), 3.79 (1H, d, J = 13.3 Hz), 2.78 (6H, s), 2.15 (3H, s), 1.76-1.73 (1H, m), 1.45-1.36 (2H, m), 1.29 (6H, dd, J = 6.2, 3.9 Hz), 0.96 (6H, dd, J = 17.4, 6.4 Hz). |
| C-60 | $^1$H-NMR ($CDCl_3$) δ: 7.38 (1H, s), 7.35 (1H, dd, J = 9.6, 3.2 Hz), 6.92 (1H, td, J = 8.5, 3.2 Hz), 6.79 (1H, dd, J = 8.9, 4.4 Hz), 5.79 (1H, d, J = 5.0 Hz), 5.64-5.60 (1H, m), 4.64 (1H, dd, J = 13.1, 3.0 Hz), 4.56-4.43 (1H, m), 4.41-4.32 (1H, m), 4.20-4.16 (2H, m), 3.87 (3H, s), 3.87-3.82 (1H, m), 3.03 (1H, dd, J = 13.3, 10.1 Hz), 2.80 (6H, s), 2.11 (3H, s), 1.79-1.73 (1H, m), 1.41 (2H, t, J = 7.1 Hz), 1.31-1.24 (6H, m), 0.96 (6H, dd, J = 18.8, 6.9 Hz). |
| C-61 | $^1$H-NMR ($CDCl_3$) δ: 7.43 (1H, s), 7.39 (1H, dd, J = 9.2, 3.2 Hz), 6.95 (1H, td, J = 8.5, 3.2 Hz), 6.80 (1H, dd, J = 8.9, 4.4 Hz), 5.48-5.45 (1H, m), 5.17-5.15 (1H, m), 4.91-4.90 (1H, m), 4.57-4.51 (1H, m), 4.41-4.32 (1H, m), 4.16-4.07 (2H, m), 3.92-3.89 (2H, m), 3.86 (3H, s), 2.14 (3H, s), 2.12-2.06 (2H, m), 1.73-1.69 (1H, m), 1.40 (2H, t, J = 7.3 Hz), 1.27 (6H, t, J = 4.1 Hz), 1.02 (3H, t, J = 7.6 Hz), 0.96 (6H, dd, J = 18.3, 6.4 Hz). |
| C-76 | $^1$H-NMR ($CDCl_3$) δ: 7.68 (1H, dd, J = 7.6, 1.6 Hz), 7.48 (1H, s), 7.32-7.27 (1H, m), 7.03 (1H, t, J = 7.1 Hz), 6.89 (1H, d, J = 7.8 Hz), 5.21-5.13 (2H, m), 4.49-4.42 (1H, m), 4.42-4.33 (1H, m), 4.26-4.16 (3H, m), 3.97 (1H, d, J = 9.2 Hz), 3.88 (3H, s), 3.82 (1H, d, J = 13.7 Hz), 2.80 (6H, s), 2.15 (3H, s), 1.92-1.81 (1H, m), 1.29 (6H, dd, J = 6.2, 2.5 Hz), 1.03 (6H, dd, J = 6.9, 0.9 Hz). |
| C-77 | $^1$H-NMR ($CDCl_3$) δ: 7.58 (1H, dd, J = 7.6, 1.6 Hz), 7.41 (1H, s), 7.29-7.24 (1H, m), 7.00 (1H, td, J = 7.3, 0.9 Hz), 6.88 (1H, d, J = 7.8 Hz), 5.67-5.59 (1H, m), 5.52 (1H, br s), 4.58 (1H, dd, J = 13.3, 3.2 Hz), 4.41-4.21 (4H, m), 3.96-3.90 (1H, m), 3.90 (3H, s), 3.17 (1H, dd, J = 13.1, 10.3 Hz), 2.81 (6H, s), 2.11 (3H, s), 1.90-1.79 (1H, m), 1.27 (6H, dd, J = 6.2, 3.9 Hz), 1.04 (6H, dd, J = 9.6, 6.9 Hz). |
| C-78 | $^1$H-NMR ($CDCl_3$) δ: 7.60 (1H, dd, J = 7.3, 1.4 Hz), 7.44 (1H, s), 7.30 (1H, td, J = 7.9, 1.5 Hz), 7.03 (1H, t, J = 7.6 Hz), 6.90 (1H, d, J = 8.2 Hz), 5.47 (1H, d, J = 9.2 Hz), 5.19 (1H, d, J = 9.6 Hz), 4.58-4.49 (1H, m), 4.40-4.07 (4H, m), 3.99-3.91 (2H, m), 3.89 (3H, s), 2.93-2.84 (1H, m), 2.14 (3H, s), 2.13-1.97 (4H, m), 1.93-1.72 (3H, m), 1.27 (6H, dd, J = 6.2, 2.1 Hz), 1.01 (6H, dd, J = 7.1, 6.6 Hz). |
| C-85 | $^1$H-NMR ($CDCl_3$) δ: 7.69-7.64 (2H, m), 7.55 (1H, dd, J = 7.6, 1.6 Hz), 7.50-7.44 (1H, m), 7.42-7.35 (2H, m), 7.31-7.27 (2H, m), 6.98 (1H, td, J = 7.6, 0.9 Hz), 6.90 (1H, dd, J = 8.5, 1.1 Hz), 6.22 (1H, d, J = 10.1 Hz), 5.63 (1H, br s), 4.91 (1H, br s), 4.66-4.56 (1H, m), 4.53 (1H, dd, J = 13.3, 3.2 Hz), 4.41 (1H, t, J = 12.1 Hz), 4.30-4.23 (1H, m), 4.04 (1H, dd, J = 12.8, |

TABLE 8-continued

| Compound number | NMR |
|---|---|
| | 3.7 Hz), 3.91 (3H, s), 3.34 (1H, dd, J = 13.5, 9.8 Hz), 2.00 (1H, dt, J = 20.9, 7.2 Hz), 1.70 (3H, s), 1.19 (6H, dd, J = 6.0, 2.7 Hz), 1.11 (6H, dd, J = 7.3, 6.9 Hz). |
| C-87 | $^1$H-NMR ($CDCl_3$) δ: 7.55 (1H, dd, J = 7.3, 1.4 Hz), 7.39 (1H, s), 7.31-7.27 (1H, m), 7.00 (1H, t, J = 7.1 Hz), 6.89 (1H, d, J = 8.2 Hz), 5.56 (2H, d, J = 8.7 Hz), 4.66 (1H, br s), 4.53-4.40 (2H, m), 4.39-4.27 (2H, m), 3.90 (3H, s), 3.86 (1H, dd, J = 12.8, 3.2 Hz), 3.38 (1H, dd, J = 13.5, 9.4 Hz), 2.12 (3H, s), 1.96-1.85 (1H, m), 1.83-1.72 (1H, m), 1.51-1.31 (4H, m), 1.25 (6H, dd, J = 6.4, 1.4 Hz), 1.04 (6H, dd, J = 6.4, 6.0 Hz), 0.85-0.75 (6H, m). |
| C-94 | $^1$H-NMR ($CDCl_3$) δ: 7.57 (1H, dd, J = 7.6, 1.1 Hz), 7.41 (1H, s), 7.29 (1H, td, J = 7.8, 1.8 Hz), 7.02 (1H, td, J = 7.7, 1.1 Hz), 6.89 (1H, d, J = 7.3 Hz), 5.57 (1H, d, J = 9.6 Hz), 5.18 (1H, br s), 4.41-4.17 (4H, m), 4.16-4.07 (1H, m), 4.00-3.91 (2H, m), 3.89 (3H, s), 2.14 (3H, s), 2.05 (2H, t, J = 7.3 Hz), 1.93-1.82 (1H, m), 1.62-1.45 (2H, m), 1.27 (6H, d, J = 5.5 Hz), 1.01 (6H, dd, J = 6.6, 4.4 Hz), 0.86 (3H, t, J = 7.3 Hz). |
| C-95 | $^1$H-NMR ($CDCl_3$) δ: 7.57 (1H, dd, J = 7.3, 1.4 Hz), 7.39 (1H, s), 7.29 (1H, dd, J = 7.8, 1.4 Hz), 7.00 (1H, t, J = 7.1 Hz), 6.89 (1H, d, J = 7.8 Hz), 5.62-5.54 (1H, m), 5.44 (1H, d, J = 10.1 Hz), 4.98 (1H, br s), 4.53 (1H, dd, J = 13.3, 3.2 Hz), 4.46-4.24 (3H, m), 3.96-3.89 (1H, m), 3.90 (3H, s), 3.29 (1H, dd, J = 13.3, 9.6 Hz), 2.12 (3H, s), 2.05 (2H, dt, J = 11.6, 3.3 Hz), 1.90-1.80 (1H, m), 1.57-1.43 (2H, m), 1.25 (6H, d, J = 6.0 Hz), 1.03 (6H, dd, J = 11.2, 6.6 Hz), 0.86 (3H, t, J = 7.3 Hz). |
| C-97 | $^1$H-NMR ($CDCl_3$) δ: 7.56 (1H, dd, J = 7.6, 1.6 Hz), 7.39 (1H, s), 7.29 (1H, dd, J = 7.8, 1.8 Hz), 7.00 (1H, t, J = 7.3 Hz), 6.89 (1H, d, J = 8.2 Hz), 5.61-5.53 (1H, m), 5.44 (1H, d, J = 9.6 Hz), 4.92 (1H, br s), 4.51 (1H, dd, J = 13.3, 3.2 Hz), 4.45-4.24 (3H, m), 3.92 (1H, dd, J = 13.5, 4.4 Hz), 3.90 (3H, s), 3.32 (1H, dd, J = 13.1, 9.8 Hz), 2.12 (3H, s), 2.04-1.92 (2H, m), 1.91-1.79 (2H, m), 1.25 (6H, d, J = 6.0 Hz), 1.03 (6H, dd, J = 10.8, 6.6 Hz), 0.86 (6H, t, J = 7.1 Hz). |
| C-127 | $^1$H-NMR ($CDCl_3$) δ: 7.66-7.51 (1H, m), 7.45-7.38 (1H, m), 7.33-7.27 (1H, m), 7.07-6.96 (1H, m), 6.89 (1H, d, J = 8.2 Hz), 5.60-5.12 (1H, m), 4.65-4.56 (1H, m), 4.50-4.15 (4H, m), 4.08-3.97 (1H, m), 3.91-3.87 (3H, m), 3.87-3.33 (2H, m), 2.21-2.12 (3H, m), 1.94-1.75 (1H, m), 1.33 (9H, s), 1.30-1.23 (6H, m), 1.05-0.98 (6H, m). |
| C-128 | $^1$H-NMR ($CDCl_3$) δ: 7.62 (1H, dd, J = 7.8, 1.4 Hz), 7.45 (1H, s), 7.29 (1H, td, J = 7.9, 1.4 Hz), 7.02 (1H, t, J = 7.6 Hz), 6.89 (1H, d, J = 7.8 Hz), 5.78 (1H, d, J = 8.7 Hz), 5.21-5.13 (1H, m), 4.64 (1H, br s), 4.40-4.28 (2H, m), 4.28-4.18 (2H, m), 3.94 (1H, dd, J = 12.4, 3.2 Hz), 3.88 (3H, s), 3.86 (1H, dd, J = 13.7, 2.3 Hz), 2.15 (3H, s), 1.95-1.82 (1H, m), 1.27 (6H, dd, J = 6.4, 2.3 Hz), 1.09 (9H, s), 1.01 (6H, dd, J = 6.6, 5.3 Hz). |
| C-129 | $^1$H-NMR ($CDCl_3$) δ: 7.59 (1H, dd, J = 7.6, 1.6 Hz), 7.40 (1H, s), 7.30-7.27 (1H, m), 7.00 (1H, td, J = 7.3, 0.9 Hz), 6.89 (1H, d, J = 8.2 Hz), 5.69-5.60 (2H, m), 5.04-4.96 (1H, m), 4.55 (1H, dd, J = 13.3, 3.2 Hz), 4.46-4.28 (3H, m), 3.90 (3H, s), 3.89 (1H, dd, J = 11.9, 3.7 Hz), 3.25 (1H, dd, J = 13.1, 9.8 Hz), 2.13 (3H, s), 1.92-1.83 (1H, m), 1.25 (6H, dd, J = 6.4, 1.8 Hz), 1.10 (9H, s), 1.03 (6H, dd, J = 11.7, 6.6 Hz). |
| C-130 | $^1$H-NMR ($CDCl_3$) δ: 7.43 (1H, s), 7.42 (1H, dd, J = 9.4, 3.0 Hz), 7.00-6.93 (1H, m), 6.81 (1H, dd, J = 9.2, 4.1 Hz), 5.51 (1H, d, J = 9.2 Hz), 5.14 (1H, d, J = 6.9 Hz), 4.91 (1H, br s), 4.41-4.30 (2H, m), 4.30-4.18 (2H, m), 3.92 (1H, dd, J = 12.6, 3.4 Hz), 3.86 (3H, s), 3.81 (1H, dd, J = 14.0, 1.6 Hz), 2.29-2.18 (1H, m), 2.14 (3H, s), 1.91-1.78 (1H, m), 1.27 (6H, dd, J = 6.0, 1.4 Hz), 1.05 (6H, dd, J = 14.2, 6.9 Hz), 1.01 (6H, d, J = 6.9 Hz). |

TABLE 8-continued

| Compound number | NMR |
|---|---|
| C-131 | $^1$H-NMR ($CDCl_3$) δ: 7.37 (1H, dd, J = 9.2, 3.7 Hz), 7.37 (1H, s), 6.93 (1H, td, J = 8.5, 3.2 Hz), 6.80 (1H, dd, J = 8.9, 4.4 Hz), 5.67-5.57 (1H, m), 5.43 (1H, d, J = 9.6 Hz), 5.22 (1H, d, J = 6.0 Hz), 4.62 (1H, dd, J = 13.3, 3.2 Hz), 4.48-4.26 (3H, m), 3.89 (1H, dd, J = 11.9, 4.1 Hz), 3.88 (3H, s), 3.11 (1H, dd, J = 13.3, 10.1 Hz), 2.30-2.19 (1H, m), 2.12 (3H, s), 1.91-1.79 (1H, m), 1.25 (6H, dd, J = 6.4, 0.9 Hz), 1.06 (6H, dd, J = 10.1, 6.9 Hz), 1.02 (6H, d, J = 6.9 Hz). |
| C-132 | $^1$H-NMR ($CDCl_3$) δ: 7.42 (1H, s), 7.37 (1H, dd, J = 8.9, 3.0 Hz), 6.96 (1H, td, J = 8.5, 3.2 Hz), 6.81 (1H, dd, J = 8.7, 4.1 Hz), 5.73 (1H, br s), 5.21-5.13 (1H, m), 4.69 (1H, s), 4.60-4.47 (1H, m), 4.38-4.32 (1H, m), 4.25-4.08 (2H, m), 3.91-3.81 (2H, m), 3.86 (3H, s), 2.25-2.18 (1H, m), 2.14 (3H, s), 1.27 (6H, dd, J = 6.2, 1.1 Hz), 1.23 (3H, d, J = 6.9 Hz), 1.03 (6H, dd, J = 14.2, 6.9 Hz). |
| C-133 | $^1$H-NMR ($CDCl_3$) δ: 7.38 (1H, s), 7.37 (1H, dd, J = 9.6, 2.3 Hz), 6.94 (1H, td, J = 8.5, 3.2 Hz), 6.80 (1H, dd, J = 8.9, 4.4 Hz), 5.66-5.59 (1H, m), 5.49 (1H, d, J = 9.2 Hz), 5.28 (1H, d, J = 6.0 Hz), 4.79-4.66 (1H, m), 4.61 (1H, dd, J = 13.3, 3.2 Hz), 4.40-4.21 (2H, m), 3.88 (3H, s), 3.80 (1H, dd, J = 12.8, 3.7 Hz), 3.12 (1H, dd, J = 13.3, 9.6 Hz), 2.26-2.17 (1H, m), 2.12 (3H, s), 1.27-1.23 (9H, m), 1.03 (6H, dd, J = 15.1, 6.9 Hz). |
| C-136 | $^1$H-NMR ($CDCl_3$) δ: 7.41(1H, s), 7.37-6.76(3H, m), 5.72-3.85(9H, m), 3.84(3H, s), 2.15(3H, s), 2.10-1.02(14H, m). |
| C-149 | $^1$H-NMR ($CDCl_3$) δ: 7.70(1H, s), 7.35-6.78(3H, m), 5.10-2.16(10H, m), 3.88(3H, s), 2.15(3H, s), 1.26-1.01(15H, m). |
| C-153 | $^1$H-NMR ($CDCl_3$) δ: 7.44(1H, s), 7.40-6.79(3H, m), 5.05-0.98(21H, m), 3.88(3H, s), 2.14(3H, s). |
| C-163 | $^1$H-NMR ($CDCl_3$) δ: 7.42(1H, s), 7.28-6.72(3H, m), 6.15-2.20(10H, m), 3.90(3H, s), 2.14(3H, s), 1.34-1.06(15H, m). |
| C-164 | $^1$H-NMR ($CDCl_3$) δ: 7.50(1H, s), 7.28-6.71(3H, m), 5.78-2.18(10H, m), 3.90(3H, s), 2.12(3H, s), 1.28-1.00(15H, m). |
| C-183 | $^1$H-NMR ($CDCl_3$) δ: 7.42-6.79(4H, m), 5.10-3.13(9H, m), 3.88(3H, s), 2.17(3H, s), 1.30-1.20(18H, m). |
| C-185 | $^1$H-NMR ($CDCl_3$) δ: 7.37(1H, s), 7.32-6.79(3H, m), 5.19-3.90(9H, m), 3.80(3H, s), 3.55(3H, s), 2.14(3H, s), 1.28--1.21(9H, m). |
| C-187 | $^1$H-NMR ($CDCl_3$) δ: 7.40(1H, s), 7.34-6.79(3H, m), 5.17-3.76(10H, m), 3.86(3H, s), 2.15(3H, s), 1.30--1.10(15H, m). |
| C-188 | $^1$H-NMR ($CDCl_3$) δ: 7.37(1H, s), 7.32-6.79(3H, m), 5.55-3.14(10H, m), 3.86(3H, s), 2.13(3H, s), 1.28--1.21(15H, m). |
| C-193 | $^1$H-NMR ($CDCl_3$) δ: 7.84-7.35(5H, m), 5.64-2.17(10H, m), 2.15(3H, s), 1.28--1.01(15H, m). |
| C-197 | $^1$H-NMR ($CDCl_3$) δ: 7.63-7.24(5H, m), 5.68-2.15(12H, m), 2.15(3H, s), 1.31-0.98(18H, m). |
| C-198 | $^1$H-NMR ($CDCl_3$) δ: 7.44(1H, s), 7.39-6.79(3H, m), 5.42-2.08(10H, m), 3.83(3H, s), 2.14(3H, s), 1.77-0.92(21H, m). |
| C-199 | $^1$H-NMR ($CDCl_3$) δ: 7.39(1H, s), 7.39-6.79(3H, m), 5.67-2.10(10H, m), 3.83(3H, s), 2.11(3H, s), 1.77-0.92(21H, m). |
| C-200 | $^1$H-NMR ($CDCl_3$) δ: 7.44-6.79(4H, m), 5.65-3.18(9H, m), 3.87(3H, s), 2.18(3H, s), 1.80-0.93(24H, m). |
| C-204 | $^1$H-NMR ($CDCl_3$) δ: 8.52(1H, s), 7.40(1H, s), 6.90-6.66(4H, m), 5.60-3.2.20(10H, m), 2.12(3H, s), 1.30-0.98(15H, m). |
| C-206 | $^1$H-NMR ($CDCl_3$) δ: 7.39(1H, s), 7.38-6.80(3H, m), 5.60-3.95(10H, m), 3.83(3H, s), 2.12(3H, s), 1.86(3H, s), 1.90-0.98(13H, m). |
| C-209 | $^1$H-NMR ($CDCl_3$) δ: 7.44(1H, s), 7.43-6.80(3H, m), 5.55-3.80(10H, m), 3.84(3H, s), 2.12(3H, s), 2.28-1.01(23H, m). |
| C-242 | $^1$H-NMR ($CDCl_3$) δ: 7.62 (1H, d, J = 7.8 Hz), 7.54-7.46 (2H, m), 7.34 (1H, s), 7.33-7.28 (1H, m), 6.07 (1H, d, J = 7.3 Hz), 5.24 (1H, d, J = 17.9 Hz), 4.75 (1H, d, J = 17.4 Hz), 4.38-4.32 (2H, m), 4.14 (1H, dd, J = 13.7, 10.5 Hz), 3.93 (1H, dd, J = 13.7, 3.2 Hz), 3.48-3.37 (1H, m), 2.27-2.21 (1H, m), 2.18 (3H, s), |

TABLE 8-continued

| Compound number | NMR |
|---|---|
| | 2.14-2.00 (2H, m), 1.86-1.53 (6H, m), 1.25 (6H, dd, J = 6.4, 4.6 Hz), 1.21 (3H, d, J = 6.4 Hz), 1.05 (6H, dd, J = 6.9, 5.0 Hz). |
| C-243 | $^1$H-NMR ($CDCl_3$) δ: 7.50-7.46 (2H, m), 7.38-7.33 (2H, m), 7.21 (1H, s), 6.09 (1H, d, J = 7.7 Hz), 5.75 (1H, t, J = 2.0 Hz), 5.07 (1H, d, J = 18.1 Hz), 4.71 (1H, d, J = 17.7 Hz), 4.38-4.28 (2H, m), 4.12 (1H, dd, J = 13.4, 10.6 Hz), 3.91 (1H, dd, J = 13.6, 3.2 Hz), 2.79-2.70 (2H, m), 2.61-2.52 (2H, m), 2.28-2.20 (1H, m), 2.17 (3H, s), 2.14-2.05 (2H, m), 1.25 (6H, dd, J = 6.3, 4.1 Hz), 1.20 (3H, d, J = 6.8 Hz), 1.06 (6H, t, J = 6.6 Hz). |
| D-2 | $^1$H-NMR ($CDCl_3$) δ: 8.07(1H, s), 7.24-6.78(5H, m), 5.13-3.21(9H, m), 3.82(3H, s), 2.08(3H, s), 1.35-1.22(9H, m). |
| D-3 | $^1$H-NMR ($CDCl_3$) δ: 7.66(1H, s), 7.58-7.00(3H, m), 6.72(1H, s), 5.67-1.84(8H, m), 2.15(3H, s), 1.33-1.00(24H, m). |
| D-5 | $^1$H-NMR ($CDCl_3$) δ: 7.41 (1H, d, J = 2.3 Hz), 7.26 (1H, s), 7.16 (1H, dd, J = 9.2, 2.7 Hz), 6.94 (1H, td, J = 8.4, 3.1 Hz), 6.79 (1H, dd, J = 8.9, 4.4 Hz), 6.31 (1H, d, J = 2.7 Hz), 5.24-5.19 (1H, m), 5.17 (2H, s), 4.67 (2H, q, J = 8.5 Hz), 4.36-4.30 (1H, m), 4.19-4.14 (1H, m), 4.01 (1H, dd, J = 14.2, 7.3 Hz), 3.83 (3H, s), 3.61 (1H, d, J = 5.0 Hz), 2.13 (3H, s), 1.25 (6H, d, J = 6.4 Hz). |
| D-9 | $^1$H-NMR ($CDCl_3$) δ: 7.26 (1H, s), 7.17-6.80(3H, m), 5.21-3.56 (8H, m), 3.84 (3H, s), 3.36 (6H, s), 2.11 (3H, s), 1.25 (6H, d, J = 6.3 Hz). |
| D-12 | $^1$H-NMR ($CDCl_3$) δ: 7.25-7.20 (2H, m), 6.95 (1H, td, J = 8.5, 2.4 Hz), 6.80 (1H, dd, J = 9.2, 4.1 Hz), 5.23 (1H, dd, J = 7.1, 3.4 Hz), 4.38-4.27 (2H, m), 4.19-4.11 (1H, m), 3.95 (1H, tt, J = 10.8, 3.8 Hz), 3.86 (3H, d, J = 1.8 Hz), 3.78 (1H, dd, J = 13.3, 2.7 Hz), 2.91 (1H, td, J = 9.8, 5.6 Hz), 2.36 (6H, d, J = 2.7 Hz), 2.12 (3H, d, J = 3.7 Hz), 1.93 (1H, dd, J = 13.5, 6.6 Hz), 1.28-1.25 (6H, m), 1.11 (1H, dd, J = 6.9, 3.2 Hz), 1.02 (6H, dq, J = 14.1, 4.0 Hz). |
| D-13 | $^1$H-NMR ($CDCl_3$) δ: 7.31 (1H, s), 7.29-7.24 (1H, m), 7.00-6.93 (1H, m), 6.81 (1H, dd, J = 9.1, 4.1 Hz), 5.34 (1H, dt, J = 10.1, 3.4 Hz), 4.61-4.55 (1H, m), 4.47-4.05 (6H, m), 3.87 (3H, s), 3.68 (1H, dd, J = 13.8, 8.4 Hz), 2.85 (6H, s), 2.12 (3H, s), 1.26 (6H, dd, J = 6.1, 1.1 Hz). |
| D-14 | $^1$H-NMR ($CDCl_3$) δ: 7.31 (1H, s), 7.23 (1H, dd, J = 8.9, 3.0 Hz), 7.01-6.91 (1H, m), 6.81 (1H, dd, J = 8.7, 4.1 Hz), 5.30-5.23 (1H, m), 4.49-4.40 (1H, m), 4.39-4.17 (5H, m), 3.86 (3H, s), 3.85-3.79 (1H, m), 3.63-3.58 (1H, m), 2.54-2.47 (1H, m), 2.12 (3H, s), 1.27-1.24 (6H, m), 1.15-1.11 (6H, m). |
| D-18 | $^1$H-NMR ($CDCl_3$) δ: 7.25-7.18 (2H, m), 6.96 (1H, tdd, J = 9.8, 4.5, 2.9 Hz), 6.80 (1H, dq, J = 8.8, 2.0 Hz), 5.24-5.21 (1H, m), 4.37-4.30 (1H, m), 4.20-4.09 (2H, m), 3.99 (1H, dq, J = 19.5, 6.0 Hz), 3.86 (3H, d, J = 2.3 Hz), 3.80 (2H, dd, J = 13.1, 6.8 Hz), 3.13 (1H, dd, J = 13.1, 6.8 Hz), 2.27 (6H, d, J = 2.3 Hz), 2.12 (3H, d, J = 2.7 Hz), 1.31-1.16 (6H, m), 0.96-0.83 (3H, m). |
| D-19 | $^1$H-NMR ($CDCl_3$) δ: 7.49-7.48 (2H, m), 6.95 (1H, td, J = 8.5, 3.3 Hz), 6.80 (1H, dd, J = 9.1, 4.1 Hz), 5.89 (1H, d, J = 3.2 Hz), 5.21 (1H, d, J = 9.5 Hz), 4.96 (1H, ddd, J = 12.8, 7.4, 5.1 Hz), 4.40-4.27 (3H, m), 3.86 (3H, s), 3.78 (1H, dd, J = 12.9, 4.3 Hz), 3.67-3.62 (2H, m), 3.46-3.42 (1H, m), 2.56-2.49 (1H, m), 2.26-2.23 (1H, m), 2.15 (3H, s), 2.05 (1H, s), 1.93 (1H, td, J = 12.2, 7.7 Hz), 1.75 (1H, dd, J = 12.7, 7.2 Hz), 1.28 (6H, d, J = 6.3 Hz), 0.98 (6H, d, J = 6.8 Hz). |
| D-20 | $^1$H-NMR ($CDCl_3$) δ: 7.41-7.37 (2H, m), 6.93 (1H, td, J = 8.4, 3.2 Hz), 6.80 (1H, dd, J = 8.8, 4.3 Hz), 5.96 (1H, d, J = 5.4 Hz), 5.68 (1H, t, J = 6.1 Hz), 5.06-5.00 (1H, m), 4.67 (1H, dd, J = 13.1, 3.2 Hz), 4.39-4.32 (2H, m), 3.87 (3H, s), 3.77 (1H, dd, J = 13.1, 4.1 Hz), 3.62 (1H, td, J = 9.5, 2.7 Hz), 3.44 (1H, dd, J = 17.9, 9.7 Hz), 3.02 (1H, dd, J = 13.1, 10.4 Hz), 2.56-2.50 (1H, m), 2.26 (1H, t, J = 10.0 Hz), 2.10 (3H, s), 2.10 (1H, tt, J = 19.9, 7.2 Hz), 1.91 |

TABLE 8-continued

| Compound number | NMR |
|---|---|
| | (1H, ddd, J = 21.1, 11.3, 6.3 Hz), 1.75 (1H, dd, J = 12.7, 6.3 Hz), 1.25 (6H, t, J = 4.3 Hz), 0.99 (6H, dd, J = 6.8, 0.9 Hz). |
| D-29 | $^1$H-NMR ($CDCl_3$) δ: 8.03-7.37(5H, m), 5.11-3.80(7H, m), 3.93(3H, s), 2.14(3H, s), 1.35-1.20(18H, m). |
| D-35 | 1H-NMR ($CDCl_3$) δ: 7.40-6.70(4H, m), 5.35-0.95(25H, m), 3.84(3H, s), 2.14(3H, s). |
| D-37 | $^1$H-NMR ($CDCl_3$) δ: 7.44-6.80(4H, m), 5.41-1.00(25H, m), 3.86(3H, s), 2.20(3H, s). |
| D-40 | $^1$H-NMR ($CDCl_3$) δ: 7.51-7.47 (1H, m), 7.41-7.18 (4H, m), 7.08-6.97 (4H, m), 5.01-4.93 (3H, m), 4.37 (1H, dq, J = 14.7, 4.2 Hz), 3.82-3.78 (6H, m), 3.33-3.31 (3H, m), 2.17-2.16 (3H, m), 1.30-1.24 (6H, m). |
| D-47 | $^1$H-NMR ($CDCl_3$) δ: 8.73-6.77(8H, m), 5.23-3.60(7H, m), 3.80(3H, s), 2.11(3H, s), 1.70(6H, d, J = 6.3 Hz). |
| D-52 | $_1$H-NMR ($CDCl_3$) δ: 7.43-6.78(8H, m), 5.22-3.43(7H, m), 3.81(3H, s), 3.79(3H, s), 2.12(3H, s), 1.23(6H, d, J = 6.3 Hz). |
| D-57 | $^1$H-NMR ($CDCl_3$) δ: 8.52-6.96(8H, m), 5.30(2H, s), 5.18(2H, s), 4.39-4.31(1H, m), 3.96(3H, s), 2.19(3H, s) 1.26 (6H, d, J = 6.3 Hz). |
| D-63 | $^1$H-NMR ($CDCl_3$) δ: 7.25-7.18 (3H, m), 7.07 (1H, dd, J = 7.3, 1.4 Hz), 7.00 (1H, s), 6.90-6.83 (4H, m), 4.33-4.27 (1H, m), 4.23-4.19 (2H, m), 3.95 (2H, t, J = 6.9 Hz), 3.86 (3H, s), 3.80 (3H, s), 3.00-2.93 (4H, m), 2.06 (3H, s), 1.23 (6H, d, J = 6.0 Hz). |
| D-65 | $^1$H-NMR ($CDCl_3$) δ: 7.25 (1H, s), 7.21 (1H, dd, J = 8.7, 3.2 Hz), 7.01-6.92 (1H, m), 6.81 (1H, dd, J = 8.9, 4.4 Hz), 5.25-5.17 (1H, m), 4.37-4.30 (1H, m), 4.25 (4H, s), 4.14-4.07 (1H, m), 3.97 (1H, dd, J = 14.2, 7.3 Hz), 3.85 (3H, s), 3.54-3.46 (1H, m), 2.38-2.28 (4H, m), 2.12 (3H, s), 1.75-1.66 (4H, m), 1.26 (6H, d, J = 6.4 Hz). |
| D-66 | $^1$H-NMR ($CDCl_3$) δ: 7.34 (1H, s), 7.18 (1H, dd, J = 9.1, 3.2 Hz), 7.00-6.95 (1H, m), 6.81 (1H, dd, J = 8.8, 4.3 Hz), 5.24 (1H, t, J = 8.2 Hz), 4.34 (1H, td, J = 12.5, 6.0 Hz), 4.16-4.03 (1H, m), 3.95 (1H, dd, J = 14.0, 7.7 Hz), 3.86 (3H, s), 3.03 (1H, d, J = 5.4 Hz), 2.79 (2H, t, J = 7.2 Hz), 2.12 (3H, s), 1.78-1.71 (2H, m), 1.43-1.31 (4H, m), 1.26 (6H, d, J = 6.3 Hz), 0.91 (3H, t, J = 7.0 Hz). |
| D-74 | $^1$H-NMR ($CDCl_3$) δ: 7.40 (1H, s), 7.19-6.82 (3H, m), 5.25-3.94 (5H, m), 4.82 (2H, s), 3.86 (3H, s), 2.05 (3H, s), 1.29-1.21 (6H, m) |
| D-80 | $^1$H-NMR ($CDCl_3$) δ: 7.62 (1H, dd, J = 8.7, 3.2 Hz), 7.30 (1H, s), 7.29-7.24 (1H, m), 6.99 (1H, dd, J = 9.2, 3.7 Hz), 5.11 (2H, s), 4.36-4.30 (1H, m), 4.25 (4H, s), 3.97 (3H, s), 2.39-2.25 (4H, m), 2.18 (3H, s), 1.76-1.63 (4H, m), 1.25 (6H, d, J = 6.4 Hz). |
| D-83 | $^1$H-NMR ($CDCl_3$) δ: 7.61 (1H, s), 7.22-7.10 (3H, m), 6.90(1H, s), 5.94-2.20 (6H, m), 2.39 (3H, s), 2.22 (3H, s), 2.15(3H, s), 1.29-1.05 (15H, d, m). |
| D-84 | $^1$H-NMR ($CDCl_3$) δ: 7.62 (1H, dd, J = 8.7, 3.2 Hz), 7.29 (1H, s), 7.29-7.24 (1H, m), 6.99 (1H, dd, J = 9.2, 4.1 Hz), 5.11 (2H, s), 4.36-4.30 (1H, m), 4.24 (4H, br s), 3.97 (3H, s), 2.18 (3H, s), 1.85 (3H, s), 1.78 (3H, s), 1.25 (6H, d, J = 6.4 Hz). |
| D-85 | $^1$H-NMR ($CDCl_3$) δ: 7.28 (1H, s), 7.20-6.77 (3H, m), 5.94-3.36 (9H, m), 3.86 (3H, s), 2.13 (3H, s), 1.26 (6H, d, J = 6.3 Hz). |
| D-86 | $^1$H-NMR ($CDCl_3$) δ: 7.77 (1H, dd, J = 7.5, 2.9 Hz), 7.66-7.60 (2H, m), 7.52 (1H, dd, J = 9.1, 5.4 Hz), 7.44 (1H, d, J = 5.4 Hz), 7.26-7.20 (1H, m), 7.01-6.94 (1H, m), 6.82 (1H, dd, J = 8.8, 4.3 Hz), 6.26-6.19 (1H, m), 5.89 (1H, d, J = 5.0 Hz), 5.36-5.21 (1H, m), 4.67-4.42 (3H, m), 4.40-4.32 (1H, m), 4.30-4.10 (2H, m), 3.91-3.78 (4H, m), 3.53-3.38 (1H, m), 2.19-2.04 (3H, m), 1.27 (6H, dd, J = 6.3, 1.8 Hz). |
| D-87 | $^1$H-NMR ($CDCl_3$) δ: 7.84-7.78 (2H, m), 7.76-7.69 (2H, m), 7.63 (1H, dd, J = 8.8, 3.4 Hz), 7.37 (1H, s), 7.32-7.20 (1H, m), 6.98 (1H, dd, J = 9.1, 4.1 Hz), 5.15 (2H, s), 4.50-4.39 (4H, m), 4.40-4.29 (1H, m), 3.97 (3H, s), 2.18 (3H, s), 1.25 (6H, d, J = 6.3 Hz). |

TABLE 8-continued

| Compound number | NMR |
|---|---|
| D-88 | $^1$H-NMR ($CDCl_3$) δ: 7.35 (1H, d, J = 5.9 Hz), 7.28-7.22 (1H, m), 6.99-6.91 (1H, m), 6.80 (1H, dd, J = 8.8, 4.3 Hz), 5.36-5.24 (1H, m), 4.49-4.00 (5H, m), 3.88-3.84 (3H, m), 3.82-3.59 (1H, m), 2.80-2.62 (3H, m), 2.39-2.15 (2H, m), 2.14 (3H, s), 1.30-1.19 (12H, m). |
| D-89 | $^1$H-NMR ($CDCl_3$) δ: 7.34 (1H, s), 7.20 (1H, dd, J = 9.1, 3.2 Hz), 7.00-6.94 (1H, m), 6.81 (1H, dd, J = 8.8, 4.3 Hz), 5.30-5.19 (1H, m), 4.42-4.27 (1H, m), 4.24-4.01 (3H, m), 3.94-3.81 (1H, m), 3.86 (3H, s), 3.48 (1H, br s), 3.17-2.98 (3H, m), 2.31-2.15 (2H, m), 2.13 (3H, s), 1.37 (6H, d, J = 6.8 Hz), 1.26 (6H, d, J = 6.3 Hz). |
| D-90 | $^1$H-NMR ($CDCl_3$) δ: 7.27 (1H, s), 7.19 (1H, dd, J = 9.1, 3.2 Hz), 6.96 (1H, td, J = 8.4, 3.2 Hz), 6.81 (1H, dd, J = 9.1, 4.1 Hz), 5.26-5.17 (1H, m), 4.39-4.28 (1H, m), 4.17-3.95 (4H, m), 3.86 (3H, s), 3.43 (1H, d, J = 5.4 Hz), 2.98-2.91 (1H, m), 2.58 (2H, t, J = 7.5 Hz), 2.13 (3H, s), 1.90 (2H, td, J = 14.2, 6.6 Hz), 1.26 (12H, d, J = 6.3 Hz). |

[Biological Test]

Usefulness of the dihydropyrimidine compound of the present invention as an active ingredient for agricultural and horticultural fungicides is illustrated in Test Examples below.

The dihydropyrimidine compounds used in the tests are shown by test in Tables 9 and 10 below. The compound numbers in Table 9 each correspond to the compound numbers in Tables 2 to 4. The compound numbers in Table 10 each correspond to the compound numbers in Tables 6 and 7.

TABLE 9

| Scab | | | Powdery mildew | | Brown rust | Gray mold |
|---|---|---|---|---|---|---|
| A-1 | A-40 | A-94 | A-1 | A-84 | A-1 | A-42 |
| A-2 | A-42 | A-95 | A-2 | A-86 | A-2 | A-58 |
| A-3 | A-44 | A-96 | A-10 | A-90 | A-10 | A-60 |
| A-5 | A-46 | A-97 | A-11 | A-91 | A-11 | A-63 |
| A-6 | A-48 | A-98 | A-14 | A-92 | A-14 | A-75 |
| A-7 | A-49 | A-99 | A-17 | A-93 | A-17 | A-76 |
| A-8 | A-51 | A-100 | A-18 | A-94 | A-23 | A-102 |

TABLE 9-continued

| Scab | | | Powdery mildew | | Brown rust | Gray mold |
|---|---|---|---|---|---|---|
| A-9 | A-58 | A-101 | A-23 | A-95 | A-24 | |
| A-10 | A-60 | A-102 | A-24 | A-96 | A-25 | |
| A-11 | A-61 | A-103 | A-31 | A-97 | A-48 | |
| A-13 | A-63 | A-104 | A-38 | A-99 | A-60 | |
| A-14 | A-67 | A-105 | A-42 | A-100 | A-61 | |
| A-15 | A-70 | A-107 | A-46 | A-101 | A-63 | |
| A-16 | A-71 | B-3 | A-48 | A-102 | A-64 | |
| A-17 | A-72 | B-7 | A-49 | A-105 | A-69 | |
| A-18 | A-75 | B-8 | A-51 | B-1 | A-70 | |
| A-19 | A-76 | B-9 | A-58 | B-3 | A-76 | |
| A-20 | A-79 | | A-60 | | A-80 | |
| A-21 | A-80 | | A-61 | | A-91 | |
| A-22 | A-81 | | A-63 | | A-93 | |
| A-23 | A-83 | | A-69 | | A-95 | |
| A-24 | A-84 | | A-70 | | A-99 | |
| A-25 | A-85 | | A-71 | | A-100 | |
| A-26 | A-87 | | A-75 | | | |
| A-31 | A-88 | | A-76 | | | |
| A-36 | A-90 | | A-79 | | | |
| A-37 | A-91 | | A-80 | | | |
| A-38 | A-93 | | A-81 | | | |

TABLE 10

| Scab | | | Powdery mildew | | | Brown rust | | Gray mold |
|---|---|---|---|---|---|---|---|---|
| C-2 | C-89 | C-180 | C-2 | C-95 | C-197 | C-2 | C-168 | C-2 |
| C-4 | C-90 | C-182 | C-4 | C-97 | C-199 | C-4 | C-170 | C-4 |
| C-6 | C-91 | C-183 | C-6 | C-99 | C-202 | C-6 | C-174 | C-24 |
| C-10 | C-93 | C-184 | C-10 | C-101 | C-207 | C-10 | C-176 | C-56 |
| C-12 | C-95 | C-186 | C-12 | C-103 | C-208 | C-22 | C-182 | C-58 |
| C-14 | C-97 | C-188 | C-14 | C-105 | C-210 | C-24 | C-197 | C-60 |
| C-15 | C-99 | C-189 | C-15 | C-107 | C-211 | C-33 | C-199 | C-62 |
| C-17 | C-101 | C-191 | C-22 | C-109 | C-213 | C-43 | C-210 | C-101 |
| C-22 | C-103 | C-197 | C-24 | C-111 | C-219 | C-45 | D-11 | C-112 |
| C-24 | C-105 | C-199 | C-29 | C-112 | D-1 | C-47 | D-20 | C-126 |
| C-25 | C-107 | C-202 | C-30 | C-115 | D-3 | C-49 | D-22 | C-148 |
| C-28 | C-109 | C-207 | C-32 | C-117 | D-11 | C-54 | D-48 | C-154 |
| C-29 | C-111 | C-208 | C-33 | C-122 | D-20 | C-56 | D-50 | C-168 |
| C-30 | C-112 | C-210 | C-34 | C-124 | D-22 | C-58 | | C-199 |
| C-32 | C-115 | C-211 | C-36 | C-126 | D-34 | C-60 | | C-202 |
| C-34 | C-117 | C-213 | C-39 | C-127 | D-35 | C-63 | | C-210 |
| C-36 | C-122 | C-219 | C-43 | C-129 | D-37 | C-67 | | D-11 |
| C-39 | C-124 | C-220 | C-45 | C-135 | D-44 | C-69 | | |
| C-41 | C-126 | C-221 | C-47 | C-137 | D-56 | C-75 | | |
| C-43 | C-127 | D-3 | C-49 | C-141 | | C-79 | | |

TABLE 10-continued

| Scab | | | Powdery mildew | | Brown rust | Gray mold |
|---|---|---|---|---|---|---|
| C-45 | C-129 | D-7 | C-51 | C-146 | C-81 | |
| C-47 | C-135 | D-8 | C-54 | C-148 | C-83 | |
| C-49 | C-137 | D-11 | C-56 | C-151 | C-87 | |
| C-51 | C-141 | D-13 | C-58 | C-154 | C-89 | |
| C-54 | C-144 | D-14 | C-60 | C-158 | C-93 | |
| C-56 | C-148 | D-16 | C-62 | C-160 | C-95 | |
| C-58 | C-151 | D-20 | C-63 | C-166 | C-97 | |
| C-60 | C-152 | D-22 | C-65 | C-168 | C-99 | |
| C-62 | C-154 | D-33 | C-67 | C-170 | C-101 | |
| C-63 | C-156 | D-34 | C-69 | C-172 | C-103 | |
| C-65 | C-158 | D-35 | C-71 | C-173 | C-107 | |
| C-67 | C-160 | D-36 | C-73 | C-174 | C-109 | |
| C-69 | C-162 | D-37 | C-75 | C-176 | C-112 | |
| C-71 | C-166 | D-39 | C-77 | C-177 | C-115 | |
| C-73 | C-168 | D-43 | C-79 | C-179 | C-117 | |
| C-75 | C-170 | D-52 | C-81 | C-180 | C-124 | |
| C-77 | C-172 | D-53 | C-83 | C-182 | C-126 | |
| C-79 | C-173 | D-54 | C-85 | C-183 | C-129 | |
| C-81 | C-174 | D-56 | C-87 | C-186 | C-135 | |
| C-83 | C-176 | D-57 | C-89 | C-188 | C-148 | |
| C-85 | C-177 | D-63 | C-90 | C-191 | C-154 | |
| C-87 | C-179 | | C-93 | C-194 | C-166 | |

(Preparation of Emulsion for Test)

5 parts by weight of the dihydropyrimidine compound of the present invention, 93.5 parts by weight of N,N-dimethylformamide, and 1.5 parts by weight of polyoxyethylene sorbitan monolaurate (TWEEN® 20) were mixed and dissolved to obtain an emulsion (I) including 5% of an active ingredient.

The control value was calculated by the following expression.

Control value (%)=100−{lesion area ratio in treated group/lesion area ratio in untreated group}×100 [Expression 1]

(Test Example 1) Apple Scab Control Test

Water was added to the emulsion (I) such that the concentration of the dihydropyrimidine compound reached 125 ppm to dissolve the emulsion, and a drug solution was obtained. Subsequently, the drug solution was sprayed onto apple seedlings (variety: "Orin", leaf stage: 3 to 4) cultivated in seedling pots. After air drying, the seedlings were inoculated with conidiospores of an apple scab pathogen (*Venturia inaequalis*) (treated group). As a control, apple seedlings that were not sprayed with the drug solution were inoculated in the same manner (untreated group). The seedlings were left to stand in a humidified room at 20° C. using a 12 hour light/dark cycle.

On the day 2 weeks after the inoculation, the leaves of the apple seedlings were visually observed to determine the lesion area ratio, and the control value was calculated.

The dihydropyrimidine compounds described in Table 9 and Table 10 were subjected to the apple scab control test. All the compounds demonstrated control values of 75% or more.

(Test Example 2) Wheat Powdery Mildew Control Test

Water was added to the emulsion (I) such that the concentration of the dihydropyrimidine compound reached 125 ppm to dissolve the emulsion, and a drug solution was obtained. Subsequently, the drug solution was sprayed onto wheat seedlings (variety: "Chihoku", leaf stage: 1 to 2) cultivated in seedling pots. After air drying, conidiospores of a wheat powdery mildew pathogen (*Erysiphe graminis* f. sp. *tritici*) were sprinkled thereon for inoculation (treated group). As a control, wheat seedlings that were not sprayed with the drug solution were inoculated in the same manner as described above (untreated group). The seedlings were left to stand in a greenhouse at 20° C.

On the 6 days after the inoculation, the leaves of the wheat seedlings were visually observed to determine the lesion area ratio, and the control value was calculated.

The dihydropyrimidine compounds described in Table 9 and Table 10 were subjected to the wheat powdery mildew control test. All the compounds demonstrated control values of 75% or more.

(Test Example 3) Wheat Brown Rust Control Test

Water was added to the emulsion (I) such that the concentration of the dihydropyrimidine compound reached 125 ppm to dissolve the emulsion, and a drug solution was obtained. Subsequently, the drug solution was sprayed onto wheat seedlings (variety: "Norin 61", leaf stage: 1 to 2) cultivated in seedling pots. After air drying, uredospores of a wheat brown rust pathogen (*Puccinia recondita*) were sprinkled on wheat seedlings sprayed with the drug solution for inoculation (treated group). As a control, wheat seedlings that were not sprayed with the drug solution were inoculated in the same manner as described above (untreated group). The seedlings were left to stand in a greenhouse at 20° C.

On the 12 days after the inoculation, the leaves of the wheat seedlings were visually observed to determine the lesion area ratio, and the control value was calculated.

The dihydropyrimidine compounds described in Table 9 and Table 10 were subjected to the wheat brown rust control test. All the compounds demonstrated control values of 75% or more.

(Test Example 4) Cucumber Gray Mold Control Test

Water was added to the emulsion (I) such that the concentration of the dihydropyrimidine compound reached 125 ppm to dissolve the emulsion, and a drug solution was obtained. Subsequently, the drug solution was sprayed onto cucumber seedlings (variety: "creeping" type, cotyledon stage) cultivated in seedling pots. After air drying, a suspension of conidiospores of a cucumber gray mold pathogen (*Botrytis cinerea*) was dropped thereon for inoculation (treated group). As a control, cucumber seedlings that were not sprayed with the drug solution were inoculated by dropping in the same manner as described above (untreated group). The seedlings were left to stand in a humidified room at 20° C.

On the 4 days after the inoculation, the leaves of the cucumber seedlings were visually observed to determine the lesion area ratio, and the control value was calculated.

The dihydropyrimidine compounds described in Table 9 and Table 10 were subjected to the cucumber gray mold control test. All the compounds demonstrated control values of 75% or more.

(Test Example 5) Wheat Powdery Mildew Seed Treatment Test

The emulsion (I) was used to treat seeds such that (weight of dihydropyrimidine compound)/(weight of seeds) reached 100 g/100 kg based on the wheat seeds (variety: "Chihoku"). These seeds were disseminated in pots, and after 8 to 10 days, conidiospores of a wheat powdery mildew pathogen (*Erysiphe graminis* f. sp. *tritici*) were sprinkled thereon for inoculation (treated group). As a control, wheat seedlings that were not treated with the drug were inoculated in the same manner as described above (untreated group). The seedlings were left to stand in a greenhouse at 20° C.

On the 7 days after the inoculation, the leaves of the wheat seedlings were visually observed to determine the lesion area ratio, and the control value was calculated.

The dihydropyrimidine compounds described in Table 11 were subjected to the wheat powdery mildew seed treatment test. All the compounds demonstrated control values of 75% or more.

TABLE 11

| Compound number |
|---|
| A-58 |
| A-60 |
| A-61 |
| A-75 |
| A-76 |
| C-54 |
| C-56 |
| C-73 |
| C-83 |
| C-85 |
| C-89 |
| C-93 |
| C-95 |
| C-97 |
| C-99 |
| C-101 |
| C-107 |
| C-112 |
| C-115 |
| C-117 |
| C-135 |
| C-148 |
| C-154 |
| C-160 |
| C-170 |
| C-176 |
| C-179 |
| C-197 |
| C-199 |
| C-207 |
| C-210 |

(Test Example 6) Wheat Powdery Mildew Soil Irrigation Treatment Test

Pots (5.5 cm×5.5 cm) in which wheat seeds (variety: "Chihoku") were disseminated were irrigated with 10 ml of a drug solution prepared by adding water to the emulsion (I) so as to have a concentration of the dihydropyrimidine compound of 100 ppm. After 8 to 10 days, conidiospores of a wheat powdery mildew pathogen (*Erysiphe graminis* f. sp. *tritici*) were sprinkled thereon for inoculation (treated group). As a control, wheat seedlings that were not treated with the drug were inoculated in the same manner as described above (untreated group). The seedlings were left to stand in a greenhouse at 20° C.

On the 7 days after the inoculation, the leaves of the wheat seedlings were visually observed to determine the lesion area ratio, and the control value was calculated.

The dihydropyrimidine compounds described in Table 12 were subjected to the wheat powdery mildew soil irrigation treatment test. All the compounds demonstrated control values of 75% or more.

TABLE 12

| Compound number |
|---|
| A-58 |
| A-60 |
| A-75 |
| A-76 |
| C-67 |
| C-73 |
| C-83 |
| C-93 |
| C-95 |
| C-99 |
| C-101 |
| C-107 |
| C-117 |
| C-148 |
| C-154 |
| C-160 |
| C-170 |
| C-179 |
| C-182 |
| C-191 |
| C-197 |
| C-199 |
| C-207 |
| C-210 |

Usefulness of the dihydropyrimidine compound of the present invention as an active ingredient of nematicides is illustrated in a Test Example below.

(Test Example 7) Efficacy Against *Meloidogyne incognita*

A suspension containing about 50/0.16 mL second-instar larvae (L2) of *Meloidogyne incognita* was poured into a 96-well microplate at 160 μL per well. Then, a drug solution prepared by adding water to the emulsion (I) so as to have a concentration of the dihydropyrimidine compound of 125 ppm was poured at 40 μL per well. The plate was left to stand under a 20° C. condition for 4 days.

Mortality was determined, and the nematode mortality rate was calculated. Those individuals that showed no movement for 10 seconds were deemed to be dead. The test repeated twice.

The compounds of compound numbers A-28, A-64, C-92, and C-145 were subjected to the efficacy test against *Meloidogyne incognita*. All the compounds demonstrated a nematode mortality rate on *Meloidogyne incognita* of 60% or more.

Usefulness of the dihydropyrimidine compound of the present invention as an active ingredient for medical/animal antifungal agents is illustrated in Test Examples below.

(Test Example 8) Antimicrobial Test Against *Fusarium graminearum*

Water was added to the emulsion (I) such that the concentration of the dihydropyrimidine compound reached 125 ppm to dissolve the emulsion, and a drug solution was obtained.

Spores of *Fusarium graminearum* were added to and dispersed in a potato sucrose yeast extract medium, and the drug solution described above was further added and mixed thereto such that the concentration of the dihydropyrimidine compound in the culture solution reached 15.6 ppm. The resulting solution was dispensed onto a 96-well microplate and cultivated in the dark at 20° C. for 4 days.

After the cultivation, the turbidity at a wavelength of 405 nm was measured by a microplate reader and compared with that in the untreated case to determine the growth inhibition rate of *Fusarium graminearum* (%).

The dihydropyrimidine compounds described in Table 13 were subject to the antimicrobial test against *Fusarium graminearum*. All the compounds demonstrated excellent growth inhibition rates of 50% or more.

TABLE 13

| Compound number |
|---|
| A-2 |
| A-14 |
| A-15 |
| A-17 |
| A-23 |
| A-24 |
| A-37 |
| A-38 |
| A-42 |
| A-46 |
| A-49 |
| A-51 |
| A-58 |
| A-60 |
| A-61 |
| A-63 |
| A-64 |
| A-69 |
| A-70 |
| A-75 |
| A-76 |
| A-79 |
| A-83 |
| A-88 |
| A-90 |
| A-92 |
| A-93 |
| A-95 |
| A-96 |
| A-97 |
| A-99 |
| A-100 |
| A-101 |

TABLE 13-continued

| Compound number |
|---|
| A-102 |
| A-105 |
| A-106 |
| A-107 |
| B-7 |
| B-8 |
| C-2 |
| C-4 |
| C-6 |
| C-10 |
| C-12 |
| C-14 |
| C-15 |
| C-22 |
| C-24 |
| C-25 |
| C-29 |
| C-32 |
| C-33 |
| C-34 |
| C-36 |
| C-39 |
| C-41 |
| C-43 |
| C-45 |
| C-47 |
| C-49 |
| C-54 |
| C-56 |
| C-58 |
| C-60 |
| C-62 |
| C-63 |
| C-67 |
| C-69 |
| C-71 |
| C-73 |
| C-75 |
| C-77 |
| C-79 |
| C-81 |
| C-83 |
| C-85 |
| C-87 |
| C-89 |
| C-93 |
| C-95 |
| C-97 |
| C-99 |
| C-101 |
| C-103 |
| C-105 |
| C-107 |
| C-109 |
| C-111 |
| C-112 |
| C-115 |
| C-117 |
| C-122 |
| C-124 |
| C-126 |
| C-127 |
| C-129 |
| C-135 |
| C-137 |
| C-141 |
| C-148 |
| C-151 |
| C-154 |
| C-156 |
| C-158 |
| C-160 |
| C-162 |
| C-168 |
| C-170 |
| C-172 |
| C-176 |
| C-179 |

TABLE 13-continued

| Compound number |
|---|
| C-182 |
| C-183 |
| C-186 |
| C-188 |
| C-194 |
| C-197 |
| C-199 |
| C-202 |
| C-207 |
| C-210 |
| C-213 |
| C-219 |
| D-1 |
| D-2 |
| D-5 |
| D-7 |
| D-8 |
| D-9 |
| D-11 |
| D-13 |
| D-14 |
| D-20 |
| D-22 |
| D-39 |
| D-40 |
| D-41 |
| D-43 |
| D-48 |
| D-49 |
| D-50 |
| D-52 |
| D-53 |
| D-54 |
| D-55 |
| D-56 |
| D-63 |

(Test Example 9) Antimicrobial Test Against *Aspergillus niger*

Spores of *Aspergillus niger* were added to and dispersed in a Vogel medium, and a dihydropyrimidine compound dissolved in dimethyl sulfoxide was added and mixed thereto at 25 ppm. The resulting solution was dispensed onto a 96-well microplate and cultivated in the dark at 25° C. for 4 days.

After the cultivation, the turbidity at a wavelength of 405 nm was measured by a microplate reader and compared with that in the untreated case to determine the growth inhibition of *Aspergillus niger* (%) was determined.

The dihydropyrimidine compounds described in Table 14 were subject to the antimicrobial test against *Aspergillus niger*. All the compounds demonstrated excellent growth inhibition rates of 50% or more.

TABLE 14

| Compound number |
|---|
| A-1 |
| A-7 |
| A-14 |
| A-23 |
| A-24 |
| A-37 |
| A-38 |
| A-42 |
| A-51 |
| A-58 |
| A-60 |
| A-61 |
| A-63 |
| A-75 |
| A-76 |
| A-79 |
| A-80 |
| A-88 |
| A-90 |
| A-93 |
| A-95 |
| A-96 |
| A-97 |
| A-100 |
| A-101 |
| A-102 |
| C-43 |
| C-54 |
| C-56 |
| C-58 |
| C-60 |
| C-62 |
| C-63 |
| C-69 |
| C-73 |
| C-75 |
| C-77 |
| C-79 |
| C-81 |
| C-83 |
| C-89 |
| C-93 |
| C-95 |
| C-99 |
| C-101 |
| C-103 |
| C-107 |
| C-109 |
| C-112 |
| C-115 |
| C-117 |
| C-124 |
| C-126 |
| C-129 |
| C-135 |
| C-137 |
| C-141 |
| C-148 |
| C-154 |
| C-160 |
| C-168 |
| C-170 |
| C-172 |
| C-176 |
| C-179 |
| C-182 |
| C-186 |
| C-188 |
| C-194 |
| C-197 |
| C-199 |
| C-202 |
| C-207 |
| C-210 |
| C-213 |
| D-11 |
| D-20 |
| D-22 |
| D-52 |
| D-53 |
| D-54 |
| D-56 |

INDUSTRIAL APPLICABILITY

Since those randomly selected from among the dihydropyrimidine compounds of the present invention exert the effects as described above, the dihydropyrimidine compound of the present invention, including the compounds that are not exemplified, are compounds having the antimicrobial and bactericidal effect and nematicidal effect, causing no phytotoxicity to plants, and giving little influence on humans, livestock, and fish, and are useful as pesticides, nematicides, and medical/animal antifungal agents.

The invention claimed is:

1. A compound of formula (I) or a salt thereof:

(I)

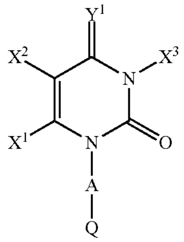

wherein, $X^1$ represents a hydrogen atom;

$X^2$ represents a group represented by $R^1O—N═CR^6$;

$R^1$ represents a substituted or unsubstituted C1-6 alkyl group;

$R^6$ represents a hydrogen atom or a substituted or unsubstituted C1-6 alkyl group;

$X^3$ represents a substituted or unsubstituted linear C1-6 alkyl group, a substituted or unsubstituted linear C2-6 alkenyl group, a substituted or unsubstituted linear C2-6 alkynyl group, a group represented by $R^1$—CO—, a substituted or unsubstituted C3-6 cycloalkyl group, a substituted or unsubstituted C6-10 aryl group, or a substituted or unsubstituted 4 to 6-membered ring heterocyclyl group, wherein substituent(s) on the linear C1-6 alkyl group, the linear C2-6 alkenyl group, the linear C2-6 alkynyl group, the C3-6 cycloalkyl group, the C6-10 aryl group, and the 4 to 6-membered ring heterocyclyl group are selected from the group consisting of:

a substituted or unsubstituted C1-6 alkyl group,
a substituted or unsubstituted C2-6 alkenyl group,
a substituted or unsubstituted C2-6 alkynyl group,
a hydroxy group,
a substituted or unsubstituted C1-6 alkoxy group,
a substituted or unsubstituted C1-6 alkylthio group,
a substituted or unsubstituted C1-6 alkylsulfinyl group,
a substituted or unsubstituted C1-6 alkylsulfonyl group,
a substituted or unsubstituted C3-6 cycloalkyl group,
a substituted or unsubstituted C6-10 aryl group,
a substituted or unsubstituted 3 to 10-membered ring heterocyclyl group,
a cyano group,
a group represented by $R^a$—CO—,
a group represented by $R^b$—O—CO—,
a group represented by $R^cR^d$N—,
a group represented by $R^cR^d$N—CO—,
a group represented by $R^a$—CO—O—,
a group represented by $R^a$—CO—$NR^e$—,
a group represented by $R^a$—CO—CO—$NR^e$—,
a group represented by $R^b$—O—CO—$NR^e$—,
a group represented by $R^cR^d$N—CO—O—,
a group represented by $R^cR^d$N—CO—$NR^e$—,
a group represented by $R^cR^d$N—CO—CO—$NR^e$—,
a group represented by $R^cR^d$N—CS—$NR^e$—,
a group represented by $R^bSO_2$—$NR^e$—,
a group represented by $R^a$O—N═$CR^f$—, and
a group represented by $R^hR^i$C═N—O—, each $R^a$ independently represents
a hydrogen atom,
a substituted or unsubstituted C1-6 alkyl group,
a substituted or unsubstituted C2-6 alkenyl group,
a substituted or unsubstituted C2-6 alkynyl group,
a substituted or unsubstituted C3-6 cycloalkyl group,
a substituted or unsubstituted C6-10 aryl group, or
a substituted or unsubstituted 3 to 10-membered ring heterocyclyl group, each $R^b$ independently represents
a substituted or unsubstituted C1-6 alkyl group, or
a substituted or unsubstituted C3-6 cycloalkyl group, each $R^c$ independently represents
a hydrogen atom,
a substituted or unsubstituted C1-6 alkyl group,
a substituted or unsubstituted C3-6 cycloalkyl group, or
a substituted or unsubstituted C6-10 aryl group, each $R^d$ independently represents
a hydrogen atom,
a substituted or unsubstituted C1-6 alkyl group, or
a substituted or unsubstituted C1-6 alkoxy group, wherein $R^c$ and $R^d$ can together form a divalent organic group, each $R^e$ independently represents
a hydrogen atom,
a substituted or unsubstituted C1-6 alkyl group, or
a substituted or unsubstituted C1-6 alkoxy group, $R^f$ represents
a hydrogen atom, or
an amino group, each $R^h$ independently represents
a substituted or unsubstituted C1-6 alkyl group, and each $R^i$ independently represents a substituted or unsubstituted C1-6 alkyl group, wherein $R^h$ and $R^i$ can together form a divalent organic group;

A represents a substituted or unsubstituted C1-6 alkylene group or a substituted or unsubstituted C2-6 alkenylene group, wherein substituent(s) on the C1-6 alkylene group and the C2-6 alkenylene group are selected from:
a hydroxy group,
a substituted or unsubstituted C1-6 alkoxy group,
a substituted or unsubstituted C2-6 alkenyloxy group,
a substituted or unsubstituted C2-6 alkynyloxy group,
a substituted or unsubstituted C3-6 cycloalkyloxy group,
a substituted or unsubstituted C6-10 aryloxy group,
a substituted or unsubstituted 3 to 6-membered ring heterocyclyloxy group,
an oxo group (O═), or
a divalent group represented by Ra1O—N═, and $R^{a1}$ represents a substituted or unsubstituted C1-6 alkyl group; and Q represents a substituted or unsubstituted C6-10 aryl group or a substituted or unsubstituted 5 to 10-membered ring heterocyclyl group.

2. An agricultural and horticultural fungicide containing a carrier and at least one selected from the group consisting of the compound according to claim 1 and a salt thereof, as an active ingredient.

3. The agricultural and horticultural fungicide according to claim 2, wherein the fungicide is suitable for seed treatment.

4. The compound or a salt thereof according to claim 1, wherein A represents a substituted or unsubstituted C1-6 alkylene group or a substituted or unsubstituted C2-6 alkenylene group, wherein substituent(s) on the C1-6 alkylene group and the C2-6 alkenylene group are selected from:

a hydroxy group, a substituted or unsubstituted C1-6 alkoxy group, an oxo group (O=), or a divalent group represented by Ra1O-N=, and $R^{a1}$ represents a substituted or unsubstituted C1-6 alkyl group.

* * * * *